United States Patent
Perez

(10) Patent No.: US 11,331,482 B2
(45) Date of Patent: *May 17, 2022

(54) SYSTEMS AND METHODS FOR MANAGING PAIN USING AN ELECTRO-DERMAL PATCH

(71) Applicant: Elira, Inc., St. Louis, MO (US)

(72) Inventor: Raul E. Perez, St. Louis, MO (US)

(73) Assignee: Elira, Inc., St. Louis, MO (US)

( * ) Notice: Subject to any disclaimer, the term of this patent is extended or adjusted under 35 U.S.C. 154(b) by 262 days.

This patent is subject to a terminal disclaimer.

(21) Appl. No.: 16/581,084

(22) Filed: Sep. 24, 2019

(65) Prior Publication Data

US 2020/0155847 A1    May 21, 2020

Related U.S. Application Data

(63) Continuation of application No. 15/337,321, filed on Oct. 28, 2016, now Pat. No. 10,463,854, which is a
(Continued)

(51) Int. Cl.
*A61N 1/36* (2006.01)
*A61B 5/0533* (2021.01)
(Continued)

(52) U.S. Cl.
CPC ........ *A61N 1/36021* (2013.01); *A61B 5/0022* (2013.01); *A61B 5/0024* (2013.01);
(Continued)

(58) Field of Classification Search
CPC .............. A61N 1/36021; A61N 1/0484; A61N 1/0456; A61N 1/0476; A61N 1/36014;
(Continued)

(56) References Cited

U.S. PATENT DOCUMENTS

| 4,803,986 A | 2/1989 | Dufresne |
| 5,263,480 A | 11/1993 | Wernicke |

(Continued)

FOREIGN PATENT DOCUMENTS

| DE | 102006053427 | 5/2008 |
| WO | 2014194200 A1 | 12/2014 |

(Continued)

OTHER PUBLICATIONS

Camilleri et al, "Effect of somatovisceral reflexes and selective dermatomal stimulation on postcibal antral pressure activity", Gastroenterology Unit, Mayo Clinic, Rochester, Minnesota 55905, Jul. 1984.
(Continued)

*Primary Examiner* — Rex R Holmes
(74) *Attorney, Agent, or Firm* — Novel IP

(57) ABSTRACT

A wearable device for treating dysmenorrhea in a patient includes a microprocessor, electrical stimulator and at least one electrode configured to deliver electrical stimulation from the external surface of the patient's epidermal layer through a range of 0.1 mm to 10 mm or a range of 0.1 mm to 20 mm of the dermis by applying electrical stimulation to the epidermis of a T9 to T12, L1, L2, L5 and/or S1 to S4 dermatomes of the patient. The device includes a pad, in which the electrode is disposed, for secure placement of the device on a skin surface of the patient. The device is adapted to provide electrical stimulation as per stimulation protocols and to communicate wirelessly with a companion control device configured to monitor and record menstruation-related patterns of the patient. The control device is also configured to monitor, record, and modify stimulation parameters of the stimulation protocols.

20 Claims, 48 Drawing Sheets

Related U.S. Application Data continuation-in-part of application No. 15/052,784, filed on Feb. 24, 2016, now Pat. No. 10,143,840, and a continuation-in-part of application No. 15/052,791, filed on Feb. 24, 2016, now Pat. No. 10,118,035.

(60) Provisional application No. 62/414,144, filed on Oct. 28, 2016, provisional application No. 62/413,213, filed on Oct. 26, 2016, provisional application No. 62/393,486, filed on Sep. 12, 2016, provisional application No. 62/378,393, filed on Aug. 23, 2016, provisional application No. 62/341,917, filed on May 26, 2016, provisional application No. 62/326,541, filed on Apr. 22, 2016, provisional application No. 62/248,059, filed on Oct. 29, 2015, provisional application No. 62/247,113, filed on Oct. 27, 2015, provisional application No. 62/246,526, filed on Oct. 26, 2015, provisional application No. 62/242,957, filed on Oct. 16, 2015, provisional application No. 62/242,944, filed on Oct. 16, 2015, provisional application No. 62/240,808, filed on Oct. 13, 2015, provisional application No. 62/237,356, filed on Oct. 5, 2015, provisional application No. 62/189,805, filed on Jul. 8, 2015, provisional application No. 62/189,800, filed on Jul. 8, 2015, provisional application No. 62/161,362, filed on May 14, 2015, provisional application No. 62/161,353, filed on May 14, 2015, provisional application No. 62/141,328, filed on Apr. 1, 2015, provisional application No. 62/141,333, filed on Apr. 1, 2015, provisional application No. 62/133,526, filed on Mar. 16, 2015, provisional application No. 62/133,530, filed on Mar. 16, 2015, provisional application No. 62/120,082, filed on Feb. 24, 2015, provisional application No. 62/120,067, filed on Feb. 24, 2015.

(51) Int. Cl.

| | | |
|---|---|---|
| *A61B 5/021* | (2006.01) | |
| *A61B 5/145* | (2006.01) | |
| *A61B 5/00* | (2006.01) | |
| *A61N 1/04* | (2006.01) | |
| *A61B 5/0205* | (2006.01) | |
| *G16H 40/67* | (2018.01) | |
| *A61B 5/259* | (2021.01) | |
| *A61B 5/369* | (2021.01) | |
| *A61B 5/389* | (2021.01) | |
| *A61B 5/0245* | (2006.01) | |
| *A61B 5/08* | (2006.01) | |
| *A61B 5/11* | (2006.01) | |
| *A61B 5/0537* | (2021.01) | |
| *A61B 5/024* | (2006.01) | |
| *A61B 5/24* | (2021.01) | |
| *A61B 5/276* | (2021.01) | |

(52) U.S. Cl.
CPC .......... *A61B 5/021* (2013.01); *A61B 5/02055* (2013.01); *A61B 5/0533* (2013.01); *A61B 5/14532* (2013.01); *A61B 5/259* (2021.01); *A61B 5/369* (2021.01); *A61B 5/389* (2021.01); *A61B 5/4836* (2013.01); *A61B 5/6802* (2013.01); *A61B 5/6824* (2013.01); *A61B 5/6833* (2013.01); *A61N 1/0456* (2013.01); *A61N 1/0476* (2013.01); *A61N 1/0484* (2013.01); *A61N 1/0492* (2013.01); *A61N 1/36031* (2017.08); *A61N 1/36034* (2017.08); *G16H 40/67* (2018.01); *A61B 5/0245* (2013.01); *A61B 5/02405* (2013.01); *A61B 5/0537* (2013.01); *A61B 5/0816* (2013.01); *A61B 5/1118* (2013.01); *A61B 5/14542* (2013.01); *A61B 5/24* (2021.01); *A61B 5/276* (2021.01); *A61B 5/4866* (2013.01); *A61B 5/4875* (2013.01); *A61B 5/7475* (2013.01); *A61B 2560/0242* (2013.01); *A61N 1/0452* (2013.01); *A61N 1/36128* (2013.01)

(58) Field of Classification Search
CPC .............. A61N 1/0492; A61N 1/36128; A61N 2001/083; A61N 1/0452; A61B 5/0024; A61B 5/02055; A61B 5/4836; A61B 5/6833; A61B 5/0476; A61B 5/6802; A61B 5/6824; A61B 5/04087; A61B 5/14532; A61B 5/021; A61B 5/0533; A61B 5/0488; A61B 5/0022; A61B 5/4866; A61B 2560/0242; A61B 5/14542; A61B 5/1118; A61B 5/0816; A61B 5/0537; A61B 5/4875; A61B 5/04001; A61B 5/0245; A61B 5/02405; A61B 5/7475; A61B 5/0424
See application file for complete search history.

(56) References Cited

U.S. PATENT DOCUMENTS

| | | | |
|---|---|---|---|
| 6,097,982 A | 8/2000 | Glegyak | |
| 6,205,359 B1 | 3/2001 | Boveja | |
| 6,325,764 B1 | 12/2001 | Griffith | |
| 6,600,953 B2 | 7/2003 | Flesler | |
| 6,718,202 B2 | 4/2004 | Mann | |
| 7,336,993 B1 | 2/2008 | Szeles | |
| 7,346,390 B1 | 3/2008 | Tumey | |
| 7,689,276 B2 | 3/2010 | Dobak | |
| 7,914,468 B2 | 3/2011 | Shalon | |
| 7,930,033 B2 | 4/2011 | Chen | |
| 7,937,145 B2 | 5/2011 | Dobak | |
| 8,145,318 B2 | 3/2012 | Van Herk | |
| 8,574,164 B2 | 11/2013 | Mashiach | |
| 8,862,238 B2 | 10/2014 | Rahimi | |
| 8,954,889 B2 | 2/2015 | Fujibayashi | |
| 9,320,471 B2 | 4/2016 | Hayes | |
| 9,339,647 B2 | 5/2016 | Strother | |
| 9,351,684 B1 | 5/2016 | Ahmad | |
| 9,956,393 B2 | 5/2018 | Perez | |
| 10,118,035 B2 | 11/2018 | Perez | |
| 10,463,854 B2* | 11/2019 | Perez ................. | A61N 1/36034 |
| 2002/0087192 A1 | 7/2002 | Barrett | |
| 2002/0087193 A1 | 7/2002 | Riddle | |
| 2003/0144708 A1 | 7/2003 | Starkebaum | |
| 2004/0254610 A1 | 12/2004 | Lin | |
| 2005/0256028 A1 | 11/2005 | Yun | |
| 2006/0195153 A1 | 8/2006 | Diubaldi | |
| 2007/0060971 A1 | 3/2007 | Glasberg | |
| 2007/0093870 A1 | 4/2007 | Maschino | |
| 2007/0123952 A1 | 5/2007 | Strother | |
| 2007/0239224 A1 | 10/2007 | Bennett | |
| 2007/0255335 A1 | 11/2007 | Herbert | |
| 2008/0086072 A1 | 4/2008 | Bonutti | |
| 2008/0132962 A1 | 6/2008 | Diubaldi | |
| 2009/0105560 A1 | 4/2009 | Solomon | |
| 2009/0132018 A1 | 5/2009 | Diubaldi | |
| 2009/0157149 A1 | 6/2009 | Wahlgren | |
| 2009/0171418 A1 | 7/2009 | Sarif | |
| 2009/0182393 A1 | 7/2009 | Bachinski | |
| 2009/0182394 A1 | 7/2009 | Bachinski | |
| 2010/0168820 A1 | 7/2010 | Maniak | |
| 2010/0228314 A1 | 9/2010 | Goetz | |
| 2010/0298895 A1 | 11/2010 | Ghaffari | |
| 2011/0193705 A1 | 8/2011 | Sekura | |
| 2011/0257711 A1 | 10/2011 | Lindner | |
| 2011/0270360 A1 | 11/2011 | Harris | |
| 2012/0010651 A1 | 1/2012 | Thramann | |

(56) References Cited

U.S. PATENT DOCUMENTS

| | | |
|---|---|---|
| 2012/0101874 A1 | 4/2012 | Ben-Haim |
| 2012/0109233 A1 | 5/2012 | Lee |
| 2012/0121735 A1 | 5/2012 | Halford |
| 2012/0172792 A1 | 7/2012 | Baynham |
| 2013/0096641 A1 | 4/2013 | Strother |
| 2013/0110201 A1 | 5/2013 | Bonde |
| 2013/0296996 A1 | 11/2013 | Wahlgren |
| 2013/0304175 A1 | 11/2013 | Voegele |
| 2013/0338729 A1 | 12/2013 | Spector |
| 2014/0031895 A1 | 1/2014 | Rahimi |
| 2014/0046423 A1 | 2/2014 | Rajguru |
| 2014/0148872 A1 | 5/2014 | Goldwasser |
| 2014/0266776 A1 | 9/2014 | Miller |
| 2014/0296935 A1 | 10/2014 | Ferree |
| 2014/0315161 A1 | 10/2014 | Sako |
| 2015/0005841 A1 | 1/2015 | Pal |
| 2015/0039047 A1 | 2/2015 | Parker |
| 2015/0148878 A1 | 5/2015 | Yoo |
| 2015/0258326 A1 | 9/2015 | Harris |
| 2017/0021171 A1 | 1/2017 | Perez |
| 2017/0021172 A1 | 1/2017 | Perez |
| 2017/0080207 A1 | 3/2017 | Perez |
| 2017/0203095 A1 | 7/2017 | Bachinski |
| 2018/0000347 A1 | 1/2018 | Perez |
| 2018/0078195 A1 | 3/2018 | Sutaria |
| 2018/0078754 A1 | 3/2018 | Perez |
| 2018/0085580 A1 | 3/2018 | Perez |
| 2018/0125689 A1 | 5/2018 | Perez |

FOREIGN PATENT DOCUMENTS

| | | |
|---|---|---|
| WO | 2015033152 A2 | 3/2015 |
| WO | 2016138176 A1 | 9/2016 |
| WO | 2016138357 A1 | 9/2016 |
| WO | 2017002104 A1 | 1/2017 |
| WO | 2017075359 A2 | 5/2017 |
| WO | 2017205047 A2 | 11/2017 |
| WO | 2018081423 A1 | 5/2018 |

OTHER PUBLICATIONS

"Feasibility Assessment of Appetite Suppression Utilizing TENS Trial-1 (FAAST-1)", Protocol No. CD-001, Revision: Version Rev 02 (Nov. 20, 2015).

Hall WJ, O'Connor PC., "A pharmacological analysis of the response of dog anterior mesenteric vein to transmural electrical stimulation", Ir J Med Sci. Jul. -Sep. 1972;141(7):113-9.

Lee SK et al, "Electroacupuncture may relax the sphincter of Oddi in humans", Gastrointest Endosc. Feb. 2001;53(2):211-6.

Lee GT., "A study of electrical stimulation of acupuncture locus tsusanli (St-36) on mesenteric microcirculation", Am J Chin Med (Gard City N Y). Jan. 1974;2(1):53-66.

Obuchowicz A, Obuchowicz E., "Plasma beta-endorphin and insulin concentrations in relation to body fat and nutritional parameters in overweight and obese prepubertal children", Int J Obes Relat Metab Disord. Sep. 1997;21(9):783-8.

Giovannini et al., "Unresponsiveness of the endorphinergic system to its physiological feedback in obesity", Appetite. Feb. 1991;16(1):39-43.

Wan et al, "The effectiveness of purgation and electroacupuncture in extrahepatic bile duct stone complicated with acute biliary pancreatitis: management of biliary stone pancreatitis through traditional Chinese medicine", Pancreas. Apr. 2011;40(3):483-4. doi: 10.1097/MPA.0b013e318205e52f.

Blaut et al, "The effect of transcutaneous nerve stimulation on intraductal biliary pressure in post-cholecystectomy patients with T-drainage", Eur J Gastroenterol Hepatol. Jan. 2003;15(1):21-6.

Kim MH, "A brief commentary: electroacupuncture may relax the contraction of sphincter of Oddi". The Journal of Alternative and Complementary Medicine. vol. 7, Supplement 1, 2001, pp. S-119-S-120.

Liu et al, "Effects of acupuncture on myoelectric activity of Oddis sphincter in humans", J Tradit Chin Med. Sep. 1993;13(3):189-90.

"D4.3: Satiety Methodology", Work Package 4, Project No. KBBE-2011-5-289800, Project Title: SATIN (Satiety Innovation), Lead Partner: University of Leeds (UNIVLEEDS). Nov. 13, 2012.

Jing Wang et al, "Effects of Cutaneous Gastric Electrical Stimulation on Gastric Emptying and Postprandial Satiety and Fullness in Lean and Obese Subjects", J Clin Gastroenterol vol. 44, No. 5, May/Jun. 2010.

Mark Johnson, "Transcutaneous electrical nerve stimulation (TENS)".

"ACUSLIM Control Your Appetite the Natural Way", Simply Good Health, Australia. Natural Remedies for Healthy Living, Nov. 21, 1997.

Furgala et al, "The effect of Transcutaneous Nerve Stimulation (TENS) on gastric electrical activity", Oct. 18, 2001, http://www.jpp.krakow.pl/journal/archive/12_01/articles/07_article.html.

Wang et al, "Effects of Cutaneous Gastric Electrical Stimulation on Gastric Emptying and Postprandial Satiety and Fullness in Lean and Obese Subjects", J Clin Gastroenterol, vol. 44, No. 5, May/Jun. 2010.

JM Lacey et al, "Acupuncture for the treatment of obesity: a review of the evidence", International Journal of Obesity (2003) 27, 419-427.

Philip V. Peplow et al, "Electroacupuncture for Control of Blood Glucose in Diabetes: Literature Review", J Acupunct Meridian Stud 2012;5(1):1-10.

Mohammad Ma'ani et al, "Nerve Supply of the Stomach and the Small Intestines", Anatomy-7, Apr. 21, 2015.

Camilleri et al, "Relation between antral motility and gastric emptying of solids and liquids in humans", The American journal of physiology, Dec. 1985.

Liu Zhicheng et al, "Effect of acupuncture on weight loss evaluated by adrenal function", Journal of Traditional Chinese Medicine 13 (3): 169-173, 1993.

J F Bergmann et al, "Correlation between echographic gastric emptying and appetite: influence of psyllium", Gut 1992; 33: 1042-1043.

Janssen et al, "Review article: the role of gastric motility in the control of food intake", Aliment Pharmacol Ther 2011; 33: 880-894.

Eva Haker et al, "Effect of sensory stimulation (acupuncture) on sympathetic and parasympathetic activities in healthy subjects", Journal of the Autonomic Nervous System 79 (2000) 52-59.

Stein Knardahl et al, "Sympathetic nerve activity after acupuncture in humans", Pain 75 (1998) 19-25.

Monique Ernst et al, "Sympathetic effects of manual and electrical acupuncture of the Tsusnali Knee Point: Comparison with the Hoku Hand point sympathetic effects", Experimental Neurology 94, 1-10 (1986).

DiLorenzo, Daniel John, "Chronic Intraneural Electrical Stimulation for Prosthetic Sensory Feedback", Proc. 1st Intl IEEE EMBS Conf Neural Eng, Mar. 20-22, 2003.

Sven Andersson, "The functional background in acupuncture effects", Scand J Rehab Med, Suppl 29: 31-60, 1993.

Akio Sato et al, "Somatosympathetic Reflexes : Afferent Fibers, Central Pathways, Discharge Characteristics", Physiological Reviews, vol. 53, No. 4, Oct. 1973.

Kazushi Nishijo et al, "Decreased heart rate by acupuncture stimulation in humans via facilitation of cardiac vagal activity and suppression of cardiac sympathetic nerve", Neuroscience Letters 227 (1997) 165-168.

D. Thomas et al, "Somatic sympathetic vasomotor changes documented by medical thermographic imaging during acupuncture analgesia", Clinical reheumatology, 1992, 11, 55-59.

Monique Ernst et al, "Sympathetic vasomotor changes induced by manual and electrical acupuncture of the Hoku Point visualized by thermography", Pain 21 (1985), 25-33.

Will Rosellini, "FDA gives nod to first fully-removable percutaneous peripheral nerve stimulation device", Peripheral Nerve Stimulation, Posted on Jul. 28, 2016.

DiLorenzo, Daniel John, "Development of a Chronically Implanted Microelectrode Array for Intraneural Electrical Stimulation for Prosthetic Sensory Feedback",MIT SM Thesis,1999.

(56) References Cited

OTHER PUBLICATIONS

Zardetto-Smith et al., "Catecholamine and NPY Efferents From the Ventrolateral Medulla to the Amygdala in the Rat",Brain Research Bulletin, vol. 38, No. 3, 1995, pp. 253-260.
Barone et al., "Gastric Distension Modulates Hypothalamic Neurons via a Sympathetic Afferent Path Through the Mesencephalic Periaqueductal Gray", Brain Research Bulletin, vol. 38, No. 3, 1995; pp. 239-251.
Brown et al., "Changes in Food Intake with Electrical Stimulation of the Ventromedial Hypothalamus in Dogs", Journal of Neurosurgery, vol. 60, 1984, pp. 1253-1257.
Daniel et al., "Criteria for Differentiation of Brown and White Fat in the Rat", Canadian Journal of Physiology and Pharmacology, vol. 47, Mar. 22, 1969; pp. 941-945.
Flaim et al., "Coupling of Signals to Brown Fat: .alpha.-and .beta.-Adrenergic Responses in Intact Rats", In Vivo Adrenergic Responses of Brown Adipose Tissue, 1976, pp. R101-R109.
Felton, D.L. and R.F. Jozefowicz, "Netter's Atlas of Human Neuroscience", Icon Learning Systems, Teterboro, NJ, 2004, p. 126.
Kolen et al., "Effects of spatially targeted transcutaneous electrical nerve stimulation using an electrode array that measures skin resistance on pain and mobility in patients with osteoarthritis in the knee: A randomized controlled trial." J. Pain, 153 (2012) 373-381, doi:10.1016/j.pain.2011.10.033.
Malesevic et al., "Classification of muscle twitch response using ANN: Application in multi-pad electrode optimization," IEEE 2010.
Malesevic et al., "Muscle twitch responses for shaping the multipad electrode for functional electrical stimulation," IEEE Journal of Automatic Control, University of Belgrade, vol. 20:53-58, 2010.
International Search Report for PCT Application No. PCT/US2016/019416, dated Jun. 21, 2016.
International Search Report for PCT Application No. PCT/US2016/059332, dated May 5, 2017.
International Search Report for PCT Application No. PCT/US2017/031769, dated Nov. 27, 2017.
International Search Report for PCT Application No. PCT/US2017/058528, dated Feb. 1, 2018.
Derry et al., "Two Sympathetic Nerve Supplies to Brown Adipose Tissue of the Rat", Canadian Journal of Physiology and Pharmacology, vol. 47, 1969, pp. 57-63.
Takahashi et al., "Hypothalamic Regulation of Lipid Metabolism in the Rat: Effect of Hypothalamic Stimulation on Lipogenesis", Journal of the Autonomic Nervous System, vol. 6, 1982, pp. 225-235.
Yuan et al, "Hypothalamic Unitary Responses to Gastric Vagal Input from the Proximal Stomach", Am J Physiol Gastrointest Liver Physiol 262:G74-G80, 1992.
Astrup A, Buemann B, Christensen NJ, Toubro S, Thorbek G, Victor OJ, Quaade F., "The effect of ephedrine/caffeine mixture on energy expenditure and body composition in obese women", Metabolism vol. 41, No. 7 (Jul.), (1992), pp. 686-688.
Astrup A, Toubro S, Christensen NJ, Quaade F., "Pharmacology of thermogenic drugs", Am.J.Clin.Nutr. (1992), pp. 246S-248S.
Tian D et al., "Study on the effect of transcutaneous electric nerve stimulation on obesity", Beijing Da Xue Xue Bao. Jun. 2003¾ 35(3):2779.
Berthoud HR, Niijima A, Sauter JF, Jeanrenaud B., "Evidence for a role of the gastric, coeliac and hepatic branches in vagally stimulated insulin secretion in the rat", J.Auton.Nerv.Syst. (1983), pp. 97-110.
Bray GA, "Obesity, a disorder of nutrient partitioning: the Mona Lisa hypothesis", American Institute of Nutrition (1991), pp. 1146-1162.
Bray GA, "Genetic, hypothalamic and endocrine features of clinical and experimental obesity", Prog.Brain Res. (1992), pp. 333-340.
Bray GA., "Reciprocal relation of food intake and sympathetic activity: experimental observations and clinical implications", Int. J.Obes.Relat Metab Disord. (2000), pp. S8-S17.

Bray GA, Gallagher TF, Jr., "Manifestations of hypothalamic obesity in man: a comprehensive investigation of eight patients and a review of the literature", Medicine (Baltimore) (1975), pp. 301-330.
Bray GA, York DA, Fisler JS., "Experimental obesity: a homeostatic failure due to defective nutrient stimulation of the sympathetic nervous system", Vitam.Horm. (1989), pp. 1-125.
Bruch H., "The Frohlich syndrome: report of the original case", 1939. Obes. Res. (1939), pp. 329-331.
Cigaina V, V, Saggioro A, Rigo V, V, Pinato G, Ischai S., "Long-term Effects of Gastric Pacing to Reduce Feed Intake in Swine" Obes. Surg. (1996), pp. 250-253.
HANS—Han's Acupoint Nerve Stimulator, http://thehanssite.com. 2012. BioBalance LLC.
Greenway FL, "The safety and efficacy of pharmaceutical and herbal caffeine and ephedrine use as a weight loss agent", Obes.Rev. (2001), pp. 199-211.
Inoue S, Bray GA, "The effects of subdiaphragmatic vagotomy in rats with ventromedial hypothalamic obesity", Endocrinology (1977), pp. 108-114.
Inoue S, Bray GA, Mullen YS, "Transplantation of pancreatic beta-cells prevents development of hypothalamic obesity in rats", Am.J.Physiol (1978), pp. E266-E271.
Jeanrenaud B., "Energy fuel and hormonal profile in experimental obesities", Experientia Suppl (1983), pp. 57-76.
King BM, Frohman LA, "The role of vagally-medicated hyperinsulinemia in hypothalamic obesity", Neurosci.Biobehav. Rev. (1982), pp. 205-214. [28] Kral JG. Vagotomy.
Niijima A, Rohner-Jeanrenaud F, Jeanrenaud B., "Role of ventromedial hypothalamus on sympathetic efferents of brown adipose tissue", Am.J.Physiol (1984), pp. R650-R654.
Pasquali R, Casimirri F, Melchionda N, Grossi G. Bortoluzzi L, Morselli Labate AM, Stefanini C, Raitano A., "Effects of chronic administration of ephedrine during very-low-calorie diets on energy expenditure, protein metabolism and hormone levels in obese subjects", Clin.Sci.(Lond) (1992), pp. 85-92.
Perkins MN, Rothwell NJ, Stock MJ, Stone TW., "Activation of brown adipose tissue thermogenesis by the ventromedial hypothalamus", Nature (1981), pp. 401-402.
Pories WJ, Swanson MS, MacDonald KG, Long SB, Morris PG, Brown BM, Barakat HA, deRamon RA, Israel G, Dolezal JM, "Who would have thought it? An operation proves to be the most effective therapy for adult-onset diabetes mellitus", Ann.Surg. (1995), pp. 339-350.
Reeves AG, Plum F., "Hyperphagia, rage, and dementia accompanying a ventromedial hypothalamic neoplasm", Arch.Neurol. (1969), pp. 616-624.
De Graaf et al, "Biomarkers of satiation and satiety", Am J Clin Nutr 2004;79:946-61.
Sakaguchi T, Bray GA, Eddlestone G., "Sympathetic activity following paraventricular or ventromedial hypothalamic lesions in rats", Brain Res.Bull. (1988), pp. 461-465.
Sauter JF, Berthoud HR, Jeanrenaud B. ,"A simple electrode for intact nerve stimulation and/or recording in semi-chronic rats", Pflugers Arch. (1983), pp. 68-69.
Seydoux J. ssimacopoulos-Jeannet F, Jeanrenaud B, Girardier L., "Alterations of brown adipose tissue in genetically obese (ob/ob) mice. I. Demonstration of loss of metabolic response to nerve stimulation and catecholamines and its partial recovery after fasting or cold adaptation", Endocrinology (1982), pp. 432-438.
Shimizu H, Shargill NS, Bray GA., "Adrenalectomy and response to corticosterone and MSH in the genetically obese yellow mouse", Am.J.Physiol (1989), pp. R494-R500. [38] Smith DK, Sarfeh J, Howard L. Truncal vagotomy.
Tokunaga K, Fukushima M, Kemnitz JW, Bray GA., "Effect of vagotomy on serum insulin in rats with paraventricular or ventromedial hypothalamic lesions", Endocrinology (1986), pp. 1708-1711.
York DA, Bray GA., "Dependence of hypothalamic obesity on insulin, the pituitary and the adrenal gland", Endocrinology (1972), pp. 885-894.
Yoshida T, Bray GA., "Catecholamine turnover in rats with ventromedial hypothalamic lesions", Am.J.Physiol (1984), pp. R558-R565.
"Stimulation of auricular acupuncture points in weight loss", Richards et al., Aust. Fam. Physician, Jul. 1998, 27 Suppl 2:S73-77.

(56) References Cited

OTHER PUBLICATIONS

Gibbons et al, "Validation of a new hand-held electronic data capture method for continuous monitoring of subjective appetite sensations", International Journal of Behavioral Nutrition and Physical Activity 2011, 8:57.
Biggs et al., "A Comparison of the Hypoalgesic Effects of Transcutaneous Electrical Nerve Stimulation (TENS) and Non-invasive Interactive Neurostimulation (InterX.RTM.) on Experimentally Induced Blunt Pressure Pain Using Healthy Human Volunteers", Neuromodulation 2012; 15: 93-99.
Jordan Kahn, "Hands on with 'i-Massager' iPhone-controlled electrical nerve stimulation and other iOS massage accessories", 9TO5Mac, http://9to5mac.com/2013/01/09/hands-on-with-i-massager-iphone-controlled-electrical-nerve-stimulation-and-other-ios-massage-accessories/ Jan. 9, 2013.
Malesevic et al., "INTFES: A multi-pad electrode system for selective transcutaneous electrical muscle stimulation". Sep. 2011.
Sauter et al., "Current threshold for nerve stimulation depends on electrical impedance of the tissue: a study of ultrasound-guided electrical nerve stimulation of the median nerve." Anesth Analg. Apr. 2009;108(4):1338-43. doi: 10.1213/ane.0b013e3181957d84.
Ronald Melzack, "Pain and the Neuromatrix in the Brain", Journal of Dental Education, vol. 65, No. 12, Dec. 2001.
Harrold et al, "Measuring appetite in humans", KissileffLaboratory for the Study of Human Ingestive Behaviour, School of Psychology, University of Liverpool. Jan. 29, 2008.
Jaime Ruiz-Tovar et al, "Percutaneous Electric Neurostimulation of Dermatome T7 Improves the Glycemic Profile in Obese and Type 2 Diabetic Patients", vol. 93. Num. 07. Aug.-Sep. 2015, doi: 10.1016/j.cireng.2014.06.013.
Jaime Ruiz-Tovar et al, "Percutaneous Electrical Neurostimulation of Dermatome T6 for Appetite Reduction and Weight Loss in Morbidly Obese Patients", Obes Surg (2014) 24:205-211, DOI 10.1007/s11695-013-1091-z.
John K. DiBaise et al, "Impact of the Gut Microbiota on the Development of Obesity: Current Concepts", Am J Gastroenterol Suppl 2012; 1:22-27; doi: 10.1038/ajgsup.2012.5.
Lim et al, "Adipose Tissue: Ability to Respond to Nerve Stimulation in vitro", Department of Nutrition and Food Science, MIT, Cambirdge 39, Science, vol. 140. 1963.
Wenwen Zeng et al, "Sympathetic Neuro-adipose Connections Mediate Leptin-Driven Lipolysis", Cell 163, 84-94, Sep. 24, 2015, http://dx.doi.org/10.1016/j.cell.2015.08.055.
Kenneth Snow, "The Use of Transcutaneous Electrical Nerve Stimulationfor the Treatment of Painful Diabetic Neuropathy", 2012 NeuroMetrix, Inc., PN2203822 Rev C.
Diyar Hussein Tahir, "A comparison of high versus low intensity transcutaneous electrical nerve stimulation for chronic pain", Zanco J. Med. Sci., vol. 15, No. (2), 2011.
Obuchowicz A et al, "Plasma beta-endorphin and insulin concentrations in relation to body fat and nutritional parameters in overweight and obese prepubetral children", Int J Obes Relat Metab Disord. Sep. 1997, 21(9):783-8.
Livingstone et al., "Methodological issues in the assessment of satiety", Scandinavian Journal of NutritionlNaringsforskning vol. 44:98-1 03,2000.

Xing et al, "Gastric Electrical-Stimulation Effects on Canine Gastric Emptying, Food Intake, and Body Weight", Obesity Research vol. 11 No. Jan. 1, 2003.
Ruffin M et al, "Electrical stimulation of the ventromedial hypothalamus enhances both fat utilization and metabolic rate that precede and parallel the inhibition of feeding behavior", Brain Res. Oct. 30, 1999;846(1):23-9, PMID: 10536210.
Cigaina V, "Gastric pacing as therapy for morbid obesity: preliminary results", Obes Surg Jun. 2002;12(3):421, PMID: 11969102.
Shafshak TS, "Electroacupuncture and exercise in body weight reduction and their application in rehabilitating patients with knee osteoarthritis", Am J Chin Med. 1995;23(1):15-25, PMID: 7598088.
Michael Camilleri, "Peripheral Mechanisms in Appetite Regulation", Gastroenterology. May 2015 ; 148(6): 1219-1233. doi:10.1053/j.gastro.2014.09.016.
Guneli E, et al, "Possible involvement of ghrelin on pain threshold in obesity", Med Hypotheses, Mar. 2010;74(3):452-4, PMID 19883981.
Thomas O. Mundinger et al, "Direct Stimulation of Ghrelin Secretion by Sympathetic Nerves", Endocrinology, Jun. 2006, 147(6):2893-2901, doi: 10.1210/en.2005-1182.
Cigaina V et al, "Plasma ghrelin and gastric pacing in morbidly obese patients", Metabolism Clinical and Experimental 56 (2007) 1017-1021.
Flint et al, "Reproducibility, power and validity of visual analogue scales in assessment of appetite sensations in single test meal studies", International Journal of Obesity (2000) 24, 38-48.
Cigaina V et al, "Gastric Pacing for Morbid Obesity: Plasma Levels of Gastrointestinal Peptides and Leptin", Obesity Research vol. 11 No. 12, Dec. 2003.
Vander Tuig JG, Knehans AW, Romsos DR., "Reduced sympathetic nervous system activity in rats with ventromedial hypothalamic lesions", Life Sci. (1982), pp. 913-920.
Takahashi K, et al., "Methodology for detecting swallowing sounds", Dysphagia. 1994 Winter;9(1):54-62.
Brian Buntz, "Brain-Zapping Wearable Device Hits Market without FDA Clearance", Posted in Mobile Health by Brian Buntz on Jun. 4, 2015.
Biegler GMBH, Stivax Neurostimulation product brochure, http://www.biegler.com/en/stivax?file=files/biegler/manuals/stivax_brochure_en.pdf. Apr. 2016.
Eagle Advancement Institute, "Pulse Stimulation Treatment (PSTIM)", http://eagleadvancementinstitute.com/pstim/Overview.asp. 2014.
Ghoname et al., "The effect of stimulus frequency on the analgesic response to percutaneous electrical nerve stimulation in patients with chronic low back pain", Anesth Analg. Apr. 1999;88(4):841-6.
Takagi K1, Yamaguchi S, Ito M, Ohshima N., "Effects of electroacupuncture stimulation applied to limb and back on mesenteric microvascular hemodynamics", Jpn J Physiol. Jun. 2005;55(3):191-203. Epub Sep. 7, 2005.
Yamaguchi S1, Ito M, Ohshima N., "Effects of electrical stimulation of the dorsal skin on systemic and mesenteric microvascular hemodynamics in anesthetized rats", Jpn J Physiol. Jun. 2002;52(3):257-65.
Interational Search Report for PCT/US20/61215, dated Mar. 4, 2021.
Written Opinion of the International Searching Authority for PCT/US20/61215, dated Mar. 4, 2021.

* cited by examiner

Front Side     Patch Configuration     Back Side

Front Side     Central Pod Configuration     Back Side
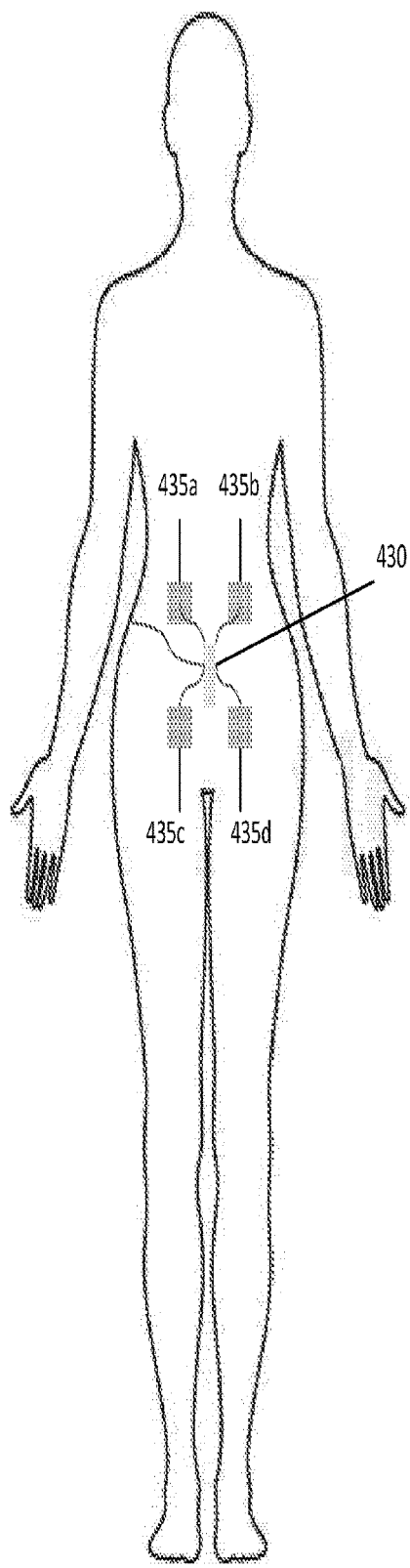
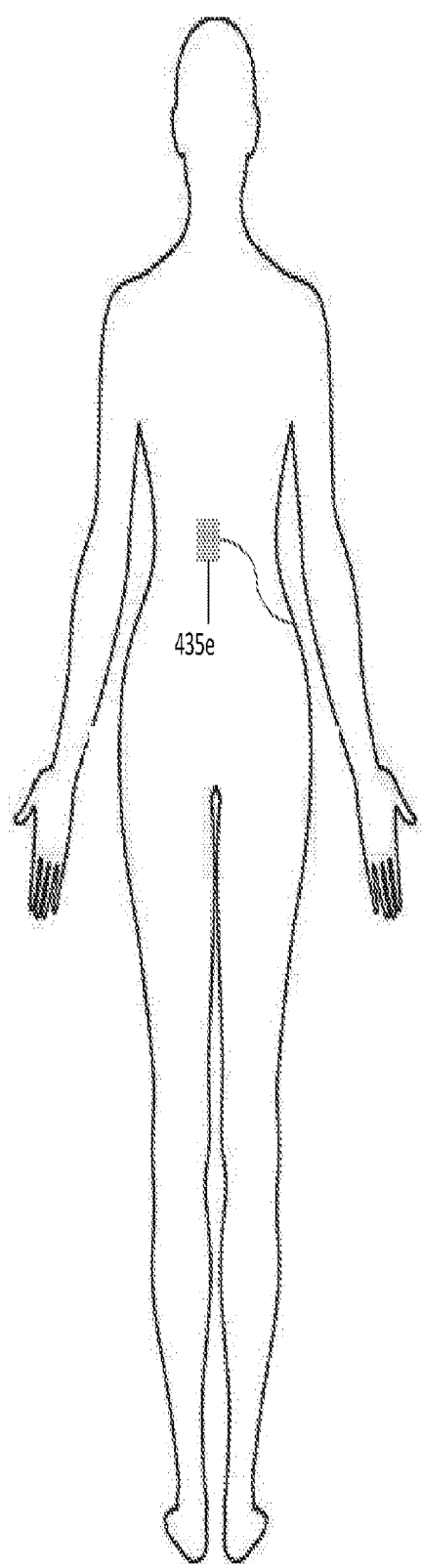
FIG. 4C                  FIG. 4D

Waistband Configuration

Front Side

Back Side

Front Side    Undergarment Configuration    Back Side

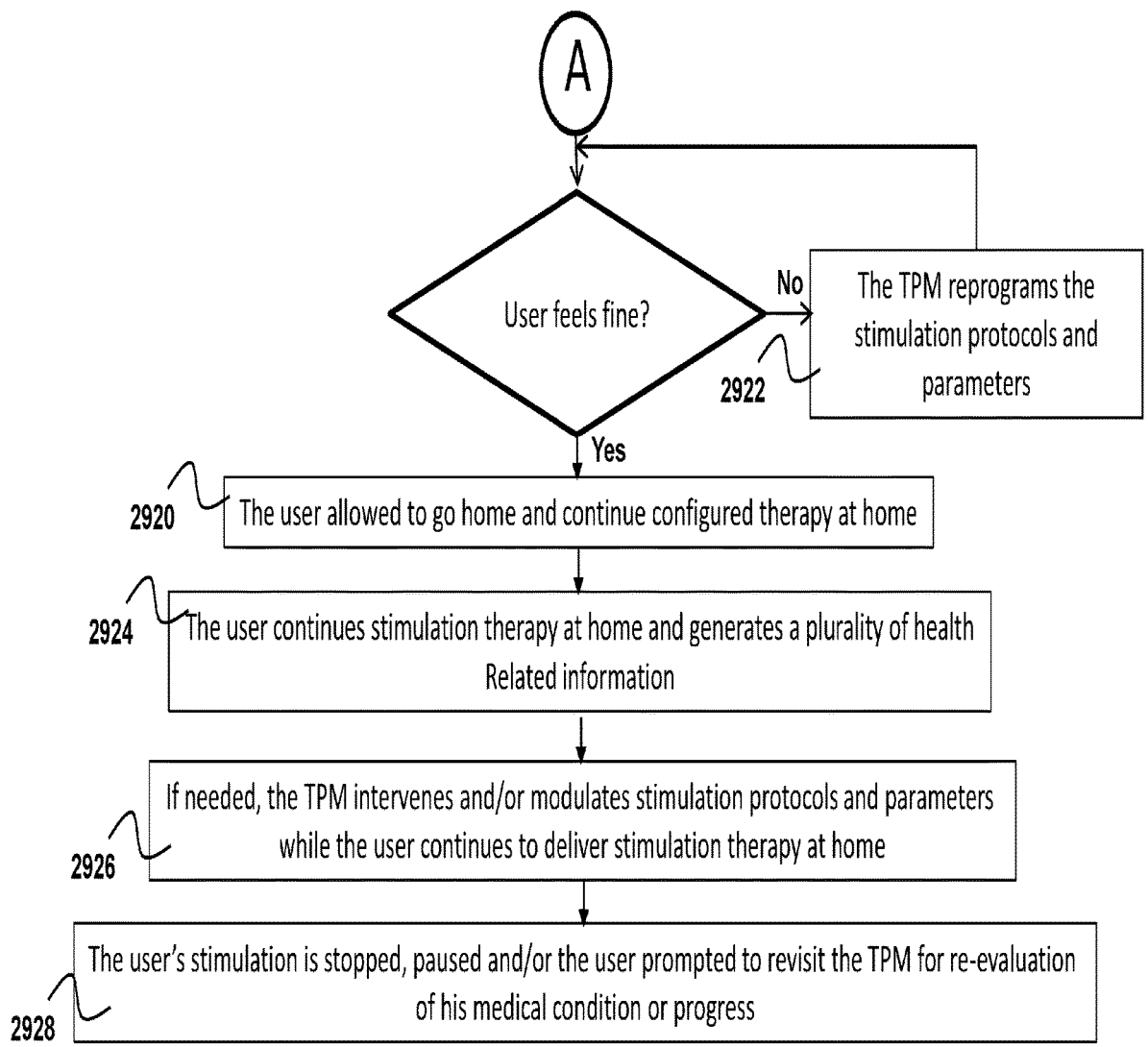
FIG. 29 (contd.)

SYSTEMS AND METHODS FOR MANAGING PAIN USING AN ELECTRO-DERMAL PATCH

CROSS-REFERENCE

The present application is a continuation application of U.S. patent application Ser. No. 15/337,321, entitled "Systems and Methods for Managing Symptoms Associated with Dysmenorrhea Using an Electro-Dermal Patch", filed on Oct. 28, 2016, and issued as U.S. Pat. No. 10,463,854 on Nov. 5, 2019, which relies on U.S. Patent Provisional Application No. 62/248,059, entitled "Systems and Methods for Enabling Pain Management Using an Electro-Dermal Patch" and filed on Oct. 29, 2015, for priority.

U.S. patent application Ser. No. 15/337,321 also relies on the following applications, for priority:

U.S. Patent Provisional Application No. 62/414,144, entitled "Systems and Methods for Enabling Appetite Modulation and/or Improving Dietary Compliance Using a Photo-Stimulator" and filed on Oct. 28, 2016;

U.S. Patent Provisional Application No. 62/413,213, entitled "Systems and Methods for Enabling Appetite Modulation and/or Improving Dietary Compliance Using an Electro-Dermal Patch" and filed on Oct. 26, 2016;

U.S. Patent Provisional Application No. 62/393,486, entitled "Systems and Methods for Enabling Appetite Modulation and/or Improving Dietary Compliance Using an Electro-Dermal Patch" and filed on Sep. 12, 2016;

U.S. Patent Provisional Application No. 62/378,393, entitled "Systems and Methods for Enabling Appetite Modulation and/or Improving Dietary Compliance Using an Electro-Dermal Patch" and filed on Aug. 23, 2016;

U.S. Patent Provisional Application No. 62/341,917, entitled "Systems and Methods for Enabling Appetite Modulation and/or Improving Dietary Compliance Using an Electro-Dermal Patch" and filed on May 26, 2016; and, U.S. Patent Provisional Application No. 62/326,541, entitled "Systems and Methods for Enabling Appetite Modulation and/or Improving Dietary Compliance Using an Electro-Dermal Patch" and filed on Apr. 22, 2016.

U.S. patent application Ser. No. 15/337,321 is also a continuation-in-part application of U.S. patent application Ser. No. 15/052,791, entitled "Systems and Methods for Enabling Appetite Modulation and/or Improving Dietary Compliance Using an Electro-Dermal Patch", filed on Feb. 24, 2016, and issued as U.S. Pat. No. 10,118,035 on Nov. 6, 2018.

U.S. patent application Ser. No. 15/337,321 is also a continuation-in-part application of U.S. patent application Ser. No. 15/052,784, entitled "Systems and Methods for Enabling Appetite Modulation and/or Improving Dietary Compliance Using an Electro-Dermal Patch", filed on Feb. 24, 2016, and issued as U.S. Pat. No. 10,143,840 on Dec. 4, 2018.

Both U.S. patent application Ser. No. 15/052,791 and U.S. patent application Ser. No. 15/052,784 rely on the following applications, for priority:

U.S. Patent Provisional Application No. 62/248,059, entitled "Systems and Methods for Enabling Pain Management Using an Electro-Dermal Patch" and filed on Oct. 29, 2015;

U.S. Patent Provisional Application No. 62/247,113, entitled "Systems and Methods for Enabling Appetite Modulation Using an Electro-Dermal Patch" and filed on Oct. 27, 2015;

U.S. Patent Provisional Application No. 62/246,526, entitled "Systems and Methods for Enabling Appetite Modulation Using an Electro-Dermal Patch" and filed on Oct. 26, 2015;

U.S. Patent Provisional Application No. 62/242,957, entitled "Systems and Methods for Enabling Appetite Modulation Using an Electro-Dermal Patch" and filed on Oct. 16, 2015;

U.S. Patent Provisional Application No. 62/242,944, entitled "Systems and Methods for Enabling Appetite Modulation Using an Electro-Dermal Patch" and filed on Oct. 16, 2015;

U.S. Patent Provisional Application No. 62/240,808, entitled "Systems and Methods for Enabling Appetite Modulation Using an Electro-Dermal Patch" and filed on Oct. 13, 2015;

U.S. Patent Provisional Application No. 62/237,356, entitled "Systems and Methods for Enabling Appetite Modulation Using Transcutaneous Electrical Neurostimulation" and filed on Oct. 5, 2015;

U.S. Patent Provisional Application No. 62/189,805, entitled "Dermatome Stimulation System" and filed on Jul. 8, 2015;

U.S. Patent Provisional Application No. 62/189,800, entitled "Dermatome Stimulation Method" and filed on Jul. 8, 2015;

U.S. Patent Provisional Application No. 62/161,362, entitled "Dermatome Stimulation Method" and filed on May 14, 2015;

U.S. Patent Provisional Application No. 62/161,353, entitled "Dermatome Stimulation System" and filed on May 14, 2015;

U.S. Patent Provisional Application No. 62/141,333, entitled "Dermatome Stimulation Method" and filed on Apr. 1, 2015;

U.S. Patent Provisional Application No. 62/141,328, entitled "Dermatome Stimulation System" and filed on Apr. 1, 2015;

U.S. Patent Provisional Application No. 62/133,530, entitled "Dermatome Stimulation Method" and filed on Mar. 16, 2015;

U.S. Patent Provisional Application No. 62/133,526, entitled "Dermatome Stimulation System" and filed on Mar. 16, 2015;

U.S. Patent Provisional Application No. 62/120,082, entitled "Dermatome Stimulation Methods" and filed on Feb. 24, 2015; and U.S. Patent Provisional Application No. 62/120,067, entitled "Dermatome Stimulation System" and filed on Feb. 24, 2015.

U.S. patent application Ser. No. 15/337,321 also relates to International Application Number PCT/US16/19416, entitled "Systems and Methods for Enabling Appetite Modulation and/or Improving Dietary Compliance Using an Electro-Dermal Patch" and filed on Feb. 24, 2016.

All of the above-mentioned applications are herein incorporated by reference in their entirety.

FIELD

The present specification relates generally to systems and methods of modulating a patient's pelvic and/or menstrual pain by delivering electrical stimulation to a predetermined area of the user's anatomy in a manner that is convenient, easy to use, and amenable to increased patient compliance. More particularly, the present specification relates to electrical stimulation devices comprising low profile, wearable, disposable skin patches or units that are easy to self-administer, programmable and monitorable using a mobile handheld device, and programmed to stimulate a patient's nerves from the external surface of the patient's epidermal layer in a manner that enables pelvic and/or menstrual pain control, modulation or suppression and also avoids adverse side effects. The present specification further relates to a low profile, wearable, disposable skin patch that is capable of integrating with, and being controlled by, a plurality of different hardware devices or software applications depending on the type, extent, nature and scope of the pelvic and/or menstrual pain modulation desired and/or the need for long term maintenance of primary and secondary dysmenorrhea.

BACKGROUND

Dysmenorrhea is the medical term used to describe pain experienced immediately before or during menstruation. The pain is usually in the pelvis or lower abdomen. Other symptoms may include back pain (typically lower back), diarrhea, or nausea. While pelvic pain may be caused by other reasons, such as and not limited to appendicitis, kidney diseases, intestinal disorders, nerve conditions, and others; in primary and secondary dysmenorrhea pain is usually felt in the lower abdomen or back. Dysmenorrhea is a major problem affecting millions of women in the US alone. The condition is believed to be one of the largest contributors to absence of women from schools, work, and social engagements, among others. Medications, such as those taken orally, to treat dysmenorrhea are known to have undesired side effects.

TENS (Transcutaneous Electrical Nerve Stimulation) devices are well known and have been disclosed as being useful in treating a variety of indications. However, conventional TENS devices are difficult to place, activate, or maintain the TENS device on her own. Additionally, the TENS device must be configured to store, deliver, and maintain a substantial current density and/or power level, which results in a large profile and difficult to wear device.

Conventional devices typically only allow for powering on to start stimulation and powering off by manual manipulation of a switch and do not allow for automatic stimulation based on sensed data or triggers without on-going management by a user. Further, prior approaches using electrical, external stimulation to treat dysmenorrhea do not have a combination of the following characteristics effective to enable a patient to independently administer the device and accompanying therapies: wearability; administration by the patient; real-time or near real-time feedback from the patient (e.g. menstrual calendar, general well-being of the wearer, others) or from wearable devices, for example, a device, with physiological sensors, configured to be worn on the human body, such as around the wrist, in order to monitor, acquire, record, and/or transmit the physiological data; the ability to stimulate multiple times per day or week; daily, or on-demand, feedback from the device to the patient; storage of stimulation parameters and other real-time inputs; and an electrical stimulation profile and a footprint conducive to long term wearability. In addition, prior art therapies which have some degree of flexibility include an electrode which must be tethered via cables to a control or power box. Prior art therapies which are wireless are typically bulky, inflexible, and not amenable to being worn for long periods of time.

Also known are electro-acupuncture techniques that are influenced by acupuncture theory of the meridians, energy channels, and their distribution for a choice of sites or accupoints to be stimulated with electricity. Electro-acupuncture and specifically, accupoint stimulation, has been generally accepted for pain relief, but are not easily managed by a patient.

Therefore, there is a need for a low profile, long lasting electrical neuro-stimulation device which is programmed, and is effective to, manage primary and secondary dysmenorrhea, and specifically menstrual pain, with minimal habituation. There is also a need for a device that can effectively integrate a patient's well-being data, menstrual calendar, and other personal information.

There is a need for an electrical neuro-stimulation device which is wearable and can be controlled, programmed, and administered by the patient, thereby enabling greater patient independence. There is also a need for an electrical neuro-stimulation device which includes real-time or near real-time feedback from patient parameters including, but not limited to, exercise, diet, hunger, appetite, well-being, menstrual calendar, intake of birth-pills, and which will be able to obtain real-time or near real-time feedback from other wearable devices, for example, a device, with physiological sensors, configured to be worn on the human body, such as around the wrist, in order to monitor, acquire, record, and/or transmit the physiological data, allowing for frequent adjustability and customization of therapy to suppress menstrual pain. There is a need for an electro-stimulation device configured to intelligently trigger and initiate stimulation automatically and without on-going management by a user. There is a need for an electrical neuro-stimulation device having the ability to modify stimulation strength and frequency based on a patient's requirement. In addition, there is a need for an electrical neuro-stimulation device capable of storing stimulation parameters and other real-time inputs, such as diary and menstrual calendar, to provide a physician and the patient with real-time records and treatment profiles. The storage would include inputs from the electrical neuro-stimulation device and from other sources of information, for example, a device, with physiological sensors, configured to be worn on the human body, such as around the wrist, in order to monitor, acquire, record, and/or transmit the physiological data.

There is also a need for an electrical neuro-stimulation device which targets menstrual pain management, does not require implantation, and does not require wires or remote electrodes to provide stimulation. There is also a need for a patient-administered, wearable electrical neuro-stimulation directed toward suppressing pain and affecting prostaglandin levels. There is a need for an electrical neuro-stimulation device having a size, shape, weight, and being composed of materials all supported by power requirements as driven by stimulation therapy, allowing the device to be wearable. Such a device would eliminate the need for heavy stimulation parameters requiring heavy power needs (which would make wearability impractical or impossible). There is also a need for an electrical neuro-stimulation device which is controllable by a companion device (such as a smartphone) and includes no visible or tactile user interface on the stimulation device itself. There is a need for an electrical neuro-stimulation device having unique electrical stimulations and 'footprints', based on electrode design and stimulation parameters, which would allow using technology other than TENS.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses an electrical stimulation device for suppressing or modulating symptoms of dysmenorrhea in a patient comprising: a housing configured to be adhered to the patient's epidermal layer; a microcontroller positioned within the housing; a transceiver positioned within the housing and in electrical communication with the microcontroller, wherein said transceiver is configured to communicate wirelessly with an external device; at least one electrode in physical contact with the housing and in electrical contact with said patient's epidermal layer; and a pulse generator positioned within the housing and in electrical communication with the microcontroller and said at least one electrode, wherein the pulse generator is configured to generate a plurality of electrical pulses adapted to penetrate, via the at least one electrode, a range of 0.1 mm to 10 mm through the patient's epidermal layer.

Optionally, the electrical stimulation device further comprises a power source, wherein said power source is a battery having a voltage in a range of 2.5 V to 4.5 V.

Optionally, the electrical stimulation device further comprises a plurality of receptor slots configured to receive additional power sources.

Optionally, the electrical stimulation device further comprises a first actuator configured to provide a visual indicator, wherein said visual indicator provides information about a power of state of the electrical stimulation device, a commencement or conclusion of a stimulation session, a malfunction of the electrical stimulation device, or a state of the power source.

Optionally, the electrical stimulation device further comprises a second actuator configured to turn the electrical stimulation device on or off.

Optionally, the electrical stimulation device further comprises a third actuator configured to provide a tactile indicator, wherein said tactile indicator provides information about a power of state of the electrical stimulation device, a commencement or conclusion of a stimulation session, a malfunction of the electrical stimulation device, or a state of the power source.

Optionally, the electrical stimulation device further comprises a fourth actuator configured to provide an auditory indicator, wherein said auditory indicator provides information about a power of state of the electrical stimulation device, a commencement or conclusion of a stimulation session, a malfunction of the electrical stimulation device, or a state of the power source.

The housing may be hermetically sealed.

Optionally, the housing further contains a first sensor, a second sensor, and a third sensor. The first sensor may be an impedance sensor configured to determine contact integrity of the at least one electrode to the patient's epidermal layer. The second sensor may be a physiological sensor configured to measure physiological parameters of the user. The third sensor may be a neural sensor configured to detect a presence of neural activity. The third sensor may be a neural sensor configured to detect an amount of neural activity and generate at least one of an indication that the electrical stimulation device is placed in a right location, an indication that the electrical stimulation device is increasing neural activity in accordance with a stimulation protocol, an indication that the patient's neural response rate is insufficient, and an indication that a stimulation protocol needs to be modified.

Optionally, the electrical stimulation device does not include an on or off switch.

The electrical stimulation device may be adapted to operate in a first state and in a second state, wherein, in the first state, the electrical stimulation device has an average current usage of less than 5 µA and wherein, in the second state, the electrical stimulation device has an average current usage of greater than 10 µA. Optionally, in the first state, the electrical stimulation device is not configured to generate said plurality of electrical pulses. Optionally, in the second state, the electrical stimulation device is configured to generate said plurality of electrical pulses. The electrical stimulation device may be configured to switch from said first state to said second state upon receiving a signal from the external device.

Optionally, the electrical stimulation device further comprises a hydrogel pad, wherein the at least one electrode is positioned in the hydrogel pad. The at least one electrode may be disposed on a lower surface of the hydrogel pad. The at least one electrode may be configured in a square wave pattern. The at least one electrode may be configured in a comb pattern, having a linear backbone with a plurality of elongated teeth extending perpendicularly therefrom. The at least one electrode may be configured in an alternating comb pattern, having a first linear backbone with a first plurality of elongated teeth extending perpendicularly therefrom and a second linear backbone, parallel to the first linear backbone, with a second plurality of elongated teeth extending perpendicularly therefrom and alternating with the first plurality of elongated teeth. The at least one electrode may be printed on a lower surface of the hydrogel pad.

The electrical stimulation device may have a first length extending from one end of the electrical stimulation device to the other end of the electrical stimulation device and a first width extending from one edge of the electrical stimulation device to the other edge of the electrical stimulation device, wherein the electrical stimulation device generates an electrical field having a length substantially equal to or greater than the first length and a width substantially equal to or greater than the first width.

The electrical stimulation device may have a substantially linear profile, a width of 2 inches or less, a length of 5 inches or less, a height of 0.25 inches or less, and a weight of 5 ounces or less.

The electrical stimulation device may have an ingress protection rating of at least IPX7, thereby adapted to enable the patient to expose the electrical stimulation device to water for at least 30 minutes without sustaining water damage to the electrical stimulation device.

Optionally, the housing comprises an elliptical shape having a first radius in a range of X to Y and a second radius in a range of X to Y.

Optionally, the electrical stimulation device further comprises an elliptically shaped controller assembly, wherein said controller assembly comprises said microcontroller, said transceiver and said pulse generator, wherein the elliptically shaped controller assembly has a top surface directed away from the patient's epidermal layer and a bottom surface directed towards the patient's epidermal layer, and wherein the top surface of the elliptically shaped controller assembly is overmolded with a material. The overmolded material may be at least one of a thermoplastic elastomer or a thermoset material. The top surface may have a plurality of slots extending through the overmolded material. Optionally, the electrical stimulation device further comprises a plurality of light emitting diodes positioned in alignment with at least one of said plurality of slots. The bottom surface may comprise a flexible circuit having a plurality of electrical contacts. Optionally, the plurality of electrical contacts comprise gold-plated copper pads etched into said flexible circuit. Optionally, a periphery of the bottom surface is covered by the overmolded material and a central portion of the bottom surface is not covered by the overmolded material. Optionally, the electrical stimulation device further comprises a gel pad, wherein the at least one electrode is positioned in the gel pad and wherein the gel pad is configured to be attached to the bottom surface of the controller assembly. Optionally, the plurality of electrical contacts and at least one electrode in the gel pad are electrically connected and said electrical connection comprises a capacitance type connection. Optionally, the electrical stimulation device further comprises a dielectric material laminated over a surface of at least one of the plurality of electrical contacts and gel pad. The transceiver, the microcontroller, the pulse generator, and a battery may be positioned between said flexible circuit and said top surface. Optionally, the controller assembly further comprises a flexible circuit upon which said microcontroller, said transceiver and said pulse generator are mounted. The flexible circuit may have a perimeter and may comprise an anchor positioned along said perimeter. The anchor may comprise a plurality of perforation holes for receiving said overmolded material.

Optionally, the electrical stimulation device comprises a memory, wherein said memory is configured to store a plurality of stimulation parameters, and wherein the microcontroller is adapted to cause the pulse generator to generate said plurality of electrical pulses in accordance with said plurality of stimulation parameters. The plurality of stimulation parameters may comprise at least two of stimulation pulse width, pulse amplitude, pulse frequency, pulse shape, duty cycle, session duration, and session frequency.

Optionally, said stimulation pulse width is in a range of 10 µsec to 100 msec, said pulse amplitude is in a range of 1 mA to 100 mA, said pulse frequency is in a range of 1 to 250 pulses per second (pps), said pulse shape is at least one of monophasic, biphasic, and sinusoidal, said duty cycle is in a range of 1% to 99%, said session duration is in a range of 1 min to 60 min, and said session frequency is based on the menstruation cycle of the user.

The microcontroller may be configured to modify said plurality of stimulation parameters based upon an input from the external device. The microcontroller may be configured to modify at least one of said stimulation pulse width, said pulse amplitude, said pulse frequency, said pulse shape, said duty cycle, said session duration, and said session frequency based upon an input of a degree of the patient's pain, wherein said input is wirelessly transmitted from the external device. The microcontroller may be configured to modify at least one of said stimulation pulse width, said pulse amplitude, said pulse frequency, said pulse shape, said duty cycle, said session duration, and said session frequency based upon an input of a degree of the patient's dysmenorrhea symptoms, wherein said input is wirelessly transmitted from the external device. The microcontroller may be configured to modify at least one of said stimulation pulse width, said pulse amplitude, said pulse frequency, said pulse shape, said duty cycle, said session duration, and said session frequency based upon an input of a degree of at least one of the patient's nausea level, discomfort-level, energy-level, and weakness-level, wherein said input is wirelessly transmitted from the external device. The microcontroller may be configured to modify at least one of said stimulation pulse width, said pulse amplitude, said pulse frequency, said pulse shape, said duty cycle, said session duration, and said session frequency based upon an input of an amount of at least one of the patient's weight and calories burned, wherein said amount is wirelessly transmitted from the external device.

Optionally, the electrical stimulation device is adapted to operate in a first state and in a second state, wherein: in the first state, the electrical stimulation device has an average current usage of less than 5 µA and the electrical stimulation device is not configured to generate said plurality of electrical pulses; in the second state, the electrical stimulation device has an average current usage of greater than 10 µA and the electrical stimulation device is configured to generate said plurality of electrical pulses; the microcontroller is configured to automatically switch from said first state to said second state upon receiving a signal from the external device; and the microcontroller is configured to automatically modify at least one of said stimulation pulse width, said pulse amplitude, said pulse frequency, said pulse shape, said duty cycle, said session duration, and said session frequency based upon an input of at least one of a degree of the patient's pain level, a degree of one or more symptoms of dysmenorrhea, a degree of the patient's nausea level, a degree of the patient's discomfort level, a degree of the patient's energy level, a degree of the patient's weakness level, an amount of the patient's weight, an amount of calories consumed by the patient, and an amount of calories expended by the patient, wherein said input is wirelessly transmitted to the transceiver of the electrical stimulation device from the external device.

The present specification also discloses method of using the electrical stimulation device comprising installing an application on the external device, wherein said application is configured to acquire patient status data and prompting, via said application, the patient to input said patient status data. The patient status data may comprise at least one of a degree of pain being experienced by the patient, and a degree of well-being being experienced by the patient. The well-being level may comprise at least one of a degree of nausea, a degree of discomfort, a degree of energy level, and a degree of weakness, being experienced by the patient.

Optionally, the method further comprises generating a modulation signal based upon said patient status data, wherein said modulation signal comprises instructions for modulating at least one of a stimulation pulse width, a pulse amplitude, a pulse frequency, a pulse shape, a duty cycle, a session duration, and a session frequency.

Optionally, the method further comprises wirelessly transmitting said modulation signal from the external device to the electrical stimulation device.

Optionally, the method further comprises receiving said modulation signal at the electrical stimulation device and using said modulation signal to modify at least one of said stimulation pulse width, said pulse amplitude, said pulse frequency, said pulse shape, said duty cycle, said session duration, and said session frequency, wherein each of said stimulation pulse width, said pulse amplitude, said pulse frequency, said pulse shape, said duty cycle, said session duration, and said session frequency are stored in a memory in the electrical stimulation device and used by the microcontroller to generate said plurality of electrical pulses.

Optionally, the method further comprises: acquiring, via said application, a first stimulation protocol; using said first stimulation protocol, within said application, to generate a first modulation signal, wherein said modulation signal comprises instructions for modulating at least one of a stimulation pulse width, a pulse amplitude, a pulse frequency, a pulse shape, a duty cycle, a session duration, and a session frequency; wirelessly transmitting said modulation signal from the external device to the electrical stimulation device; and using said modulation signal to modify at least one of said stimulation pulse width, said pulse amplitude, said pulse frequency, said pulse shape, said duty cycle, said session duration, and said session frequency, wherein each of said stimulation pulse width, said pulse amplitude, said pulse frequency, said pulse shape, said duty cycle, said session duration, and said session frequency are stored in a memory in the electrical stimulation device and used by the microcontroller to generate said plurality of electrical pulses. Optionally, the method further comprises: acquiring, via said application, a second stimulation protocol, wherein said second stimulation protocol is different from the first stimulation protocol; using said second stimulation protocol, within said application, to generate a second modulation signal, wherein said second modulation signal comprises instructions for modulating at least one of the stimulation pulse width, the pulse amplitude, the pulse frequency, the pulse shape, the duty cycle, the session duration, and the session frequency; wirelessly transmitting said second modulation signal from the external device to the electrical stimulation device; and using said second modulation signal to modify at least one of said stimulation pulse width, said pulse amplitude, said pulse frequency, said pulse shape, said duty cycle, said session duration, and said session frequency, wherein each of said stimulation pulse width, said pulse amplitude, said pulse frequency, said pulse shape, said duty cycle, said session duration, and said session frequency.

The present specification also discloses a method of using the electrical stimulation device comprising installing an application on the external device, wherein said application is configured to acquire patient status data and prompting, via said application, the patient to input a request to modulate said plurality of electrical pulses.

Optionally, the method further comprises generating a modulation signal for said request to modulate said plurality of electrical pulses.

Optionally, the method further comprises wirelessly transmitting said modulation signal from the external device to the electrical stimulation device.

Optionally, the method further comprises receiving said modulation signal at the electrical stimulation device and using said modulation signal to modify at least one of said stimulation pulse width, said pulse amplitude, said pulse frequency, said pulse shape, said duty cycle, said session duration, and said session frequency, wherein each of said stimulation pulse width, said pulse amplitude, said pulse frequency, said pulse shape, said duty cycle, said session duration, and said session frequency are stored in a memory in the electrical stimulation device and used by the microcontroller to generate said plurality of electrical pulses.

Optionally, the method further comprises using said application to generate a modulation signal, wherein said modulation signal is determined based upon the patient's request to modulate said plurality of electrical pulses and a plurality of values, each of said values representing a numerical limit to at least one of a stimulation pulse width, a pulse amplitude, a pulse frequency, a pulse shape, a duty cycle, a session duration, and a session frequency. Optionally, the method further comprises wirelessly transmitting said modulation signal from the external device to the electrical stimulation device and using said modulation signal to modify at least one of said stimulation pulse width, said pulse amplitude, said pulse frequency, said pulse shape, said duty cycle, said session duration, and said session frequency, wherein each of said stimulation pulse width, said pulse amplitude, said pulse frequency, said pulse shape, said duty cycle, said session duration, and said session frequency are stored in a memory in the electrical stimulation device and used by the microcontroller to generate said plurality of electrical pulses.

The present specification also discloses a method of using the electrical stimulation device comprising: mounting the electrical stimulation device to the patient's epidermal layer; and generating said plurality of electrical pulses such that at least one of the patient's epidermis of a T9 to T12 dermatomes, L1, L2, L5 dermatomes, and/or a sacral dermatome, such as the S1 to S4 dermatomes is electrically stimulated.

The present specification also discloses a method of decreasing a symptom of dysmenorrhea of a patient, comprising: positioning an electrical stimulation device on an epidermal layer of said patient, wherein the electrical stimulation device comprises a housing configured to adhere to the patient's epidermal layer, a microcontroller positioned within the housing, a transceiver positioned within the housing and in electrical communication with the microcontroller, wherein said transceiver is configured to communicate wirelessly with an external device, at least one electrode in electrical contact with the microcontroller and in electrical contact with said patient's epidermal layer and a pulse generator positioned within the housing and in electrical communication with the microcontroller and said at least one electrode, wherein the pulse generator is configured to generate a plurality of electrical pulses adapted to penetrate, via the at least one electrode, a range of 0.1 mm to 10 mm through the patient's epidermal layer; and generating said plurality of electrical pulses such that at least one of the patient's epidermis of a T9 to T12 dermatomes, L1, L2, L5 dermatomes, and/or a sacral dermatome, such as the S1 to S4 dermatomes is electrically stimulated.

Optionally, the electrical stimulation device comprises a memory, wherein said memory is configured to store a first plurality of stimulation parameters, and wherein the microcontroller is adapted to cause the pulse generator to generate said plurality of electrical pulses in accordance with said first plurality of stimulation parameters. The first plurality of stimulation parameters may comprise at least two of stimulation pulse width, pulse amplitude, pulse frequency, pulse shape, duty cycle, session duration, and session frequency.

Optionally, said stimulation pulse width is in a range of 10 μsec to 500 msec, said pulse amplitude is in a range of 1 mA to 100 mA, said pulse frequency is in a range of 1 pulse per second (pps) to 125 pps, said pulse shape is at least one of monophasic, biphasic, and sinusoidal, said duty cycle is in a range of 1% to 99%, said session duration is in a range of 30 min to 60 min, and said session frequency is based on at least one of the menstrual cycle of the user and occurrences of pain experienced by the user.

Optionally, the method further comprises: installing an application on the external device; using said application, acquiring patient status data over a period of time, said patient status data including at least one of a level of pain, a level of well-being, a level of nausea, an amount of the patient's weight; after said period of time, generating a stimulation parameter modulation signal based upon said patient data; and wirelessly transmitting the stimulation parameter modulation signal to the electrical stimulation device. Optionally, upon initiation of operation, said microcontroller causes the plurality of electrical pulses to be generated using the first plurality of stimulation parameters and wherein, after said period of time, said microcontroller causes the plurality of electrical pulses to be generated using a second plurality of stimulation parameters, said second plurality of stimulation parameters being determined based upon said stimulation parameter modulation signal. Optionally, the electrical stimulation device is adapted to operate in a first state and in a second state, wherein: in the first state, the electrical stimulation device has an average current usage of X to less than 5 µA and the electrical stimulation device is not configured to generate said plurality of electrical pulses; in the second state, the electrical stimulation device has an average current usage of greater than 10 µA and the electrical stimulation device is configured to generate said plurality of electrical pulses; the microcontroller is configured to automatically switch from said first state to said second state upon receiving a signal from the external device; and the microcontroller is configured to automatically modify at least one of said stimulation pulse width, said pulse amplitude, said pulse frequency, said pulse shape, said duty cycle, said session duration, and said session frequency based upon said stimulation parameter modulation signal.

The present specification also discloses a method of modulating, decreasing, or suppressing a condition arising from dysmenorrhea, comprising: positioning an electrical stimulation device on an epidermal layer of said patient, wherein the electrical stimulation device comprises: a housing configured to adhere to the patient's epidermal layer, a processor positioned within the housing, a transceiver positioned within the housing and in electrical communication with the processor, at least one electrode in electrical contact with the processor and in electrical contact with said patient's epidermal layer, a pulse generator positioned within the housing and in electrical communication with the processor and said at least one electrode, wherein the pulse generator is configured to generate a plurality of electrical pulses adapted to penetrate, via the at least one electrode, a range of 0.1 mm to 10 mm through the patient's epidermal layer, and a memory in communication with the processor, wherein said memory is configured to store a first plurality of stimulation parameters, wherein the processor is adapted to cause the pulse generator to generate said plurality of electrical pulses in accordance with said first plurality of stimulation parameters, and wherein the first plurality of stimulation parameters comprise a pulse width in a range of 10 µsec to 1 msec, a pulse amplitude in a range of 1 mA to 100 mA, a pulse frequency in a range of 1 pps to 125 pps, a pulse duty cycle in a range of 1% to 99%, a session duration in a range of 30 min to 60 min, and a number of sessions based on at least one of occurrences of pain experienced by the user and menstrual cycle of the user; and generating said plurality of electrical pulses such that at least one of the patient's epidermis of a T9 to T12 dermatomes, L1, L2, L5 dermatomes, and/or a sacral dermatome, such as the S1 to S4 dermatomes is electrically stimulated.

Optionally, the pulse width is equal to 200 µsec, the pulse amplitude is equal to 5 mA, the pulse frequency is equal to 20 Hz, the pulse duty cycle equals 100%, the session duration equals 30 minutes, and the number of sessions is 1 session per day.

Optionally, the method further comprises: installing an application on a mobile device; using said application, acquiring patient status data over a period of time, said patient status data including at least one of a level of pain, a level of well-being, a level of nausea, an amount of the patient's weight; after said period of time, generating a stimulation parameter modulation signal based upon said patient data; causing the stimulation parameter modulation signal to be wirelessly transmitted to the electrical stimulation device; and causing the plurality of electrical pulses to be generated using a second plurality of stimulation parameters, said second plurality of stimulation parameters being determined based upon said stimulation parameter modulation signal.

Optionally, if the level of pain is above a threshold level, the second plurality of stimulations has at least one of a pulse width, a pulse amplitude, a pulse frequency, a pulse duty cycle, a session duration, or a number of sessions that is increased relative to the first plurality of stimulation parameters.

Optionally, if the level of pain is below a threshold level, the second plurality of stimulations has at least one of a pulse width, a pulse amplitude, a pulse frequency, a pulse duty cycle, a session duration, or a number of sessions that is decreased relative to the first plurality of stimulation parameters.

Optionally, if the level of nausea is above a threshold level, the second plurality of stimulations has at least one of a pulse width, a pulse amplitude, a pulse frequency, a pulse duty cycle, a session duration, or a number of sessions that is decreased relative to the first plurality of stimulation parameters.

Optionally, if the level of well-being is above a threshold level, the second plurality of stimulations has at least one of a pulse width, a pulse amplitude, a pulse frequency, a pulse duty cycle, a session duration, or a number of sessions that is increased relative to the first plurality of stimulation parameters.

Optionally, if the level of well-being is below a threshold level, the second plurality of stimulations has at least one of a pulse width, a pulse amplitude, a pulse frequency, a pulse duty cycle, a session duration, or a number of sessions that is decreased relative to the first plurality of stimulation parameters.

The present specification also discloses a device for treating symptoms of dysmenorrhea in a patient, comprising a microcontroller, a wireless transceiver, a battery, one on/off switch, a pulse generator, and at least one electrode, wherein said device is configured to deliver electrical stimulation from the external surface of the patient's epidermal layer through a range of 0.1 mm to 10 mm or a range of 0.1 mm to 20 mm of the dermis by applying said electrical stimulation to any one of an epidermis of a T9 to T12 dermatomes, L1, L2, L5 dermatomes, and/or a sacral dermatome, such as the S1 to S4 dermatomes of said patient.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 4C illustrates a location and configuration of an electro-dermal patch device in accordance with various embodiments of the present specification;

FIG. 4D illustrates a location and configuration of an electro-dermal patch device in accordance with various embodiments of the present specification;

DETAILED DESCRIPTION

Figure 1A:
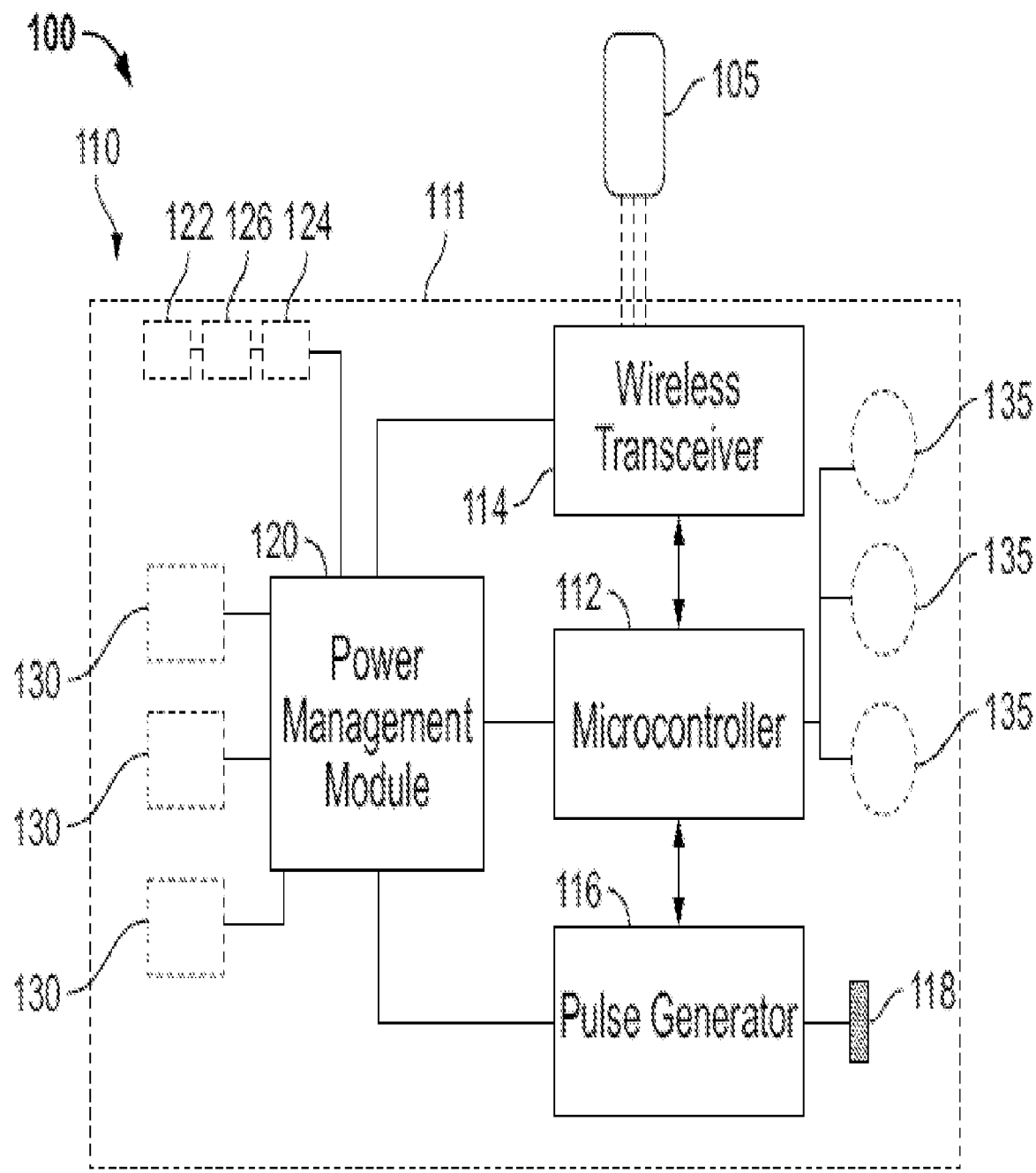
FIG. 1A is a block diagram of a system for stimulating nerves and nerve endings in body tissue, in accordance with various embodiments of the present specification.

The present specification is directed toward systems and methods of managing different types of pelvic pain or lower GI pain, such as dysmenorrhea, including modulating menstrual pain, by delivering electrical stimulation to a predetermined area of the user's anatomy in a manner that is convenient, easy to use, and amenable to increased patient compliance. In an embodiment, the principles, treatment methodologies, and devices of the present specification may also be used for treating any pelvic or lower GI pain, such as, but not limited to ovulation pain; pain associated with post-partum condition; ovarian cyst related pain; fibroid related pain; pain associated with endometriosis; pain related to or caused by pelvic inflammatory disease (PID); pain related to irritable bowel syndrome (IBS) and/or Crohn's disease; pain related to or caused by diverticulitis; and/or lower back pain (either as an isolated condition or related to any of the above-mentioned conditions).

The term "modulating" refers to any form of regulation, manipulation or control to change a given variable from one state to another state. More particularly, the present specification relates to electrical stimulation devices comprising low profile, wearable, and optionally disposable skin patches or devices that are configured for placement on a patient's lower abdominal area. In an embodiment, at least a portion of the devices or patches may be placed on the patient adjacent to the umbilicus bilaterally up to a distance towards the edge of the trunk. In an embodiment, at least a portion of the devices or patches may be placed at a distance ranging from 1.5 inches from the umbilicus bilaterally up to the edge of the trunk. In an embodiment, at least a portion of the devices or patches may be placed at or near a patient's pubic bone, bilaterally. In an embodiment, at least a portion of the devices or patches may be placed at or near a patient's tailbone.

Optionally, the devices or patches of the present specification may be placed at or near a patient's front and lateral T9 to T12 dermatomes, L1, L2, L5 dermatomes, and/or a sacral dermatome, such as the S1 to S4 dermatomes.

In an embodiment, the devices and/or patches of the present specification are easy to self-administer, programmable and monitorable using a mobile handheld device, and programmed to stimulate, from the external surface of the patient's epidermal layer through a range of 0.1 mm to 10 mm of the dermis or through a range of 0.1 mm to 20 mm of the dermis, nerves located proximate to the front and lateral T9 to T12 dermatomes, L1, L2, L5 dermatomes, and/or a sacral dermatome, such as the S1 to S4 dermatomes in a manner that enables modulation of dysmenorrhea symptoms including a patient's menstrual pain, and that avoids feeling of dizziness or nausea, headaches and minimizes habituation. In various embodiments, a stimulation depth through the patient's epidermal layer ranges from 0.1 mm to 0.5, 1, 2, 3, 4, 5, 6, 7, 8, 9, 10, 11, 12, 13, 14, 15, 16, 17, 18, 19, 20 mm or any increment therein.

The present specification further relates to a low profile, wearable, disposable skin patch that is capable of integrating with, and being controlled by, a plurality of different hardware devices or software applications depending on the type, extent, nature and scope of the pelvic and/or menstrual pain modulation desired, including immediate, pelvic and/or menstrual pain reduction or long term pelvic and/or menstrual pain management.

An electrical neuro-stimulation device, in the form of an electro-dermal patch (EDP) is disclosed that, in various embodiments, is configured as a discrete, disposable and waterproof adhesive patch or pad for placement on a user's skin, particularly on the regions encompassing the front and lateral T9 to T12 dermatomes, L1, L2, L5 dermatomes, and/or a sacral dermatome, such as the S1 to S4 dermatomes. In various embodiments, the EDP is wireless and incorporates flexible circuits and elastomeric overmolding, making the device waterproof and flexible enough to be able to mold to body contours for greater comfort and permanent wearability. In some embodiments, the EDP device also modulates prostaglandin production.

In some embodiments, the electrical neurostimulation device is provided in the form of a band, such as a waist band, which is configured to be placed on the user similar to a large band with means to attach its two ends, such as clasps, buttons, zippers, hooks, snaps, Velcro, string, or any other attachment mechanisms. The electrodes are placed within the band, which may be made of cloth or some form of elastic material. In embodiments, the electrodes are removable or are in the forms of removable patches. In embodiments, the band is provided in varying sizes to accommodate users of different body-shapes and sizes. The band may be attached by the user to place its electrodes on the user's skin, particularly on the regions encompassing the front and lateral T9 to T12 dermatomes, L1, L2, L5 dermatomes, and/or a sacral dermatome, such as the S1 to S4 dermatomes. In embodiments, the band includes at least four electrodes such that on wearing the band, at least two of its negative electrodes are placed on both sides of the umbilicus (at varying distances) and at least two of its positive electrodes are paced over the pubic bone. In embodiments, the band includes a fifth optional electrode lead that is placed on the back near the tailbone. In embodiments, the band with five electrodes has a sixth optional electrode lead that is placed on the back near the tailbone. The band may incorporate most features of the EDP, and may also enable separating its electrodes in order to separately clean the band when required.

In some other embodiments, the electrical neuro-stimulation device is provided in the form of a single patch, which is configured to be placed on the user such that at least two of its negative electrodes are placed on both sides of the umbilicus and at least two of its positive electrodes are placed over the pubic bone. In the embodiments, the electrodes are placed in a unified manner on the patch. In one embodiment, the patch is square-shaped. In other embodiments, the electrode/pad combination may have a shape including any one of irregular, rectangular, circular, elliptical, and triangular.

In yet other embodiments, the electrical neuro-stimulation device is provided in the form of a star-shaped, an octopus-shaped, or a squid-shaped patch, which is configured such that its electrode leads protrude outwards in different directions from a central pod. In embodiments, the star-shaped patch has four electrodes, which are configured to be placed on the user such that at least two of its negative electrodes are placed on both sides of the umbilicus and at least two of its positive electrodes are placed over the pubic bone. In embodiments, the star-shaped patch has a fifth optional electrode lead that is placed on the back near the tailbone. In embodiments, the star-shaped patch with five electrodes has a sixth optional electrode lead that is placed on the back near the tailbone.

The patches may be attached by the user to place its electrodes on the user's skin, particularly on the regions encompassing the front and lateral T9 to T12 dermatomes, L1, L2, L5 dermatomes, and/or a sacral dermatome, such as the S1 to S4 dermatomes. The patches may incorporate most features of the EDP, and may also enable separating its electrodes in order to separately clean the patch when required.

In still other embodiments, the electrical neuro-stimulation device is provided in the form of a type of underwear, which is configured to be worn by the user, similar to an underpants. The underwear may be of any of the available shapes and sizes, such as but not limited to a thong, high-waist underpants, low-waist underpants, and boy shorts-style underpants. In embodiments, electrodes are placed within the underwear. In embodiments, the electrodes are removable or are in forms of removable patches. In embodiments, the underwear is provided in varying sizes to accommodate users of different body-shapes and sizes. The underwear may be worn by the user to place its electrodes on the user's skin, particularly on the regions encompassing the front and lateral T9 to T12 dermatomes, L1, L2, L5 dermatomes, and/or a sacral dermatome, such as the S1 to S4 dermatomes. In embodiments, the underwear includes at least four electrodes such that on wearing the underwear, at least two of its negative electrodes are placed on both sides of the umbilicus and at least two of its positive electrodes are placed over the pubic bone. In embodiments, the underwear includes a fifth optional electrode lead that is placed on the back near the tailbone. In embodiments, the underwear with five electrodes has a sixth optional electrode lead that is placed on the back near the tailbone. The band may incorporate most features of the EDP, and may also enable separating its electrodes in order to separately clean the band when required.

In embodiments of the present specification, the electro-dermal patch device is wearable and can be controlled and programmed by the patient, allowing the patient to administer therapy and eliminating the need for frequent patient visits to a medical professional.

In embodiments, the electrical neuro-stimulation device is configured to be placed on the user such that at least two of its negative electrodes are placed on both sides of the umbilicus and at least two of its positive electrodes are placed over the pubic bone, with optional electrodes at or near the user's tailbone.

In optional embodiments, the electro-dermal patch device is designed to be placed on regions that may encompass the front and lateral thoracic dermatomes including T9 to T12 dermatomes, L1, L2, L5 dermatomes, and/or a sacral dermatome, such as the S1 to S4 dermatomes of the patient.

In embodiments, the electro-dermal device can be used to deliver therapy on a pre-programmed basis. In an embodiment, the electro-dermal device can be used to deliver therapy that is timed to coincide with pain event spikes recorded in a patient diary that is used to form an evolving topographical pain map. In yet other embodiments, therapy can be delivered via a rescue session in an "on-demand" mode.

In embodiments, the electro-dermal patch device is wirelessly coupled to a companion device (e.g. smartphone, watch, or tablet) which can be used to program the electro-dermal patch device, allowing the patient to self-administer therapy on-demand. In some embodiments, therapy provided by the electro-dermal patch device is coupled with a storage or recording (for keeping a log of the therapy) and patient compliance reminders. The benefits provided by having a wearable and self-administered electro-dermal patch device include, among others, greater patient independence and improved patient compliance to stimulation protocols, with resultant increased efficacy, and the ability to modify stimulation parameters based on real-time feedback provided to the electro-dermal patch device by the patient and other devices.

In some embodiments, the electro-dermal patch device is driven by an algorithm derived from patient input data and monitored data. In embodiments, the data relates to incidents of pelvic and/or menstrual pain. In an embodiment, the pelvic pain results from dysmenorrhea. In the case of dysmenorrhea, the system is driven by data that tracks information pertaining to the user's (woman's) monthly patterns of ovulation and menstruation. In embodiments, the algorithm monitors the onset and duration of the menstruation cycle. In an average cycle that lasts for 28 days, the pain could increase before the onset of menstruation, and in some cases around the days of ovulation.

In embodiments, the system learns the behavior of user's body based on the experience of pain, and on the menstruation and ovulation cycles. Adjustments to the algorithm, and therefore stimulation, may be made both manually by the patient and/or automatically by the device itself or the companion device.

In some embodiments, the algorithm is also derived from monitored parameters, such as prostaglandin levels, which are typically measured in a clinical setting. Lower levels of prostaglandin might result in lower pelvic and/or menstrual pain. In most cases, the heavier the bleeding, the more likely the pain experienced by the user. Prostaglandins are found in the endometrium, which is the lining of uterus (which thickens and grows under the influence of estrogen). Progesterone causes the endometrial layer to shed. Menstrual bleeding is a combination of removal of the endometrial layer and actual bleeding that causes some blood vessels to open. Thus, more pain is likely with more bleeding, as greater levels of prostaglandin are released.

In addition, menorrhagia is a measurable parameter that is indicative of the amount of blood flow/loss. Menorrhagia may be measured by the number of pads and/or tampons that are used, the saturation of the pad and/or tampon, and the frequency of use during a menstrual cycle. A higher rate of pad/tampon changes generally indicates greater loss of blood and therefore more pain. In embodiments, the user inputs data pertaining the number of pads and/or tampons that are changed, to the system responsible for interfacing with the user and tracking data. In embodiments, other parameters used include the quality of blood during menstruation, the level of pelvic and/or menstrual pain, number of days that the user is bleeding, water retention, diet, change in weight, and salt intake.

In embodiments, well-being parameters include one or more symptoms that indicate that the production of prostaglandin is affected, including but not limited to nausea, headache, diarrhea, and fatigue. These parameters are measured at baseline and over time during treatment and are used as inputs to titrate therapy. Adjustments to the algorithm, and therefore stimulation, are made either manually by the patient or automatically by the electro-dermal patch device itself or the companion device or both. In accordance with some aspects of the present specification, a medical professional can flexibly program the electro-dermal patch and still direct the patient, only allowing the patient to adjust device parameters (for greater patient independence) but within restricted bounds or predetermined parameters.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

For purposes of the present specification, direct electrical stimulation refers to where the electrical field generated by the EDP is in contact with the anatomical structure being stimulated.

For purposes of the present specification, the terms "trigger" and "triggering" do not necessarily imply immediately triggering stimulation. "Trigger" and "triggering" are defined as initiating or starting the execution of a protocol that will result in stimulation over a predefined period.

In the description and claims of the application, each of the words "comprise" "include" and "have", and forms thereof, are not necessarily limited to members in a list with which the words may be associated.

As used herein, the indefinite articles "a" and "an" mean "at least one" or "one or more" unless the context clearly dictates otherwise.

The terms "patient", "individual", "person", and "user" are used interchangeably throughout this specification and refer to the person that is receiving treatment or stimulation from the devices and methods of the present specification.

The term "epidermal layer" means the outer most layer of a person's skin and shall be construed to cover all variants of the word "epidermal", including epidermis.

Throughout this specification, the term "power source" is used to represent any energy providing device, including a lithium-ion battery, a betavoltaic battery, a solar cell, nickel-cadmium battery, a fuel cell, a mobile phone, or remote charging station.

The term "controller" is used to denote a processing unit configured to control the initiation of stimulation, termination of stimulation, and type and/or extent of stimulation and shall include the terms "control unit", "processing unit", "microcontroller", "microprocessor", or "processor".

The term "pulse generator" means a device configured to generate electrical pulses in accordance with instructions from a controller. It should be appreciated that the pulse generator and controller can be integrated into a single device or multiple devices.

The term "electrode" is used to refer to a conducting material that is capable of receiving electrical pulses and communicating them to another surface.

The term "modulation" or "modulating" means any form of regulation, manipulation or control to change a given variable from one state to another state.

Any increases or decreases in levels or rates are determined by the following formula

[(New Level or Rate)−(Old Level or Rate)]/(Old Level or Rate).

The phrase "at least one of x, y, and z" means that only one of x or y or z need to be true or present in order to satisfy that limitation.

The term "dermatome" refers to an area of skin that is primarily innervated and/or supplied by a specific spinal nerve.

The term "meridian" refers to low resistance fluid channels where various chemical and physical transports take place and are individual pathways which exist among the subcutaneous tissues and serve as channels for the flow of interstitial microscopic fluid throughout the body.

Electro-Dermal Patch System

FIG. 1A is a block diagram illustration of a system 100 for stimulating or modulating nerves and nerve endings in body tissues, in accordance with an embodiment of the present specification. The system 100 comprises an electro-dermal patch (EDP) device 110 in data communication with a companion device 105. In various embodiments, the companion device 105 is further capable of being in data communication with a remote patient care facility, data server and/or patient care personnel. The companion device 105, comprising a computer readable medium and processor, can be any type of computing and communication device, including a computer, server, mobile phone, gateway, laptop, desktop computer, netbook, personal data assistant, remote control device or any other device capable of accessing a cellular, Internet, TCP/IP, Ethernet, Bluetooth, wired, or wireless network.

The electro-dermal patch device 110, in various embodiments, has a housing 111 comprising a microprocessor or microcontroller 112 electronically connected to a transceiver 114 to wirelessly communicate with the companion device 105, a pulse generator 116 to generate a plurality of electrical pulses for application through one or more electrodes 118 and a power management module 120, such as a lithium-ion battery, a betavoltaic battery, a solar cell, nickel-cadmium battery, or a fuel cell. In some embodiments, the power management module 120 comprises a battery having a voltage in a range of 1.5 V to 4.5 V (for a single battery). The voltage depends on the chemistry of the battery being used. In other embodiments, the power management module 120 includes a plurality of batteries stacked in series to increase the voltage supply, wherein per battery voltage ranges from 1.5 V to 4.5 V. The power management module 120 has one or more additional receptor slots 130 to enable snap on or clip on attachment of a disposable electronic assembly that includes a battery for providing additional backup charge to the electro-dermal patch device 110.

Optionally, the housing 111 also comprises one or more actuators 122 such as push buttons or switches to switch the device 110 on/off and to enable user control or settings of a plurality of stimulation therapy protocols such as for toggling stimulation up or down, one or more visual indicators 124, such as LEDs (Light Emitting Diodes), and one or more tactile and audio indicators 126, such as a vibrator, buzzer or beeper to provide feedback to a user, such as about the on/off state of the electro-dermal patch device 110, commencement or conclusion of therapy, battery charge/discharge, and/or malfunction of the electro-dermal patch device 110, among other information. In one embodiment, the one or more actuators 122 includes a touch sensitive screen that enables (using an accelerometer) the user to finger-tap to control and adjust stimulation therapy protocols while the electro-dermal patch device 110 is still worn by the user. Still further embodiments may include (additionally or alternatively) control interfaces on the EDP such as, but not limited to, a slider on the surface of the EDP, an infrared interface wherein communication between the EDP 110 and the companion device 105 is achieved by transmission of infrared radiation, a magnetic interface wherein an external magnet or electro-magnet activates a reed switch or GMR (giant magnetoresistance) device or sensor positioned on the EDP 110, or an audible (speaker) command input interface. It should also be appreciated that, in one embodiment, the EDP comprises no such on/off actuators or stimulation toggling actuators and is entirely controlled by an external device, as described below.

In various embodiments, the housing 111 is sealed so that it is waterproof or water-resistant. In some embodiments, the housing 111 is hermetically sealed to be airtight. In various embodiments, the housing 111 is molded from polymeric materials such as, but not limited to, polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or poly-lactide (PL/DLA) co-polymers, PLLA-polyglycolic acid (PGA) co-polymers, and photocrosslinkable polymers. In some embodiments, the housing 111 is of transparent polymeric material to allow visibility of the contained electronic components and circuitry.

In various embodiments, the microprocessor 112 is in electronic communication with one or more sensors 135 to generate data representative of various physiological parameters of an individual, such as the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and/or UV radiation exposure and absorption. In certain cases, the data representative of the various physiological parameters are the signal or signals themselves generated by the one or more sensors 135 and in certain other cases the data is calculated by the microprocessor 112 based on the signal or signals generated by the one or more sensors 135. Methods for generating data representative of various physiological parameters and sensors to be used therefore are well known to persons of ordinary skill in the art.

Table 1 provides several examples of well-known parameters and the sensor used to measure the parameter. The types of data listed in Table 1 are intended to be examples of the types of data that can be generated by the one or more sensors 135. It is to be understood that other types of data relating to other parameters can be generated by the electro-dermal patch device 110 without departing from the scope of the present specification. It is further understood that the sensors may be located in the housing 111, as shown in FIG. 1A, or remotely positioned from the housing 111 and configured to be electronic communication, via the wireless transceiver 114, with the microcontroller 112.

TABLE 1

| Parameter | Sensor |
| --- | --- |
| Heart Rate/Pulse Rate | EKG (2 Electrodes)/BVP (LED Emitter and Optical Sensor) |
| Beat-to-Beat Variability | EKG (2 Electrodes) |
| EKG Skin Surface Potential | EKG (3-10 Electrodes) |
| Respiration Rate | Chest Volume Change (Strain Gauge) |
| Skin Temperature | Surface Temperature Probe (Thermistors) |
| Core Temperature | Esophageal or Rectal Probe (Thermistors) |
| Heat Flow | Heat Flux (Thermopile) |
| Galvanic Skin Response | Skin Conductance (2 Electrodes) |
| EMG Skin Surface Potential | EMG (3 Electrodes) |
| EEG Skin Surface Potential | EEG (Multiple Electrodes) |
| EOG Eye Movement | Thin Film Piezoelectric Sensors |
| Blood Pressure | Electronic Sphygmomanometer |
| Body Fat | Body Impedance (2 Active Electrodes) |
| Activity | Accelerometer |
| Oxygen Consumption | Oxygen Uptake (Electro-chemical) |
| Glucose Level | Electro-chemical sensors, Optical techniques, Aqueous techniques (tears, saliva, and sweat), and Iontophoresis techniques. |
| Body Position | Mercury Switch Array, Accelerometer |
| Muscle Pressure | Thin Film Piezoelectric Sensors |
| UV Radiation | UV Sensitive Photo Cells |
| Blood oxygen saturation | Pulse oximeter |

The microprocessor 112 is programmed to summarize and analyze the data representative of the physiological parameters of the individual. For example, the microprocessor 112 can be programmed to calculate an average, minimum or maximum heart rate or respiration rate over a defined period of time, such as ten minutes. The electro-dermal patch device 110 is also able to derive information relating to the individual's physiological state based on the data representative of one or more physiological parameters. The microprocessor 112 is programmed to derive such information using known methods based on the data representative of one or more physiological parameters. Table 2 provides examples of the type of information that can be derived, and indicates some of the types of data that can be used therefor.

TABLE 2

| Derived Information | Data Used |
| --- | --- |
| Activity level | Heart rate, pulse rate, respiration rate, heat flow, activity, oxygen consumption |
| Basal metabolic rate | Heart rate, pulse rate, respiration rate, heat flow, activity, oxygen consumption, glucose level |
| Basal temperature | Skin temperature, core temperature |
| Calories burned | Heart rate, pulse rate, respiration rate, heat flow, activity, oxygen consumption |
| Maximum oxygen consumption rate | EKG, heart rate, pulse rate, respiration rate, heat flow, blood pressure, activity, oxygen consumption |
| Relaxation Level | EKG, beat-to-beat variability, heart rate, pulse rate, respiration rate, skin temperature, heat flow, galvanic skin response, EMG, EEG, blood pressure, activity, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |

Additionally, the electro-dermal patch device 110 may also generate data indicative of various contextual parameters relating to the environment surrounding the individual. For example, the electro-dermal patch device 110 can generate data representative of the air quality, sound level/quality, light quality or ambient temperature near the individual, or the global positioning of the individual. The electro-dermal patch device 110 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

In one embodiment, the electro-dermal patch device 110 includes at least one or a combination of the following three sensors 135: 1) an impedance or bio-impedance sensor to determine electrode integrity, i.e. whether the electrode is functioning properly or damaged or to detect and confirm contact integrity of the one or more electrodes 118 with tissues to be stimulated. In another embodiment, an impedance or bio-impedance sensor is used to detect and confirm contact integrity of the one or more electrodes 118 with tissues to be stimulated, 2) an accelerometer to monitor user activity such as walking, running, exercises, distance covered, sleep detection, sensing user input to the electro-dermal patch device 110, 3) a neural activity monitor to detect presence of neural activity as well as an amount of neural activity (firing rate).

In one embodiment, the electro-dermal patch device 110 only includes one or a combination of the following three sensors 135, and no other sensors: 1) an impedance or bio-impedance sensor to determine electrode integrity, i.e. whether the electrode is functioning properly or damaged, to detect and confirm contact integrity of the one or more electrodes 118 with tissues to be stimulated and accordingly modify or manage stimulation therapy. In another embodiment, an impedance or bio-impedance sensor is used to detect and confirm contact integrity of the one or more electrodes 118 with tissues to be stimulated, 2) an accelerometer to monitor user activity such as walking, running, exercises, distance covered, sleep detection, sensing user input to the electro-dermal patch device 110, 3) a neural activity monitor to detect presence of neural activity as well as an amount of neural activity (firing rate). With respect to confirming contact integrity, it should be appreciated that, in one embodiment, sufficient contact integrity of the one or more electrodes 118 is defined in terms of achieving a predefined amount of electrode impedance with the patient's epidermal layer, such as in the range of 200 to 1000 ohms, as measured by the impedance sensor.

In another embodiment, the electro-dermal patch device 110 only includes one or a combination of the following two sensors 135, and no other sensors: 1) an impedance or bio-impedance sensor to determine electrode integrity, i.e. whether the electrode is functioning properly or damaged, to detect and confirm contact integrity of the one or more electrodes 118 with tissues to be stimulated and accordingly modify or manage stimulation therapy and/or 2) a neural activity monitor to detect presence of neural activity as well as an amount of neural activity (firing rate). With respect to confirming contact integrity, it should be appreciated that, in one embodiment, sufficient contact integrity of the one or more electrodes 118 is defined in terms of achieving a predefined amount of electrode impedance with the patient's epidermal layer, such as in the range of 200 to 1000 ohms, as measured by the impedance sensor.

The neural sensor is used to generate a plurality of feedback such as, but not limited to, an indication that the electro-dermal patch device 110 is placed in the right location or area, an indication that the electro-dermal patch device 110 is increasing neural-activity in line with, and in accordance with, a stimulation protocol or an indication that the neural response rate is too slow or insufficient and, therefore, the stimulation protocol needs to be modified. Such plurality of feedback generated by the neural sensor is provided to the user through a Health Management software application running on the user's hand-held computing device such as a smartphone, PDA, tablet that, in various embodiments, functions as the companion device 105. In some embodiments, the neural sensor connects to at least one of the one or more stimulation electrodes 118 while in some alternate embodiments, the neural sensor connects to at least one additional sensing electrode in addition to the one or more stimulation electrodes 118. In some embodiments, the electro-dermal patch device 110 also includes a glucose sensor to monitor the user's blood glucose level.

In some embodiments, the electrodes 118 are in the housing 111, while in other embodiments, the electrodes 118 are removably connectable to the housing 111. In one embodiment, the electrodes 118 are configured to be partially or wholly positioned in the housing 111 and extend outward to be in electrical communication with a hydrogel pad. In another embodiment, the electrodes 118 are configured to be snap-on electrodes where the electrodes 118 are removably connectable to an exterior surface of the housing 111. This allows for the electrode 118 and/or hydrogel pad to be removed and replaced with a new electrode 118 and hydrogel pad, thereby reusing the electrical dermal patch device 110 with the new electrode and hydrogel pad and minimizing the cost of electrodes that fail after just a few days of use.

Figure 1B:
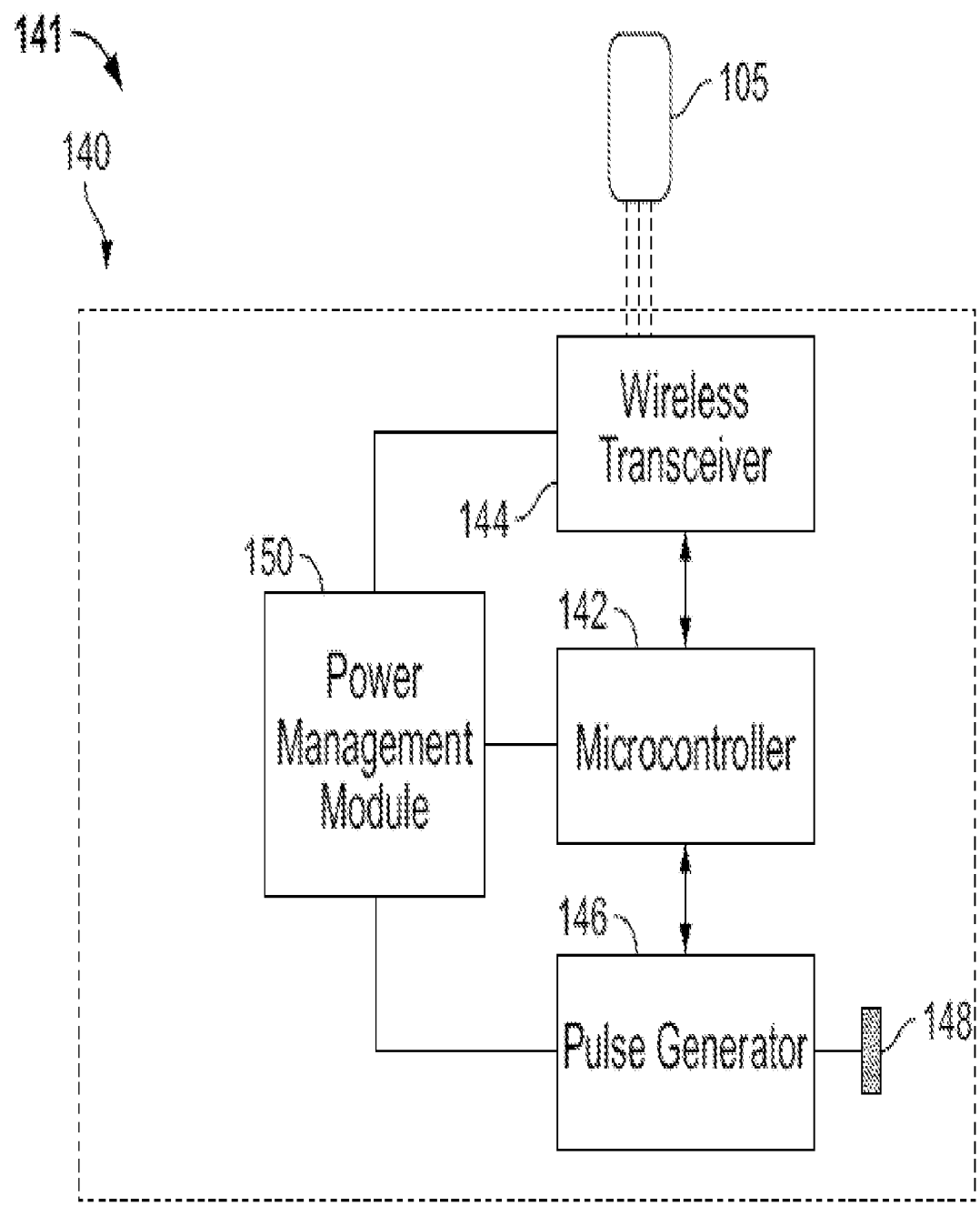
FIG. 1B is a block diagram of a system for stimulating or modulating nerves and nerve endings in body tissues, in accordance with another embodiment of the present specification.

FIG. 1B is a block diagram illustration of a system 141 for stimulating or modulating nerves and nerve endings in body tissues, in accordance with another embodiment of the present specification. In some embodiments, referring to FIG. 1B, the electro-dermal patch device (EDP) 140 includes a microcontroller 142, wireless transceiver 144, a power management module 150, such as a lithium-ion battery, a betavoltaic battery, a solar cell, nickel-cadmium battery, or a fuel cell, a pulse generator 146, and at least one electrode 148, and includes no other physical inputs or sensors on the EDP 140 itself. The remaining inputs are on the companion device 105 and are actuated through the wireless coupling of the companion device 105 and EDP 140.

In some embodiments, rather than including a physical on/off switch, the EDP 140 depicted in FIG. 1B is always using at least a minimum amount of power such that an 'off' state refers to a low power state. While no stimulation is being provided, there is, at a minimum, a periodic 'wake-up' of the EDP 140 to check for communication from the companion device 105. The 'wake-up' places the device in an 'on' state and, in some embodiments, includes no stimulation wherein the EDP 140 runs diagnostics for reporting to the companion device 105. Therefore, while in the 'off' state, the EDP 140 is constantly using a very low amount of power, is not providing stimulation, and is either awaiting a signal from the companion device or is performing diagnostics or other non-stimulation activities requiring very little power. In some embodiments, the energy usage is less than 5 µA average current or in the range of 0.1 µA to 5 µA average current while in the 'off' state and greater than 10 µA average current while in the 'on' state. In some embodiments, the energy usage is at least 1 µA greater while in the 'on' state than while in the 'off' state. Once the EDP 140 receives a signal from the companion device 105 to initiate stimulation, it enters the 'on' state and uses an amount of energy associated with the level of stimulation. In another embodiment, the EDP 140 uses no energy while in an 'off' state and must be awakened, or switched to an 'on' state, by a signal from the companion device.

Figure 1C:
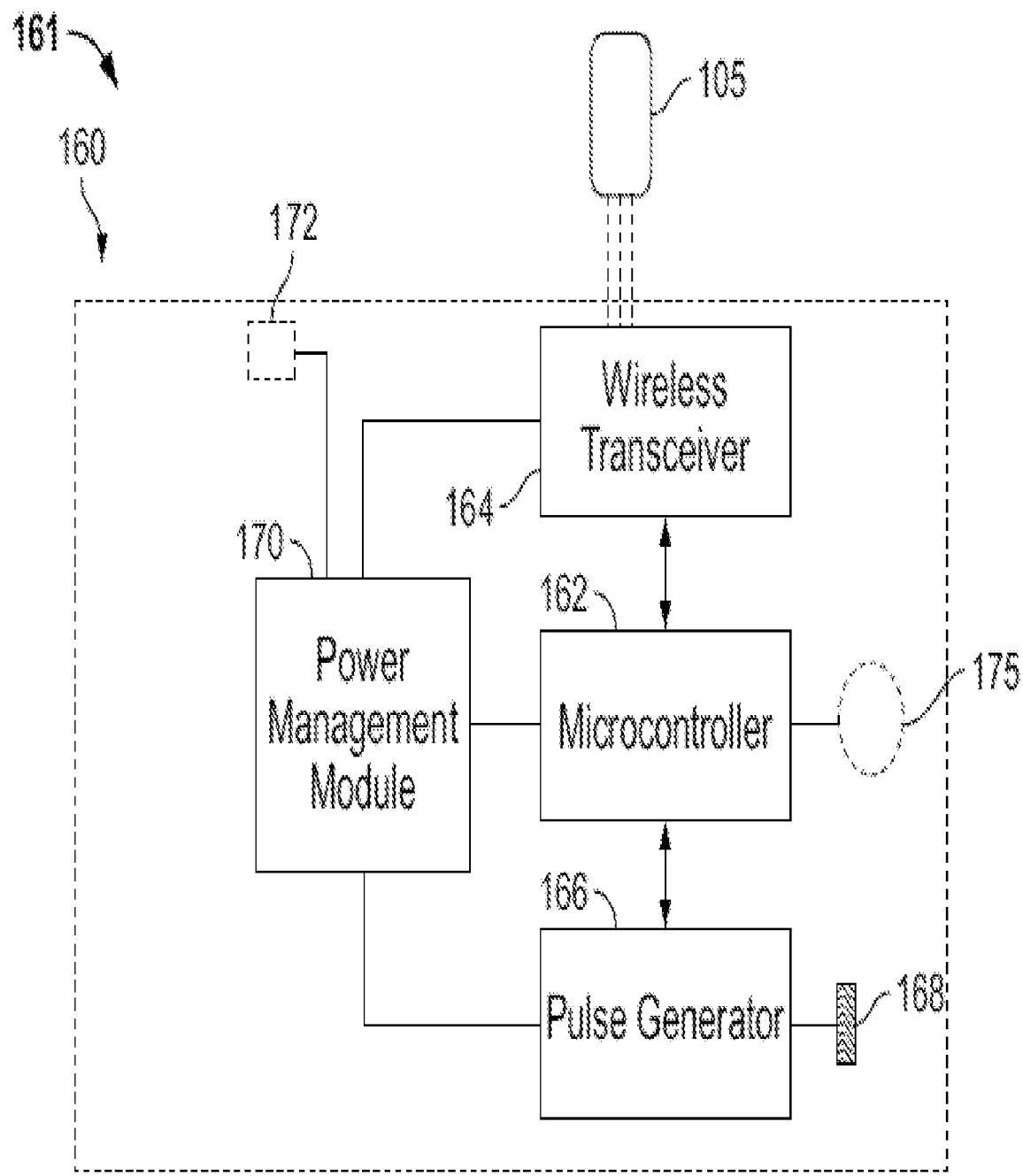
FIG. 1C is a block diagram of a system for stimulating or modulating nerves and nerve endings in body tissues, in accordance with yet another embodiment of the present specification.

FIG. 1C is a block diagram illustration of a system 161 for stimulating or modulating nerves and nerve endings in body tissues, in accordance with yet another embodiment of the present specification. In some embodiments, referring to FIG. 1C, the electro-dermal patch device (EDP) 160 includes a microcontroller 162, wireless transceiver 164, a power management module 170, such as a lithium-ion battery, a betavoltaic battery, a solar cell, nickel-cadmium battery, or a fuel cell, a pulse generator 166, one electrode 168, an optional single actuator 172 to turn the EDP 160 on or off, one sensor 175 for sensing a physiological parameter of the patient, and includes no other physical inputs on the EDP 160 itself. In one embodiment, the sensor 175 is a neural sensor. The remaining inputs are on the companion device 105 and are actuated through the wireless coupling of the companion device 105 and EDP 160.

In accordance with various aspects of the present specification, each component (power management module, microprocessor or microcontroller, pulse generator, transceiver, and one or more electrodes) of the electro-dermal patch may be positioned in a separate housing, in a separate device, or otherwise physically remote from each other. For example, as described with reference to FIG. 1A, the electro-dermal patch device 110 comprises a power management module 120, microprocessor or microcontroller 112, pulse generator 116, transceiver 114, and one or more electrodes 118 in a housing 111, where the one or more electrodes 118 are in physical communication with a hydrogel pad.

Figure 1D:
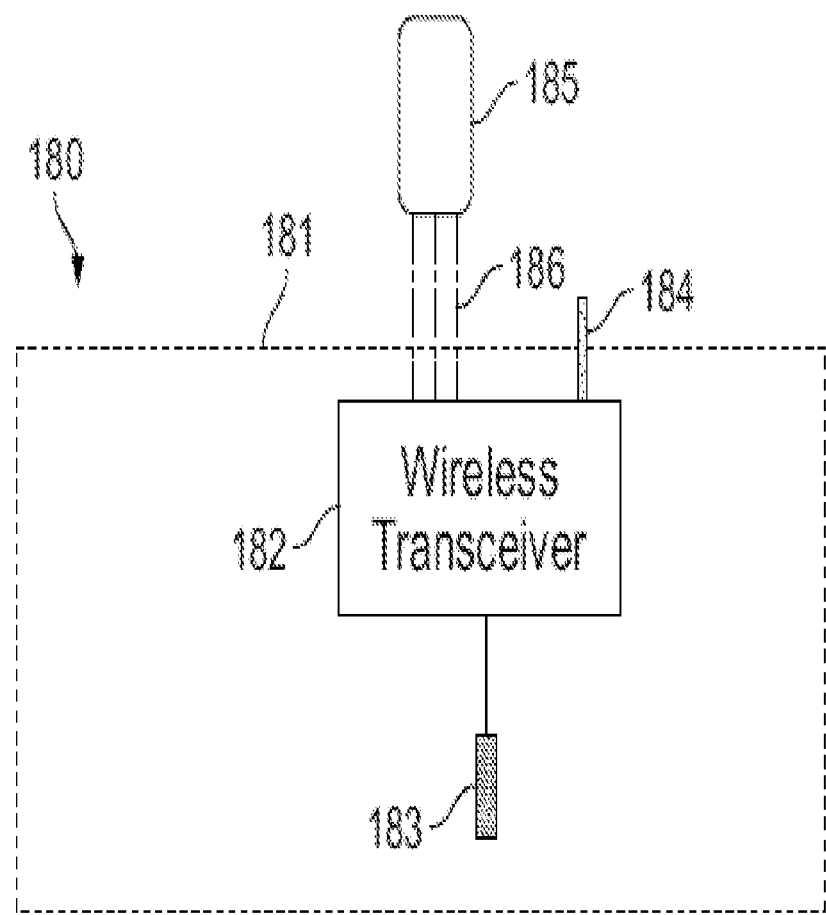
FIG. 1D is a block diagram of a system for stimulating or modulating nerves and nerve endings in body tissues, in accordance with yet another embodiment of the present specification.

However, in a first alternative embodiment as shown in FIG. 1D, the electro-dermal patch device 180 comprises a transceiver 182 having an antenna 184 for receiving electrical pulse signals 186 and an electrode 183, which may or may not be in physical contact with a hydrogel pad. A housing 181 may be positioned around the transceiver 182 and electrode 183 or a substrate carrier may be used to support a low-profile transceiver and/or electrode circuit without any additional housing structure. In this embodiment, an external device 185 comprises the power source, controller, and pulse generator adapted to generate a plurality of electrical pulses, as described earlier with reference to FIGS. 1A through 1C. The external device 185 may be a watch, mobile phone, a sensor pod configured to attach to the patient using a strap or band, or other wearable device. The external device 185 wirelessly transmits the electrical pulses 186 to the transceiver 182 which, in turn, transmits the electrical pulses to the electrode 183 and, thereafter, to the patient's epidermal layer through the hydrogel pad.

Figure 1E:
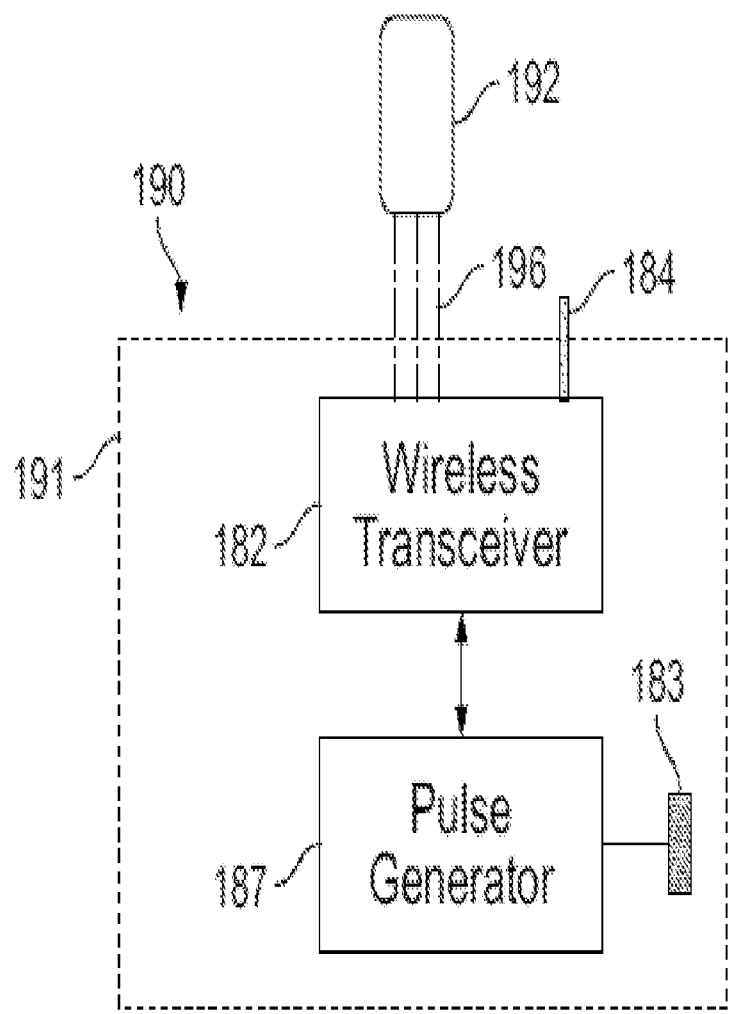
FIG. 1E is a block diagram of a system for stimulating or modulating nerves and nerve endings in body tissues, in accordance with still another embodiment of the present specification.

In a second alternative embodiment, as shown in FIG. 1E, the EDP device 190 comprises a transceiver 182 having an antenna 184 for receiving signals 196, a pulse generator 187, and an electrode 183 in physical communication with a hydrogel pad. A housing 191 may be positioned around the transceiver 182, pulse generator 187, and electrode 183. In this embodiment, an external device 192 comprises the power source and controller adapted to generate an electrical signal, power signal, or data signal 196 that is wirelessly transmitted to transceiver 182 and, in turn, to the pulse generator 187 and used by the pulse generator 187 to generate a plurality of electrical pulses. The external device 192 may be a watch, mobile phone, a sensor pod configured to attach to the patient using a strap or band, or other wearable device. The electrical pulses are communicated to the electrode 183 and, thereafter, to the patient's epidermal layer through an optional hydrogel pad.

Figure 1F:
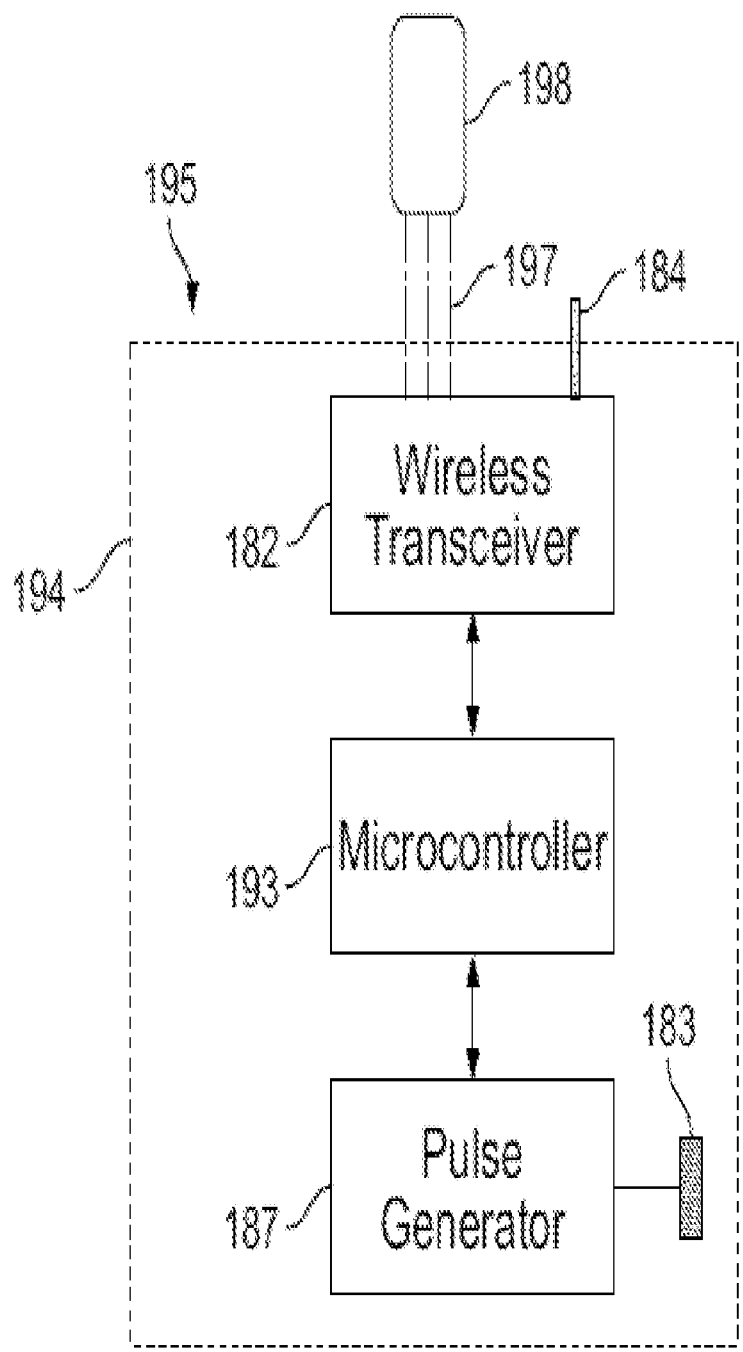
FIG. 1F is a block diagram of a system for stimulating or modulating nerves and nerve endings in body tissues, in accordance with yet another embodiment of the present specification.

In a third alternative embodiment, as shown in FIG. 1F, the EDP device 195 comprises a transceiver 182 having an antenna 184 for receiving power signals 197, a microprocessor or microcontroller 193, a pulse generator 187, and an electrode 183 in physical communication with a hydrogel pad. A housing 194 may be positioned around the transceiver 182, microcontroller 193, pulse generator 187, and electrode 183. In this embodiment, an external device 198 comprises a power source and transceiver adapted to generate the power signal 197 that is wirelessly transmitted to the transceiver 182 of the EDP device 195 and, in turn, to the microcontroller 193 and pulse generator 187 which generates a plurality of electrical pulses. The external device 198 may be a watch, mobile phone, a sensor pod configured to attach to the patient using a strap or band, or other wearable device. The electrical pulses are communicated to the electrode 183 and, thereafter, to the patient's epidermal layer through an optional hydrogel pad.

In a fourth alternative embodiment, each of the power source, controller, pulse generator, transceiver, electrode, and hydrogel pad are combined altogether in a single housing. In a fifth alternative embodiment, the controller, pulse generator, and/or transceiver are combined together in a first housing while the electrode, power source, and/or hydrogel pad are in a disposable second housing, thereby allowing the electrode, power source, and hydrogel to be disposed of when exhausted. Accordingly, the controller, pulse generator, and/or transceiver could be reused and connected to a second electrode, power source, and/or hydrogel pad, yielding a refreshed device.

It should be appreciated that each of the above embodiments can be implemented without a transceiver, replacing the wireless communication with a wired connection between the external device and the electro-dermal patch. It should also be appreciated that, for each embodiment, signal processing to determine data indicative of a physiological condition can be done at the sensor level, i.e. in the impedance or other sensor, at the controller level in the EDP device, or at the external device level using a mobile application software or other program.

Electro-Dermal Patch (EDP) Device Configurations

In accordance with an aspect of the present specification, the electro-dermal patch device 110 is configured as a wearable and disposable skin patch. In embodiments, the EDP device is configured as a wearable device. In alternative embodiments, the EDP device is configured within a housing such that the housing is configured to be worn by the user. Exemplary wearable housing for EDP devices include waist band, and undergarment. In embodiments, the EDP is configured to include electrodes that are spread out while in contact with the user's skin, and are connected to a common pod. In embodiments, the EDP includes a separate patch for each electrode that is attachable to the user's skin. In embodiments, the skin patch is adhesively attached to the user's skin with a pair of removable and replaceable conductive hydrogel pads. Alternatively, the conductive hydrogel pads are a permanent part of the electro-dermal patch device 110 and the entire assembly is disposed of once the battery depletes. The hydrogel pads provide electrical continuity from the EDP device to a user's skin surface. Hydrogel consists of a water based absorbing polymer and a water based electrolyte. Electrical current is transmitted to the skin via the electrolyte in the hydrogel. In various embodiments, both the hydrogel and the electrolyte within meet the requirements of biocompatibility as defined by ISO 10993-5,10, which is incorporated herein by reference. In some embodiments, the EDP device uses 'foam electrodes' with either dry or wet conductive gels applied to the center of the electrode assembly. The foam is placed along the perimeter of the electrode assembly and provides adhesion to the skin. The gel is the conductive medium between the electrode metal and the skin. The 'foam electrodes' are impervious to water since the foam is closed cell and acts as a barrier to water ingress to the conductive gel.

In accordance with an aspect of the present specification, the electro-dermal patch device 110 is configured to be worn for prolonged usage, such as for at least a few minutes, a few hours, or 1, 2, 3, 4, 5, 6, 7, 8, 9, 10, 11, 12, 13, 14 days or up to 3 months continuously or any increment therein, and removed solely for the purpose of recharging and/or changing the replaceable conductive hydrogel pads. The adhesive of the pads is preferably biocompatible to prevent skin irritation due to prolonged usage of the patch. Loctite®, manufactured by Henkel, is a non-limiting example of a medical or biocompatible adhesive. The adhesive of the pads provides sufficient attachment integrity of the EDP to the user's skin. In various embodiments, the EDP has an average minimum 'peel strength' in a range of 1.3 to 1.7 Newton and preferably 1.5 Newton on living skin. In one embodiment, the EDP device uses the KM30B hydrogel, manufactured by Katecho Inc., having a 'peel strength' in a range of 1 to 2.5 Newton. Persons of ordinary skill in the art would appreciate that 'peel strength' is the force required to remove or peel off the EDP, having adhesive pads, from the user's skin and is a measure of the attachment integrity of the EDP. 'Peel strength' is typically quantified by pulling the device from a flexible end or edge at an angle of 90 degrees from the skin surface at a peel rate that ranges from 100 to 500 mm/minute. In alternate embodiments, placement of the electro-dermal patch device 110 is accomplished using a band, strap or a belt, multiple patches connected together by a pod, an undergarment, or any other (discussed in context of FIGS. 4A-4D and 5A-5E). It should be appreciated that the term "adhered" is intended to encompass all forms of achieving device-to-skin contact, including adhesives, bands, straps, or belts.

In accordance with some embodiments, the one or more electrodes 118 enable the electro-dermal patch device 110 to provide electrical stimulation therapy, from the external surface of the patient's epidermal layer through a range of 0.1 mm to 10 mm or a range of 0.1 mm to 20 mm of the dermis, to a user. In various embodiments, a stimulation depth through the patient's epidermal layer ranges from 0.1 mm to 0.5, 1, 2, 3, 4, 5, 6, 7, 8, 9, 10, 11, 12, 13, 14, 15, 16, 17, 18, 19, 20, 21, 22, 23, 24, or 25 mm or any increment therein. An embodiment of the present specification uses two electrodes disposed in hydrogel pads. The electrode pads are disposed on the surface of the skin of the user to pass electrical pulses through the skin and stimulate nerves and nerve endings in body tissues under the skin in the region of the electrodes.

Figure 2A:
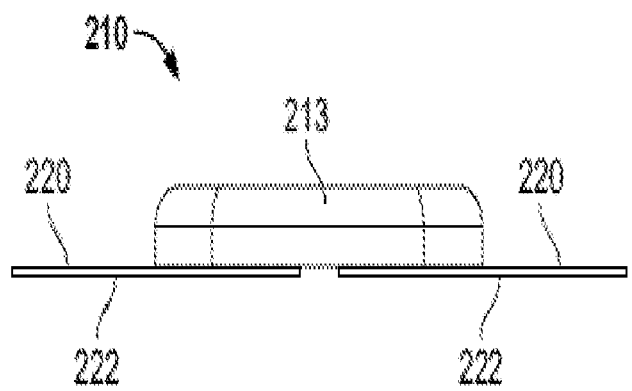
FIG. 2A is a side perspective view of an electro-dermal patch (EDP) device, in accordance with some embodiments of the present specification.
Figure 2B:
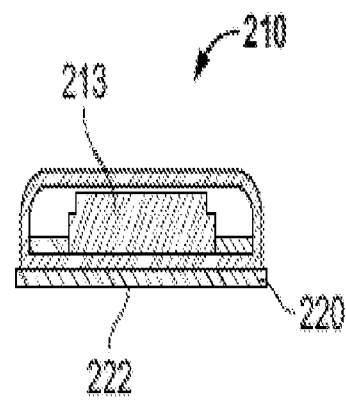
FIG. 2B is a front perspective view of the electro-dermal patch device of FIG. 2A.
Figure 2C:
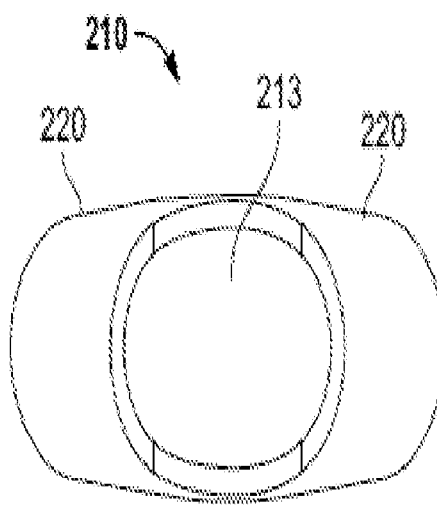
FIG. 2C is a top perspective view of the electro-dermal patch device of FIG. 2A.

FIGS. 2A, 2B and 2C are respectively side, front and top perspective views of an electro-dermal patch device 210, in accordance with an embodiment, having a pair of conductive hydrogel pads 220 and a device housing 213. The housing 213 includes the microcontroller, pulse generator, wireless transceiver, and power management module of the system described with reference to FIG. 1A. The electrodes extend from the housing 213 and into the pads 220 for placement proximate the skin surface of a patient. In one embodiment, the pads 220 have at least one and sometimes more electrodes (not shown) disposed or printed on a lower surface 222 of the pads 220. The pads 220, when adhered to a user's skin, enable the electrodes to be in direct contact with the outer surface of the skin. In embodiments, the pads comprise at least four electrodes or leads that are spread out within housing 213 such that the pads are in contact with the areas of user's skin that address pelvic and/or menstrual pain. In various embodiments, the electrodes can be in the form of typical gel-based skin electrodes, gel-less skin electrodes, or skin puncturing or skin abrading electrodes in order to reduce skin-electrode impedance. In various embodiments, the electrode surface area ranges from 0.1 inches$^2$ to 10 inches$^2$, 0.001 inches$^2$ to 0.1 inches$^2$, or 0.001 inches$^2$ to 10 inches$^2$.

In an alternate embodiment, referring again to FIGS. 2A-2C, the housing 213 is detachable from the hydrogel pads 220 and can be snap-connected to the hydrogel pads 220.

The skin patches or pads 220 can have different shapes and sizes for different body types and areas of stimulation. In some embodiments, the patches or pads are irregularly shaped. In various embodiments, the patches or pads 220 are rectangular having a length of about 2 inches, a breadth of about 1 inches and a thickness of about 0.2 inches. In another embodiment, the patches or pads 220 are rectangular having a length of about 3 to 5 inches, a breadth of about 0.5 to 2.5 inches and a thickness of about 0.10-0.30 inches. In various other embodiments, the patches or pads 220 are round or circular having a diameter of about 2 to 4 inches and a thickness of about 0.10 to 0.30 inches. In still other embodiments, the patches or pads 220 are square having sides of about 2 to 4 inches and a thickness of about 0.10 to 0.30 inches. The patches or pads 220 can have other sizes and shapes such as, but not limited to, elliptical or triangular. In other embodiments, the electrode/pad combination may have a shape including any one of irregular, rectangular, circular, square, elliptical, and triangular and wherein, at its thickest would be between 0.25 to 5 inches in thickness. In another embodiment, the device would comprise two of such electrode/pad combinations placed side by side.

In other embodiments, the device comprises four to six such electrode/pad combinations that are placed at different sites on the body of the user. In embodiments, the electrode/pad combinations are placed at front and lateral T9 to T12 dermatomes, L1, L2, L5 dermatomes and/or a sacral dermatome such as the S1 to S4. In embodiments, the electrode/pad combinations are placed by the user on the skin below the belly-button, in the supra pubic area. In embodiments, at least two electrodes are placed on the skin at roughly 1.5 inches on either side of the belly-button. Moreover, at least two electrodes are positioned on either side of the belly button and on the skin over the pubic bones. In some embodiments, one or two electrodes are positioned on the skin at the back of the user, near the tailbone.

Figure 3A:
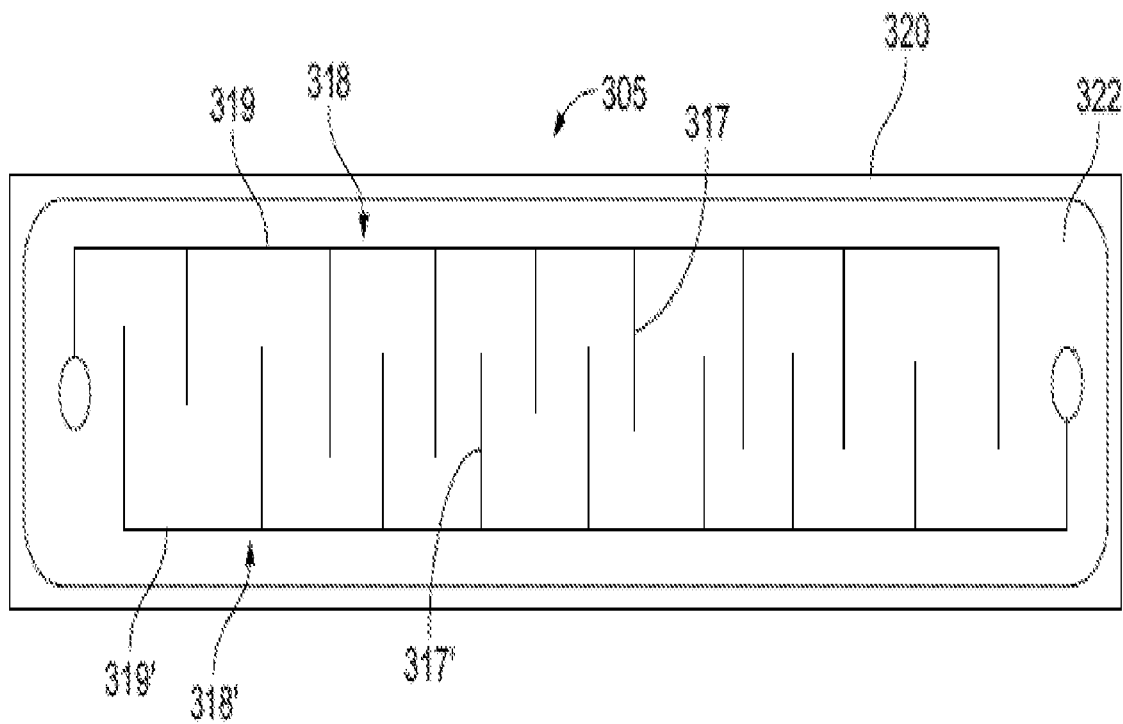
FIG. 3A illustrates a first pattern of electrodes, in accordance with certain embodiments.
Figure 3B:
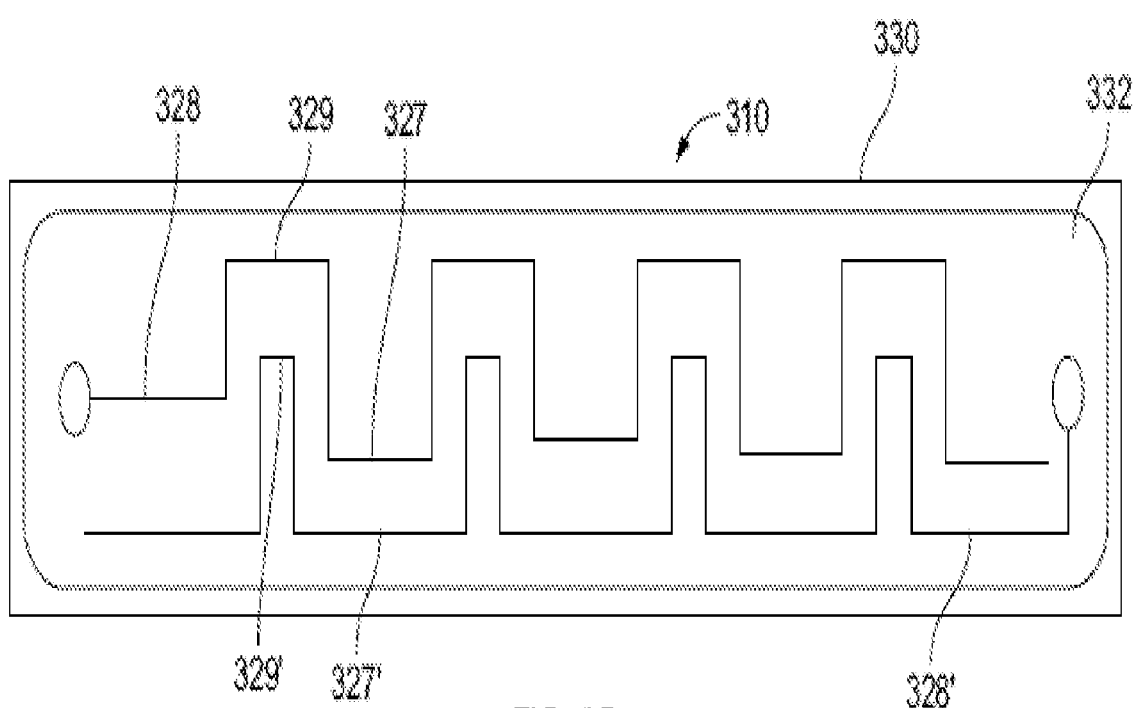
FIG. 3B illustrates a second pattern of electrodes, in accordance with certain embodiments.

In accordance with various embodiments, the electrodes are disposed or printed on the bottom surface 222 of the pads 220 in the form of a plurality of patterns or geometries. FIGS. 3A and 3B illustrate, respectively, a first pattern 305 and a second pattern 310 of first 318, 318' and second electrodes 328, 328'. Referring to FIG. 3A, in one embodiment, the electrodes 318, 318' each have a 'comb' like pattern comprising an elongate 'backbone' 319, 319' with a plurality of 'teeth' 317, 317' extending perpendicularly therefrom. The two electrodes 318, 318' are positioned facing one another such that the 'teeth' 317 of a first electrode 318 are configured to alternate between the 'teeth' 317' of a second electrode 318'. Referring to FIG. 3B, in one embodiment, the electrodes 328, 328' each have a 'square wave' pattern comprising a plurality of peaks 329, 329' and valleys 327, 327'. In one embodiment, the peaks 329 of a first electrode 328 are wider than the peaks 329' of a second electrode 328' such that the peaks 329' of the second electrode 328' fit within the peaks 329 of the first electrode 328. Referring to FIGS. 3A and 3B simultaneously, the patterns 305, 310 are printed on the lower adhesive surface 322, 332 of skin patches or pads 320, 330. Persons of ordinary skill in the art should appreciate that the first and second patterns 305, 310 are only exemplary. In alternative embodiments, the patches or pads are configured to be placed at locations on a user's skin, which are spread-out in different directions. In an embodiment, one patch/pad may be configured to be located on one side of, and above the belly-button, another patch/pad is configured to be located on the same side but below the belly-button. Similarly, two more patches/pads may be located on the other side, one above and one below, the belly-button. Further patches/pads may be configured to be located on the back side of the user near the tail bone. In embodiments, as discussed above and in context of FIGS. 4A-4D and 5A-5E, the patches/pads are configured in housings of various shapes and sizes so as to be able to reach out each location desired by the user, in order to manage pelvic and/or menstrual pain. In some embodiments, the skin patches or pads 320, 330 are transparent such that the pattern of electrodes 318, 318', 328, 328' are visible to the user through the patches or pads 320, 330.

In accordance with various embodiments, the electrical field generated by the electrodes, such as the electrodes 318, 318', 328, 328', is shallow and widely distributed to spread over a sufficiently large area of application of a stimulation therapy. The characteristics of the electrical field generated depend at least upon: a distance between the electrodes and the pattern or geometry of the electrodes on the patch or pad. In accordance with an embodiment, the distance between the two electrodes 318, 318' and 328, 328' is fixed along the entire length of the electrodes 318, 318', 328, 328'. In one embodiment, the electrical field generated by the electrodes is distributed along an area of attachment of the electro-dermal patch device and penetrates a depth of up to 20 mm from the skin surface. In other words, in various embodiments, the electrical field generated by the neuro-stimulation device has a width and length equal to the width and length of the device footprint and a depth sufficient to target neural tissue within 20 mm of the surface of the skin.

In another embodiment, an electrical dermal patch comprises an electrode that is at least partially affixed within the housing and not removably attached to a surface of the housing. The contact surface area of such electrode is in a range of 0.1 in$^2$ to 10 in$^2$, or, more preferably, 0.5 in$^2$ to 4 in$^2$ and the programmable current ranges from 100 µA to 500 mA, or, more preferably, 2 mA to 50 mA. In these embodiments, the current density of the electrical dermal patch is in a range of 10 µA/in$^2$ to 5000 mA/in$^2$, more preferably 25 µA/in$^2$ to 1000 mA/in$^2$, and even more preferably 0.5 mA/in$^2$ to 100 mA/in$^2$. The total contact surface area of the electrical dermal patch in this configuration is equal to the contact surface area of its electrode(s) plus a small additional amount for peripheral portions of the housing, which typically will not amount to more than an additional 5-10% more contact surface area relative to the electrode(s) surface area.

It should be appreciated that, in any configuration described below, one or multiple electrodes may be attached to the housing, or integrated into the housing, each having the characteristics described above, without departing from the scope of this specification. In embodiments, four or more electrodes are fixedly attached to the housing. In other embodiments, four or more electrodes are movably attached to a housing. In other embodiments, at least four electrodes are fixedly attached to the housing, and additional electrodes are movably attached to the housing.

In an embodiment, the EDP device is configured as a large, square area patch device. In this embodiment, the electrical neuro-stimulation device is configured to be placed on the user such that at least two of its negative electrodes are placed on both sides of the umbilicus and at least two of its positive electrodes are placed over the pubic bone, with an optional electrode placed on the patient's back. In other embodiments, the electrode/pad combination may have a shape including any one of irregular, rectangular, circular, square, elliptical, and triangular. In addition, in other embodiments, the positive and negative electrode placement may be altered such that it still achieves the objectives of the present specification.

In accordance with an aspect of the present specification, the electro-dermal patch device (EDP) is configured as a wearable and disposable skin patch. In embodiments, the EDP device is configured as a wearable device. In some embodiments, the EDP device is placed at or near an 'area of interest' on the user's body to provide stimulation therapies for a plurality of conditions or treatments. In alternative embodiments, the EDP device is configured within a housing such that the housing is configured to be worn by the user.

Figure 4A:
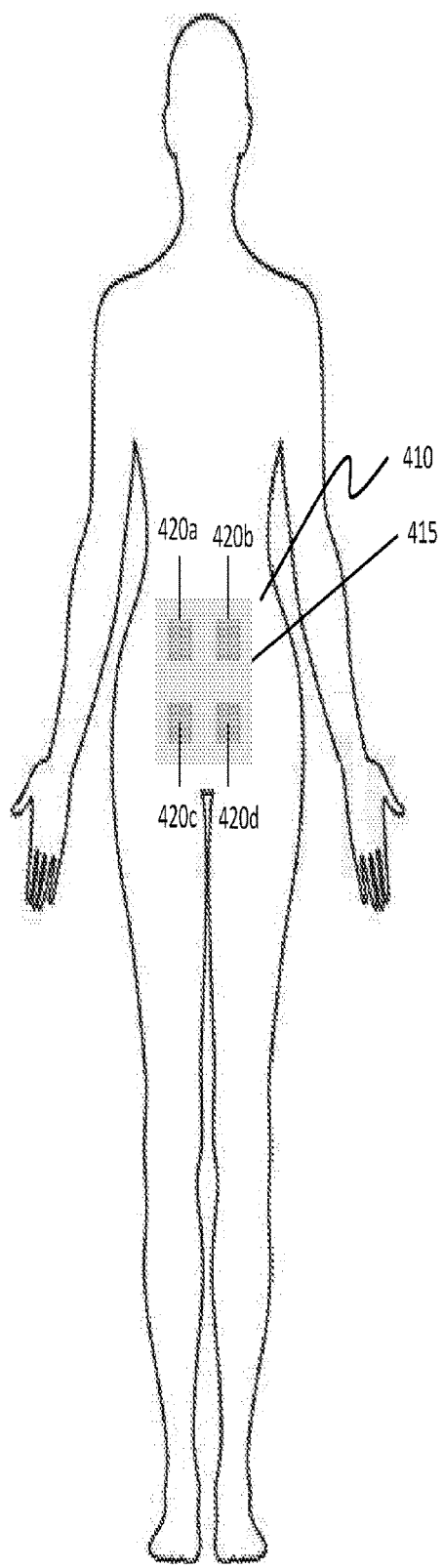
FIG. 4A illustrates a location and configuration of an electro-dermal patch device in accordance with various embodiments of the present specification.
Figure 4B:
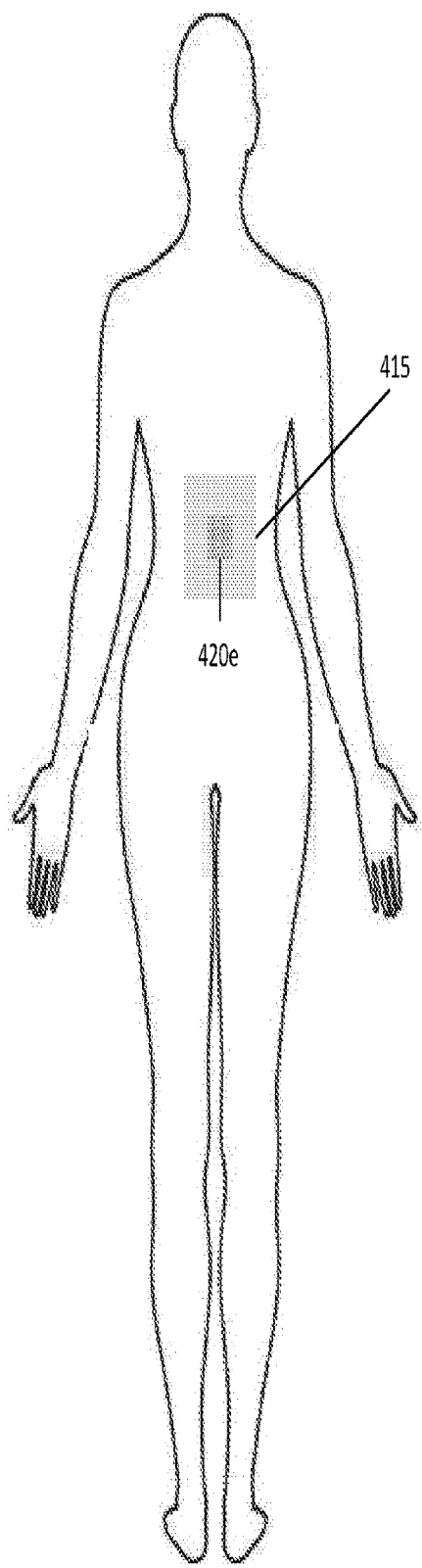
FIG. 4B illustrates a location and configuration of an electro-dermal patch device in accordance with various embodiments of the present specification.

FIGS. 4A and 4B are respectively front and back views of an electro-dermal patch device 410, in accordance with an embodiment, including device housing 415 and conductive pads 420a, 420b, 420c, and 420d, and optional pad 420e. Housing 415 includes the microcontroller, pulse generator, wireless transceiver, and power management module of the system described with reference to FIG. 1A. Electrodes extend from housing 415 and into pads 420a, 420b, 420c, and 420d, and optional pad 420e for placement proximate the skin surface of a patient. In one embodiment, the pads 420*a*, 420*b*, 420*c*, and 420*d*, and optional pad 420*e* have at least one and preferably two electrodes disposed or printed on a lower surface of the pads 420*a*, 420*b*, 420*c*, and 420*d*, and optional pad 420*e*. The pads 420*a*, 420*b*, 420*c*, and 420*d*, and optional pad 420*e*, when adhered to a user's skin, enable the electrodes to be in direct contact with the outer surface of the skin. In various embodiments, the electrodes can be in the form of typical gel-based skin electrodes, gel-less skin electrodes, or skin puncturing or skin abrading electrodes in order to reduce skin-electrode impedance. In various embodiments, the electrode surface area ranges from 0.1 inches$^2$ to 10 inches$^2$, 0.001 inches$^2$ to 0.1 inches$^2$, or 0.001 inches$^2$ to 10 inches$^2$.

In various embodiments, housing 415 is sealed so that it is waterproof or water-resistant. In some embodiments, housing 415*a* is hermetically sealed to be airtight. In various embodiments, housing 415*a* is molded from polymeric materials such as, but not limited to, polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked transpolyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, and photocrosslinkable polymers. In some embodiments, housing 415 is of transparent polymeric material to allow visibility of the contained electronic components and circuitry.

EDP device 410 of FIGS. 4A and 4B is for illustration purposes, and the actual shape and size of EDP device may be provided in various configurations to accommodate comfort preferences of or size variances of different users. The skin patches or pads 420*b*, 420*c*, 420*d*, and optionally 420*e* can have different shapes and sizes for different body types and areas of stimulation. In some embodiments, the patches or pads are irregularly shaped. In various embodiments, the patches or pads 420 are rectangular having a length of about 2 inches, a breadth of about 1 inches and a thickness of about 0.2 inches. In another embodiment, the patches or pads 420 are rectangular having a length of about 3 to 5 inches, a breadth of about 0.5 to 2.5 inches and a thickness of about 0.10-0.30 inches. In various other embodiments, the patches or pads 420 are round or circular having a diameter of about 2 to 4 inches and a thickness of about 0.10 to 0.30 inches. In still other embodiments, the patches or pads 420 are square having sides of about 2 to 4 inches and a thickness of about 0.10 to 0.30 inches. The patches or pads 420 can have other sizes and shapes such as, but not limited to, elliptical or triangular. In other embodiments, the electrode/pad combination may have a shape including any one of irregular, rectangular, circular, square, elliptical, and triangular and wherein, at its widest, would be between 0.25 to 5 inches in width, at its tallest would be between 0.25 to 5 inches in height, and at its thickest would be between 0.25 to 5 inches in thickness. In another embodiment, the device would comprise two of such electrode/pad combinations placed side by side.

In alternative embodiments, the patches or pads 420 are configured to be placed at locations on a user's skin, which are spread-out in different directions. In an embodiment, one patch/pad may be configured to be located on one side of, and above the belly-button, another patch/pad is configured to be located on the same side but below the belly-button. Similarly, two more patches/pads may be located on the other side, one above and one below, the belly-button. Further patches/pads may be configured to be located on the back side of the user near the tail bone.

In an alternate embodiment, the housing 415 is detachable from the conductive pads 420*a*, 420*b*, 420*c*, 420*d*, and optionally 420*e* and can be snap-connected to the pads. In one embodiment, the electrodes are configured to be partially or wholly positioned in housing 415 and extend outward to be in electrical communication with conductive pads. In another embodiment, the electrodes are configured to be snap-on electrodes where the electrodes are removably connectable to an exterior surface of housing 415. This allows for the electrode and/or hydrogel pad to be removed and replaced with a new electrode and hydrogel pad, thereby reusing the electrical dermal patch device 410 with the new electrode and hydrogel pad and minimizing the cost of electrodes that fail after just a few days of use.

In embodiments, EDP device 410 may include system components similar to the EDP device in communication with a companion device, described in context of FIGS. 1A to 1F. In embodiments, a housing 415 includes the electronics, sensors, and other components that comprise the electrodermal device.

In embodiments, EDB device 410 is positioned and/or fitted on the user such that housing 415 is placed at an appropriate location, such that electrodes coming into contact with at least one or a combination of dermatomes T9 to T12, L1, L2, L5 and/or S1 to S4 dermatomes, for treating dysmenorrhea and/or pelvic pain. In embodiments, two of the negative electrodes are placed on either side of the umbilicus, or the belly button, on one or more of the dermatomes such as T9 to T12. Additionally, at least two of the positive electrodes are placed over the pubic bone on either side of the umbilicus, such as on L1. In embodiments, an optional electrode is placed on the back of the user, such as on L2, L5, and/or S1 to S4 dermatomes.

In other embodiments, the electrical neuro-stimulation device is provided in the form of a star-shaped, an octopus-shaped, or a squid-shaped patch, which is configured such that its electrode leads protrude outwards in different directions from a central pod, as shown in FIGS. 4C and 4D, in front and rear views, respectively. FIGS. 4C and 4D, in accordance with an embodiment, include device housing 430 and conductive pads 435*a*, 435*b*, 435*c*, and 435*d*, and optional pad 435*e*. Housing 430 includes the microcontroller, pulse generator, wireless transceiver, and power management module of the system described with reference to FIG. 1A. Electrodes extend outwards from housing 430 and into pads 435*a*, 435*b*, 435*c*, and 435*d*, and optional pad 435*e* for placement proximate the skin surface of a patient. In one embodiment, the pads 435*a*, 435*b*, 435*c*, and 435*d*, and optional pad 435*e* have at least one and preferably two electrodes disposed or printed on a lower surface of the pads 435*a*, 435*b*, 435*c*, and 435*d*, and optional pad 435*e*. The pads 435*a*, 435*b*, 435*c*, and 435*d*, and optional pad 435*e*, when adhered to a user's skin, enable the electrodes to be in direct contact with the outer surface of the skin. In various embodiments, the electrodes 435*a*, 435*b*, 435*c*, and 435*d*, and optional pad 435*e* are movably connected to housing 430, such that the electrodes 435*a*, 435*b*, 435*c*, and 435*d*, and optional pad 435*e* can be attached to at different locations on the user's skin, while each location is independent from the other. In various embodiments, the electrodes can be in the form of typical gel-based skin electrodes, gel-less skin electrodes, or skin puncturing or skin abrading electrodes in order to reduce skin-electrode impedance. In various embodiments, the electrode surface area ranges from 0.1 inches$^2$ to 10 inches$^2$, 0.001 inches$^2$ to 0.1 inches$^2$, or 0.001 inches$^2$ to 10 inches$^2$.

In various embodiments, housing 430 is sealed so that it is waterproof or water-resistant. In some embodiments, housing 430 is hermetically sealed to be airtight. In various embodiments, housing 430 is molded from polymeric materials such as, but not limited to, polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, and photocrosslinkable polymers. In some embodiments, housing 430 is of transparent polymeric material to allow visibility of the contained electronic components and circuitry.

EDP device of FIGS. 4C and 4D is for illustration purposes, and the actual shape and size of EDP device may be provided in various configurations to accommodate comfort preferences of or size variances of different users. The skin patches or pads 435a, 435b, 435c, and 435d, and optional pad 435e can have different shapes and sizes for different body types and areas of stimulation. In some embodiments, the patches or pads are irregularly shaped. In various embodiments, the patches or pads 435 are rectangular having a length of about 2 inches, a breadth of about 1 inches and a thickness of about 0.2 inches. In another embodiment, the patches or pads 435 are rectangular having a length of about 3 to 5 inches, a breadth of about 0.5 to 2.5 inches and a thickness of about 0.10-0.30 inches. In various other embodiments, the patches or pads 435 are round or circular having a diameter of about 2 to 4 inches and a thickness of about 0.10 to 0.30 inches. In still other embodiments, the patches or pads 435 are square having sides of about 2 to 4 inches and a thickness of about 0.10 to 0.30 inches. The patches or pads 435 can have other sizes and shapes such as, but not limited to, elliptical or triangular. In other embodiments, the electrode/pad combination may have a shape including any one of irregular, rectangular, circular, square, elliptical, and triangular and wherein, at its widest, would be between 0.25 to 5 inches in width, at its tallest would be between 0.25 to 5 inches in height, and at its thickest would be between 0.25 to 5 inches in thickness. In another embodiment, the device would comprise two of such electrode/pad combinations placed side by side.

In alternative embodiments, the patches or pads 435 are configured to be placed at locations on a user's skin, which are spread-out in different directions. In an embodiment, one patch/pad 435a may be configured to be located on one side of, and above the belly-button, another patch/pad 435c is configured to be located on the same side but below the belly-button. Similarly, two more patches/pads 435b and 435d may be located on the other side, one above and one below, the belly-button. Further patches/pads, such as 435e, may be configured to be located on the back side of the user near the tail bone.

In an alternate embodiment, the housing 430 is detachable from the conductive pads 435a, 435b, 435c, and 435d, and optional pad 435e and can be wire-connected to the pads. In one embodiment, the electrodes are configured to be movable connected electrically to housing 430. In another embodiment, the electrodes are configured to be removably connectable to housing 430. This allows for the electrode and/or hydrogel pad to be removed and replaced with a new electrode and hydrogel pad, thereby reusing the electrical dermal patch device 435 with the new electrode and hydrogel pad and minimizing the cost of electrodes that fail after just a few days of use.

In embodiments, EDP device shown in FIGS. 4C and 4D may include system components similar to the EDP device in communication with a companion device, described in context of FIGS. 1A to 1F. In embodiments, housing 430 includes the electronics, sensors, and other components that comprise the electro-dermal device.

In embodiments, EDB device shown in FIGS. 4C and 4D is positioned and/or fitted on the user such that housing 430 is placed at an appropriate location, such that electrodes coming into contact with at least one or a combination of dermatomes T9 to T12, L1, L2, L5 and/or S1 to S4 dermatomes, for treating dysmenorrhea and/or pelvic pain. In embodiments, two of the negative electrodes are placed on either side of the umbilicus, or the belly button, on one or more of the dermatomes such as T9 to T12. Additionally, at least two of the positive electrodes are placed over the pubic bone on either side of the umbilicus, such as on L1. In embodiments, an optional electrode is placed on the back of the user, such as on L2, L5, and/or S1 to S4 dermatomes. In embodiments, the star-shaped patch 430 has four electrodes 435a, 435b, 435c, and 435d, which are configured to be placed on the user such that at least two of its negative electrodes are placed on both sides of the umbilicus and at least two of its positive electrodes are placed over the pubic bone. In embodiments, electrodes 435a and 435b are placed on either side of the umbilicus over one or the other of T9 to T12 dermatomes. In embodiments, electrodes 435c and 435d are placed on either side of the umbilicus over L1. In embodiments, the star-shaped patch has a fifth optional electrode lead 435e that is placed on the back near the tailbone. In embodiments, the star-shaped patch with five electrodes has a sixth optional electrode lead (not shown) that is placed on the back near the tailbone. In embodiments, the optional electrodes, such as 435e, is placed on the back over L2, L5, and/or S1 to S4 dermatomes. The patches may be attached by the user to place its electrodes on the user's skin, particularly on the regions encompassing the front and lateral T9 to T12 dermatomes, L1, L2, L5 dermatomes, and/or a sacral dermatome, such as the S1 to S4 dermatomes. The patches may incorporate most features of the EDP, and may also enable separating its electrodes in order to separately clean the patch when required.

Figure 5A:
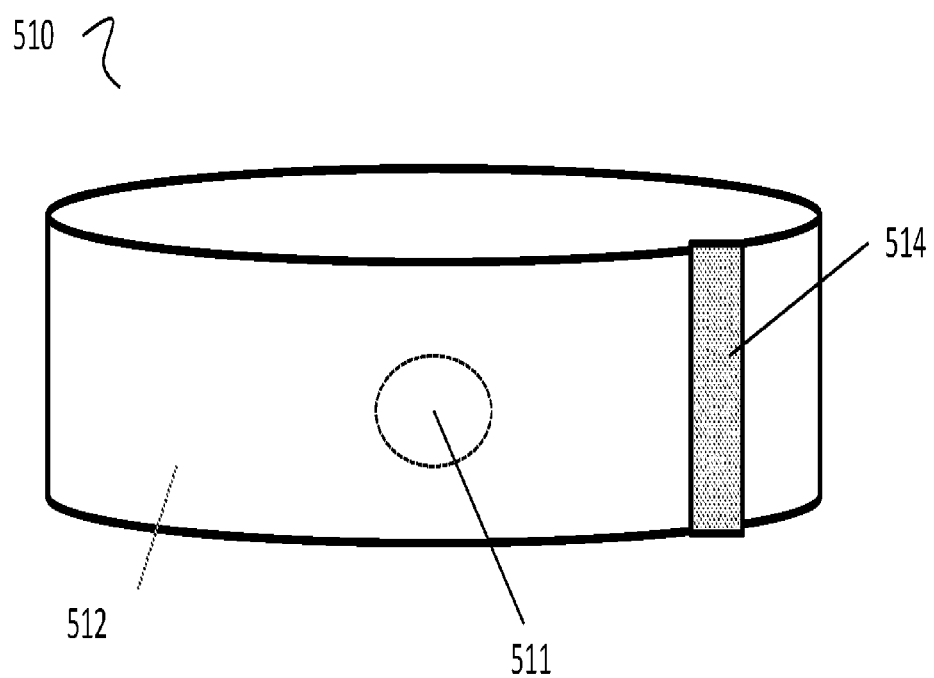
FIG. 5A illustrates an electro-dermal band device in accordance with various embodiments of the present specification.

Referring to FIG. 5A, in an embodiment, an EDP device is configured as an electro-dermal band (EDB) device 510. In embodiments, EDB device 510 is worn by a user in a manner similar to a waist band or a belt 512, such that EDB device 510 is secured comfortably around the user's epidermis, such as around the waist. EDB device 510 of FIG. 5A is for illustration purposes, and the actual shape and size of EDB device may be provided in various configurations to accommodate comfort preferences of different users. In embodiments, EDB device 510 may be made from a natural material, a synthetic material, or a combination of natural and synthetic material. In embodiments, EDB device 510 may include system components similar to the EDP device in communication with a companion device, described in context of FIGS. 1A to 1F. In embodiments, a housing 511 includes the electronics, sensors, and other components that comprise the electro-dermal device. In an embodiment, EDB device 510 includes a flat band with an inner surface that is in contact with the user's body, and an outer surface opposite to the inner surface. In embodiments, housing 511 (shown as a dotted structure on EDB 510) may be placed on the inner surface of EDB device 510 such that when worn by the user, housing 511 is in direct contact with the user's epidermis. In embodiments, EDB device 510 is tied around the user such that housing 511 is placed at an appropriate location, such as the T9 to T12, L1, L2, L5 and/or S1 to S4 dermatomes, for dysmenorrhea. Housing 511 includes at least four electrodes that are positioned over either side of the umbilicus over one or other of the T9 to T12, L1, L2, L5 and/or S1 to S4 dermatomes.

In various embodiments, housing 511 is sealed so that it is waterproof or water-resistant. In some embodiments, housing 511 is hermetically sealed to be airtight. In various embodiments, housing 511 is molded from polymeric materials such as, but not limited to, polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, and photocrosslinkable polymers. In some embodiments, housing 511 is of transparent polymeric material to allow visibility of the contained electronic components and circuitry.

Figure 5B:
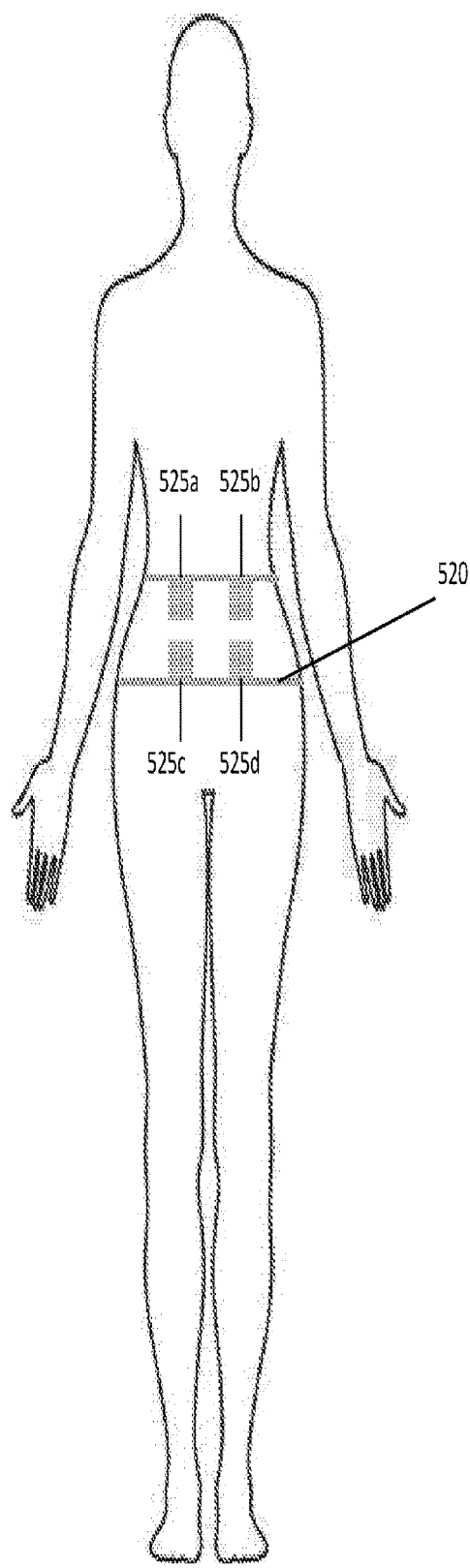
FIG. 5B illustrates a location and configuration of an electro-dermal band device in accordance with various embodiments of the present specification.
Figure 5C:
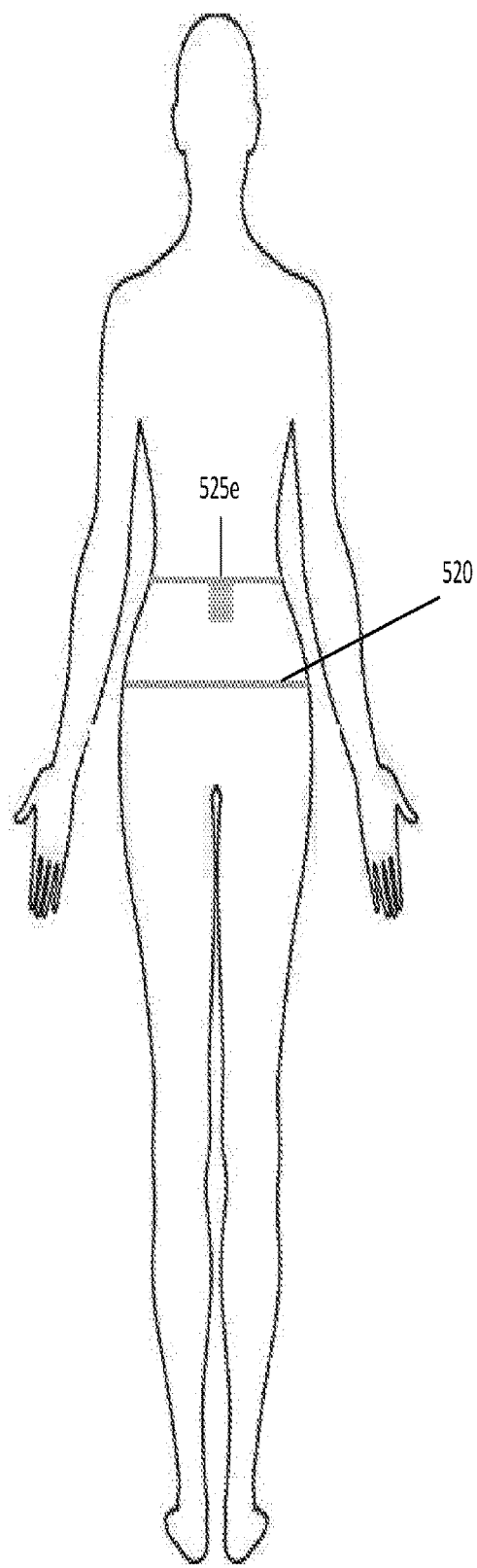
FIG. 5C illustrates a location and configuration of an electro-dermal band device in accordance with various embodiments of the present specification.

Housing 511 comprises electrodes (not shown), which may be placed within housing 511. FIG. 5A illustrates an embodiment where the electrodes are fixed with housing 511. FIGS. 5B and 5C illustrate an alternative embodiment of the waist band configuration of FIG. 5A, where the electrodes are removably connectable on an inner surface of a band 520. In embodiments, band 512 and band 520 are similarly configured. In one embodiment, electrodes 525a, 525b, 525c, and 525d, and an optional electrode 525e, are configured to be partially or wholly positioned separately within band 520. In embodiments, electrodes 525a, 525b, 525c, and 525d, and an optional electrode 525e are in electrical communication with a hydrogel pad. In another embodiment, electrodes 525a, 525b, 525c, and 525d, and an optional electrode 525e are configured to be snap-on electrodes where the electrodes are removably connectable to an interior surface of band 520. This allows for the electrode and/or hydrogel pad to be removed and replaced with a new electrode and hydrogel pad, thereby reusing the electrical dermal band device 510 with the new electrode and hydrogel pad and minimizing the cost of electrodes that fail after just a few days of use. In an embodiment, electrodes 525a, 525b, 525c, and 525d, and an optional electrode 525e, are placed in separate pockets fixed within internal surface of band 520. The electrodes are positioned such that they come into contact with at least one or a combination of dermatomes T9 to T12, L1, L2, L5 and/or S1 to S4 dermatomes, for treating dysmenorrhea and/or pelvic pain. In an embodiment, electrodes 525a, 525b, 525c, and 525d, and an optional electrode 525e are connected to a an EDB device (not shown), which is placed within a housing on the internal surface of band 520. In another embodiment, each of electrodes 525a, 525b, 525c, and 525d, and an optional electrode 525e are placed within separate housings that are removably attached to internal surface of band 520.

Referring to FIGS. 5A, 5B, and 5C, in embodiments, housing(s) may be removably attached to band of 512 and/or 520 of their respective EDB device, such that band 512 and/or 520 may be cleaned if and when required, while the housing(s) and its components including electrodes and sensors remain unharmed during the cleaning process. In some embodiments, EDB device on bands 512 and/or 520 includes one or more electrodes placed at appropriate locations along its inner surface, and may not include a housing.

In embodiments, band 512/520 may be tied around the waist of the user, like a belt. Two ends of band 512/520 may be joined together with any of the known joining mechanisms. FIG. 5A illustrates an embodiment of a fastener, for example a Velcro fastener, which may be used for clothes or other materials consisting two overlapping strips. Referring FIG. 5A, the two ends of band 512 may overlap at an area 514 that uses an adjustable fastening mechanism. In another embodiment, a buckle mechanism may be used to fasten band 512/520. In another embodiment, a hook and eye closure mechanism may be used to fasten band 512/520.

Figure 5D:
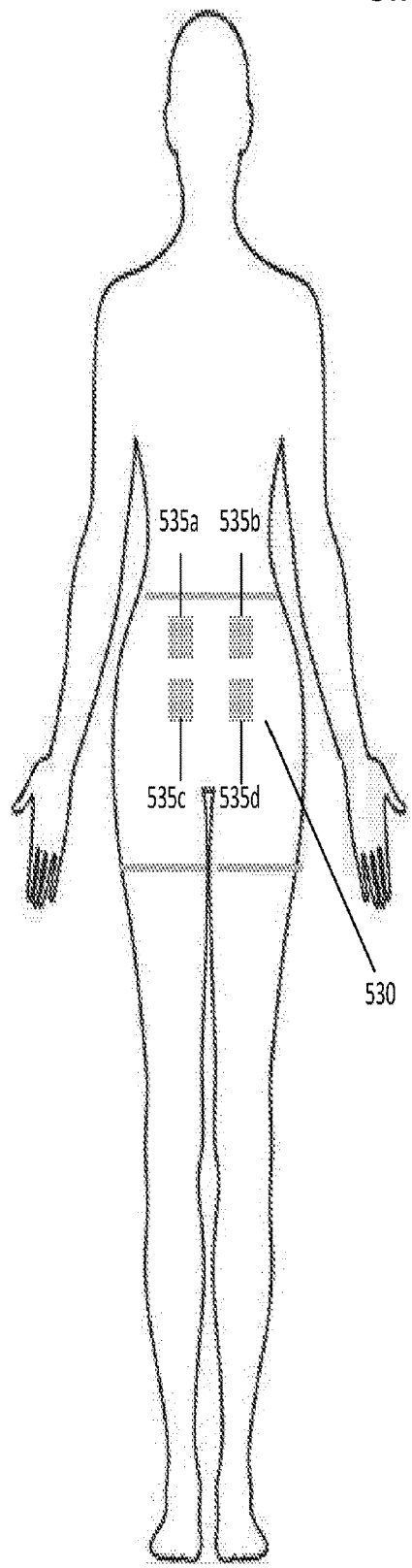
FIG. 5D illustrates a location and configuration of an electro-dermal device in accordance with various embodiments of the present specification, in an undergarment configuration.
Figure 5E:
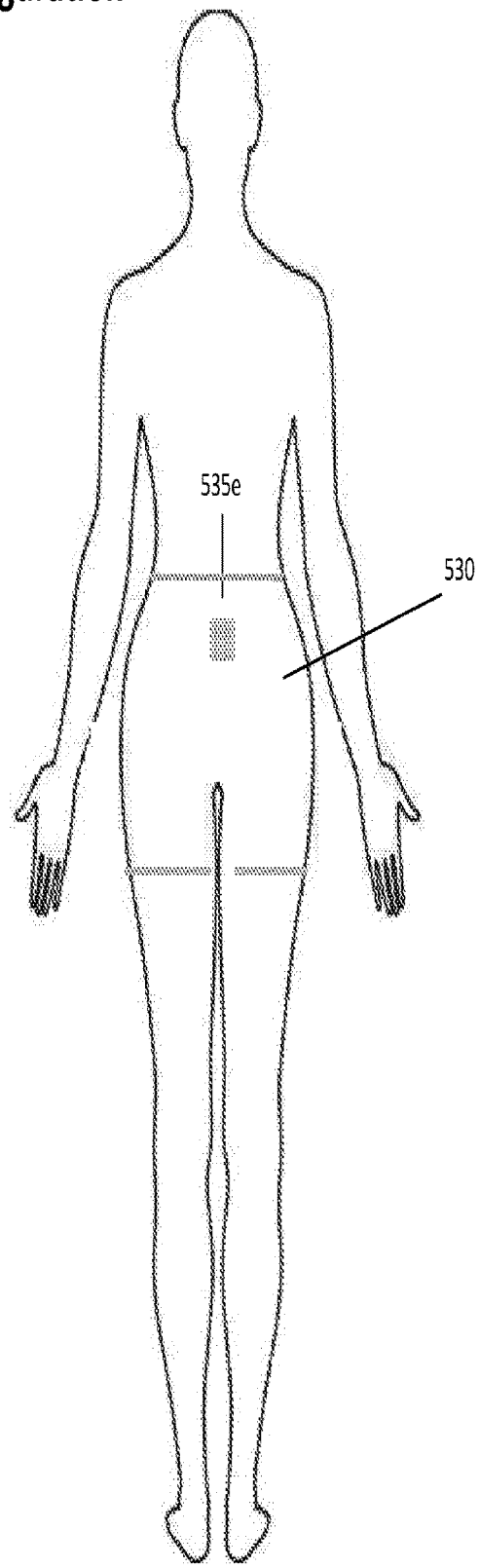
FIG. 5E illustrates a location and configuration of an electro-dermal device in accordance with various embodiments of the present specification, in an undergarment configuration.

In still other embodiments, the electrical neuro-stimulation device is provided in the form of a type of undergarment, which is configured to be worn by the user, similar to underpants, as shown in FIGS. 5D and 5E. The underwear 530 may be of any of the available shapes and sizes, such as but not limited to a thong, high-waist underpants, low-waist underpants, and boy shorts-style underpants. In embodiments, electrodes are placed within the underwear.

FIGS. 5D and 5E are respectively front and back views of underwear 530, in accordance with an embodiment, including conductive pads 535a, 535b, 535c, and 535d, and optional pad 535e. Each conductive pad or electrode may be placed in a separate housing, or alternatively, may be electrically connected to a common housing (not shown). Each housing includes the microcontroller, pulse generator, wireless transceiver, and power management module of the system described with reference to FIG. 1A. Electrodes extend from the housings and into pads 535a, 535b, 535c, and 535d, and optional pad 535e for placement proximate the skin surface of a patient. In one embodiment, the pads 535a, 535b, 535c, and 535d, and optional pad 535e have at least one and preferably two electrodes disposed or printed on a lower surface of the pads 535a, 535b, 535c, and 535d, and optional pad 535e. The pads 535a, 535b, 535c, and 535d, and optional pad 535e, when adhered to a user's skin, enable the electrodes to be in direct contact with the outer surface of the skin. In various embodiments, the electrodes can be in the form of typical gel-based skin electrodes, gel-less skin electrodes, or skin puncturing or skin abrading electrodes in order to reduce skin-electrode impedance. In various embodiments, the electrode surface area ranges from 0.1 inches$^2$ to 10 inches$^2$, 0.001 inches$^2$ to 0.1 inches$^2$, or 0.001 inches$^2$ to 10 inches$^2$.

In various embodiments, the housings are sealed so that they are waterproof or water-resistant. In some embodiments, housings are hermetically sealed to be airtight. In various embodiments, housings are molded from polymeric materials such as, but not limited to, polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, and photocrosslinkable polymers. In some embodiments, housings are of transparent polymeric material to allow visibility of the contained electronic components and circuitry.

EDP device shown in FIGS. 5D and 5E is for illustration purposes, and the actual shape, size, and position each pad may be provided in various configurations to accommodate comfort preferences of or size variances of different users. The skin patches or pads 535a, 535b, 535c, and 535d, and optional pad 535e can have different shapes and sizes for different body types and areas of stimulation. In some embodiments, the patches or pads are irregularly shaped. In various embodiments, the patches or pads 535a, 535b, 535c, and 535d, and optional pad 535e are rectangular having a length of about 2 inches, a breadth of about 1 inches and a thickness of about 0.2 inches. In another embodiment, the patches or pads 535a, 535b, 535c, and 535d, and optional pad 535e are rectangular having a length of about 3 to 5 inches, a breadth of about 0.5 to 2.5 inches and a thickness of about 0.10-0.30 inches. In various other embodiments, the patches or pads 535a, 535b, 535c, and 535d, and optional pad 535e are round or circular having a diameter of about 2 to 4 inches and a thickness of about 0.10 to 0.30 inches. In still other embodiments, the patches or pads 535a, 535b, 535c, and 535d, and optional pad 535e are square having sides of about 2 to 4 inches and a thickness of about 0.10 to 0.30 inches. The patches or pads 535a, 535b, 535c, and 535d, and optional pad 535e can have other sizes and shapes such as, but not limited to, elliptical or triangular. In other embodiments, the electrode/pad combination may have a shape including any one of irregular, rectangular, circular, square, elliptical, and triangular and wherein, at its widest, would be between 0.25 to 5 inches in width, at its tallest would be between 0.25 to 5 inches in height, and at its thickest would be between 0.25 to 5 inches in thickness. In another embodiment, the device would comprise two of such electrode/pad combinations placed side by side.

In an alternate embodiment, the housings are detachable from the conductive pads 535a, 535b, 535c, and 535d, and optional pad 535e and can be snap-connected to the pads. In one embodiment, the electrodes are configured to be partially or wholly positioned in the housings and extend outward to be in electrical communication with conductive pads. In another embodiment, the electrodes are configured to be snap-on electrodes where the electrodes are removably connectable to an exterior surface of their housing. This allows for the electrode and/or hydrogel pad to be removed and replaced with a new electrode and hydrogel pad, thereby reusing the underwear 530 with the new electrode and hydrogel pad and minimizing the cost of electrodes that fail after just a few days of use.

In embodiments, the housings may include system components similar to the EDP device in communication with a companion device, described in context of FIGS. 1A to 1F. In embodiments, the housings includes the electronics, sensors, and other components that comprise the electro-dermal device.

In embodiments, the electrodes 535a, 535b, 535c, 535d, and optional electrode 535e are removable or are in forms of removable patches. In embodiments, the underwear is provided in varying sizes to accommodate users of different body-shapes and sizes. The underwear may be worn by the user to place its electrodes on the user's skin, particularly on the regions encompassing the front and lateral T9 to T12 dermatomes, L1, L2, L5 dermatomes, and/or a sacral dermatome, such as the S1 to S4 dermatomes. In embodiments, the underwear includes at least four electrodes such that on wearing the underwear, at least two of its negative electrodes are placed on both sides of the umbilicus and at least two of its positive electrodes are placed over the pubic bone. In embodiments, the underwear includes a fifth optional electrode lead that is placed on the back near the tailbone. In embodiments, the underwear with five electrodes has a sixth optional electrode lead that is placed on the back near the tailbone. In embodiments, two of the negative electrodes are placed on either side of the umbilicus, or the belly button, on one or more of the dermatomes such as T9 to T12. Additionally, at least two of the positive electrodes are placed over the pubic bone on either side of the umbilicus, such as on L1. In embodiments, an optional electrode is placed on the back of the user, such as on L2, L5, and/or S1 to S4 dermatomes. The undergarment may incorporate most features of the EDP, and may also enable separating its electrodes in order to separately clean the undergarment when required.

Companion Device/Control

Referring back to FIG. 1A, the electro-dermal patch device 110 is in data communication with and controlled by the companion device 105 in accordance with an aspect of the present specification. The companion device 105 is further capable of being in data communication with a remote patient care facility and/or patient care personnel. The companion device 105 is in data communication with the electro-dermal patch device 110 through a direct link to drive therapy. In accordance with a preferred embodiment, the companion device 105 is a hand-held computing device such as a watch, wristband, smartphone, tablet, or PDA that controls the electro-dermal patch device 110 through a wireless connection, such as Bluetooth, WiFi or any other private/public cellular or TCP/IP network such as the Internet. In some embodiments, the companion device is physically separated from and external to the EDP, hence referred to as a separate or external device. In some embodiments, the companion device may be a wearable activity monitor that tracks heart rates, movement, and other physiological data. In some embodiments, the EDP may be integrated into a wearable activity monitor and communicate with an external device, such as a smartphone, that is executing a software application in data communication with the wearable activity monitor.

The companion device 105 is configured to monitor and record ('learn') patterns of a patient's menstrual occurrences and experiences, and monitor and record, learn, and optionally, modify or enable a clinician to modify the stimulation parameters of the stimulation protocols delivered by the electro-dermal patch device 110. In an embodiment, an average cycle of 28 days is experienced by the user. The first day is the day of onset of menstruation. Consequently, the eleventh to fourteenth days are typically when ovulation occurs. In an embodiment, pain records provided by the user are correlated with the menstruation cycle to learn and develop a pain topography, which may evolve by learning more occurrences and experiences over a period of time. The stimulation parameters, including frequency and measure of stimulation, may be modified accordingly. In some embodiments, therapy provided by the electro-dermal patch device 110 is coupled with both recordings (keeping a log of the therapy) and patient compliance reminders provided by the companion device 105.

FIG. 35 is a depiction of a graphical user interface with a visual light bar, which may be displayed through companion device 105 coupled with EDP device 110. The figure is described in greater details in the subsequent paragraphs, and is presented here as an example of a graphical user interface provided by companion device 105. In the example, a scale of 1 to 10 is used to prompt the user to reflect the degree of pain that is experienced. In another embodiment, a range of 0 to 100 may be selected for the light bar to denote a patient's degree of pain. The degree of pain recorded by the device may subsequently be used to trigger the frequency and measure of stimulation therapy, in order to treat pelvic pain and/or dysmenorrhea.

With reference to FIG. 1A, in accordance with an aspect, the companion device 105, which is a hand-held computing device (such as a smartphone, tablet, PDA) in various embodiments, runs or implements a Health Management software Application (HMA). The HMA activates, deactivates and controls the electro-dermal patch device 110 to provide a plurality of stimulation therapies or protocols in accordance with various embodiments. In an embodiment, the graphical user interface of FIG. 35 is integrated with the HMA. In some embodiments, the HMA activates, deactivates and controls the electro-dermal patch device 110 by pairing or syncing the hand-held computing device (wirelessly or through a wired connection) with the electro-dermal patch device 110. In some embodiments, the HMA pairs or syncs and controls more than one electro-dermal patch device 110 worn by the user for treating a combination of conditions.

In still further embodiments, the HMA is capable of also communicating (via pairing or syncing) with a third party device (including a third party application software on an external device), with physiological sensors, configured to be worn on the human body, such as around the wrist, in order to monitor, acquire, record, and/or transmit the physiological data, to receive and integrate exercise and weight loss information, along with one or more electro-dermal patch devices 110 of the present specification.

In some embodiments, multiple electro-dermal patch (EDP) devices 110 are networked together with a single companion device 105 to aggregate data feedback from the EDP devices 110. The aggregated data is then used to modify stimulation parameters and develop more precise stimulation algorithms. In various embodiments, the companion device 105 enables social networking with friends and family, provides voice recognition and voice feedback, and includes anti-hacking data protection for HIPAA compliance. In some embodiments, the wireless connection (for pairing or syncing) is optionally compliant with HIPAA and other regulatory body requirements and laws relating to OUS (Outside United States) countries for patient data privacy. In various embodiments, the wireless connection is encrypted to prevent hacking of the device to retrieve patient data and/or inappropriately stimulate the patient and/or destroy the device.

Figure 6A:
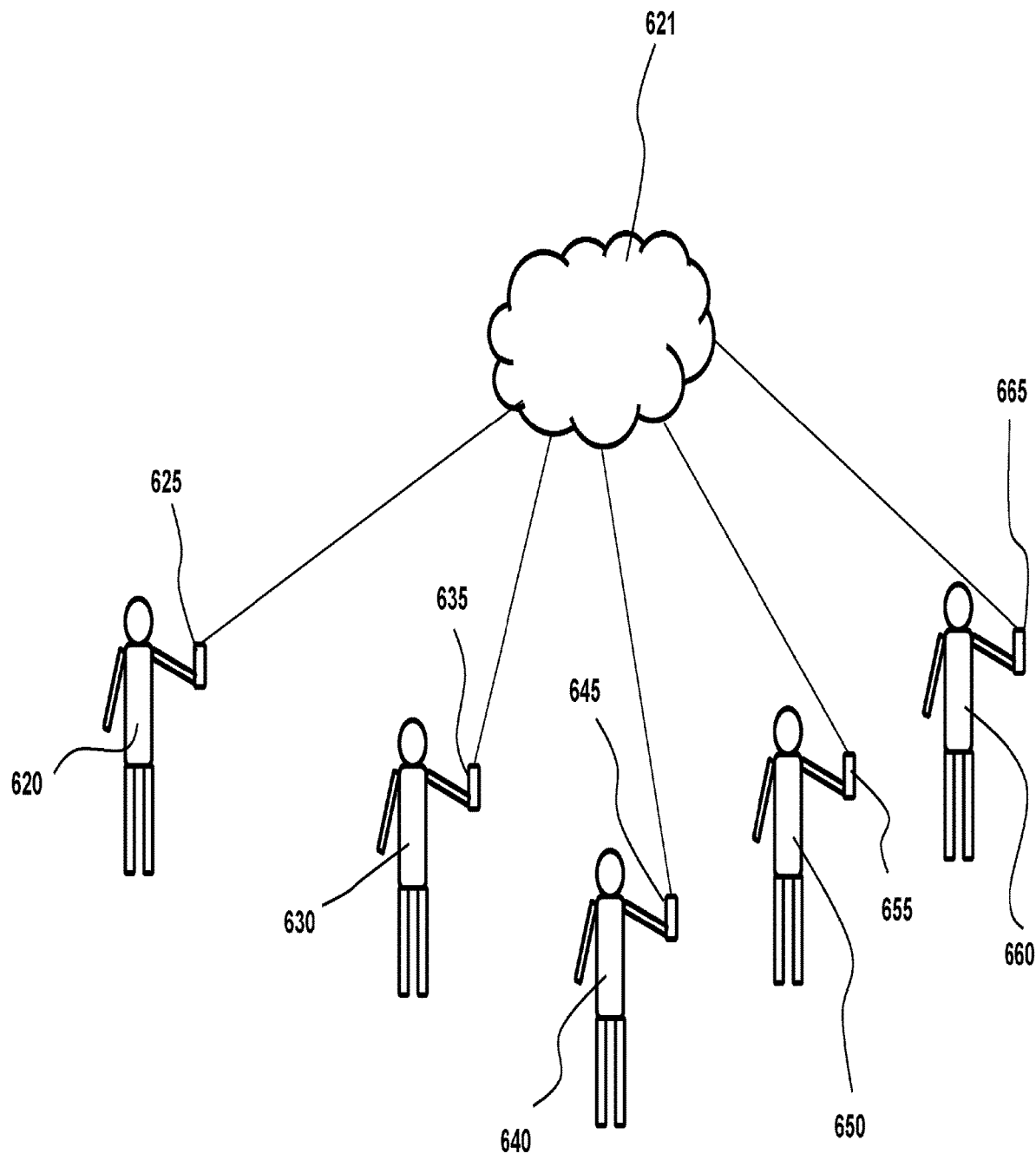
FIG. 6A is a schematic diagram of a plurality of electro-dermal patch users with companion devices shared over a common network connection, in accordance with one embodiment of the present specification.

In various embodiments, as shown in FIG. 6A, using companion devices 625, 635, 645, 655, 665 multiple EDP users 620, 630, 640, 650, 660 respectively, can network with one another and communicate regarding their therapy over a shared network connection 621, such as a cloud based connection, which can lead to improved patient compliance to stimulation protocols, with resultant increased dietary compliance. For example, networked EDP users could share and exchange experiences, menstrual pain levels, progress, dietary ideas, and success stories. In some embodiments, networked exchanges are automatically input into companion devices, resulting in changes to therapy provided by the EDP devices. For example, in one embodiment, aggregated dosing data is used to reset baseline default dosing settings to provide different dietary recommendations. Traditionally, small group clinical studies are performed to obtain data used for creating dosing strategies. By networking EDP users through companion devices, larger amounts of aggregated user settings can be obtained automatically, for example, via a cloud based connection, and used to automatically fine tune dosing settings. In some embodiments, EDP users have the ability, over a network connection, to share data among friends and family who are also users. Further, in some embodiments, users connected to a group, for example, My Days™, Lily Period Tracker™, Period Calendar™, Period Tracker™ Clue™, Moov™, My Cycles™, MonthPal™, Pink Pad™, Lychee™, and the like, can receive "group therapy" support in the form of input, as needed or at periodic intervals, from a moderator or therapist. In embodiments, the "groups" also enable communication between EDP devices, between users, and between users and a moderator or therapist. Such interconnectivity among friends, groups, and moderators/therapists provides a larger support network for EDP users and promotes user compliance.

Figure 6B:
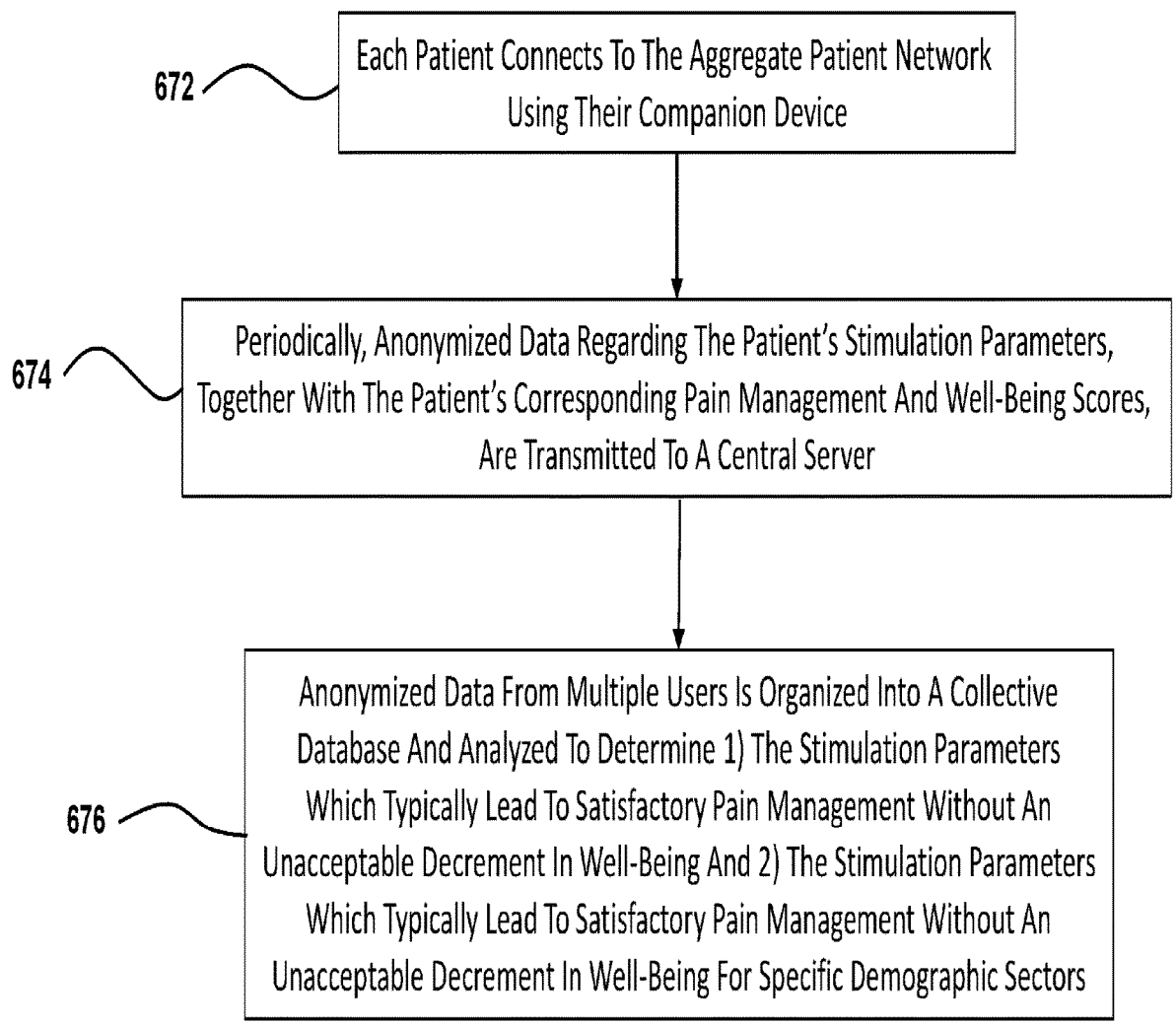
FIG. 6B is a flow chart listing the steps in one embodiment of a method of aggregating, organizing, and analyzing stimulation parameters and patient's pain profile, and well-being scores for a plurality of patients, each having an EDP device with linked companion device connected to an aggregate patient network.

In some embodiments, an EDP user network functions as a dosing settings and dietary information exchange. For example, in an aggregate patient data network, multiple different patients have an EDP communicating with a personal companion device. FIG. 6B is a flow chart listing the steps in one embodiment of a method of aggregating, organizing, and analyzing stimulation parameters and pain-management and well-being scores for a plurality of patients, each having an EDP device with linked companion device connected to an aggregate patient network. At step 672, each patient connects to the aggregate patient network using their companion device. At step 674, periodically, e.g. several times a day, once a day, 2-6 times a week, or any such increment, anonymized data regarding the patient's stimulation parameters including, but not limited to, stimulation pulse width, pulse amplitude, pulse frequency, pulse shape, duty cycle, session duration, and session frequency, together with the patient's corresponding pain-management and well-being scores (different types of scores being collectively referred to as patient status data), are transmitted to a central server, or set of servers.

At the central server, at step 676, the anonymized data from multiple users are organized into a collective database and analyzed to determine 1) the stimulation parameters including, but not limited to, stimulation pulse width, pulse amplitude, pulse frequency, pulse shape, duty cycle, session duration, and session frequency, which typically lead to satisfactory pain management without an unacceptable decrement in well-being and 2) the stimulation parameters including, but not limited to, stimulation pulse width, pulse amplitude, pulse frequency, pulse shape, duty cycle, session duration, and session frequency, which typically lead to satisfactory pain management without an unacceptable decrement in well-being for specific demographic sectors. In some embodiments, patient status data such as pain management and well-being scores are aggregated into a composite score. The user can share her composite score (along with treatment or stimulation settings that led to the composite score) with friends and family via social networking, to illicit advice, encouragement and compare progress.

It should be appreciated that while in some embodiments data regarding the patients' stimulation parameters is anonymized, in some embodiments the data may not be anonymized if the patients sign away their respective privacy rights.

In various embodiments, pain management and well-being scores across demographic profiles are analyzed to determine what stimulation settings achieve optimum pain management and well-being levels or scores for a given age, gender, BMI, ethnicity, menstrual cycles, ovulation cycles, pain during menstruation and/or ovulation, or overall menstrual pain management goal. Thus, for a given user, once the optimum stimulation settings are identified, it is then determined how stimulation settings for the given user must be modified in order to match those optimum stimulation settings, and a modulation signal is transmitted in order to establish those new (optimum) stimulation settings.

Figure 6C:
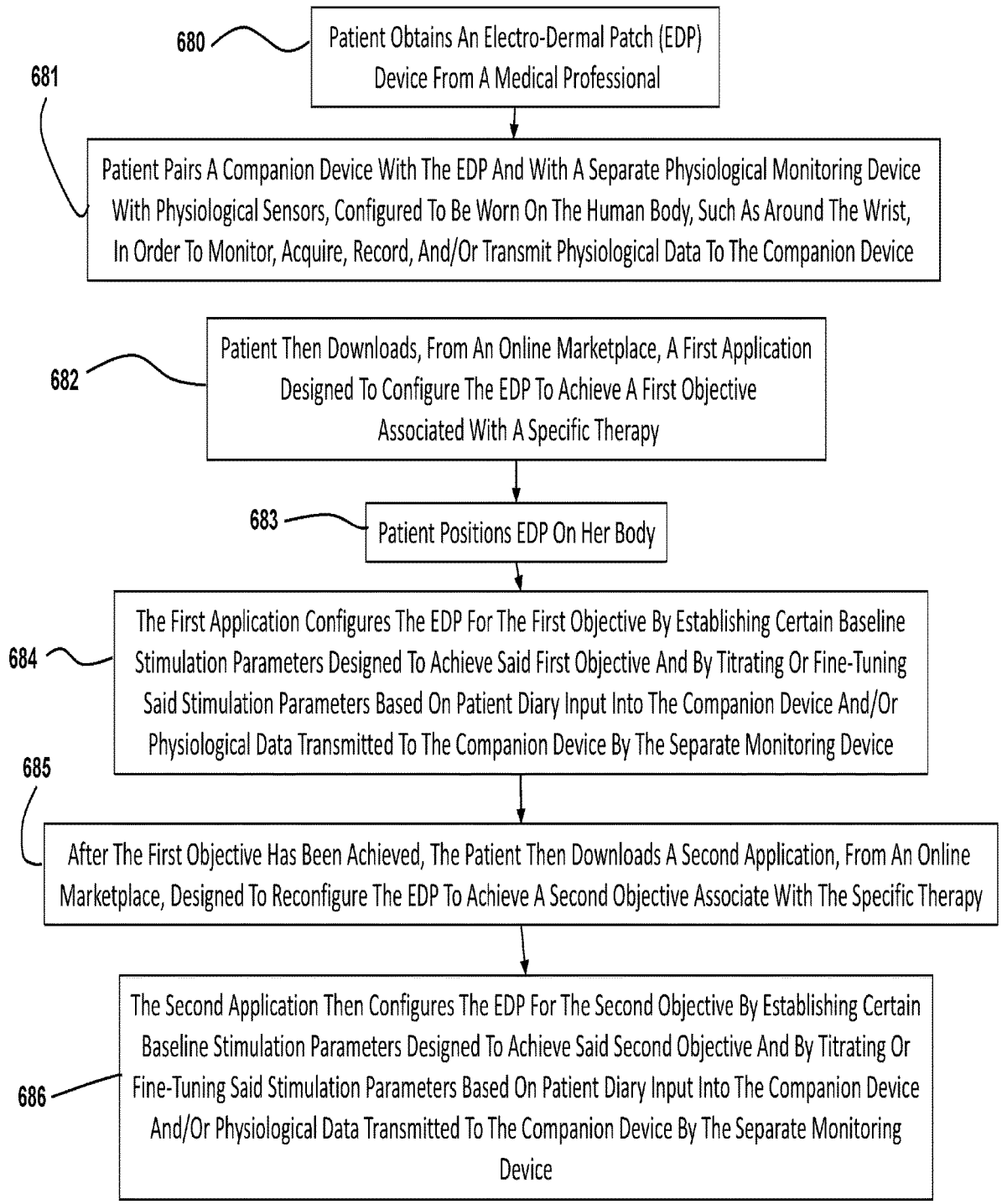
FIG. 6C is a flow chart illustrating the steps involved in using one or more downloadable applications to configure and reconfigure stimulation provided by an electro-dermal patch (EDP) device, in accordance with one embodiment of the present specification.

In various embodiments, the EDP device, and the electrical stimulation it delivers, is configurable and re-configurable for different therapies and for different aspects within a specific therapy. For example, regarding pain management, the patient and/or companion device can configure the EDP to deliver electrical stimulation in an effort to manage pain associated with menstruation in the patient and then, once the pain is effectively managed, reconfigure the EDP to deliver electrical stimulation to anticipate and block menstrual pain every month. This can be accomplished via one or more applications downloaded to the companion device. FIG. 6C is a flow chart illustrating the steps involved in using one or more downloadable applications to configure and reconfigure stimulation provided by an electro-dermal patch (EDP) device, in accordance with one embodiment of the present specification. At step 680, a patient obtains an EDP from a medical professional. At step 681, the patient pairs a companion device with the EDP and with a separate physiological monitoring device with physiological sensors, configured to be worn on the human body, such as around the wrist, in order to monitor, acquire, record, and/or transmit physiological data to the companion device, wherein the companion device is adapted to create and modify stimulation parameters based on the monitored physiological data. At step 682, the patient then downloads, from an online marketplace, a first application designed to configure the EDP to achieve a first objective associated with a specific therapy, for example, initial pain management. The patient positions the EDP on the body at step 683. The first application, at step 684, configures the EDP for the first objective by establishing certain baseline stimulation parameters designed to achieve said first objective and by titrating or fine-tuning said stimulation parameters based on patient diary input into the companion device and/or physiological data transmitted to the companion device by the separate monitoring device. After the first objective has been achieved, at step 685, the patient then downloads a second application, from an online marketplace, designed to reconfigure the EDP to achieve a second objective associated with the specific therapy, for example, maintaining the pain management.

In various embodiments, one or both of the first and second applications is available from the online marketplace for a fee. Additionally, both the first and second applications may be separate and distinct applications which reside on the companion device, are separately obtained by accessing the on-line application marketplace associated with the companion device, and are activated, and executed, by clicking on separate and distinct icons from the companion device's home screen. In another embodiment, the first application may be downloaded from the on-line application marketplace associated with the companion device and may be activated, and executed, by clicking on separate and distinct icons from the companion device's home screen while the second application, and all subsequent applications responsible for modulating the EDP's stimulation parameters, are downloaded by accessing a marketplace of such applications through the first application. Specifically, the first application provides a gateway to a database, or library, of additional applications which may provide for different stimulation parameters based on inputs, level of pain, and other criteria that differ from the first application, or each other.

The second application, at step 686, then configures the EDP for the second objective by establishing certain baseline stimulation parameters designed to achieve said second objective and by titrating or fine-tuning said stimulation parameters based on patient diary input into the companion device and/or physiological data transmitted to the companion device by the separate monitoring device. In one embodiment, for pain management, the stimulation parameters for the first objective (manage initial pain associated with menstruation) are more focused on patient diary record of experienced pain and well-being as inputs to titrate therapy while the stimulation parameters for the second objective (on-going menstrual pain management) are more focused on menstrual cycle and calendar information as an input to titrate therapy. While menstrual pain management has been used to describe the method above for modifying therapy provided by the EDP, in various embodiments, the method of using one or more online applications to configure and reconfigure the stimulation parameters of the EDP can be used on any condition receptive to electrical stimulation therapy.

In various embodiments, the EDP and companion device are open source to allow for the creation of applications for the devices designed to enact therapy methods similar to the one described above. In another embodiment, a single master application downloadable to a companion device is responsible for controlling the EDP and setting initial stimulation parameters. This master application may come with the EDP upon initial purchase or may be separately purchasable or downloadable for a free from an online marketplace. In various embodiments, further software upgrades, such as in-application or "in-app" purchases, can be obtained, for a fee, within the master application and used to fine-tune therapy. In various embodiments, such software upgrades include, for example, new menstrual cycle tracking applications, new diet plans, new exercise plans, and improved fitness tracking, among others. In various embodiments, these software upgrades are created by third parties or by the creator of the master application. In some embodiments, new applications or software upgrades to a master application reconfigure the EDP to provide electrical stimulation targeting different conditions. For example, in various embodiments, applications or upgrades reconfigure baseline EDP stimulation parameters to treat other conditions including, but not limited to, nausea and headaches associated with menstruation, pain associated with endometriosis, obesity, diabetes, back pain, and urinary incontinence. In some embodiments, the electrical components of the device are the same and the patient uses a different, disposable electrode patch portion and repositions the device on her body. These applications and upgrades modify the algorithms used by the companion device to change the stimulation parameters for the EDP to treat the different conditions.

For example, in one embodiment, a patient initially uses the EDP for menstrual pain management in a method similar to that described above. She then downloads a fee-based online application to the companion device which then reconfigures the EDP stimulation to target appetite suppression to treat her obesity. She can then use her initial application to return the EDP back to pain management settings in anticipation of her next menstrual cycle. She could continually download new applications and upgrades and reconfigure the EDP to treat a plurality of different conditions and go back and forth between different conditions. It would be preferred that, for the non-dysmenorrhea applications, such as urinary incontinence, back pain, and peripheral neuropathy, including diabetic peripheral neuropathy, a completely different application be downloaded while for new or different menstrual pain management plans, it would be preferred to download additional applications through the first downloaded menstrual pain management application itself, thereby avoiding having multiple different and distinct menstrual pain management applications on the companion device's home screen.

Because the presently disclosed embodiments are directed to medical treatments, it is imperative that patient specific data, such as data representing specific stimulation settings and patient status data, are stored, transmitted, and verified in a manner that is secure and subject to authentication. In one embodiment, data transmissions between the EDP, the companion device, and any remote server(s) are subject to verification and authentication, such as by using checksums, private and public keys, and other forms of verification known in the art. If, at any time, one or more of the data transmissions fail to be properly verified or authenticated, any new or modulated stimulation settings associated with such data transmissions are discarded or otherwise set aside and only a previous stimulation setting associated with a fully verified and/or authenticated complete set of data transmissions is used. Alternatively, the system may lock the use of any stimulation setting until such data transmissions can be fully verified, along with any new or modulated stimulation settings associated therewith.

Figure 6D:
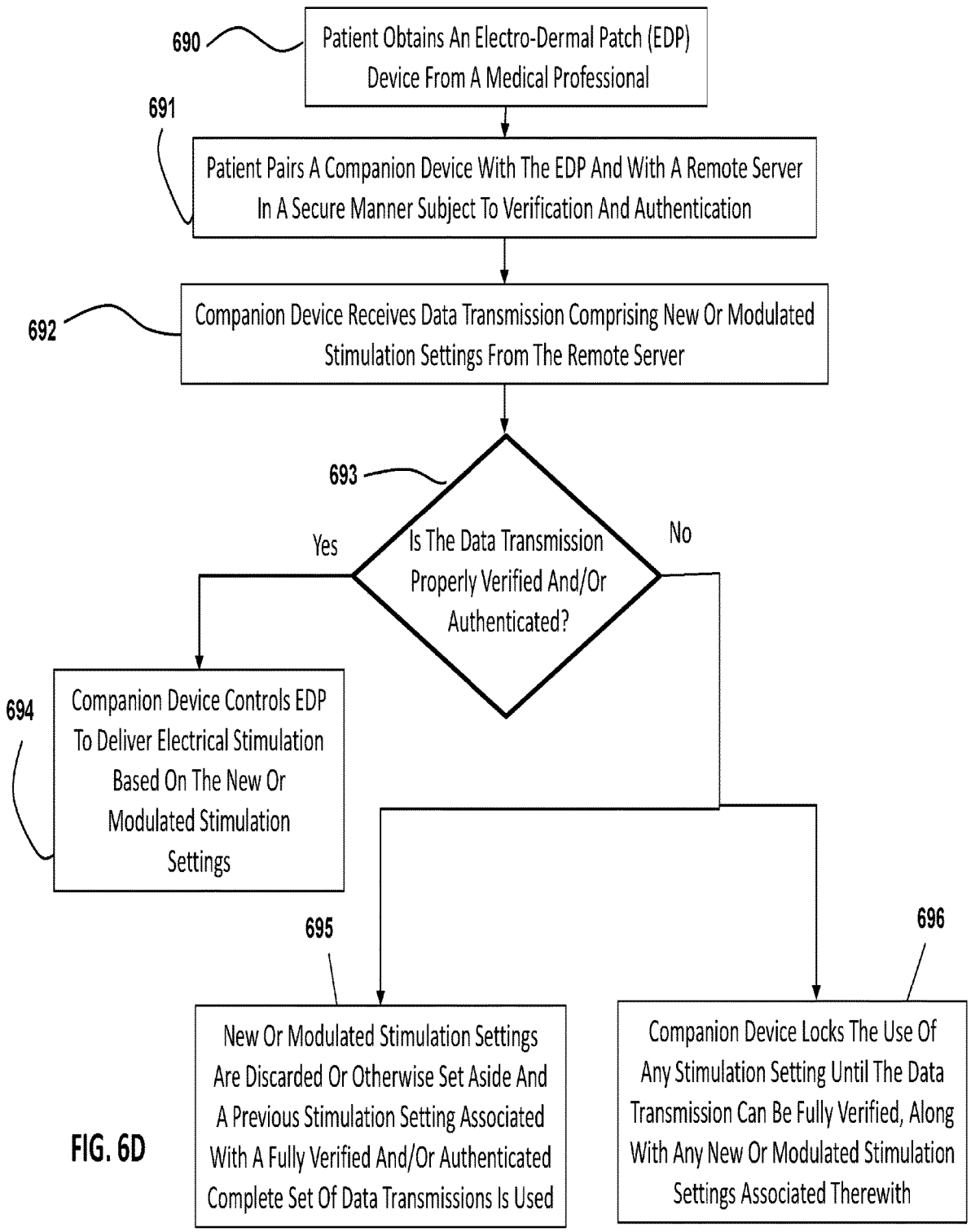
FIG. 6D is a flow chart illustrating the steps involved in a method of a companion device verifying and/or authenticating data transmission received from a remote server, in accordance with some embodiments of the present specification.

FIG. 6D is a flow chart illustrating the steps involved in a method of a companion device verifying and/or authenticating data transmission received from a remote server, in accordance with some embodiments of the present specification. At step 690, a patient obtains an electro-dermal patch (EDP) device from a medical professional. The patient pairs a companion device with the EDP and with a remote server, in a secure manner subject to verification and authentication, at step 691. At step 692, the companion device receives a data transmission comprising new or modulated stimulation settings from the remote server. The companion device then checks if the data transmission is properly verified and/or authenticated at step 693. In one embodiment, if the data transmission is properly verified and/or authenticated, the companion device controls the EDP to deliver electrical stimulation based on the new or modulated stimulation settings at step 694. In one embodiment, if the data transmission is not properly verified and/or authenticated, the new or modulated stimulation settings are discarded or otherwise set aside and a previous stimulation setting associated with a fully verified and/or authenticated complete set of data transmissions is used at step 695. In another embodiment, if the data transmission is not properly verified and/or authenticated, the companion device locks the use of any stimulation setting until the data transmission can be fully verified, along with any new or modulated stimulation settings associated therewith at step 696.

In another embodiment, communications between an EDP, companion device and any remote server(s) may comprise an indication, such as a packet header, identifier, tag, or other representation, of whether the specific EDP involved in the data transmissions is a device that has been sold subject to FDA regulatory approval or whether it is a device that has not been sold subject to FDA regulatory approval. Depending on such an identifier (indicative of government regulatory governance, or some extent thereof), different data processing may occur. For example, if the companion device or remote server(s) determine the EDP in question is subject to FDA approval (based on an identifier being stored in a memory within the EDP), it may cause a different or higher level of encryption, authentication, and/or verification to be applied to the stored data or to data transmissions. In one case, all data transmissions to and from the EDP, between the EDP and companion device, and/or between the companion device and remote server(s) are encrypted, authenticated, and anonymized subject to verification. In another case, only data transmissions containing patient-specific stimulation settings or patient status data are encrypted, authenticated, and/or subject to verification while all other data transmissions are not encrypted.

If, on the other hand, the companion device or remote server(s) determines the EDP in question is not subject to FDA approval (based on an identifier being stored in a memory within the EDP), it may cause a lower level of encryption, authentication, and/or verification to be applied to the stored data or to data transmissions relative to the FDA case. In one embodiment, no data transmissions to and from the EDP, between the EDP and companion device, and/or between the companion device and remote server(s) are encrypted, authenticated, and subject to verification. In another case, only data transmissions containing patient-specific stimulation settings or patient status data are authenticated and/or subject to verification and no data transmissions are encrypted.

Figure 6E:
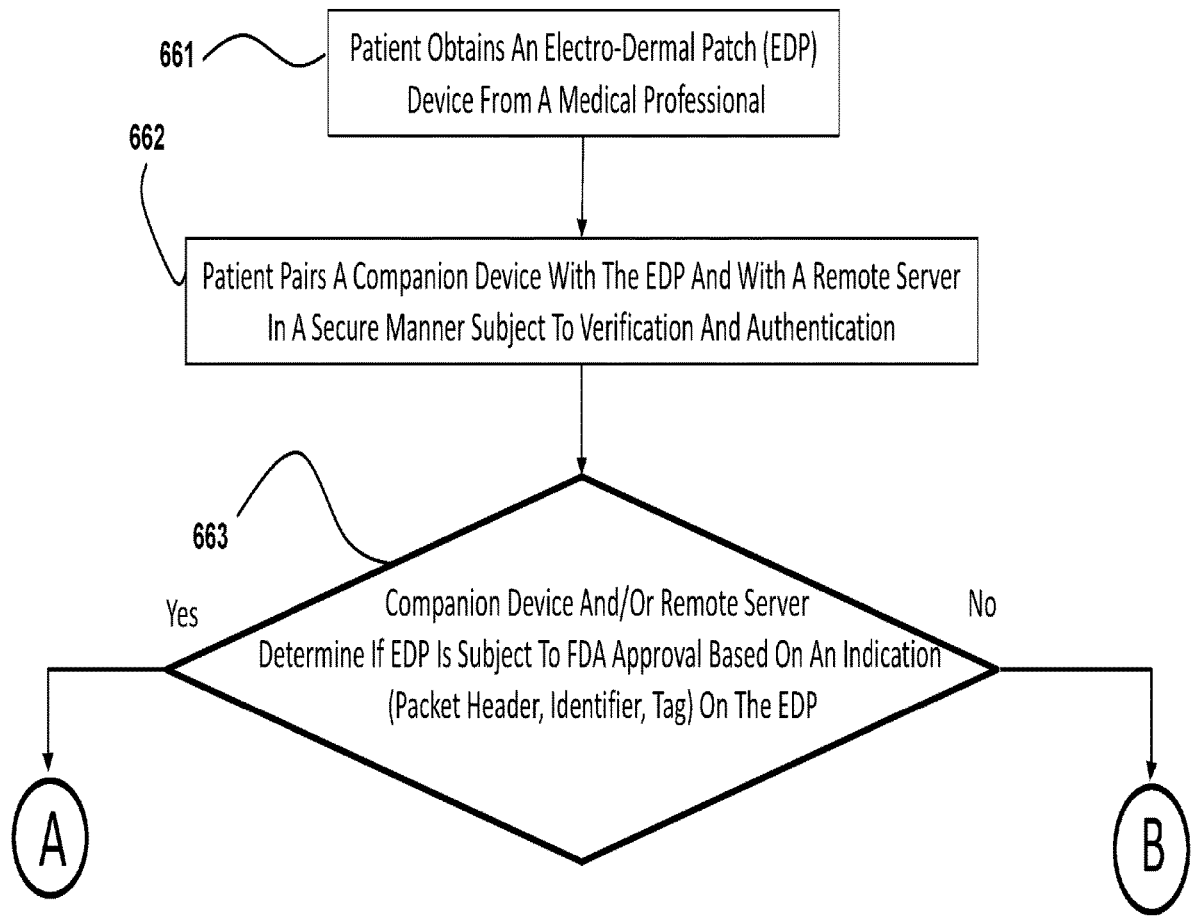
FIG. 6E is a flow chart illustrating the steps involved in a method of encrypting, authenticating, and/or verifying data transmissions between an EDP, companion device, and remote server based on FDA approval status of the EDP, in accordance with some embodiments of the present specification.
Figure 6E:
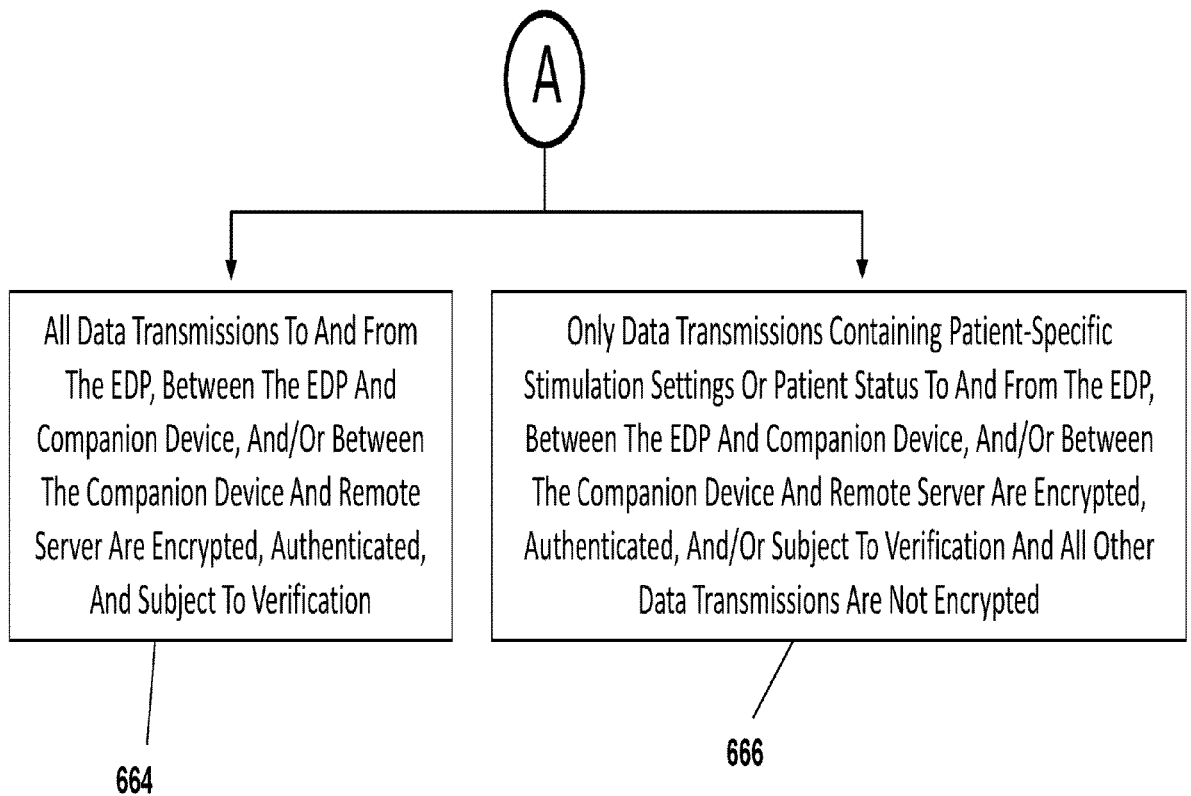
Figure 6E:
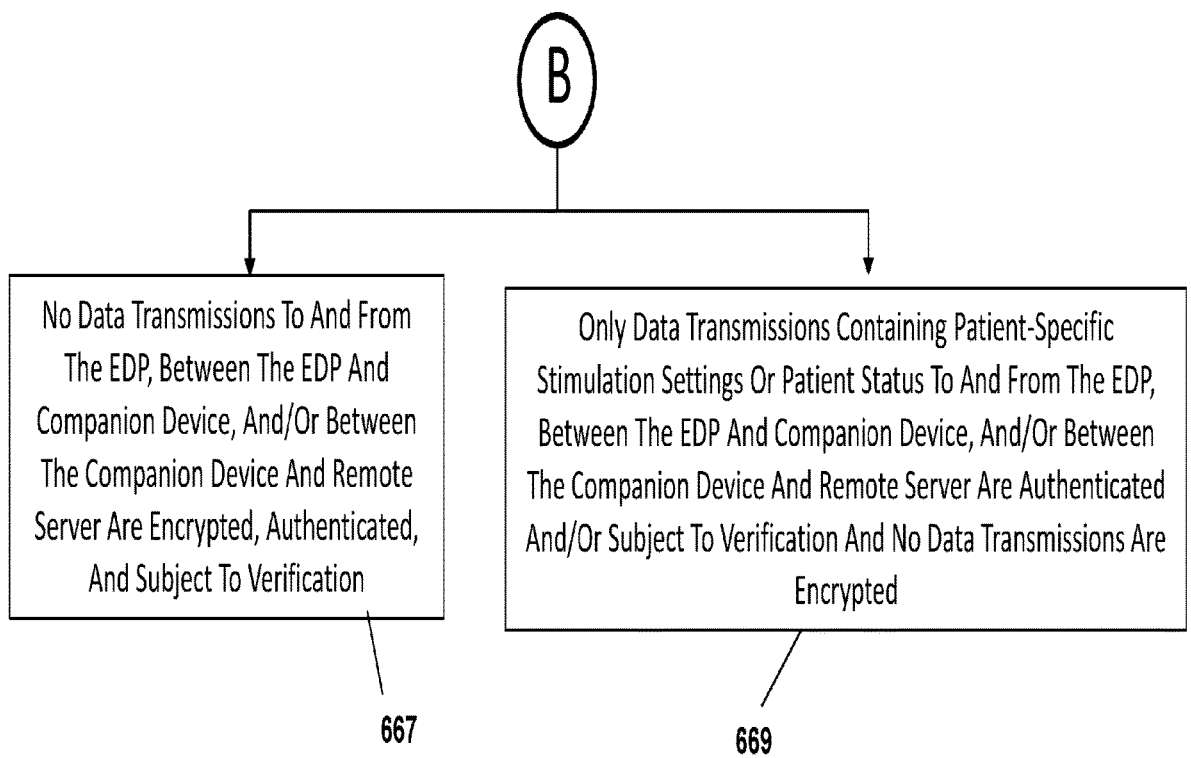

FIG. 6E is a flow chart illustrating the steps involved in a method of encrypting, authenticating, and/or verifying data transmissions between an EDP, companion device, and remote server based on FDA approval status of the EDP, in accordance with some embodiments of the present specification. At step 661, a patient obtains an electro-dermal patch (EDP) device from a medical professional. The patient pairs a companion device with the EDP and with a remote server, in a secure manner subject to verification and authentication, at step 662. At step 663, the companion device and/or remote server determine if the EDP is subject to FDA approval based on an indication (packet header, identifier, tag) on the EDP. In one embodiment, if it is determined that the EDP is subject to FDA approval, then all data transmissions to and from the EDP, between the EDP and companion device, and/or between the companion device and remote server are encrypted, authenticated, and subject to verification at step 664. In another embodiment, at step 666, if it is determined that the EDP is subject to FDA approval, only data transmissions containing patient-specific stimulation settings or patient status to and from the EDP, between the EDP and companion device, and/or between the companion device and remote server are encrypted, authenticated, and/or subject to verification and all other data transmissions are not encrypted. In another embodiment, if it is determined that the EDP is not subject to FDA approval, then no data transmissions to and from the EDP, between the EDP and companion device, and/or between the companion device and remote server are encrypted, authenticated, and subject to verification at step 667. In another embodiment, at step 669, if it is determined that the EDP is not subject to FDA approval, only data transmissions containing patient-specific stimulation settings or patient status to and from the EDP, between the EDP and companion device, and/or between the companion device and remote server are authenticated and/or subject to verification and no data transmissions are encrypted.

In accordance with an aspect of the present specification, patient status data and, if needed, stimulation setting, parameters and protocols are transmitted to insurance companies to support medical treatments, such as endometrial ablation surgeries (for menorrhagia, for example), hysterectomy, or other insurance claims, or for other general insurance data needs. In some embodiments, such data transmission may be subjected to encryption, authentication and verification as described at step 666.

The Health Management Application (hereinafter also referred to as 'HMA') of the present specification comprises a plurality of programmatic instructions and algorithms and implements a plurality of GUIs (Graphical User Interface) to enable a plurality of functions, non-limiting examples of which are described henceforth.

Referring back to FIG. 1A, in various embodiments, the HMA enables confirming linkup to the electro-dermal patch device 110 and displaying battery life of the electro-dermal patch device 110.

The HMA enables generating an audio and/or visual indicator on the hand-held computing device 105 indicating that a) the electro-dermal patch device 110 has been properly placed on the user's body by, for example, confirming sufficient electrode and tissue contact or integrity, b) the one or more electrodes 118 is aged or compromised (ascertained by, for example, impedance measurements) and needs to be replaced. In some embodiments, electrode and tissue contact integrity and electrode integrity, i.e. whether the electrode is functioning properly or damaged, are checked through at least one impedance or bio-impedance sensor of the electro-dermal patch device 110. In other embodiments, an acoustic sensor, capable of sensing specific acoustic signals unique to an area of the human body, is used to determine if the electro-dermal patch device 110 has been properly positioned on the user's body. In various embodiments, sufficient electrode and tissue contact or integrity is defined as achieving electrode impedance in a range of 200 ohms to 1000 ohms. In one embodiment, pulse amplitude is automatically adjusted by virtue of there being a constant current source (from one or more batteries). A constant current source circuit automatically adjusts the pulse to maintain a programmed amplitude in the event of electrode-tissue interface impedance changes. This automatic adjustment may be programmed to occur for voltages ranging from 0.1V to 500V. Accordingly, the pulse amplitude is automatically modulated in order to maintain a constant current source.

The HMA also enables analyzing sensed neural activity prior to the commencement of a stimulation therapy to assess and indicate to the user that the electro-dermal patch device 110 has been placed at an appropriate location, such as at or near the T9 to T12, L1, L2, L5 and/or S1 to S4 dermatomes for dysmenorrhea. In various embodiments, the accuracy or appropriateness of the electro-dermal patch device location is assessed through the neural activity monitor of the electro-dermal patch device 110. In various embodiments, neural activity sensing or monitoring is accomplished by using a sense amplifier circuit to measure neural activity and output a representative signal to the microcontroller or microprocessor of the electro-dermal patch device 110. The microcontroller algorithmically processes the data to determine if there is neural activity. In some embodiments, the sense amplifier circuit measures neural activity signals directly using the same electrodes used for stimulation. In other embodiments, the sense amplifier circuit measures neural activity signals separately using different electrodes than those used for stimulation. In still other embodiments, the sense amplifier circuit measures neural activity signals using both the same electrodes used for stimulation and different electrodes than those used for stimulation. In various embodiments, the sense amplifier circuit incorporates a gain in a range of 1 to 100,000,000 and all values in between, and incorporates a bandpass filter of 0.1 Hz to 10,000 Hz and all combinations in between. These functions are accomplished using conventional analog circuitry known in the art, such as operational amplifier circuits and transistor circuits. In one embodiment, a process used by the microprocessor to process the sensed neural activity comprises counting the number of events within a predetermined time period. In other embodiments, the process is modified to add moving averages in the form of finite impulse response (FIR) or infinite impulse response (IIR) digital filters.

The HMA, in embodiments, enables the user to self-administer therapy, including the ability to stimulate multiple times per day, thereby accelerating treatment effect and efficacy. In embodiments, the HMA prompts users to enable stimulation multiple times per day at the onset of or shortly before the onset of menstruation and throughout the duration of the menstruation, and at the onset of or shortly before the onset of ovulation and throughout the duration of ovulation. The HMA may trigger stimulation prompts to the user while learning user-triggered stimulations and correlating them with occurrences of menstruation and/or ovulation and user-experiences. In various embodiments, the self-administration is on-demand and is actuated via a button on the companion device 105 used to trigger the electro-dermal patch device 110. Triggering the electro-dermal patch device 110 is defined as triggering a protocol or rescue session that may result in stimulation over a predefined period and does not necessarily indicate electrical stimulation begins immediately. The companion device 105 and/or electro-dermal patch device 110 include pre-programmed restrictions which prevent the patient from over-stimulating. In addition, the companion device 105 and/or electro-dermal patch device 110 include triggers which prompt the patient to stimulate based upon time of day, historical trends in experience of menstrual pain.

The HMA also enables analyzing sensed neural activity during a stimulation therapy to assess effectiveness of the stimulation. Depending upon the effectiveness, the Health Management application may automatically recommend and/or implement adjustments or modifications to a plurality of stimulation parameters. In some embodiments, the recommended adjustments to the plurality of stimulation parameters must be accepted or authorized for implementation by at least one of the user (that is, the patient) and/or the remote patient care facility or personnel. In various embodiments, neural activity is sensed using a sense amplifier circuit as described above.

The HMA enables the user to input her current pain experience, or any other physical or physiological parameter linked to pelvic pain and/or dysmenorrhea through a GUI screen and provides real-time or near real-time integration of feedback from patient parameters such as, but not limited to, pain suppression and well-being, recorded in a patient daily diary, from the patient and obtaining real-time or near real-time integration of feedback, such as amount of physical exercises performed, from other wearable devices, for example, a device, with physiological sensors, configured to be worn on the human body, such as around the wrist, in order to monitor, acquire, record, and/or transmit the physiological data, allowing for frequent adjustability and customization of therapy as needed. The integration of feedback from the patient and from other devices allows for modification of therapy, as needed. As is commonly known, women who frequently exercise experience reduced frequency and/or severity of at least primary form of dysmenorrhea. The integration of feedback from the patient and from other devices allows for modification of therapy, as needed, to suppress pain and other symptoms and treat dysmenorrhea.

The HMA enables providing recording, storage and display of all stimulation parameters and other real-time inputs, such as diary and monitoring of menstruation calendar, to provide the physician and patient real-time records and treatment profiles. The information stored includes a combination of inputs from the stimulation device and from other sources of information, for example, from a device, with physiological sensors, configured to be worn on the human body, such as around the wrist, in order to monitor, acquire, record, and/or transmit the physiological data.

The HMA enables presenting GUI screens to enable the user to provide inputs such as, but not limited to, menstrual calendar; frequency, severity, and anatomical location of pain experienced; and the like. In embodiments, the HMA adjusts the algorithm, and therefore stimulation, based on prompts that are made both manually by the patient and automatically by the device itself or the companion device. In some embodiments, the HMA prompts the user to wear the device based on calendrical information or an application that follows menstrual cycles. The HMA may prompt the user with reminders. In some embodiments, the HMA and/or menstrual cycle applications require a number of cycles to 'learn' the behavior of the user's cycle. In some embodiments, the HMA and/or menstrual cycle applications require 0-5 cycles to 'learn' the behavior of the user's cycle.

In some embodiments, the algorithm is also derived from monitored parameters, such as prostaglandins levels, which are typically measured in a clinical setting. Lower levels of prostaglandin might result in lower pelvic and/or menstrual pain. In most cases, the heavier the bleeding, the more likely the pain experienced by the user. Prostaglandins are found in the endometrium, which is the lining of uterus (which thickens and grows under the influence of estrogen). Progesterone causes the endometrial layer to shed. Menstrual bleeding is a combination of removal of the endometrial layer and actual bleeding that causes some blood vessels to open. Thus, more pain is likely with more bleeding, as greater levels of prostaglandin are released.

In addition, menorrhagia is a measurable parameter that is indicative of the amount of blood flow/loss. Menorrhagia may be measured by the number of pads and/or tampons that are used, the saturation of the pad and/or tampon, and the frequency of use during a menstrual cycle. A higher rate of pad/tampon changes generally indicates greater loss of blood and therefore more pain. In embodiments, the user feeds data pertaining the number of pads and/or tampons that are changed, to the system responsible for interfacing with the user and tracking data. In embodiments, other parameters used include the quality of blood during menstruation, the level of pelvic and/or menstrual pain, number of days that the user is bleeding, water retention, diet, change in weight, and salt intake.

In embodiments, well-being parameters include one or more symptoms that indicate that the production of prostaglandin is affected, including but not limited to nausea, headache, diarrhea, and fatigue. These parameters are measured at baseline and over time during treatment and are used as inputs to titrate therapy. Adjustments to the algorithm, and therefore stimulation, are made either manually by the patient or automatically by the electro-dermal patch device itself or the companion device or both. In accordance with some aspects of the present specification, a medical professional can flexibly program the electro-dermal patch and still direct the patient, only allowing the patient to adjust device parameters (for greater patient independence) but within restricted bounds or predetermined parameters.

The HMA further enables providing feedback from the electro-dermal patch device to the patient.

The HMA also enables receiving, processing and analyzing data generated by a uterine contraction sensor, such as an acoustic sensor, included as one of the sensors 135, in some embodiments. Data obtained by the uterine contraction sensor can be used to trigger stimulation.

The HMA enables generating and displaying a plurality of charts or graphs representative of the user's standard menstrual calendar, pain experiences, and other symptoms such as dizziness or nausea over a period of time such as daily, weekly or monthly.

The HMA enables managing and generating prompts (audio, visual and/or tactile) with respect to a plurality of compliance aspects such as, but not limited to: stimulation therapy compliance—prompts the user if the user forgets to wear/attach/apply the electro-dermal patch device and/or disables a recommended duration or frequency of stimulation therapy; prompts the user with respect to a stimulation protocol that a scheduled stimulation is going to begin in the next T minutes, 10 minutes for example, and presenting the user with an option to disable the scheduled stimulation which if not disabled allows the scheduled stimulation to begin after T minutes. The prompts are intended to encourage patient compliance and, in some embodiments, include composite scores and displays for overall patient progress. In embodiments, the prompts are provided to the user according to the user's menstruation and ovulation cycle. In an example, the user is prompted just before the onset of menstruation, at the onset of menstruation, and through the duration of the menstruation. Similarly, the user may be prompted at the onset of ovulation and through the duration of ovulation.

The HMA enables recommending and/or implementing modification to stimulation patterns or protocols when receiving an input from the user that the user is encountering a feeling of discomfort or uncomfortable sensation at the stimulation site during and/or after stimulation.

The HMA further enables assessing stimulation habituation, and incidents of discomfort in the user and accordingly modifying the stimulation patterns or protocols. In various embodiments, these events are input into the electro-dermal patch device or companion device by the patient. For example, in one embodiment, the patient can input, via a GUI on one or both devices, nausea events, dyspepsia events or pain events. The microprocessor then algorithmically processes these events and accordingly modifies stimulation.

The HMA enables the remote patient care facility and/or patient care personnel to access (via cellular and/or private or public wired or wireless networks such as the Internet) a plurality of user's health related information and stimulation induced nausea, dyspepsia, and habituation events. In some embodiments, the Health Management application periodically transmits the user's health related information apart from enabling the remote patient care facility and/or patient care personnel to access such information in real time or on demand, if required. In various embodiments, the user's authorization is needed to allow such access to the user's health related information.

The HMA also enables detecting removal of the electro-dermal patch device—the impedance or bio-impedance electrode enables the Health Management application to regularly or continuously monitor electrode and skin contact impedance. This allows the Health Management application to detect whether the electro-dermal patch device has been removed or worn by the user. In embodiments, the EDP device is intended to be used for a few days a month, as-needed and/or on-demand. The HMA learns the user's behavior related to use of the EDP device, based on user-input. In embodiments, the learned behavior indicates the user's health related information. In embodiments, where the electro-dermal patch device is configured for use on as-needed or on-demand basis, any missing user health related information is treated as non-occurrence of any stimulation event.

The HMA also enables providing unique electrical stimulation characteristics and 'footprints', based on electrode design and stimulation parameters, allowing the patient to use a variety of methodologies for stimulation.

In still a further non-limiting example, the HMA enables doctors or medical personnel to tell new patients about their medical practice.

In still further non-limiting examples, the HMA enables patients to view their medical personnel and request an appointment with the office; enables setting of daily reminders for prescribed vitamins and supplements; enables patients to pose queries to their doctors or medical personnel; enables communicating schedules of pelvic and/or menstrual pain management, dysmenorrhea, and hygiene seminars and support groups, to the patients; enables medical personnel to communicate healthy recipes with the patients to support their continued pelvic and/or menstrual pain management and dysmenorrhea; enables medical personnel as well as patients to journalize daily thoughts and progress notes; enables information exchange with third party applications; enables patients to track their water intake along with food consumed; enables automatic tracking of calories, protein, fat and carbohydrates consumed by patients; enables scanning of barcodes of package food to allow patients to see the nutritional information, and have it logged automatically to the feed consumed daily diary; enables physicians or medical personnel to enter specific goals for their patients; enables physicians to share their patient status data, with approval from their patients, with the fellow practice/department physicians to solicit better recommendations for the patients; enables instilling exercising habits in the patients since women who frequently exercise experience reduced frequency and/or severity of at least primary form of dysmenorrhea; enables physicians and other medical personnel to send out push notifications to their patients to keep the patients engaged and motivated towards their pelvic pain management, dysmenorrhea, and health goals. In still further non-limiting examples, the HMA enables patients to track whether they are taking specific medications that affect pelvic pain and/or dysmenorrhea, such as hormones; and also track consumption of birth control pills.

It should be appreciated that in various embodiments, the user's plurality of health related information is utilized by the Health Management application to suggest and/or implement a plurality of recommendations comprising stimulation patterns or protocols, medication (such as an amount of insulin intake, for example), dietary and/or activities plans.

In some embodiments, the plurality of recommendations is auto generated by the Health Management application and presented to the user for user's authorization for implementation. In some embodiments, the plurality of recommendations auto generated by the Health Management application are presented to the remote patient care facility and/or personnel for authorization or approval and thereafter either implemented or presented again to the user for a final authorization for implementation. In some embodiments, the Health Management application receives a plurality of recommendations prescribed by the remote patient care facility and/or personnel based on the user's plurality of health related information.

In various embodiments, the user is presented, on one or more GUIs, a plurality of recommendations, which are auto generated by the Health Management application as well as those received as prescriptions or recommendations from the remote patient care facility or personnel, the reasons for each of the plurality of recommendations, authorizations/approvals or disapprovals against each of the plurality of recommendations as received from the remote patient care facility or personnel, and annotations or notes from the remote patient care facility or personnel describing reasons for approving or disapproving each of the plurality of recommendations that were generated by the Health Management application. The user then reviews and authorizes/approves or disapproves implementation of each of the plurality of recommendations. In some embodiments, however, authorizations to implement the plurality of recommendations may not be required from the user and/or the remote patient care facility or personnel. For example, in one embodiment wherein the electro-dermal patch device is worn 24 hours per day, the number of stimulation sessions per a specified time period is automatically titrated up or down based on the recommendations. In another embodiment, the duration of stimulation is automatically titrated up or down based on the recommendations. In other embodiments, other stimulation parameters are changed automatically based on the recommendations.

Figure 7:
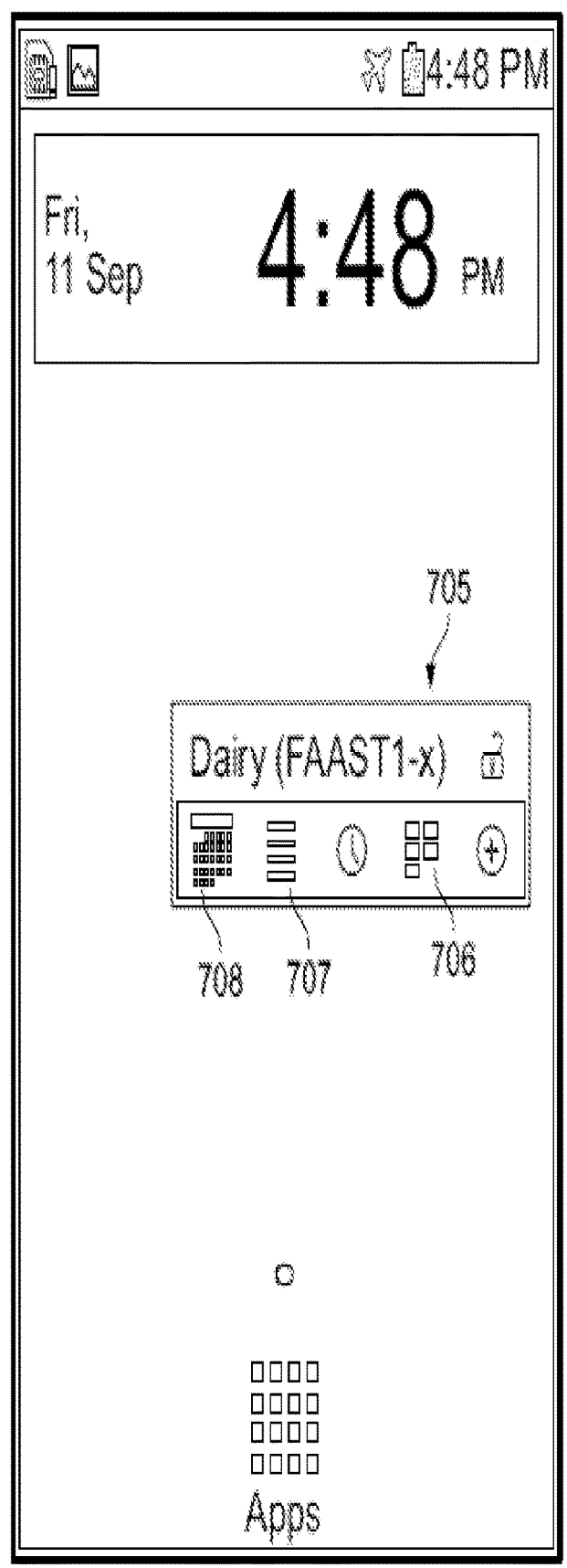
FIG. 7 is a screen shot of a companion device depicting a diary widget, in accordance with one embodiment of the present specification.

In various embodiments, the companion device includes a 'diary' for the patient to input, track, record, and display patient parameters. FIG. 7 is a screen shot of a companion device depicting a diary widget 705, in accordance with one embodiment of the present specification. The diary widget 705 includes icons enabling the patient to input and view entries in the diary. The diary widget 705 includes a quick entry buttons icon 706 which, when pressed, causes the companion device to display buttons for making diary entries. The diary widget 705 also includes a list view of diary entries icon 707 which, when pressed, causes the companion device to display the diary in a list format. The diary widget 705 also includes a calendar view of diary entries icon 708 which, when pressed, causes the companion device to display the diary in a calendar format.

Figure 8:
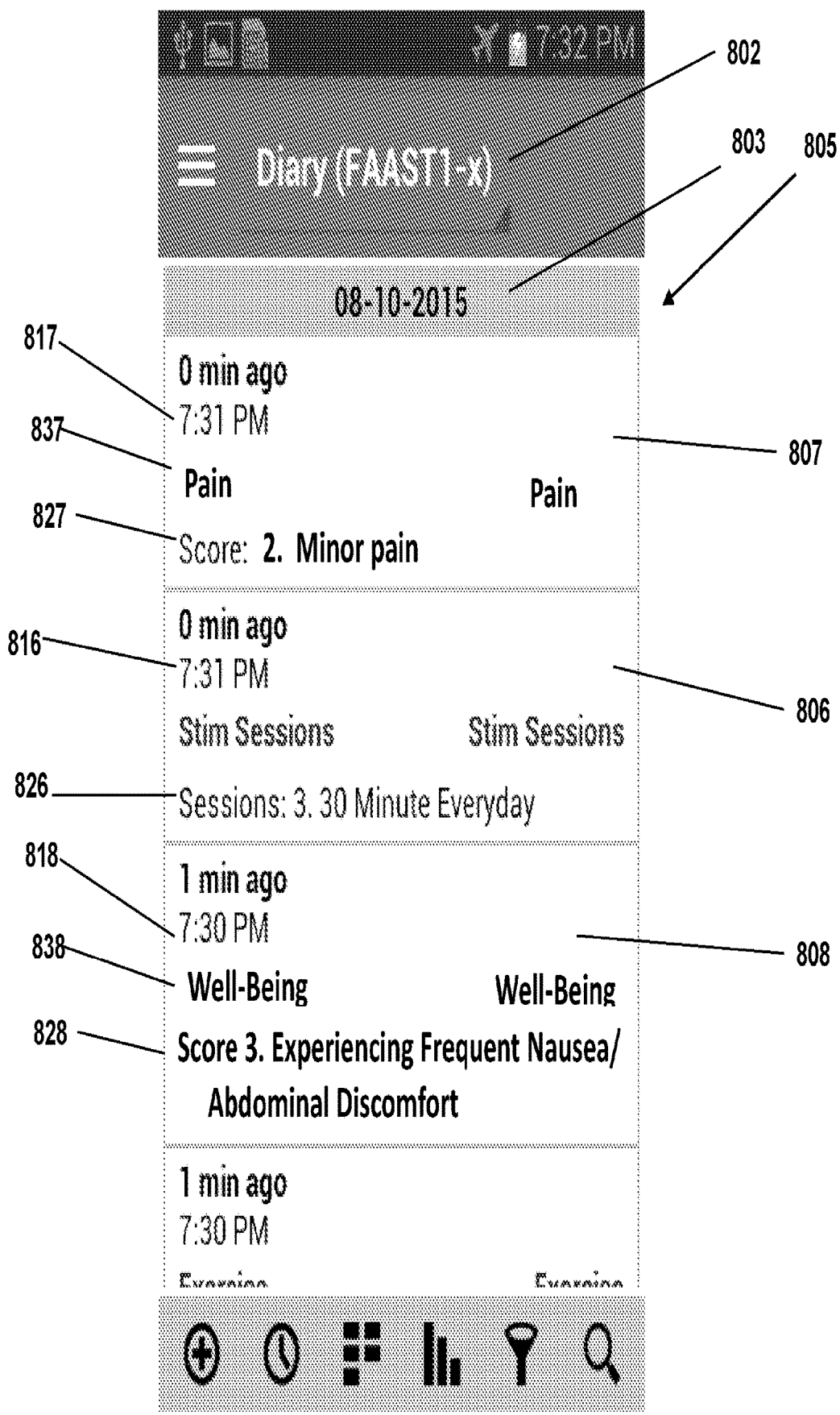
FIG. 8 is a screen shot of a companion device depicting a list view of diary entries, in accordance with one embodiment of the present specification.

FIG. 8 is a screen shot of a companion device depicting a list view of diary entries 805, in accordance with one embodiment of the present specification. The list view of diary entries 805 is accessed by pressing the list view of diary entries icon 807 as shown on FIG. 8. In various embodiments, the list view of diary entries 805 displays entries input by the patient for instances such as stimulation sessions 806 and patient parameters, for example, pain 807 and well-being 808. The stimulation session entry 806 displays the time 816 of the entry and details 826 of the stimulation session. Each patient parameter entry 807, 808 displays the time 817, 818 of the entry, the type of parameter 837, 838, and a score with description 827, 828 associated with the entry. The list view of diary entries 805 also displays the date 803 and the name of the diary 802 being viewed.

Figure 9:
FIG. 9 is a screen shot of a companion device depicting a calendar view of diary entries, in accordance with one embodiment of the present specification.

FIG. 9 is a screen shot of a companion device depicting a calendar view of diary entries 905, in accordance with one embodiment of the present specification. The calendar view of diary entries 905 is accessed by pressing the calendar view of diary entries icon 708 as shown on FIG. 7. The calendar view of diary entries 905 displays the days 906 of the month being viewed. Pressing on an individual day displays the diary entries for that day as a list 907. The patient can scroll through the list 907 to view entries. The calendar view of diary entries 905 also displays the month and year 903 and the name of the diary 902 being viewed.

Figure 10:
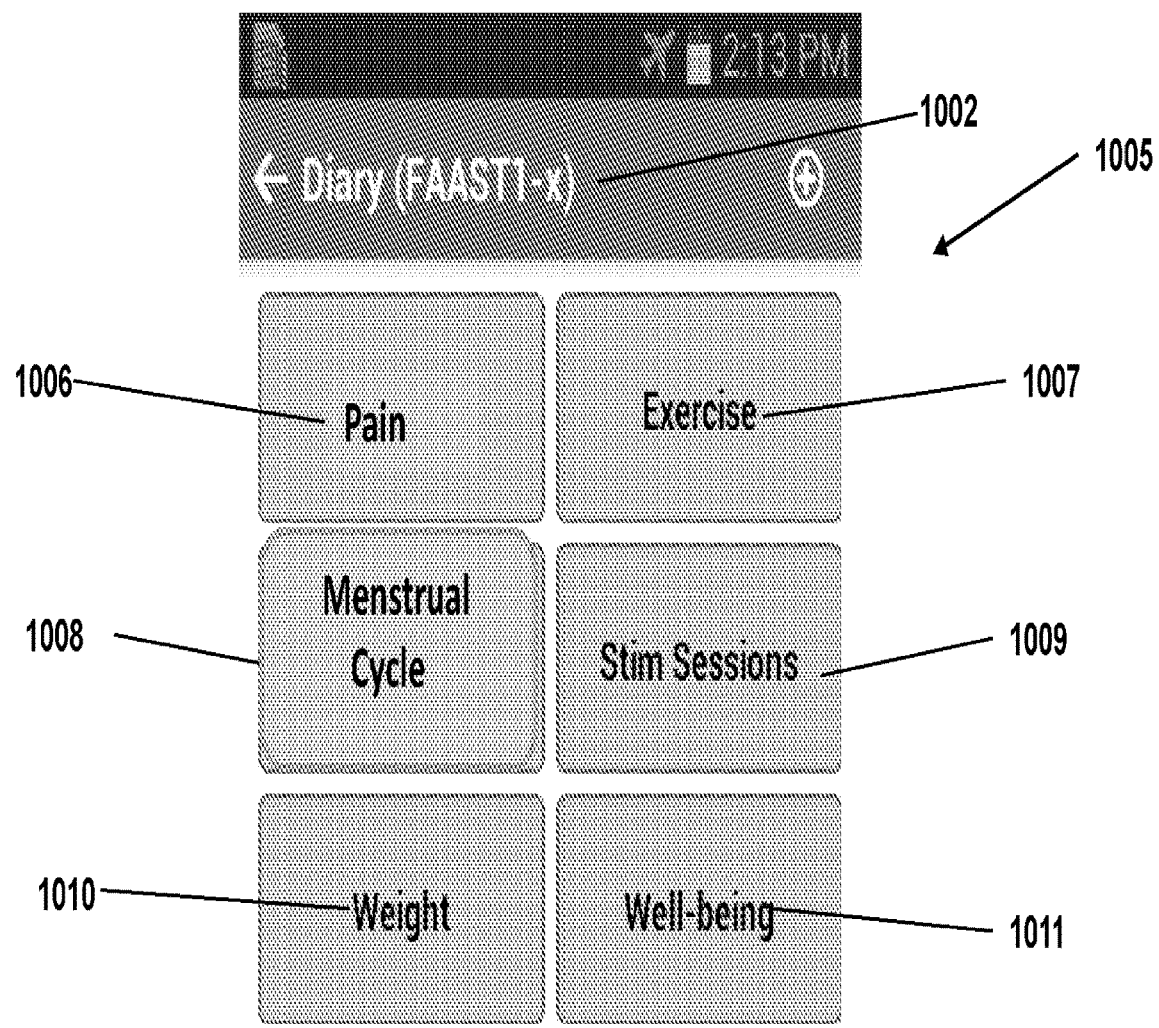
FIG. 10 is a screen shot of a companion device depicting a quick entry buttons view, in accordance with one embodiment of the present specification.

FIG. 10 is a screen shot of a companion device depicting a quick entry buttons view 1005, in accordance with one embodiment of the present specification. The quick entry buttons view 1005 is accessed by pressing the quick entry buttons icon 706 as shown on FIG. 7. In one embodiment, the quick entry buttons view 1005 includes six quick entry buttons: pain 1006, exercise 1007, menstrual cycle 1008, stim (that is, stimulation) sessions 1009, weight 1010, and well-being 1011. The quick entry buttons depicted in FIG. 10 are exemplary only and not intended to be limiting. In an embodiments, a quick entry button view is provided for hormonal intake or intake of birth control pills. In other embodiments, fewer or additional quick entry buttons are included on the quick entry buttons view. Pressing on any one of the quick entry buttons 1006, 1007, 1008, 1009, 1010, 1011 causes the companion device to display an entry screen for the chosen button. The quick entry button view 1005 also displays the name of the diary 1002 being viewed.

Figure 11:
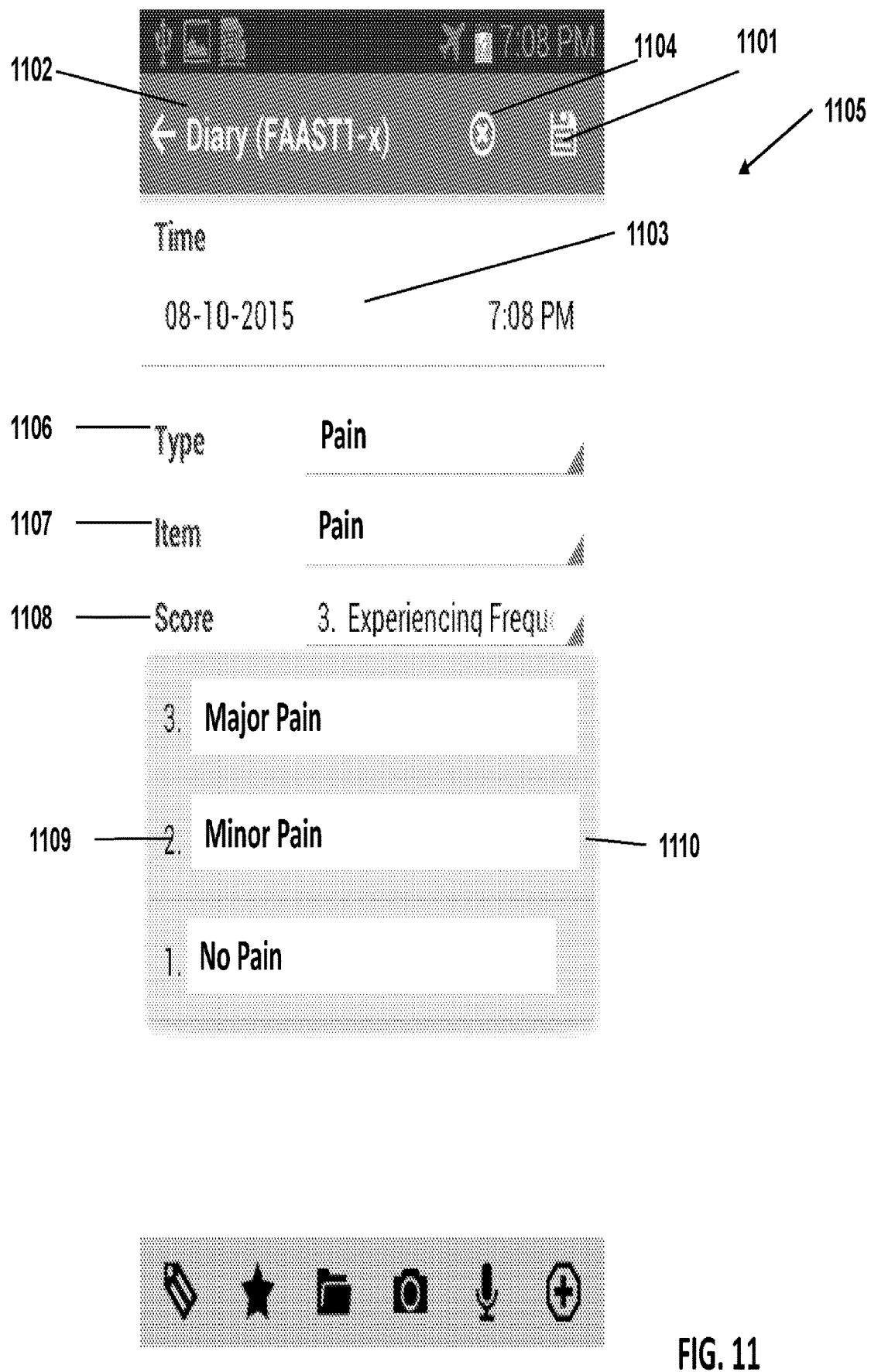
FIG. 11 is a screen shot of a companion device depicting a pain entry screen, in accordance with one embodiment of the present specification.

FIG. 11 is a screen shot of a companion device depicting a pain entry screen 1105, in accordance with one embodiment of the present specification. The pain entry screen 1105 allows the user to enter the type 1106 and item 1107 of patient parameter, in this case pain, and a score 1108 associated with the parameter. The score 1108 has a numerical value 1109 and a description 1110 associated therewith to help the patient determine which score best fits the current parameter. In some embodiments, for pain, the description relates to a level of pain associated with menstruation, which the patient is experiencing. In some embodiments, the score ranges from 1 to 3. The pain entry screen 1105 also displays the time and date 1103 the entry is being entered and the name of the diary 1102. The patient can save the entry by pressing the disk icon 1101 or cancel the entry by pressing the X icon 1104.

Figure 12:
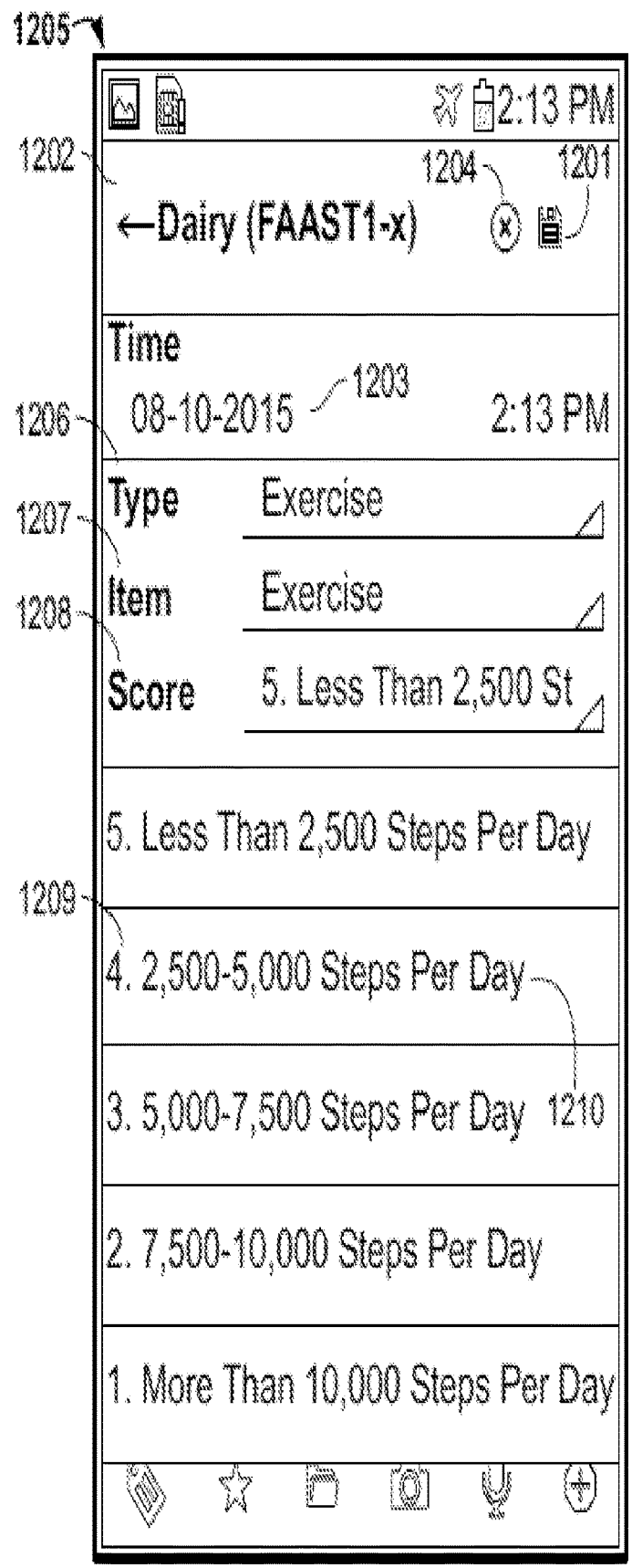
FIG. 12 is a screen shot of a companion device depicting an exercise entry screen, in accordance with one embodiment of the present specification.

FIG. 12 is a screen shot of a companion device depicting an exercise entry screen 1205, in accordance with one embodiment of the present specification. The exercise entry screen 1205 allows the user to enter the type 1206 and item 1207 of patient parameter, in this case exercise, and a score 1208 associated with the parameter. The score 1208 has a numerical value 1209 and a description 1210 associated therewith to help the patient determine which score best fits the current parameter. In some embodiments, for exercise, the description relates to how many steps the patient took per day. In some embodiments, the score ranges from 1 to 5. The exercise entry screen 1205 also displays the time and date 1203 the entry is being entered and the name of the diary 1202. The patient can save the entry by pressing the disk icon 1201 or cancel the entry by pressing the X icon 1204.

Figure 13:
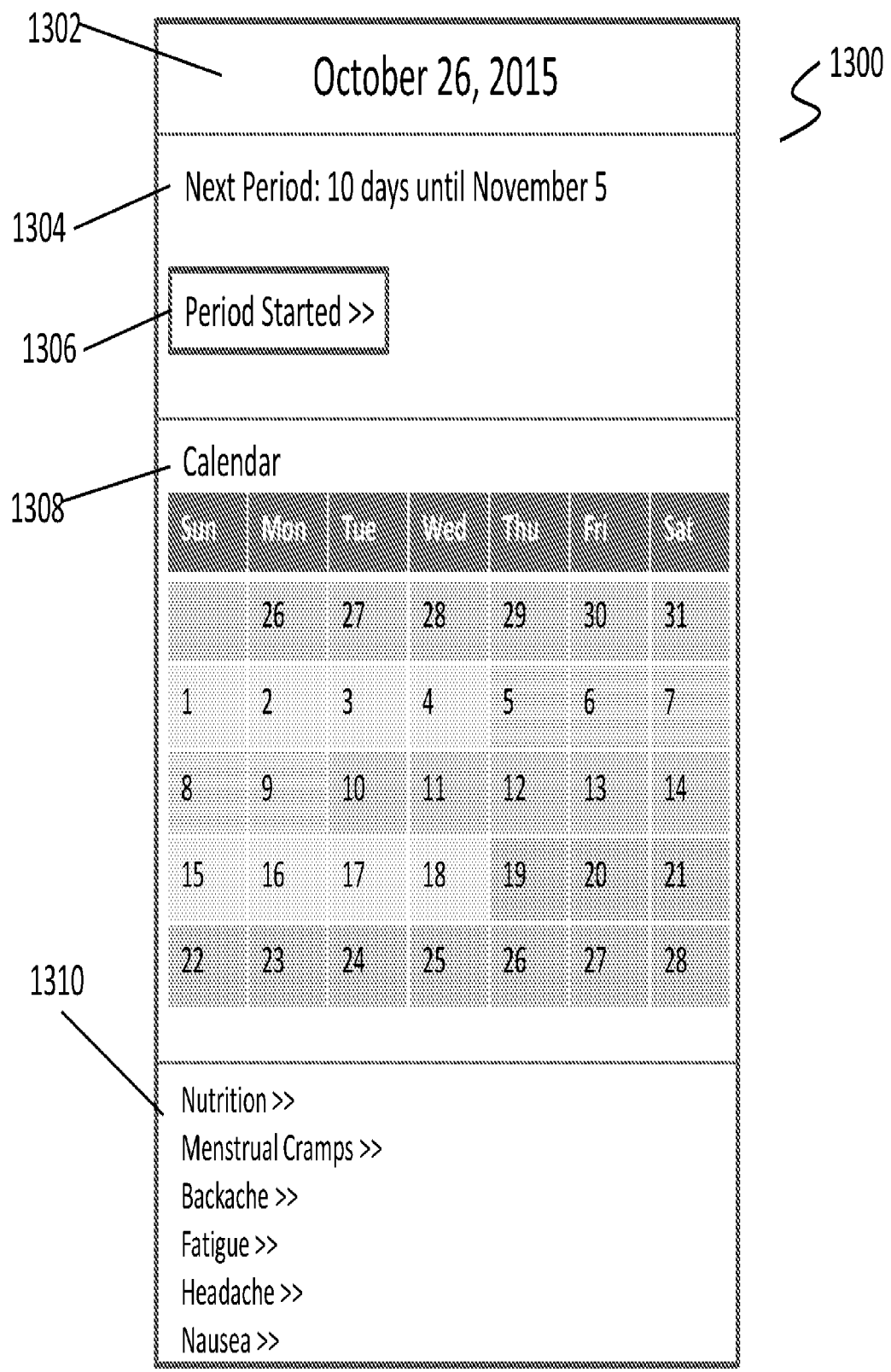
FIG. 13 is a screen shot of a companion device depicting a menstrual cycle entry screen, in accordance with one embodiment of the present specification.

FIG. 13 is a screen shot of a companion device depicting a menstrual cycle entry screen, in accordance with one embodiment of the present specification. The menstrual cycle entry screen is a screen of a companion device depicting an exemplary user-interface 1300, in accordance with an embodiment of the present specification. Interface 1300 may include a current date 1302, a date 1304 of next menstruation cycle, a button 1306 that may be selected by a user in case menstruation cycle starts, a calendar 1308 illustrating the dates for at least the next four weeks and highlighting the dates of expected menstruation cycle, fertility window, or any other date that may have been noted by the user to be of significance. Interface 1300 may also include a list view 1310 including a list of buttons that may be selected to access different topics related to the user's personal interests. The user may be able to add/edit information in the form of data, notes, and the like, through options available through view 1310. In embodiments, default information may be presented to the user. In embodiments, user may be provided access to information that is automatically determined through parameters monitored by an EDP device and/or a combination of the EDP device and the application running on the companion device.

For example, view 1310 may allow access to information pertaining user's nutrition, including calories intake, calories burnt, diet chart, and the like. This view may also provide advanced data that correlates nutrition intake to frequency and severity of menstrual pain or pain resulting from dysmenorrhea. The user may be able to view monitored data and/or data added by the user herself, pertaining frequency and severity of menstrual cramps. Additional physiological parameters including and not limited to energy levels, backache, fatigue, headache, and nausea, may also be monitored by the wearable device(s) and/or recorded by the user. In embodiments, emotional experiences can be recorded by the user. In embodiments, time and date of each entry made by the user is also noted.

Interface 1300 may also present a record of electrical stimulations provided to the user through the EDP device. The information may be used to observe patters of stimulations, and to customize the patterns either automatically or through user intervention. In some embodiments, for stimulation session, the description relates to how often stimulation was delivered per day and for how long the stimulation was applied during each session.

In embodiments, interface 1300 may include different combinations of graphical layout and information buttons that provide access to the user about menstruation-related parameters. In embodiments, the user may be provided with an option to interact on a social-networking platform where different users of the software application share their notes and experiences. In embodiments, interface 1300 may also provide to the user an ability to track intake of birth control pills and correlate this information with dysmenorrhea and related symptoms. Interface 1300 may also be able to suggest to the user ways to increase probability of conception.

While software application (app) described herein is an exemplary application that may be linked with the EDP device worn by the user, through a wireless link; other software applications that are known and commercially available may also be integrated over a communication link with the EDP device. Examples of such apps may include My Days, Lily Period Tracker, Period Calendar, Clue, Moov™, Period Tracker, My Cycles, MonthPal, Pink Pad, Lychee, and the like.

Figure 14:
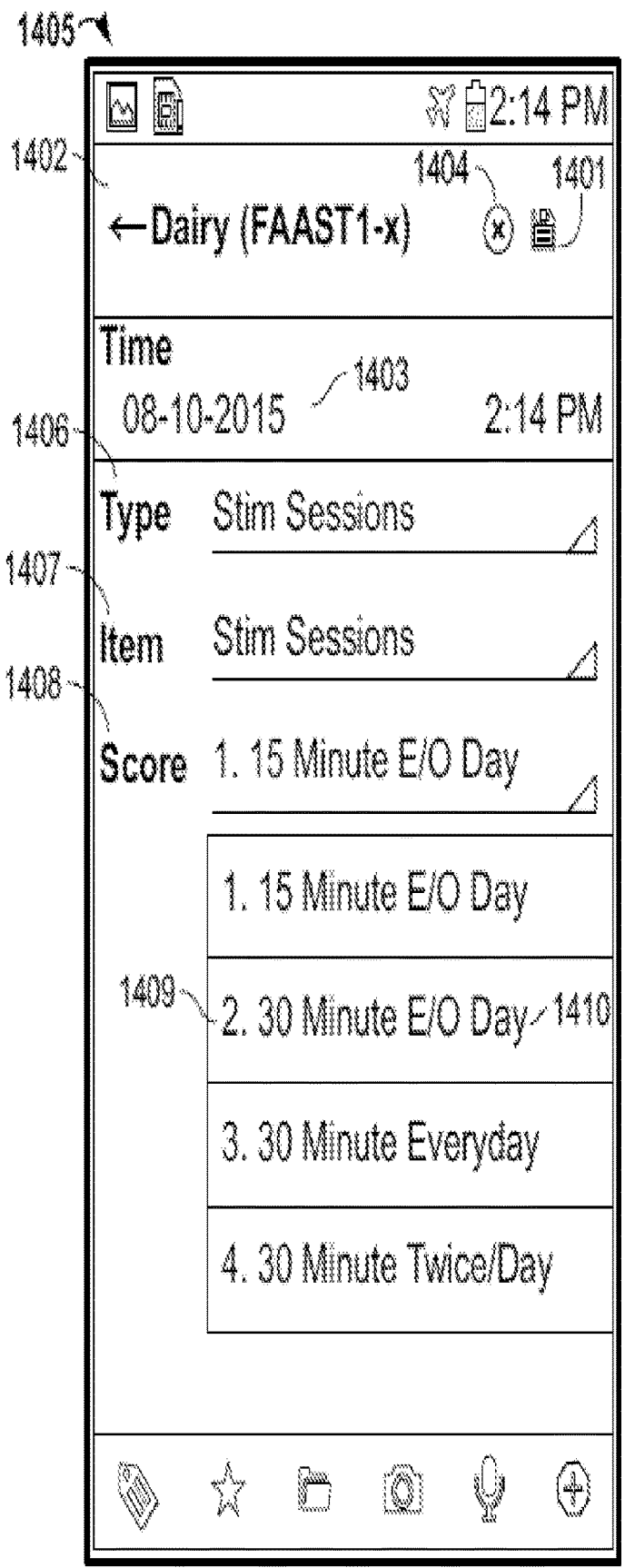
FIG. 14 is a screen shot of a companion device depicting a stimulation session entry screen, in accordance with one embodiment of the present specification.

FIG. 14 is a screen shot of a companion device depicting a stimulation session entry screen 1405, in accordance with one embodiment of the present specification. The stimulation session entry screen 1405 allows the user to enter the type 1406 and item 1407 of session, in this case a stimulation session, and a level 1408 associated with the session. The level 1408 has a numerical value 1409 and a description 1410 associated therewith to help the patient determine which level best represents what was applied during the current session. In some embodiments, for stimulation session, the description relates to how often stimulation was delivered per day and for how long the stimulation was applied during each session. In some embodiments, the level ranges from 1 to 4. The stimulation session entry screen 1405 also displays the time and date 1403 the entry is being entered and the name of the diary 1402. The patient can save the entry by pressing the disk icon 1401 or cancel the entry by pressing the X icon 1404.

Figure 15:
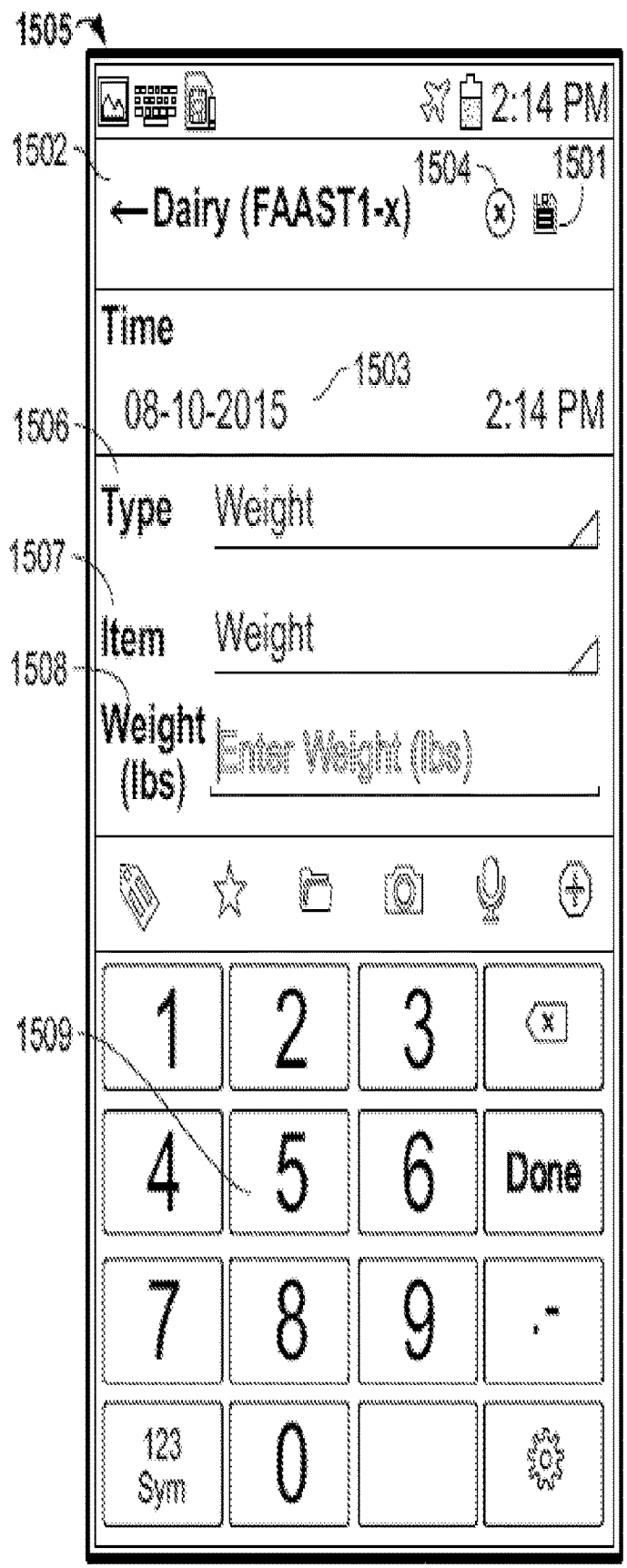
FIG. 15 is a screen shot of a companion device depicting a weight entry screen, in accordance with one embodiment of the present specification.

FIG. 15 is a screen shot of a companion device depicting a weight entry screen 1505, in accordance with one embodiment of the present specification. The weight entry screen 1505 allows the user to enter the type 1506 and item 1507 of patient parameter, in this case weight, and a weight in pounds 1508 associated with the parameter. In embodiments, the weight is tracked and monitored so that the system can differentiate between water weight, which may be different from the actual weight due to water retention, and actual weight. The weight entry screen 1505 includes a numeric keypad 1509 for the patient to use to enter the weight. The weight entry screen 1505 also displays the time and date 1503 the entry is being entered and the name of the diary 1502. The patient can save the entry by pressing the disk icon 1501 or cancel the entry by pressing the X icon 1504.

Figure 16:
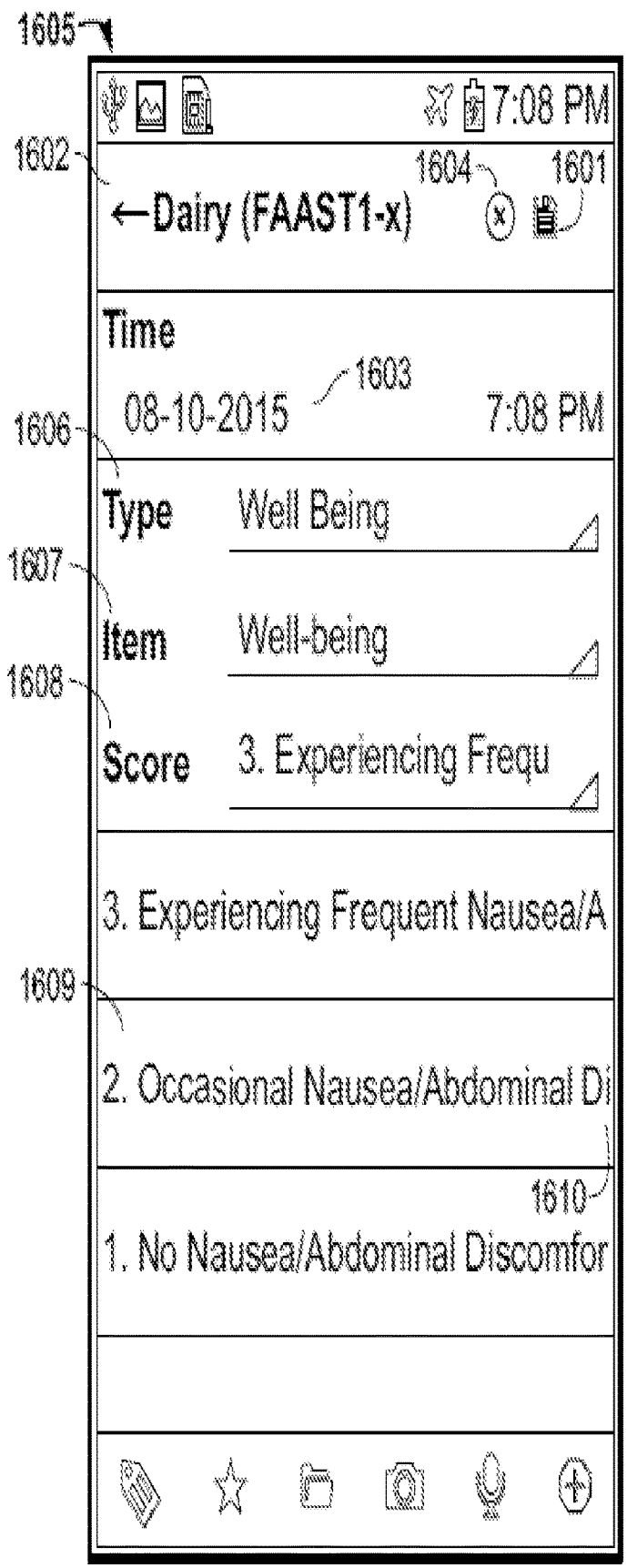
FIG. 16 is a screen shot of a companion device depicting a well-being entry screen, in accordance with one embodiment of the present specification.

FIG. 16 is a screen shot of a companion device depicting a well-being entry screen 1605, in accordance with one embodiment of the present specification. The well-being entry screen 1605 allows the user to enter the type 1606 and item 1607 of patient parameter, in this well-being, and a score 1608 associated with the parameter. The score 1608 has a numerical value 1609 and a description 1610 associated therewith to help the patient determine which score best fits the current parameter. In some embodiments, for well-being, the description relates to a level of nausea, dyspepsia and/or abdominal discomfort the patient is experiencing. In some embodiments, the score ranges from 1 to 3. The well-being entry screen 1605 also displays the time and date 1603 the entry is being entered and the name of the diary 1602. The patient can save the entry by pressing the disk icon 1601 or cancel the entry by pressing the X icon 1604. Referring to FIG. 16, in some embodiments, the nausea associated with well-being refers to nausea as a result of over-stimulation provided by the EDP, and is distinct and different from the nausea a patient might experience associated with her menstrual cycle, as described with reference to FIG. 13.

It should be appreciated that the HMA incorporates GUIs that present scales, surveys, or questionnaires designed to quantitatively assess one or more of a person's feeling of menstrual pain or dysmenorrhea symptoms, level of well-being, level of nausea, level of dyspepsia, and changes thereto.

In general, each such scale is a form of a visual analog scale (VAS). A VAS is question-based assessment mechanism, where a visual measure is associated with each question and where answering the question requires selecting a quantifiable position within that visual measure, indicative of a particular level or degree. The scale is typically composed of lines (of varying length) with words anchored at each end, describing the extremes (that is, 'I am not experiencing pain at all' on the left to 'I am experiencing severe pain' on the right). Patients are asked to make a mark across the line corresponding to their feelings. Quantification of the measurement is done by measuring the distance from the left end of the line to the mark. In some embodiments, VAS may be used to assess sensations of pain, overall quality of life and degree of well-being. In embodiments, the pain assessments may be for reasons related to pelvic pain, dysmenorrhea, migraine, or any other.

Figure 24:
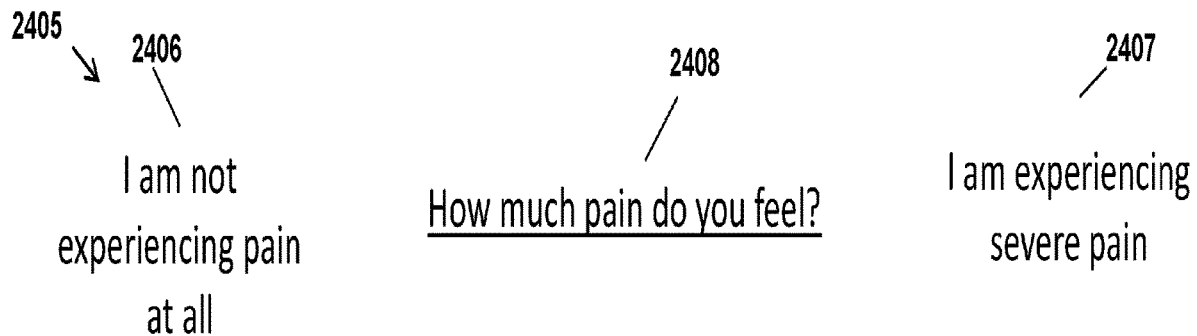
FIG. 24 is a Visual Analogue Scale (VAS) questionnaire for assessing a feeling of menstrual pain, in accordance with an embodiment.

FIG. 24 illustrates a VAS questionnaire 2405 for assessing pain sensations associated with dysmenorrhea. The questionnaire 2405 presents a patient with a leading question, such as, "how much pain do you feel?" while the two extremities 2406, 2407 of the scale line 2408 are anchored with words that describe the feeling of least and maximum pain. In one embodiment the two extremities 2406, 2407 are described as "I am not experiencing pain at all" and "I am experiencing severe pain", respectively.

Figure 25:
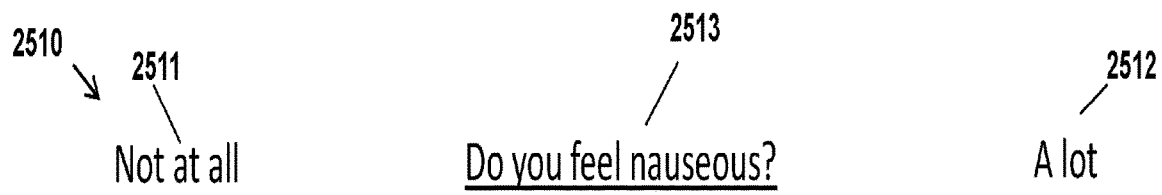
FIG. 25 is a VAS questionnaire for assessing a feeling of nausea, in accordance with an embodiment.

FIG. 25 illustrates a VAS questionnaire 2510 for assessing a degree of nausea. The questionnaire 2510 presents the patient with a leading question, such as, "Do you feel nauseous?" while the two extremities 2511, 2512 of the scale line 2513 are anchored with words that describe the feeling of least and maximum fullness. In one embodiment the two extremities 2511, 2512 are described as "Not at all" and "A lot", respectively.

Figure 26:
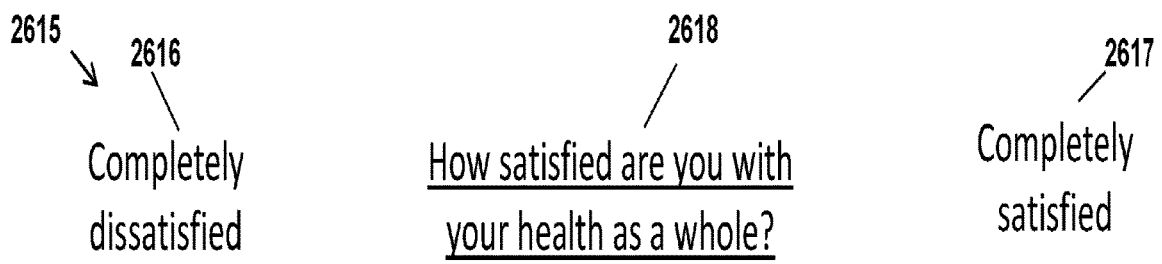
FIG. 26 is a VAS questionnaire for assessing a degree of well-being, in accordance with an embodiment.

FIG. 26 illustrates a VAS questionnaire 2615 for assessing a degree of well-being. The questionnaire 2615 presents the patient with a leading question, such as, "How satisfied are you with your health as a whole?" while the two extremities 2616, 2617 of the scale line 2618 are anchored with words that describe the feeling of least and maximum well-being. In one embodiment the two extremities 2616, 2617 are described as "Completely dissatisfied" and "Completely satisfied", respectively.

Persons of ordinary skill in the art should appreciate that the leading question and anchoring words at the two extremities of the scale, for each questionnaire of FIGS. 24 through 26, may be linguistically modified in alternate embodiments without departing from the assessment objective or the feeling to be assessed. For example, in an alternate embodiment the questionnaire may present the leading question as "How strong is your pain now?" while the two extremities are described as "Extremely" and "Not at all". Additionally, other intermediate language may be used between the two extremes.

A Numerical Rating Scale (NRS) is another example of a scale that can be used to assess the feeling of menstrual pain. A NRS is 11, 21 or 101 point scale where the end points are the extremes of "no pain" and "pain as bad as it could be", or "worst pain". The NRS can be graphically or verbally delivered. When presented graphically the numbers are often enclosed in boxes and the scale is referred to as an 11 or 21 point box scale depending on the number of levels of discrimination offered to the patient. Thus, NRS is a segmented numeric version of the visual analog scale (VAS) in which a patient selects a whole number (such as, 0-10 integers) that best reflects the intensity of their pain. Following is an exemplary 0-10 NRS rating scale:

| Rating | Pain Level |
|---|---|
| 0 | No Pain |
| 1-3 | Mild Pain (nagging, annoying, interfering little with ADLs (Activities of Daily Life)) |
| 4-6 | Moderate Pain (interferes significantly with ADLs) |
| 7-10 | Severe Pain (disabling; unable to perform ADLs) |

Another example of a scale, for assessing menstrual pain, is a Verbal Rating Scale (VRS). A VRS consists of a list of adjectives describing different levels of pain intensity: no pain, mild pain, moderate pain, severe pain, extreme pain, and worst pain. The scores 0, 2, 4, 6, 8, and 10 are assigned to each of the verbal descriptors, with "none" scored as 0 to "worst pain" scored 10, with higher numbers associated with more intense adjectives. Patients are asked to pick the word that best describes their pain intensity, and their VRS intensity score is the number associated with the word they choose.

Faces Pain Scale-Revised (FPS-R) is another scale for assessing menstrual pain. The FPS consists of seven line-drawn faces presented in a horizontal format, representing no pain to worst pain. In 2001, the FPS was revised by Hicks et al. to make it more suitable for use with widely used metric scoring 0-10 scale, using visual depictions of faces to represent increasing levels of pain intensity along a six-face continuum. Patients are instructed to point to the face that best represents the intensity of their pain; the scores 0, 2, 4, 6, 8, and 10 are assigned to each face consecutively, with higher numbers representing more painful faces.

Another example scale, for assessing menstrual pain, is the McGrill Pain Questionnaire that consists of 20 groups of words (subclasses) that can be used to describe pain and a pain rating index. The patient chooses words to describe the pain she is experiencing. The 20 subclasses of words are broken down into four major groups to describe the sensory qualities of the pain (e.g., throbbing, sharp, stabbing), the effects of the pain (e.g., sickening, blinding, grueling), the overall experience of the pain (e.g., annoying, intense, unbearable), and miscellaneous characteristics of the pain (e.g., radiating, piercing, nagging). Each word chosen is assigned a rank value and these values are used to determine the pain rating index (PRI). The PRI ranges from 0 (no pain) to 5 (excruciating pain).

The Menstrual Distress Questionnaire (MDQ) is yet another tool, for assessing menstrual distress, and comprises a list of symptoms which a patient may be asked to rate on a six-point scale ranging from no experience of the symptom to disturbing experiences. The questionnaire may contain descriptions of symptoms classified in to different categories. In an embodiment, the symptoms are classified as pain, concentration, behavior change, autonomic reaction, water retention, negative affect, arousal, and control. Each set of symptoms may be assessed on a scale, such as a six-point scale, ranging from having no effect at all to being partially disabling. In an embodiment, a set of questions are presented to the user based on one or more symptoms indicated by the user. In another embodiment, a set of questions is presented to the user based on the score indicated by the user on scales corresponding to different symptoms.

Still another tool, for assessing effects of dysmenorrhea, is the Menstrual Attitudes Questionnaire (MAQ). The MAQ consists of 33 items involving five factors: menstruation as a debilitating, bothersome and/or natural event, anticipation and prediction of the onset of menstruation, and denial of any effect of menstruation. The 33-item MAQ consisting of five subscales and items or factors are scored on a 6 or 7 point scale–1 (strongly disagree) to 6 or 7 (strongly agree).

The Woods' Daily Health Diary (WDHD) identifies all menstrual symptoms experienced as distressing. The scale has a total of 67 items. The first 57 items assess various symptoms on a severity scale ranging from 0, not present, to 4, extreme; the remaining items focus on behaviors such as exercise and diet in relation to the symptoms experienced.

As discussed above, VAS questionnaires can be designed to assess aspects such as, but not limited to, health-related overall quality of life, degree of nausea, degree of pain felt, degree of well-being, and degree of dyspepsia. For example, in one embodiment, to assess degree of dyspepsia a VAS questionnaire may present a leading question, such as, "Has your ability to eat or drink (including when, what, and how much) been disturbed by your stomach problems in the last 2 weeks?" with the two extremities of the scale being described as "Extremely" and "Not at all".

As discussed earlier, the Health Management application is capable of communicating (via pairing or syncing) with a third party device (including a third party application software on an external device), with physiological sensors, configured to be worn on the human body, such as around the wrist, in order to monitor, acquire, record, and/or transmit the physiological data, to receive and integrate exercise information, along with one or more electro-dermal patch devices of the present specification. It should be appreciated that the third party device, whether it is a third party application software on an external device or a second external device entirely (such as, but not limited to, a watch, or another medical device), is enabled to obtain information from the EDP device of the present specification, either directly from the EDP device, directly from the Health Management application, or directly from a server in data communication with the EDP device or the Heath Management application of the present specification. Consequently, the third party application or the second external device can display any information gathered by the EDP device and/or Health Management application, including patient diary inputs, the patient's level of pain, the patient's level of wellbeing, the patient's level of nausea, the stimulation settings, or an aggregate/composite score which aggregates any of the data tracked by the third party device with any of the data tracked by the EDP device and/or Health Management application to yield a single composite score.

The third party device, in various embodiments, may track one or any combination of the following patient related data: heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and/or UV radiation exposure and absorption or any other parameter listed in Tables 1 and Table 2 above, data representative of the air quality, sound level/quality, light quality or ambient temperature near the patient, or the global positioning of the patient, patient's weight, food consumed, type and amount of activity or exercise (such as steps take, swimming, running).

Electro-Dermal Patch Device Placement

In various embodiments, the electro-dermal patch device (such as the electro-dermal patch device 110 of FIG. 1A through 1C) of the present specification is placed at or near an 'area of interest' on the user's body to provide stimulation therapies for a plurality of conditions or treatments.

In various embodiments, the 'area of interest' comprises a dermatome. As understood by persons of ordinary skill in the art, a dermatome is an area of skin supplied by sensory neurons that arise from a spinal nerve ganglion. There are 8 cervical nerves (C1 being an exception with no dermatome), 12 thoracic nerves, 5 lumbar nerves and 5 sacral nerves. Each of these nerves relays sensation from a particular region of skin to the brain.

In some embodiments, the 'area of interest' comprises a thoracic dermatome, such as the user's front or lateral T9 to T12 dermatomes, L1, L2, L5 dermatomes and/or a sacral dermatome, such as the S1 to S4 dermatomes. The sacral nerves are responsible for part of the sensory perception and the movements of the lower extremities of the human body. From the S1, S2, S3 and S4 arise the pudendal nerve and parasympathetic fibers whose electrical potential supply the descending colon and rectum, urinary bladder and genital organs.

In some embodiments, the 'area of interest' comprises at least one of the patient's L1, L2, L5, S1, S2, S3, S4, T9, T10, T11, and T12 dermatomes.

In some embodiments, the 'area of interest' comprises at least one of the patient's L1, L2, L5, S1, S2, S3, S4, frontal and lateral T9, T10, T11, and T12 dermatomes and does not include any portion of the patient's T9, T10, T11, and T12 posterior dermatomes.

In alternate yet less preferred embodiments, the 'area of interest' comprises one or more meridians.

In an embodiment, an EDP device with at least four electrodes, or at least four EDP devices with one electrode each, are placed on the user's skin. One electrode each is positioned on either side of the umbilicus at approximately 1.5 inches away from the umbilicus. Further, one electrode each is positioned on either pubic bone, on each side of the umbilicus. In an embodiment, at least one and at most two electrodes are additionally placed on the back on the user, near the tail bone.

Figure 17A:
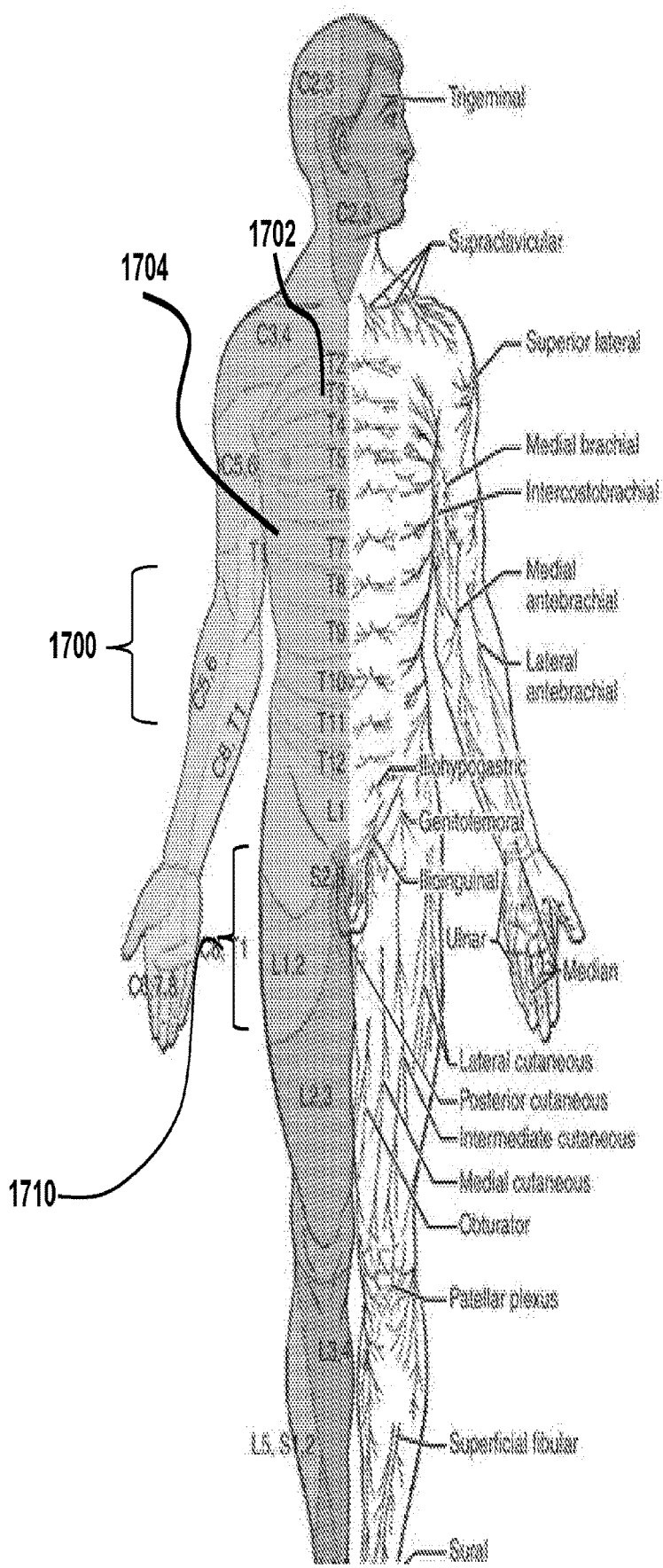
FIG. 17A is an illustration depicting the distribution of the front and lateral T9-T12 dermatomes and L1, L2, S2 and S3 dermatomes of a human body.

FIG. 17A is an illustration depicting a distribution 1700 of the T9 to T12 dermatomes and distribution 1710 of the L1, L2, S2 and S3 dermatomes across the front of a human body. The frontal dermatome is defined as the front and lateral thoracic dermatome which expressly do not include the back or spinal roots of the patient. In various embodiments, EDP devices of the present specification are positioned on the surface of the epidermis on a front portion 1702 or a lateral portion 1704 of the T9 to T12 dermatomes. The electrode(s) positioned in the pads or skin patches of EDP device then provide electrical stimulation to the epidermis of the targeted dermatome(s). T9 to T12, L1, L2 and L5 dermatomes are anatomically identifiable as follows:

T9-Intersection of the midclavicular line and the horizontal level at three quarters of the distance between the level of the xiphoid process and the level of the umbilicus.

T10—Intersection of the midclavicular line, at the horizontal level of the umbilicus.

T11—Intersection of the midclavicular line, at the horizontal level midway between the level of the umbilicus and the inguinal ligament.

T12—Intersection of the midclavicular line and the midpoint of the inguinal ligament.

L1—Midway between the key sensory points for T12 and L2.

L2—On the anterior medial thigh, at the midpoint of a line connecting the midpoint of the inguinal ligament and the medial epicondyle of the femur.

L5—On the dorsum of the foot at the third metatarsophalangeal joint.

T11 and T12 vertebrae differ from the other thoracic vertebrae in lacking facets for the ribs on their transverse processes, which additionally are shorter here; also, they are more similar in size and function to the lumbar vertebrae.

Figure 17B:
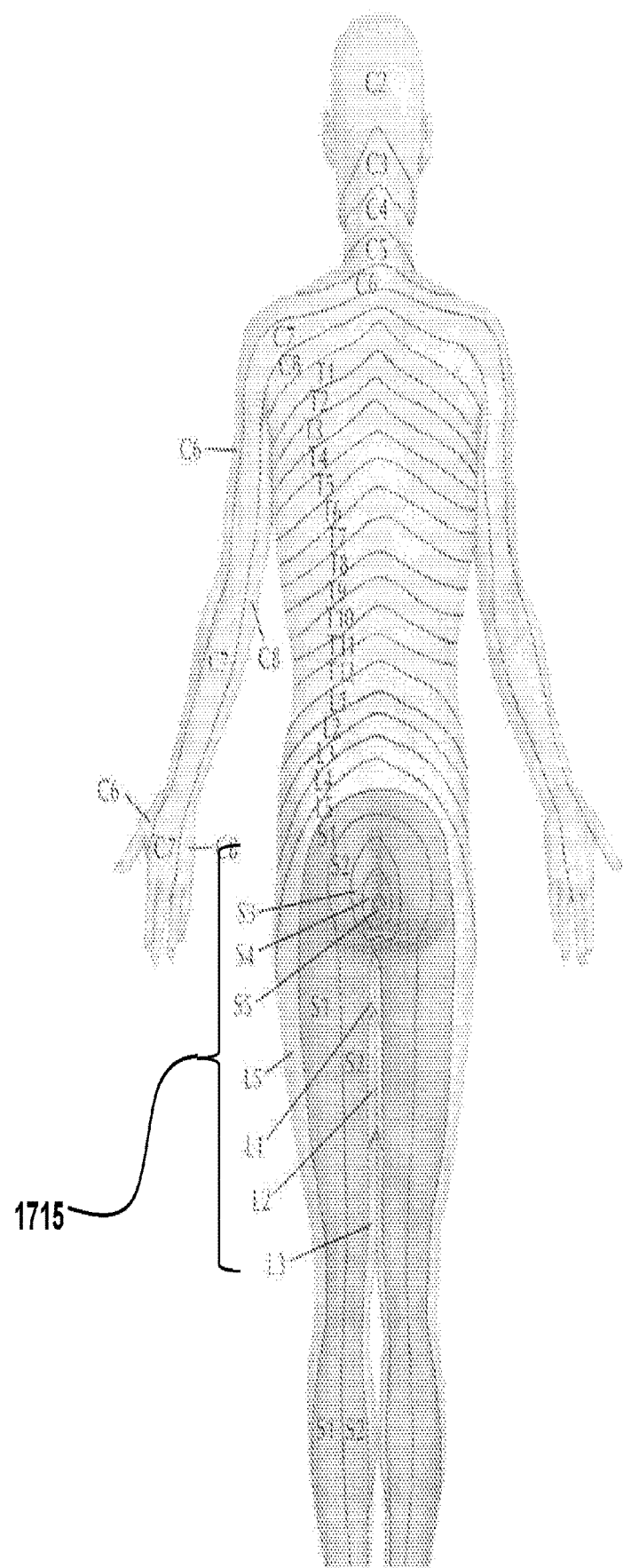
FIG. 17B is an illustration depicting the distribution of L1, L2, L5 and S1 to S4 dermatomes of a human body.

FIG. 17B is an illustration depicting the distribution 1715 of the S1—S4, L1, L2, L5 dermatomes across a perineum and back lower limbs of a human body. Referring to FIGS. 17A and 17B simultaneously, in various embodiments, EDP devices of the present specification are positioned on the surface of the epidermis on a front distribution 1710 or back distribution 1715 of the S1-S4, L1, L2, L5 dermatomes respectively. The electrode(s) positioned in the pads or skin patches of EDP device then provide electrical stimulation to the epidermis of the targeted dermatome(s). The S1 to S4 dermatomes are anatomically identifiable as follows:

S1—On the lateral aspect of the calcaneus.

S2—At the midpoint of the popliteal fossa.

S3—Over the tuberosity of the ischium or infragluteal fold.

S4—In the perineal area, less than one cm lateral to the mucocutaneous zone.

Figure 17C:
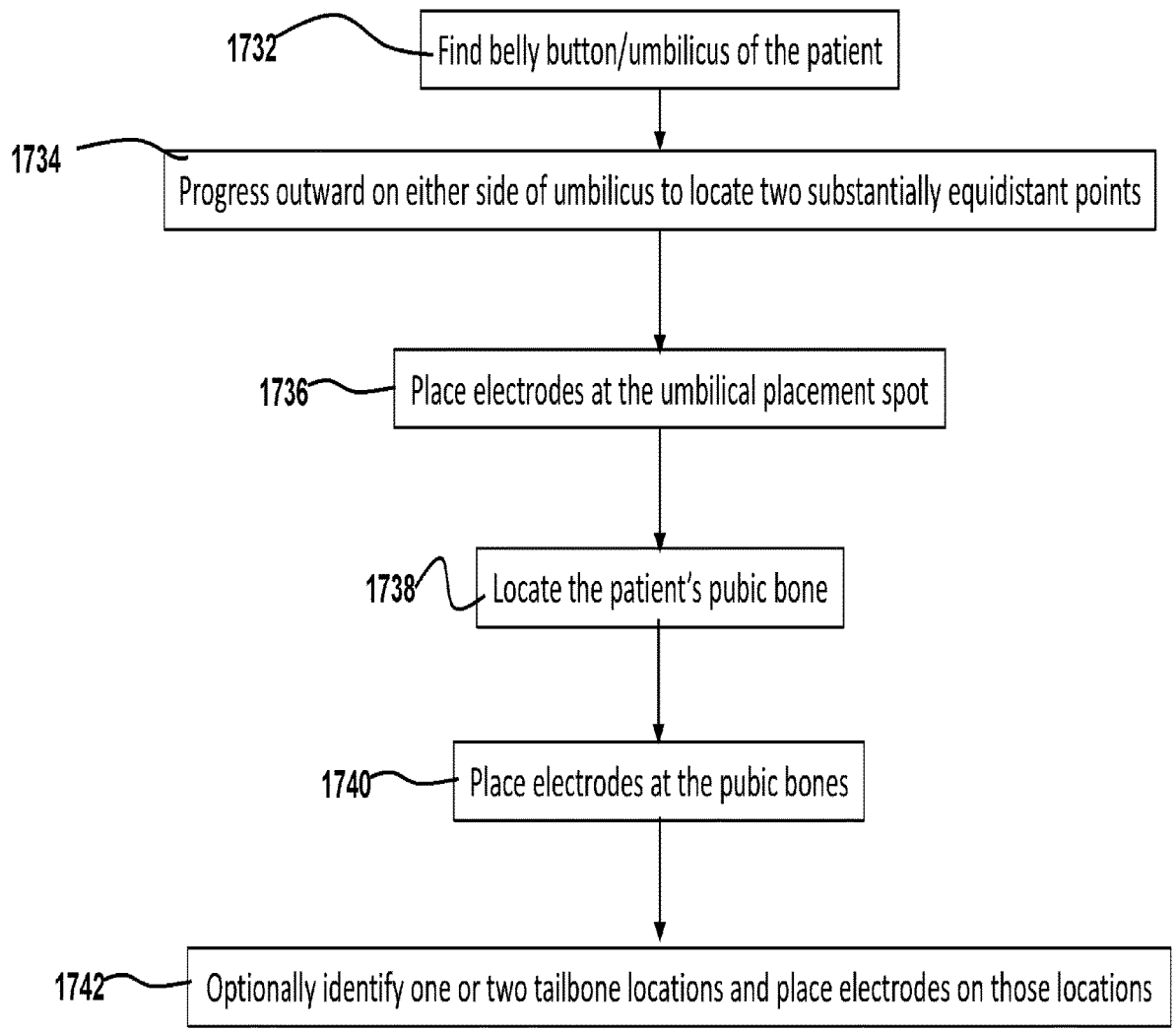
FIG. 17C is a flow chart listing the steps involved in one method of identifying a proper placement location for an electro-dermal patch on a patient, in accordance with one embodiment of the present specification.

FIG. 17C is a flow chart listing the steps involved in one method of identifying a proper placement location for an electro-dermal patch on a front thoracic surface of a patient, in accordance with one embodiment of the present specification. At step 1732, the patient, a physician, or anyone placing the EDP device on the patient, finds the umbilicus or belly button of the patient. The person applying the device then progresses outward on either side of the umbilicus of the patient at step 1734, identifying two substantially equidistant points. At step 1736, in an embodiment, at least a portion of the devices or patches may be placed on the patient adjacent to the umbilicus bilaterally up to a distance towards the edge of the trunk. In an embodiment, at least a portion of the devices or patches may be placed at a distance ranging from 1.5 inches from the umbilicus bilaterally up to the edge of the trunk.

In an embodiment, at least a portion of the devices or patches may be placed at or near a patient's pubic bone, bilaterally. In an embodiment, at least a portion of the devices or patches may be placed at or near a patient's tailbone.

At step 1738, the person applying the device identifies the pubic bones of the patient. At step 1740, the person applying the device places electrodes on the pubic bone.

In an optional step 1742, the person applying the device may locate at least one, and up to two tailbone locations and place appropriate electrodes or leads on that location.

It should be noted that in some embodiments, such as the waistband and undergarment configuration, it may only be necessary to locate one placement point, since the electrodes will be accurately positioned within the device obviating the need to individual placement.

Referring back to FIG. 1A, in various embodiments, at least one thoracic dermatome, from T9 to T12, at least one of L1, L2, L5 dermatomes and/or at least one sacral dermatome, from S1 to S4, is stimulated by the electro-dermal patch device 110 to provide electrical stimulation therapy, from the external surface of the patient's epidermal layer through 10 mm or 20 mm of the dermis, wherein the one or more electrodes 118 are configured to be positioned in skin patches or pads as described with reference to FIGS. 2A through 2C, FIGS. 3A, 3B, and 4A through 4C.

The prior art has focused on one of three different approaches: 1) stimulating the back, near the spinal root, 2) providing percutaneous electrical stimulation, which requires an electrode to be implanted, or 3) stimulating using conventional acupuncture meridians. However, the electrodermal patch device 110 of the present specification provides electrical stimulation, from the external surface of the patient's epidermal layer through 10 mm or 20 mm of the dermis, and targets front or lateral thoracic dermatomes T9 to T12, L1, L2, L5 dermatomes and/or sacral dermatomes, in accordance with various embodiments, having nerves that are closer to the skin surface. The electro-dermal patch device 110 of the present specification generates an electrical field, defined as voltage over distance, which penetrates to a shallower depth compared to stimulation encountered in the prior art. This allows the electro-dermal patch device 110 to have relatively smaller electrodes 118, lowers the current density and therefore the device requires less power than prior art devices to affect target tissues. The electrical field generated by the EDP device 110 is a function of at least the electrode geometry, electrode-tissue interface impedance, and the stimulating current amplitude. Providing an integrated device design and targeting the front and lateral thoracic dermatomes T9 to T12, L1, L2, L5 dermatomes and/or sacral dermatomes allows the patient to apply the electro-dermal patch device and stimulation independently. Prior art devices, particularly those stimulating the back (posterior side), require a medical professional for application.

Thus, in accordance with some aspects of the present specification, electrical stimulation from the external surface of the patient's epidermal layer through 10 mm or 20 mm of the dermis (using the electro-dermal patch device 110 of FIG. 1A) provides for a non-invasive treatment of pain management, prostaglandin production modulation and other symptoms due to conditions like dysmenorrhea. In various embodiments, a stimulation depth through the patient's epidermal layer ranges from 0.1 mm to 0.5, 1, 2, 3, 4, 5, 6, 7, 8, 9, 10, 11, 12, 13, 14, 15, 16, 17, 18, 19, 20 mm or any increment therein.

Stimulation Reaction Thresholds

Figure 18A:
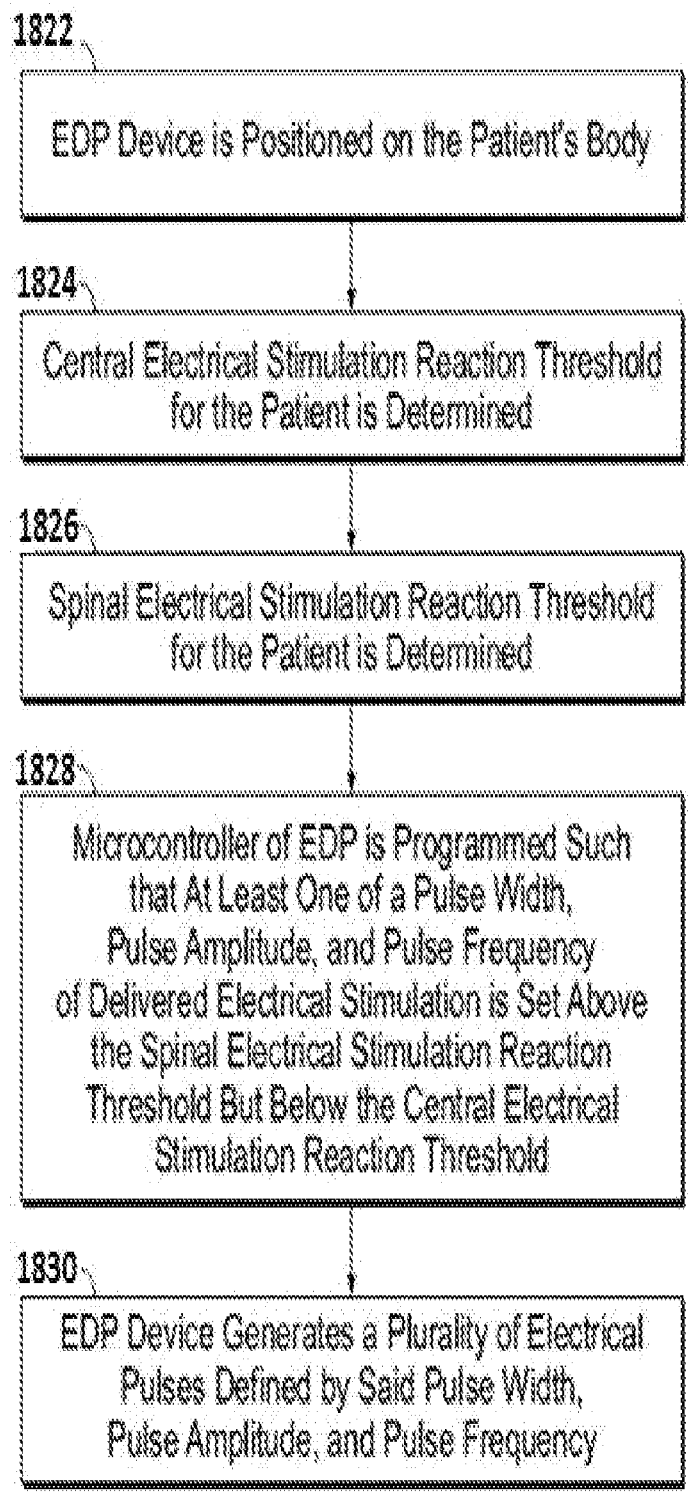
FIG. 18A is a flow chart illustrating the steps involved in a method of determining stimulation reaction thresholds and using an electro-dermal patch (EDP) device to manage menstrual pain in a patient, in various embodiments of the present specification.

FIG. 18A is a flow chart illustrating the steps involved in one embodiment of a method of determining stimulation reaction thresholds and using an electro-dermal patch (EDP) device to manage menstrual pain in a patient. At step 1822, the EDP device is positioned on the patient's body. At step 1824, a central electrical stimulation reaction threshold for the patient is determined. Then, at step 1826, a spinal electrical stimulation reaction threshold for the patient is determined. A microcontroller of the EDP device is then programmed, at step 1828, such that at least one of a pulse width, pulse amplitude, and pulse frequency of delivered electrical stimulation is set above the spinal electrical stimulation reaction threshold but below the central electrical stimulation reaction threshold. At step 1830, the EDP device then generates a plurality of electrical pulses defined by the pulse width, pulse amplitude, and pulse frequency set at step 1828.

Figure 18B:
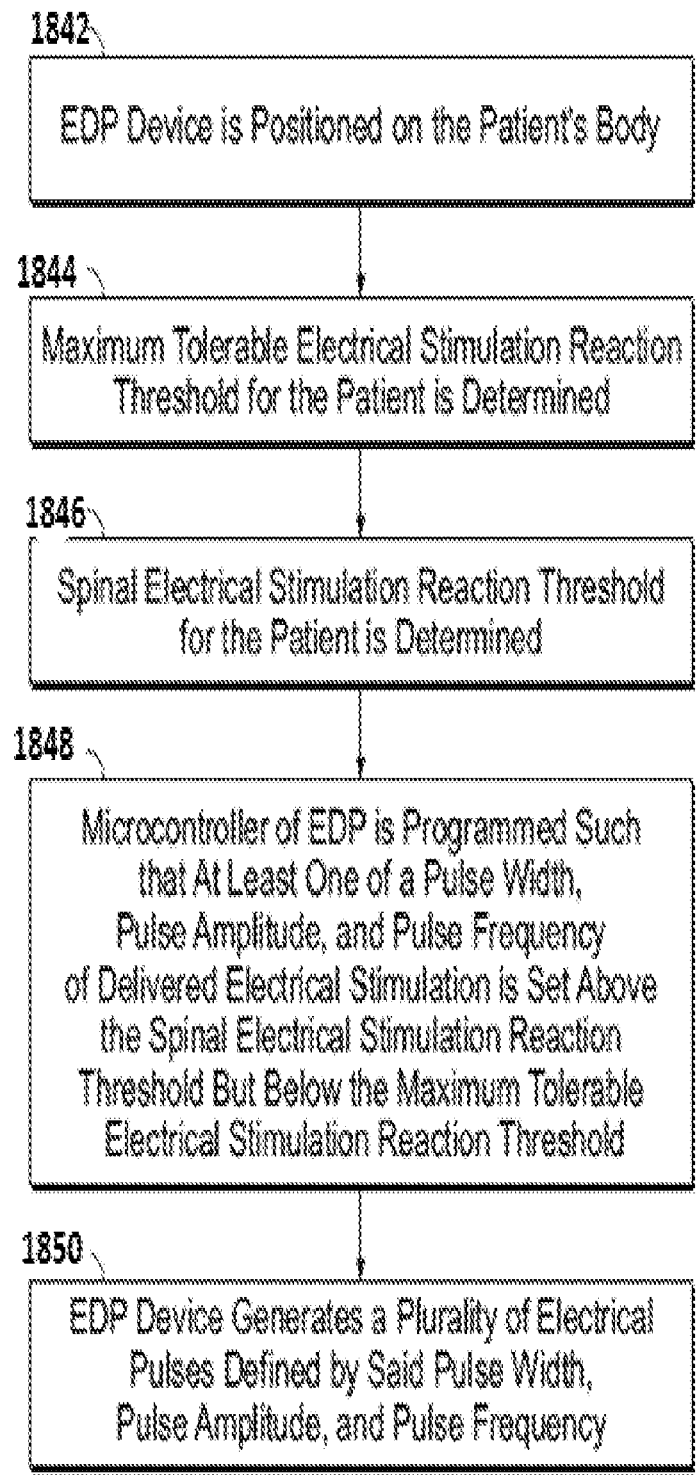
FIG. 18B is a flow chart illustrating the steps involved in a method of determining stimulation reaction thresholds and using an electro-dermal patch (EDP) device to manage menstrual pain in a patient, in various embodiments of the present specification.

FIG. 18B is a flow chart illustrating the steps involved in another embodiment of a method of determining stimulation reaction thresholds and using an electro-dermal patch (EDP) device to modulate menstrual pain in a patient. At step 1842, the EDP device is positioned on the patient's body. At step 1844, a maximum tolerable electrical stimulation reaction threshold, which can be measured as a pain sensation, for the patient is determined. Then, at step 1846, a spinal electrical stimulation reaction threshold for the patient is determined. A microcontroller of the EDP device is then programmed, at step 1848, such that at least one of a pulse width, pulse amplitude, and pulse frequency of delivered electrical stimulation is set above the spinal electrical stimulation reaction threshold but below the maximum tolerable electrical stimulation reaction threshold. At step 1850, the EDP then generates a plurality of electrical pulses defined by the pulse width, pulse amplitude, and pulse frequency set at step 1848.

Stimulation Patterns/Protocols to Drive Therapy

As discussed earlier, the user's plurality of health related information, such as the user's menstruation cycle; frequency and severity of pain; experience of backache, headache, nausea, emotional swings; stimulation induced nausea, and habituation events—is utilized by the Health Management application to suggest and/or implement a plurality of recommendations comprising stimulation patterns or protocols, medication (such as an amount of insulin intake or vitamin supplements, for example), dietary and/or activities plans. It should be appreciated that this integrated system provides users with a degree of independence and encourages patient compliance. Notwithstanding the above, however, the present application does apply to having physicians set or modify the stimulation protocols, either directly programming the EDP, programming the EDP through the companion device, or remotely communicating a desired protocol from a remote server or third party computing device to either the EDP directly or via the companion device. It should be noted the protocols may be used to manage symptoms associated with dysmenorrhea as well as pain associated with ovulation. Ovulation pain, pelvic pain, and menstrual pain may also be targeted during rescue sessions.

In various embodiments, recommendations related to stimulation patterns or protocols comprise driving, setting, customizing or adjusting a plurality of stimulation parameters such as, but not limited to, the number of stimulation sessions per day; duration of each stimulation; time or moment of application of the stimulation sessions; intensity of stimulations, stimulation pulse shape, frequency, width and amplitude; stimulation duty cycle; stimulation continuity profile; minimum and maximum overall duration or course of stimulation treatment in days, weeks or months. Following are exemplary standard setting ranges for some of the stimulation parameters:

Pulse Width: 10 μsec to 500 msec; pulse width is often fixed with the remaining parameters being adjustable Pulse Amplitude: 100 μA to 500 mA, less than 60 mA, 100 μA to 500 mA, 1 mA to 30 mA user adjustable, other adjustments set by a clinician, 15 mA to 30 mA, 5 mA to 45 mA, 1 mA to 50 mA, 1 mA to 100 mA into a 1 kΩ load pre-set range, and any increment therein Pulse Frequency: 1 Hz to 10,000 Hz, preferably 1 Hz to 100 Hz, with high frequency (>50 Hz) below the threshold of motor contraction preferable to low frequency (<10 Hz); 20 Hz to 100 Hz, and preferably 80 Hz; 1-250 pps (pulses per second)—20 to 80 pps having an analgesic effect with 80 pps providing the most profound inhibition of C-fiber-evoked flexion reflex without variation Pulse train repetition rate: approximately 1 Hz Pulse Pattern: continuous, burst, random frequency, modulated amplitude, modulated frequency, modulated pulse duration Pulse Shape: Monophasic, biphasic, sinusoidal, symmetrical biphasic, asymmetrical biphasic, spike-like biphasic Duty Cycle: 1% to 99%

Stimulation Session Duration: 1 min to 120 min or 50 ms to 120 min or 30 min ON/30 min OFF or 60 min ON/60 min OFF or X min ON/X min OFF; Matching ON/OFF sessions; Wake time ranging from 0 to 24 hours and any increment within, wherein ON/OFF session are implement only during wake time and no sessions are provided in times outside of the wake time.

Number of Stimulation Sessions/Day: 1 to 24, or based on experiences of symptoms related to dysmenorrhea, and simulation session duration, For example, a 60 minute simulation session in an ON/OFF equivalent time pattern would yield 6 ON sessions in a 12 hour period. It should be noted that the stimulation session time can vary, and therefore, the number of stimulation sessions per day can vary as well; Preset to an average cycle length of 5 days; HMA-driven after a period of 0-5 months once the application has 'learned' the user's cycle Burst Mode (that is, a burst of programmable pulses at a rate): 0.1 Hz to 100 Hz Ramp Up/Down Mode (that is, the time it takes to go from no stimulation to a peak or steady state (Ramp Up) and the time it takes to go from peak or steady state stimulation to no stimulation (Ramp Down)): 0.1 sec to 60 sec Modulated Mode: Range between 1%-100% amplitude, modulating up/down over a period of 0.1 sec-60 sec; modulation can be linear or sinusoidal; that is, in "modulated mode" the amplitude varies between 1% and 100% of a target amplitude (such as 10 mA) and this amplitude variation occurs over a period of 0.1 seconds to 60 seconds Electrode impedance (that is, the electrode-tissue interface impedance): 100 ohms to 5 kilo-ohms, 10 ohms to 5 kilo-ohms, 200 ohms to 1000 ohms, or 1 kilo-ohms to 100 kilo-ohms In some embodiments, the electro-dermal patch device provides electrical stimulation having the following parameters which are adjustable by the patient using the companion device:

Monophasic pulse shape with an active charge balancing phase

Pulse Width: 25 μsec to 500 msec in steps of 25 μsec

Pulse Amplitude: 0.1 mA to 500 mA in steps of 1 mA

Pulse Frequency: from 1 Hz, 5 Hz, 10 Hz, 15 Hz, 20 Hz, 25 Hz, 30 Hz, 40 Hz, 50 Hz, 60 Hz, 70 Hz, 80 Hz, 90 Hz, 100 Hz Stimulation Session Duration: from 5 min to 60 min in alternating equivalent time ON/OFF periods. For example, 60 min ON/60 min OFF.

Stimulation Session Duration: 1 min to 12 hr

Number of Stimulation Sessions/Day: 1 to 24, or based on experiences of symptoms related to dysmenorrhea, and simulation session duration, For example, a 60 minute simulation session in an ON/OFF equivalent time pattern would yield 6 ON sessions in a 12 hour period. It should be noted that the stimulation session time can vary, and therefore, the number of stimulation sessions per day can vary as well.

It should be appreciated that any initial or default stimulation parameters, which are implemented upon starting the device and without the benefit of any user input regarding their menstrual pain level, well-being status, nausea status or other information, may be universally fixed for all persons or may be based upon any one or a combination of the following parameters of the person: age, gender, ethnicity, weight, body mass index, body fat percentage, and/or race. Therefore, stimulation dosing may be initially based on categorizing the individual into one or more template groups and choosing a corresponding protocol. For example, one may classify individuals into various groups, such as a combination of age and gender for example (females 65 and over, females 55 to 64, females 45 to 54, females 35 to 44, females 25 to 34, females 24 and under). Additionally, the initial stimulation settings may be based on any parameters indicative of the patient's menstrual cycle.

It should further be appreciated that any selected stimulation parameters may be titrated for a given patient. Specifically, they may be adjusted upward or downward based on the amount of stimulation felt by the patient and/or immediately reported feelings of pain, nausea, or other discomfort.

In some embodiments, the stimulation continuity profile may be, for each stimulation session duration the stimulation profile applied, continuous; intermittent including short intervals of Y seconds of no stimulation; step-up stimulation wherein the stimulation amplitude and/or frequency increases at a predefined rate from commencement to completion of a stimulation session duration; or step-down stimulation wherein the stimulation amplitude and/or frequency decreases at a predefined rate from commencement to completion of a stimulation session duration. In some embodiments, the stimulation continuity profile may vary on a day to day basis. In embodiments, stimulation sessions may be active only a few days commencing from just prior to the onset of menses through the duration of the menstrual cycle. Similarly, the stimulation sessions may also be active during the days of ovulation and may be begin just prior to the onset of ovulation. Therapy prior to or at the onset of menses may be initiated based on information from a calendar, an application which follows menstrual cycles, or symptomatology, such as rescue sessions, as further described below.

In some embodiments, the time or moment of application of stimulation sessions may be, for example, 't' minutes at a certain time in a day, wherein 't' is within a range of 1 min to 60 min; at the onset of menstruation or menstrual pain and/or right before an expected menstrual pain event based on the user's recorded profile.

In accordance with an aspect of the present specification, the user as well as the remote patient care facility or personnel are able to control and adjust the plurality of stimulation parameters through the Health Management application and/or by the user via actuators 122 such as buttons or switches of FIG. 1A. In some embodiments, the remote patient care facility or personnel is authorized to control and adjust all stimulation parameters while the user is enabled to control and adjust a subset of the stimulation parameters with or without authorization/approval of the remote patient care facility or personnel. For example, the user may be allowed to change the number of stimulation sessions per day from, for example, 2 sessions per day to 1 session per day; stimulation session duration from, for example, 30 minutes to 60 minutes; and/or stimulation pulse amplitude from, for example, 1 mA to 30 mA. In one embodiment, the maximum change is limited to a predefined amount or multiple of the prior settings.

In a preferred embodiment, the user is able to increase the stimulation pulse amplitude from a minimal default amplitude setting of, say, 1 mA to a 'sensory threshold' corresponding to amplitude where the user can just feel the stimulation. The user may then save the 'sensory threshold' setting and continue stimulation at this setting. The sensory perception varies from person to person and therefore in various embodiments the 'sensory threshold' ranges from about 5 mA to 10 mA on the lower side and from about 20 mA to 30 mA on the higher side.

In some embodiments, a stimulation protocol includes alternating stimulation sessions between a first session having a low pulse frequency, for example, less than 50 Hz, followed by a second session having a high pulse frequency, for example, greater than 50 Hz.

In still further embodiments, the user may be able to control and adjust the subset of stimulation parameters within the standard settings ranges, such as those described above, or within a narrower band of range or constrained range within the standard settings ranges. For example, the user may be allowed to modify the stimulation pulse width, amplitude and frequency by no more than +/−50% from the original, default or standard setting. In another example, the user may be allowed to modify all stimulation parameters by +/−10% (from the original, default or standard setting) except for allowing the amplitude to decrease unbounded in order to address safety and/or comfort reasons. User modification of the stimulation parameters beyond the constrained range may require authorization from the remote patient care facility or personnel. In some embodiments, the range within which the user is able to control and adjust the subset of stimulation parameters is set by the remote patient care facility or personnel. Also, in some embodiments, the user may be allowed to control and adjust stimulation parameters within a first range at the onset of therapy, but as therapy progresses the user is allowed to control and adjust stimulation parameters within a second range wherein the second range is narrower, limited or constrained compared to the first range.

It should be appreciated that the type and number of stimulation parameters that the user is allowed to control and adjust can vary in multiple embodiments.

In accordance with an aspect of the present specification, the Health Management software application provides a plurality of pre-configured default or standard stimulation protocols to drive therapy for a plurality of conditions related to dysmenorrhea.

Example Stimulation Protocols for Treating Dysmenorrhea

In various embodiments, a standard stimulation protocol, for stimulating the T9 to T12, L1, L2, L5 and/or S1 to S4 dermatome(s) for managing pain associated with menstruation, may comprise a plurality of pre-configured standard settings such as at least three setting options, for example mild, optimal, intense. For example, an embodiment of a standard optimal stimulation protocol comprises a 12 hour period of sessions, with alternating ON/OFF stimulation times of 30 min to 60 min at an intensity that doesn't bother the patient, but can still be felt by them, such as at a frequency of 80 Hz and at a 'sensory threshold' amplitude of 20 mA. In some embodiments, a latency effect is encountered with stimulation wherein the stimulation is provided for a specific amount of time and the effect is not witnessed until a certain amount of time has passed and/or the effect remains for a certain amount of time post stimulation.

In some embodiments, a general stimulation protocol for managing pain associated with menstruation includes a stimulation on period of one hour, followed by a 20 to 30 minute off or break period, followed by another one hour on period, and so on. This protocol is continued for a predetermined period or for the entire time a patient is awake. The stimulation is then switched off while the patient is asleep as she is generally not feeling pain while asleep and the stimulation could prevent the patient from staying asleep. In some embodiments, during general stimulation, the on periods and off periods are equal in time. For example, in one embodiment, each one hour on period is followed by a one hour off period. In one embodiment, each on and off period has a duration of one hour and 6 on and 6 off sessions are provided in a single day. In another embodiment, each on and off period has a duration of 30 minutes and 12 on and 12 off sessions are provided in a single day. In yet another embodiment, each on and off period has a duration of 15 minutes and 24 on and 24 off sessions are provided in a single day.

Some embodiments additionally comprise a custom setting option that allows the user to adjust or set the subset of stimulation parameters, which he is allowed to control, within constrained ranges. It should be appreciated that the number of pre-configured settings (such as mild, optimal, intense) may vary across various embodiments. Also, the stimulation protocol, with its mild, optimal and intense configurations, is only exemplary and may vary across various embodiments and for targeting specific conditions such as only menstrual cramps M. For example, a stimulation protocol directed towards prostaglandin modulation, may include a stimulation pulse width of 200 sec, pulse amplitude corresponding to the user's 'sensory threshold' such as 20 mA, pulse frequency of 80 Hz, stimulation session duration of 30 minutes and one session per day for 4 weeks.

In accordance with an aspect of the present specification, the Health Management application recommends and periodically adjusts the stimulation protocols or patterns based on the user's health related information, such as the user's pain profile and stimulation induced nausea, dyspepsia, habituation events. The Health Management application monitors compliance of the user to the recommended optimal stimulation protocol. The user's pain and compliance profile is recorded and displayed to the user in the form of charts, graphs, tables or any other visual format as would be advantageously evident to persons of ordinary skill in the art.

Various embodiments also comprise allowing on-demand stimulation in addition to or in lieu of the standard stimulation protocol pre-configured settings (for example mild, optimal, intense). On-demand stimulations, also referred to hereinafter as "rescues", are applied at the onset of unexpected menstrual pain and/or at a potential occurrences of pain events as known from the user's pain profile, such as but not limited to ovulation pain. While the user is allowed on-demand stimulations as well as customized stimulation protocols, in various embodiments the Health Management application is programmed to ensure (such as by continuous monitoring, limited or restricted control access to only the subset of stimulation parameters and/or restricting the user control access to only a constrained range within the standard settings ranges) that the user does not over or under stimulate, thereby resulting in habituation or ineffective stimulation. For example, the user may be allowed to add to the number of daily sessions, over and above those scheduled based on the standard protocol settings (mild, optimal, intense), but subject to some limitations or restrictions. For example, the user may have five additional "rescues" in the first month of the stimulation therapy, declining to 4 daily in the second month, and 3 daily in the third month of therapy. It should be appreciated that the limitations are critical to avoiding habituation over time. Also, the number of stimulation sessions may be restricted and then may decline and/or the stimulation intensity, such as the amplitude and frequency, may be allowed to be adjusted up or down by a set amount, for example by +/−10%.

In some embodiments, the electro-dermal patch device of the present specification is sized in the form of a skin patch that covers multiple dermatomes such as, for example, both of the T11 and T12 dermatomes or one or more of the L1, L2, L5 or S1-S4 dermatomes. In alternate embodiments, the user may use a first electro-dermal patch on a T9 to T12, L1, L2, L5, S1 to S4 dermatome and a second electro-dermal patch on a different T9 to T12, L1, L2, L5, S1 to S4 dermatome. In such cases, the Health Management application may alternatingly stimulate the various dermatomes to treat dysmenorrhea. It should be noted, that the various suggestions and recommendations auto generated by the Health Management application, for initial fresh stimulation protocols, patterns and parameter settings as well as those related to adjusting these stimulation protocols and settings may, in various embodiments, be implemented by the user only after an approval and advice from the remote patient care facility and/or personnel. In some embodiments, however, prior approval from the remote patient care facility or personnel may not be required. The Health Management application enables the user to set an option of prior approval or disable this option.

Method of Use

In accordance with various aspects of the present specification, the user is enabled to apply or use the electro-dermal patch device of the present specification with no or minimal intervention from a physician. In some embodiments, the user visits his physician for just one session wherein, depending upon the user's medical condition, the physician may prescribe the electro-dermal patch device of the present specification to the user along with the stimulation configuration, from the external surface of the patient's epidermal layer through 10 mm or 20 mm of the dermis, of the electro-dermal patch device, as described with reference to FIG. 1A through 1C. In various embodiments, a stimulation depth through the patient's epidermal layer ranges from 0.1 mm to 0.5, 1, 2, 3, 4, 5, 6, 7, 8, 9, 10, 11, 12, 13, 14, 15, 16, 17, 18, 19, 20 mm or any increment therein. During the session, the physician instructs the user in identifying appropriate areas of stimulation, such as T9 to T12, L1, L2, L5 and/or S1 to S4 dermatomes, and also provides an orientation to the user regarding use and functions of the electro-dermal patch device. In various embodiments, the appropriate areas of stimulation may be identified, for example, by one or more temporary tattoos (such as a small dot) or an image of the user may be taken with a mark or icon locating the appropriate area on the user's body. During the session, the physician may further help the user to download the Health Management application on the user's computing device, such as her smartphone, tablet, PDA, laptop, computer and demonstrate pairing or syncing of the application to the user's computing device. The user may at this time or at a later time enable the Health Management application to be in communication with the physician or a remote patient care facility.

In alternate embodiments, the physician's intervention for initial set-up and use orientation of the electro-dermal patch device may not be required at all. In such embodiments, the user simply buys the electro-dermal patch device that comes along with a compact disk comprising detailed audio-visual tutorials demonstrating use, application download instructions, functions and identification of appropriate areas of stimulation. Additionally or alternatively, the audio-visual tutorials may be made accessible to the user via a dedicated website also hosting a web version of the Health Management application.

In various embodiments, therapy provided by the electro-dermal patch (EDP) devices of the present specification is driven or triggered by a plurality of variables. These variables can be entered by the patient or a medical professional into the companion device, sensed by a sensor on the EDP, transmitted to the companion device or EDP by a separate device, for example, a device, with physiological sensors, configured to be worn on the human body, such as around the wrist, in order to monitor, acquire, record, and/or transmit the physiological data, or can be acquired by a combination of any of the above means. In various embodiments, the variables are stored, preset, and/or measured or input on a regular, predetermined basis or time period. In some embodiments, the variables include primary variables which comprise primary drivers to any therapy regimen and secondary variables which comprise secondary indicators which may or may not affect the regimen. Some variables, such as weight in pounds, are entered into the patient diary based on their actual value while other variables, such as menstrual pain and well-being, are given a score based on a predefined score value range or a scale such as the Visual Analogue Scale (VAS). The treatment algorithm of the companion device analyzes these scores in comparison to predefined limits and automatically modifies therapy accordingly. In some embodiments, the algorithm analyzes these scores on a daily basis. In other embodiments, the algorithm analyzes the scores every other day, every third day, every fourth day, every fifth day, every sixth day, or once per week. In various embodiments, the score values range from 0 to 100. In a preferred embodiment, the score values range from 1 to 10 and, more preferably, from 1 to 5 or 1 to 3, depending on the variable. In some embodiments, a high numerical score value indicates electrical stimulation therapy provided by the EDP is inadequate and additional stimulation is needed. A lower numerical score value indicates electrical stimulation therapy provided by the EDP is excessive and stimulation needs to be reduced. Conversely, in other embodiments, a high numerical score value indicates stimulation is excessive and needs to be reduced and a low numerical score value indicates stimulation is inadequate and needs to be increased. In some embodiments, a numerical score value proximate the middle of the score range indicates therapy is appropriate and can remain unchanged.

In one embodiment, the system uses one or more of the following triggers to initiate stimulation or modulate stimulation settings: a patient's glycemic level, metabolism levels, hemoglobin A1c, and/or blood sugar. Using physiological sensors or external devices which already measure metabolism, blood sugar, glycemic levels, or hemoglobin A1c, the companion device gathers such data, integrates it with existing patient status data related to ovulation or menstruation, and generates a modulated stimulation setting, which may include a signal to initiate therapy, change therapy or cease therapy, based on an integrated patient status data profile. In one embodiment, a patient's increased blood sugar levels cause the stimulation settings to be modulated upward in order to increase the rate, frequency, or overall amount of stimulation.

In some embodiments, therapy is driven by a set of three primary drivers. The primary drivers include: pain or dysmenorrhea symptoms (menstrual cramps, backache, headache, etc.) which is defined by the patient; menstrual cycle, defined as frequency of menstruation; and well-being, defined as simply how good the patient feels. In some embodiments, well-being is further subdivided specifically into feelings of nausea, headache, backache, discomfort, energy level, and weakness/strength. Each of these primary drivers can be attributed a score which is entered into the companion device, as depicted in FIGS. 11, 13, and 16.

For example, for menstrual cycle, referring to FIG. 13, the patient can enter the start date of her menstrual cycle, the length of her menstrual cycle in days, and the timing, based on day of the month, she experiences any symptoms associated with menstruation, including, but not limited to, menstrual cramps, backache, fatigue, headache, and nausea.

In other embodiments, rather than a scale to determine the presence or absence of pain, the system presents the patient with a scale configured to record changes in her pain after stimulation. For example, in an embodiment, a pain change score scale extends from 1 to 3 wherein 1 is indicative of no change, 2 is indicative of some change, and 3 is indicative of significant change in pain after stimulation. If a patient reports a 1, no change in pain after stimulation, stimulation parameters are increased.

For pain, referring to FIG. 11, the patient can enter a pain score from 1 to 3, wherein 1 indicates the patient experienced no pain, 2 indicates the patient experienced minor pain, and 3 indicates the patient experienced major pain. In some embodiments, a pain score having a higher numerical value indicates pain management is inadequate and the patient requires greater stimulation. The treatment algorithm of the companion device recognizes the need for greater stimulation as indicated by the higher score and titrates therapy accordingly. For example, in one embodiment, if the patient enters a pain score greater than 1 in the patient diary over a period of four to seven consecutive days within a menstruation period, the algorithm uses the score to incrementally increase the duration of each stimulation session or to increase the number of stimulation sessions per day. A pain score of 1 indicates stimulation is adequate and does not need to be changed, in accordance with some embodiments. Alternatively, in some embodiments, a lower appetite score indicates stimulation needs to be decreased. For example, if the patient enters a pain score of 1 for three consecutive days within the menstruation period, stimulation sessions are decreased in duration and frequency.

In other embodiments, rather than a scale to determine the presence or absence of pain, the system presents the patient with a scale configured to record changes in her pain after stimulation. For example, in an embodiment, a pain change score scale extends from 1 to 3 wherein 1 indicates no change, 2 indicates some change, and 3 indicates significant change in pain after stimulation. If a patient reports a 1, no change in pain after stimulation, stimulation parameters are increased.

As discussed earlier, in some embodiments the primary drivers such as pain or dysmenorrhea symptoms are alternately assessed on at least one of a plurality of scientific scales such as, but not limited to, Visual Analogue Scale (VAS), Numerical Rating Scale (NRS), Verbal Rating Scale (VRS), Faces Pain Scale-Revised (FPS-R), McGill Pain Questionnaire, Menstrual Distress Questionnaire (MDQ), Menstrual Attitudes Questionnaire (MAQ), Woods' Daily Health Diary (WDHD).

For well-being, in one embodiment and referring to FIG. 16, the patient can enter a score from 1 to 3, wherein 1 indicates no nausea/abdominal discomfort, 2 indicates occasional nausea/abdominal discomfort, and 3 indicates the patient is experiencing frequent nausea/abdominal discomfort. In some embodiments, for well-being, a higher score indicates stimulation is too intense, causing the patient to experience nausea, and that a reduction in stimulation is needed. The treatment algorithm of the companion device recognizes the need for reduced stimulation as indicated by the higher score and titrates therapy accordingly. For example, in one embodiment, if the patient enters a well-being score of 3 in the patient diary for three consecutive days, the algorithm uses the score to incrementally reduce the number of stimulation sessions per day or week and/or the length of each stimulation session. In one embodiment, parameter modifications based on well-being scores supersede those based on pain scores and/or menstrual cycle dates. These primary drivers are tracked to determine how best to modify stimulation on an on-going basis to provide the patient with the proper amount of stimulation such that the patient does not experience feelings of nausea, dyspepsia, does not experience low energy or weakness, and does not experience pain. The tracking of these variables allows for automatic modification of stimulation parameters, based on predefined variable ranges and limits, to provide the patient with a therapeutic stimulation protocol without the need of constant management by the patient.

In some embodiments, therapy is further driven by a set of two secondary indicators. The secondary indicators include patient weight and calories expended/exercise. Weight can be entered in pounds and calories expended/exercises can be attributed a score which is entered into the companion device, as depicted in FIGS. 15 and 12. For example, for weight, referring to FIG. 15, the patient can enter her weight in pounds using a keypad on the companion device. In one embodiment, the patient enters her weight in the patient diary on a weekly basis. In other embodiments, the companion device is configured to communicate wirelessly with a wireless scale (i.e. bathroom scale) such that the patient's weight is automatically entered into the companion device when the patient weighs herself on the scale. This improves system accuracy by eliminating the possibility of the patient entering an incorrect weight. In addition, the system can track how often and when the patient weighs herself, send reminders, and titrate therapy based on the communicated weight. In embodiments, the weight is tracked to monitor water weight, which may indicate occurrences of water retention before and during menstruation and/or ovulation. The water weight can be compared to the actual weight. In various embodiments, the companion device is configured to communicate wirelessly with a separate device capable of measuring a plurality of physiological parameters, including, but not limited to, patient weight, body fat, lean mass, and body mass index (BMI). Data from these parameters is automatically input into a treatment algorithm of the companion device and is used to drive therapy by modifying electrical stimulation parameters.

For calories expended/exercise, referring to FIG. 12, the patient can enter an exercise score from 1 to 5, wherein 1 indicates the patient took more than 10,000 steps in a single day, 2 indicates the patient took 7,500-10,000 steps in a single day, 3 indicates the patient took 5,000-7,500 steps in a single day, 4 indicates the patient took 2,500-5,000 steps in a single day, and 5 indicates the patient took less than 2,500 steps in a single day. In some embodiments, the secondary indicators further include fitness input (from a separate device, for example, a device, with physiological sensors, configured to be worn on the human body, such as around the wrist, in order to monitor, acquire, record, and/or transmit the physiological data) and biological inputs (such as prostaglandin levels).

Similar to the primary drivers, these secondary indicators can be tracked to determine how best to modify stimulation on an on-going basis to provide the patient with the proper amount of stimulation. In some embodiments, the secondary indicators possess less value compared to the primary drivers in determining how best to modify the EDP stimulation parameters. Although embodiments having three primary drivers and one secondary indicator have been discussed, additional embodiments having greater or fewer primary drivers and/or secondary indicators are possible and the variables presented are not intended to be limiting. In various embodiments, the companion device is configured to communicate wirelessly with a separate device capable of measuring a plurality of physiological parameters, including, but not limited to, uterine contraction. Data from these parameters is automatically input into a treatment algorithm of the companion device and is used to drive therapy by modifying electrical stimulation parameters.

In embodiments, the electro-dermal device can be used to deliver therapy on a pre-programmed basis. In an embodiment, the electro-dermal device can be used to deliver therapy that is timed to coincide with pain event spikes recorded in a patient diary that is used to form an evolving topographical pain map. In other embodiments, menstrual diaries, both 3$^{rd}$ party and/or included with the devices of the present specification, are used to automatically trigger onset of therapy prior to menses. Menstrual diaries can also be used to create an evolving topographical pain map, wherein the system learns the unique pain characteristics and behaviors of the patient. In some embodiments, well-being and pain scale scoring are recorded and added to the menstrual diaries for graphical presentation to the patient, automatic titration and/or triggering of therapy, and automated menstrual coaching. In some embodiments, pain scale scoring uses a standardized HRQL questionnaire and/or VAS visual or verbal pain scale. In yet other embodiments, therapy can be delivered via a rescue session in an "on-demand" mode.

Figure 19:
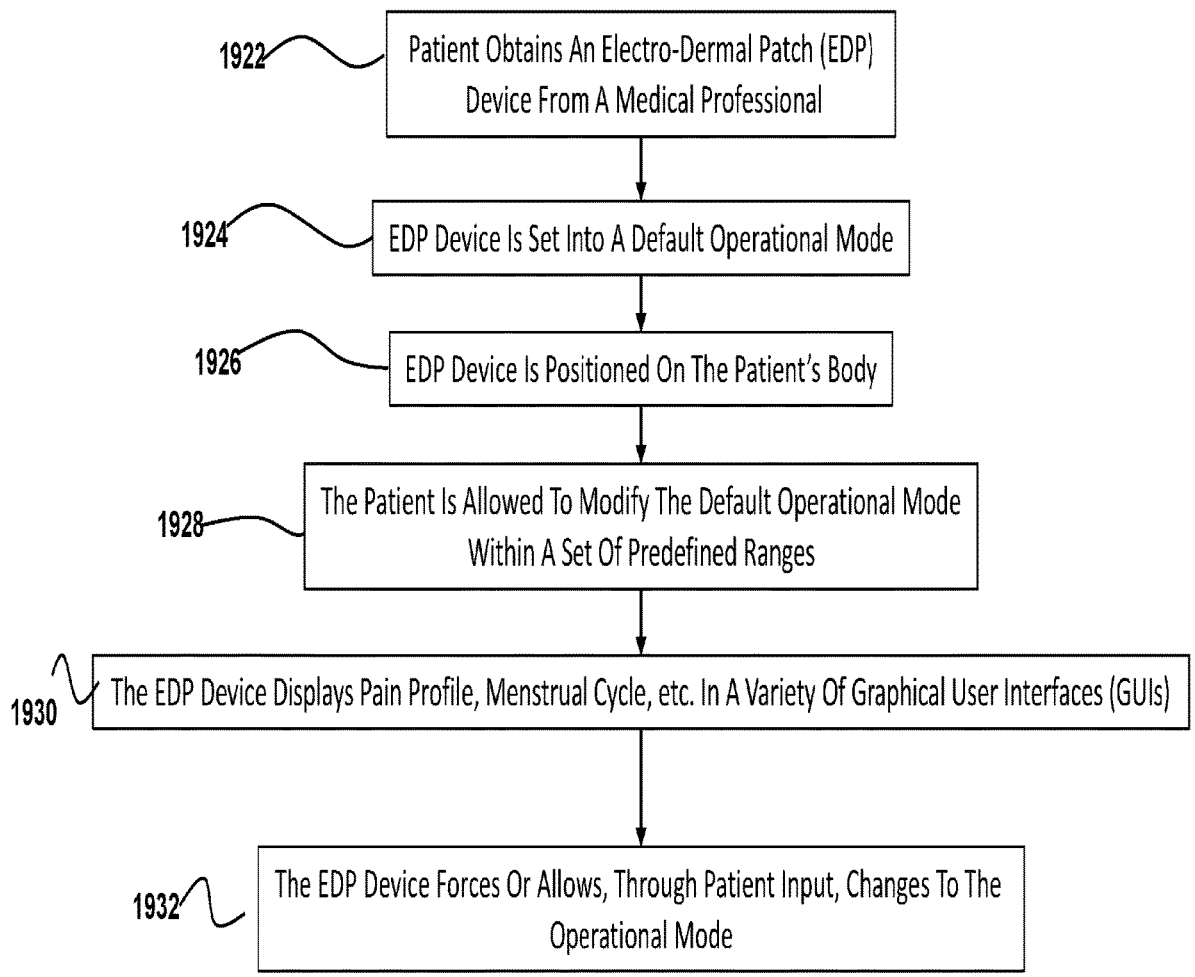
FIG. 19 is a flow chart illustrating the steps involved in one embodiment of a method of using an electro-dermal patch device to treat symptoms of dysmenorrhea in a patient.

FIG. 19 is a flow chart illustrating the steps involved in one embodiment of a method of using an electro-dermal patch device to treat symptoms of dysmenorrhea in a patient, showing a device that can be used to deliver therapy on a pre-programmed basis or in a default operational mode. At step 1922, a patient obtains an electro-dermal patch (EDP) device, in accordance with the devices disclosed in the present specification, from a medical professional.

The EDP device is set into a default operational mode, either by the patient or by the medical professional, at step 1924. In some embodiments, the default operational mode includes the following stimulation parameters and parameter ranges: pulse width in a range of 10 μsec to 10 msec; pulse amplitude in a range of 1 mA to 100 mA; pulse frequency in a range of 1 Hz to 10,000 Hz; pulse duty cycle in a range of 1% to 99%; session duration in a range of 1 min to 60 min in an alternating ON/OFF configuration; and 1 to 24 sessions per day, preferably in the duration of a user's wake time. In an embodiment, a wake time of 12 hours, with alternating ON/OFF sessions, is used. A wake time of 12 hours is only exemplary and, in various embodiments, wake time of any length ranging from 0 to 24 hours, and any increment therein, may be used. In a preferred embodiment, the default operational mode includes the following stimulation parameters: pulse width equal to 200 μsec; pulse amplitude equal to 10 mA; pulse frequency equal to 80 Hz; pulse duty cycle equaling 99%; session duration equaling 60 minutes; and 6 ON/OFF cycles per day. In another embodiment, the session duration equals 30 minutes, which corresponds to 12 ON/OFF cycles per 12 hour period. Then, at step 1926, the EDP device is positioned on the patient's body, either by the patient or by the medical professional. The patient is allowed to modify the default operational mode within a set of predefined ranges at step 1928, and as described above. The patient may modify the default operational mode based upon patient feedback or feedback provided by a separate wearable device, for example, a device, with physiological sensors, configured to be worn on the human body, such as around the wrist, in order to monitor, acquire, record, and/or transmit the physiological data. At step 1930, the EDP device displays pain profile, menstrual cycle, stimulation sessions, and the like, in a variety of graphical user interfaces (GUIs). Other parameters may also be listed, and the list in step 1930 is not intended to be limiting. The EDP device forces or allows, through patient input, changes to the operational mode in the case of an adverse effects or habituation or to conserve battery at step 1932. The EDP device forces the changes when feedback data provided by the device or another wearable device falls outside preset ranges indicating habituation is occurring. In some embodiments, habituation occurs when pain returns over time despite electrical stimulation via the stimulation protocols disclosed in the present specification, indication a loss of pain management.

Figure 20:
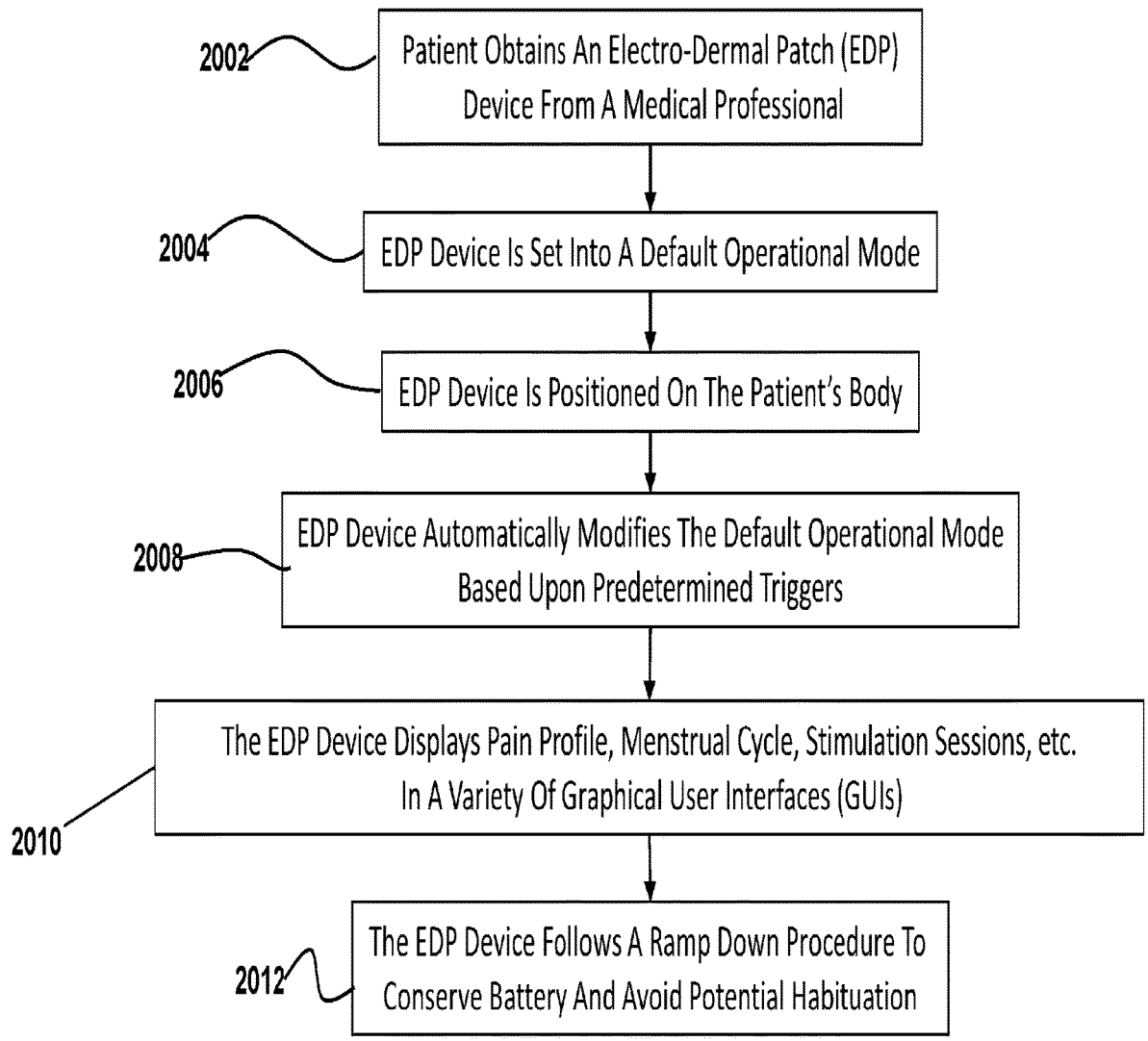
FIG. 20 is a flow chart illustrating the steps involved in another embodiment of a method of using an electro-dermal patch device to treat symptoms of dysmenorrhea in a patient.

FIG. 20 is a flow chart illustrating the steps involved in another embodiment of a method of using an electro-dermal patch device to treat symptoms of dysmenorrhea in a patient, that can be used to deliver therapy that is timed to coincide with pain event spikes recorded in a patient diary that is used to form an evolving topographical pain map. At step 2002, a patient obtains an electro-dermal patch (EDP) device, in accordance with the devices disclosed in the present specification, from a medical professional. The EDP device is set into a default operational mode, either by the patient or by the medical professional, at step 2004. In various embodiments, the default operational mode includes the stimulation parameters and parameter ranges listed above with respect to FIG. 19. Then, at step 2006, the EDP device is positioned on the patient's body, either by the patient or by the medical professional. The EDP device automatically modifies the default operational mode based upon predetermined triggers at step 2008. In various embodiments, the triggers include, but are not limited to, a. a calendar that counts the days to the next menstrual period and activates stimulation therapy before the expected date, for example 2 to 3 days before the expected date;

b. halting use of birth control pills, which can result in menstruation within about 24 hours, so the birth control pill cycle can act just like a calendar, triggering therapy around the time of stopping the pill;

c. patient well-being—many women experience changes in well-being or other body signals that announce onset of menstruation, so these signals, felt and recorded by the patient, can be used to trigger therapy; and d. detection of uterine contractions.

Trigger data is collected from patient diary recording of pain and well-being, and data from a separate device, with physiological sensors, configured to be worn on the human body, such as around the wrist, in order to monitor, acquire, record, and/or transmit the physiological data, transmitted to the companion device.

In one embodiment, for example, the patient records a pain diary entry with a score of 1, wherein the patient experienced no pain at all. In some embodiments, one or more scores of 1 on pain triggers the companion device to automatically decrease therapy parameters, for example, a decrease in stimulation intensity, duration, or sessions. At step 2010, the EDP device displays pain profile, menstrual cycle, stimulation sessions, and the like in a variety of graphical user interfaces (GUIs). Other parameters may also be listed, and the list in step 2010 is not intended to be limiting. The EDP device then follows a ramp down procedure, wherein stimulation parameters are decreased sequentially or halted altogether, at step 2012.

Figure 21:
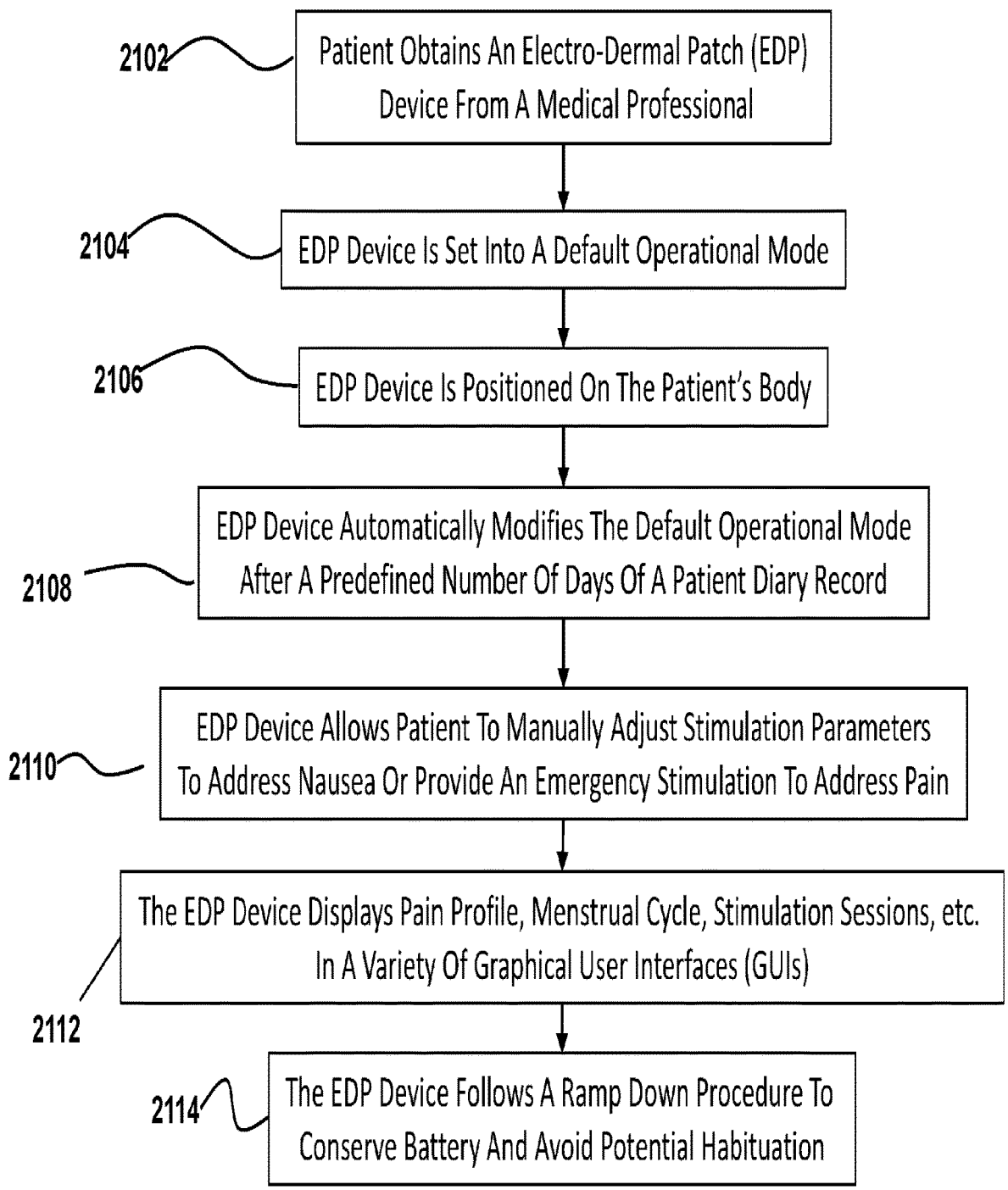
FIG. 21 is a flow chart illustrating the steps involved in another embodiment of a method of using an electro-dermal patch device to treat symptoms of dysmenorrhea in a patient.

FIG. 21 is a flow chart illustrating the steps involved in another embodiment of a method of using an electro-dermal patch device to treat symptoms of dysmenorrhea in a patient, in a therapy "on-demand"/rescue session mode. At step 2102, a patient obtains an electro-dermal patch (EDP) device, in accordance with the devices disclosed in the present specification, from a medical professional. The EDP device is set into a default operational mode, either by the patient or by the medical professional, at step 2104. In various embodiments, the default operational mode includes the stimulation parameters and parameter ranges listed above with respect to FIG. 19. Then at step 2106, the EDP device is positioned on the patient's body, either by the patient or by the medical professional. The EDP device automatically modifies the default operational mode after either a pain threshold or after a predefined number of days of a patient diary record of pain profile, menstruation cycle, and the like at step 2108. In various embodiments, the predefined number of days is in a range of 1 to 7 days. In one embodiment, the predefined number of days is 30 days. In one embodiment, the predefined number correlates to the number of days within a cycle as determine by the learned behavior or pattern of the user. In one embodiment, in combination with step 2108, the EDP device allows the patient to manually adjust stimulation parameters to provide emergency stimulation to address pain at step 2110. At step 2112, the EDP device displays pain profile, menstrual cycle, stimulation sessions, and the like, in a variety of graphical user interfaces (GUIs). Other parameters may also be listed, and the list in step 2112 is not intended to be limiting. The EDP device then follows a ramp down procedure, wherein stimulation parameters are decreased sequentially, to conserve battery and avoid potential habituation at step 2114.

Figure 22:
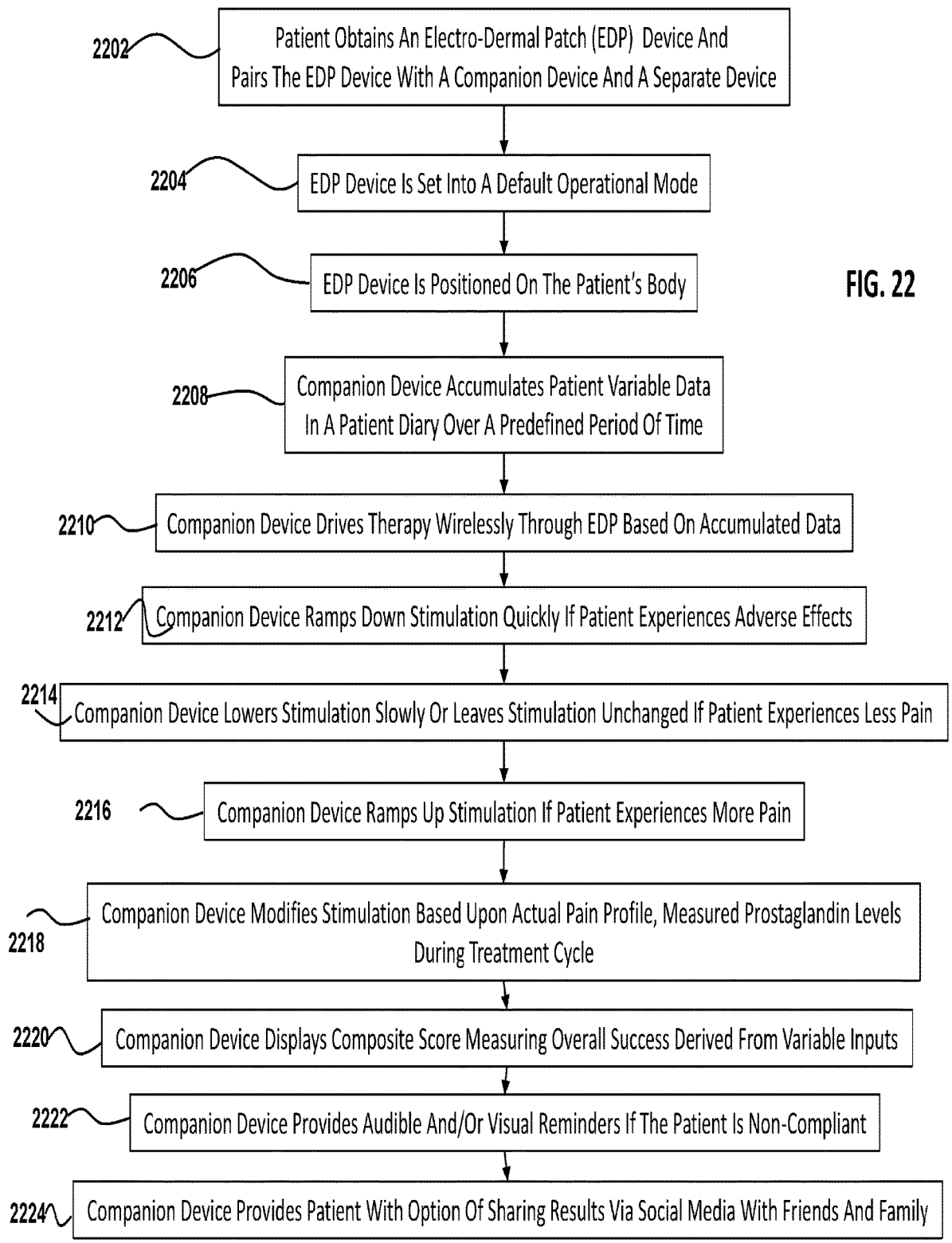
FIG. 22 is a flow chart illustrating the steps involved in another embodiment of a method of using an electro-dermal patch device to treat symptoms of dysmenorrhea in a patient.

FIG. 22 is a flow chart illustrating the steps involved in yet another embodiment of a method of using an electro-dermal patch device to treat symptoms of dysmenorrhea in a patient. At step 2202, the patient obtains an electro-dermal patch (EDP) device and pairs the EDP device with a companion device, such as a smartphone, and a separate device, for example, a device, with physiological sensors, configured to be worn on the human body, such as around the wrist, in order to monitor, acquire, record, and/or transmit the physiological data. In some embodiments, pairing with the separate device can be done anytime within a treatment cycle. In different embodiments, a treatment cycle lasts from a few minutes to a few days and is typically correlated with the duration of menses or ovulation. At step 2204, the device is set into a default operational mode. In some embodiments, the default operational mode includes the stimulation parameters and parameter ranges listed above with respect to FIG. 19 and includes periodic stimulation.

The EDP device is positioned on the patient's body at step 2206. At step 2208, the companion device accumulates patient variable data, including, but not limited to, pain profile, menstrual cycle, well-being, and the like, in a patient diary over a predefined period of time. In some embodiments, the companion device accumulates data over a range of 1 to 7 days. In one embodiment, the companion device accumulates data for 30 days. In one embodiment, the predefined number correlates to the number of days within a cycle as determine by the learned behavior or pattern of the user. Then, at step 2210, the companion device drives stimulation therapy wirelessly through the EDP device based on accumulated patient diary data over the treatment cycle. During the treatment cycle, if the patient experiences adverse side effects, the companion device ramps down stimulation parameters quickly at step 2212. During the treatment cycle, if the patient experiences decrease in pain or other symptoms of dysmenorrhea, the companion device slowly lowers stimulation to a minimum threshold or leaves stimulation unchanged at step 2214. During the treatment cycle, if the patient experiences an increase in pain or other symptoms of dysmenorrhea, the companion device ramps up stimulation accordingly at step 2216. At step 2218, the companion device modifies stimulation based upon actual weight loss, measured pain experiences, measured prostaglandin levels, or indicators of other symptoms of dysmenorrhea, during the treatment cycle. At step 2220, the companion device displays a composite score measuring overall success derived from the variable inputs. If the patient is non-compliant, the companion device will provide audible and/or visual reminders to the patient at step 2222. Optionally, at step 2224, the companion device provides the patient with the option of sharing her results via social media with designated friends and family.

In an alternate embodiment, the companion device first accumulates patient diary data before the EDP device is set into the default operation mode. Referring to FIG. 22, in this alternate embodiment, step 2208 is performed prior to step 2204. The remaining steps proceed in the same order.

In other embodiments, a patient is provided with manual options of operating the EDP device. The patient may operate the device at low, medium, and high settings, based on the patient variable data. For example, in one embodiment, a patient starts the EDP device at a high setting but begins to experience adverse side effects. The patient then resets the EDP device to the medium setting, and then to the low setting. Eventually, the patient experiences pain and resets the EDP device to the medium setting. In some embodiments, this protocol is driven by a therapy intensity scale, such as 1 to 5 or 1 to 10, or a graphic on the display of the companion device. In some embodiments, manual operation using low, medium, and high settings is coupled with the protocols described with reference to FIGS. 19-22 to establish baseline EDP device settings.

Figure 23:
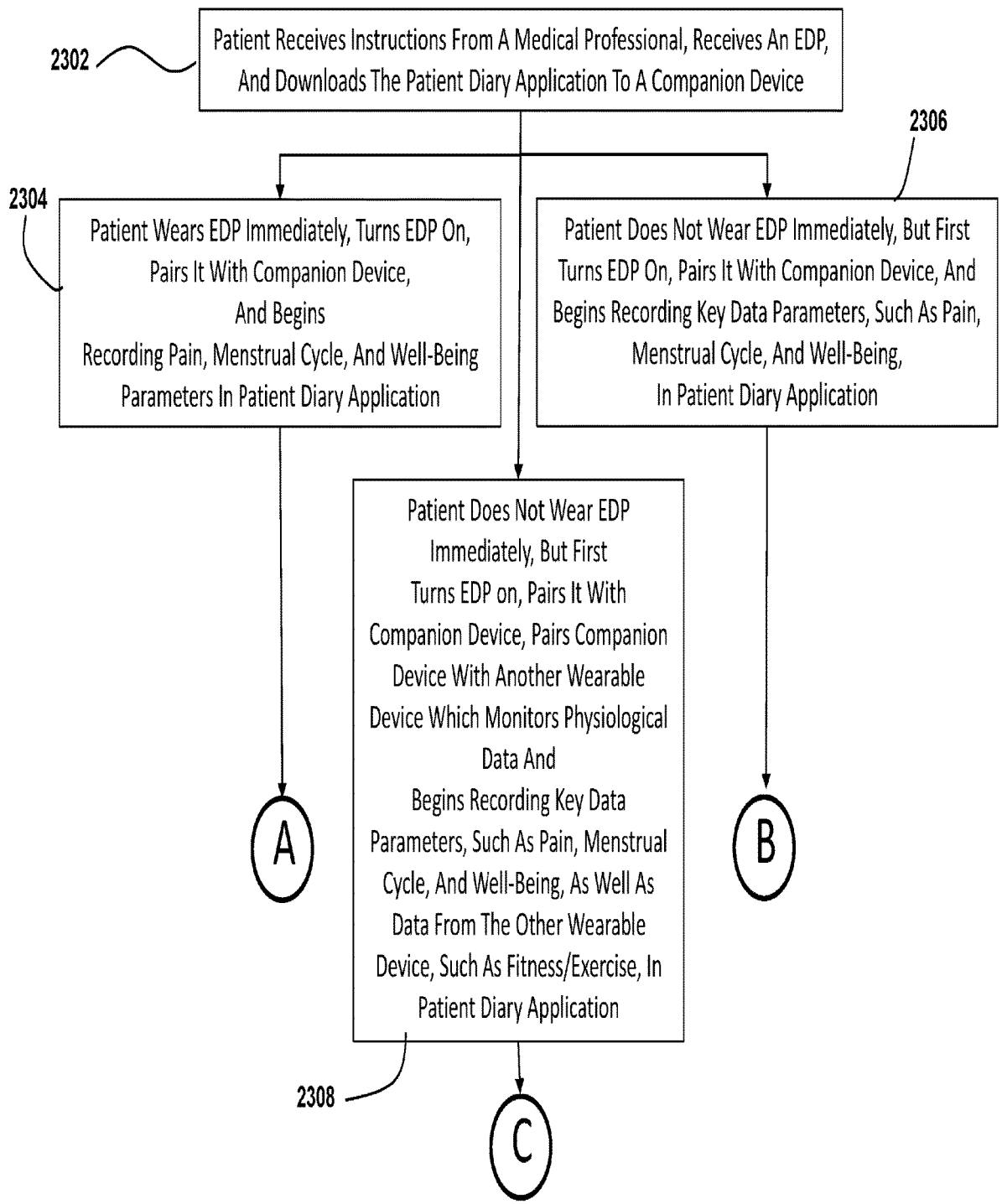
FIG. 23 is a flow chart illustrating the steps involved in yet other embodiments of methods of using an electro-dermal patch device to treat symptoms of dysmenorrhea in a patient.
Figure 23:
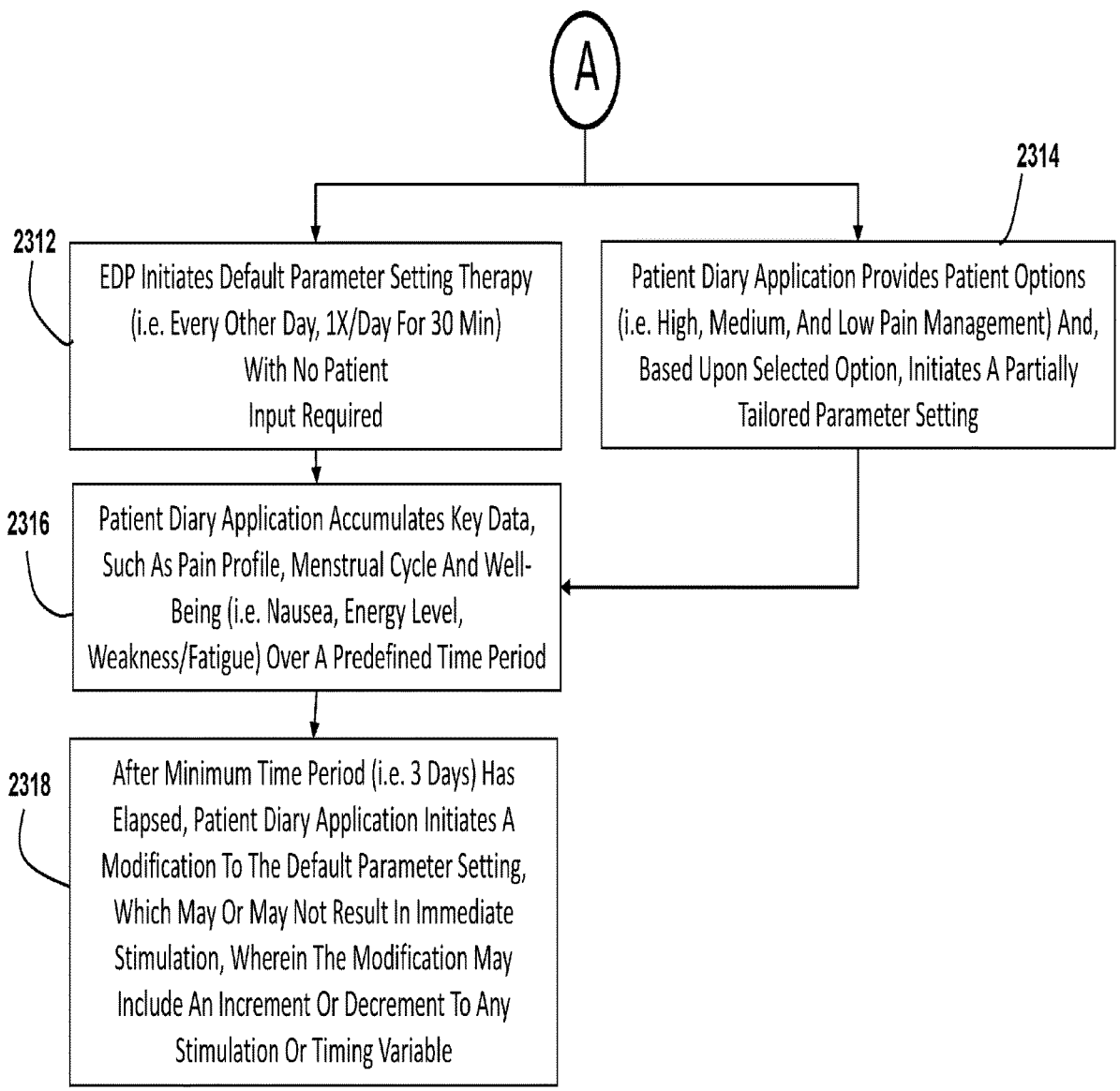
Figure 23:
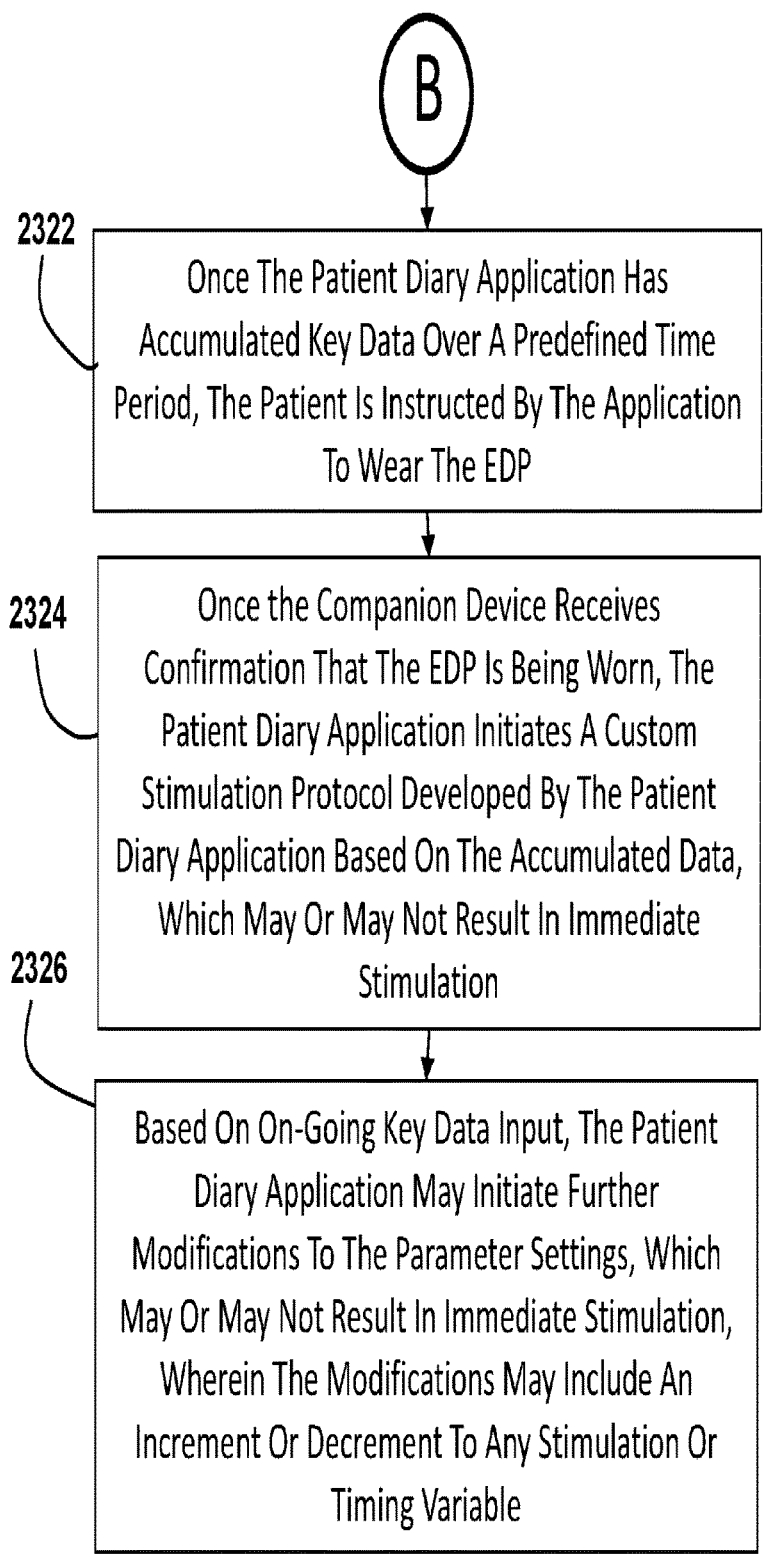
Figure 23:
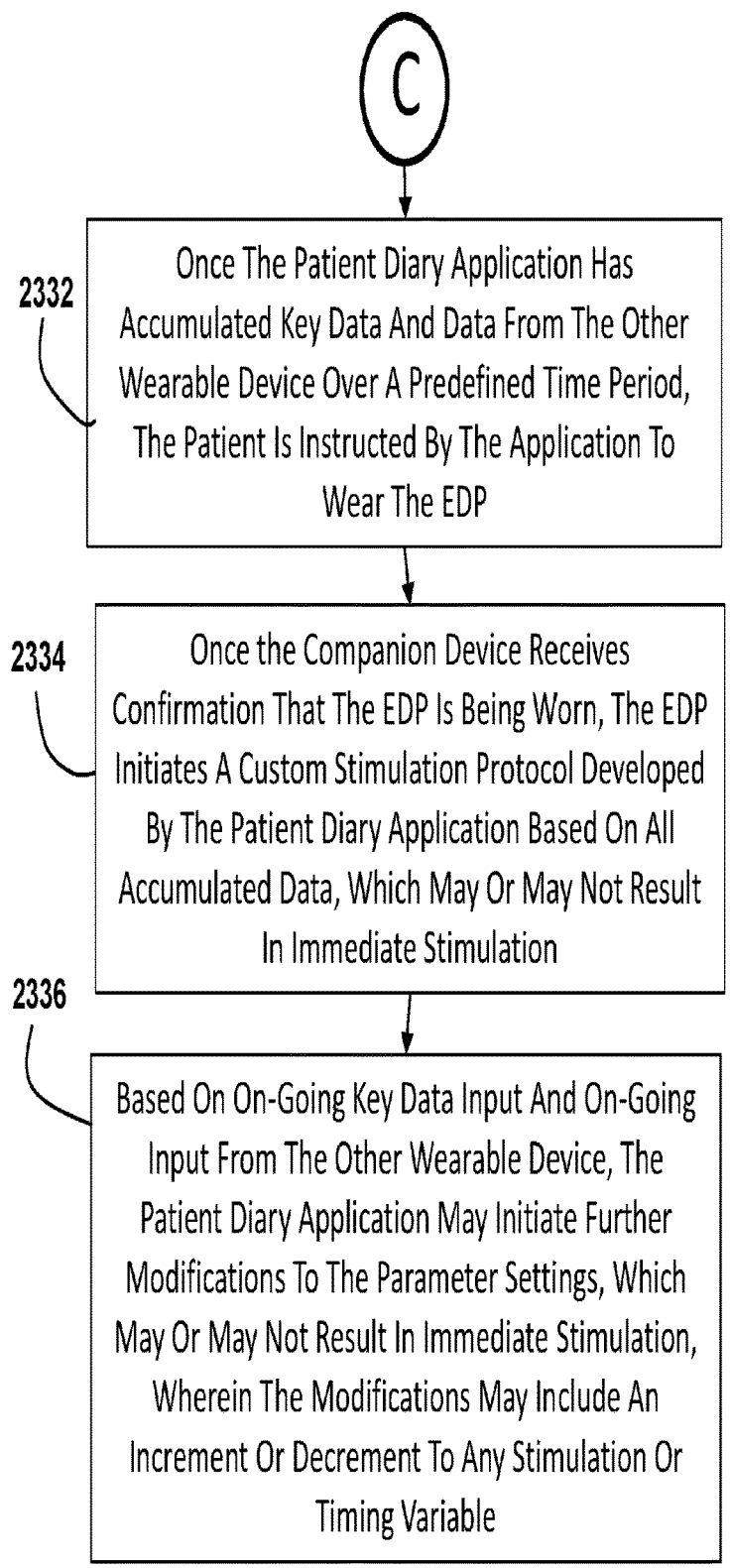

FIG. 23 is a flow chart illustrating the steps involved in yet other embodiments of methods of using an electro-dermal patch device to treat dysmenorrhea in a patient. At step 2302, a patient receives instructions from a medical professional, receives an electro-dermal patch (EDP) device, and downloads a patient diary application to a companion device, such as a smartphone. Optionally, at step 2304, the patient wears the EDP immediately, turns it on, and pairs it with the companion device such that the companion device begins recording pain, menstrual cycle, and well-being parameters in the patient diary application. In one embodiment, the EDP then initiates default parameter setting therapy with no patient input required at step 2312. The patient diary application then accumulates key data, such as pain profile, menstruation cycle, and well-being (i.e. nausea, energy level, weakness/fatigue) over a predefined time period at step 2316. After a minimum time period has elapsed at step 2318, the patient diary application initiates a modification to the default parameter setting, which may or may not result in immediate stimulation, wherein the modification may include an increment or a decrement to any stimulation or timing variable.

Alternatively, in another embodiment, following step 2304 wherein the patient wears the EDP immediately, the patient diary application provides the patient various options (i.e. high, medium, and low appetite control) at step 2314 and, based upon the selected option, initiates a partially tailored parameter setting. The patient diary application then continues to accumulate key data and initiate parameter setting modifications, as detailed in steps 2316 and 2318 respectively.

Optionally, in another embodiment, following step 2302 wherein the patient receives the EDP and downloads the patient diary application, the patient does not wear the EDP immediately at step 2306, but first turns the EDP on, pairs it with the companion device, and begins recording key data parameters, such as pain, menstrual cycle, and well-being, in the patient diary application. At step 2322, once the patient diary application has accumulated key data over a predefined time period, the patient is instructed by the application to wear the EDP. Then, at step 2324, once the companion device receives confirmation that the EDP is being worn, the patient diary application initiates a custom stimulation protocol developed by the patient diary application based on the accumulated data, which may or may not result in immediate stimulation. Based on on-going key data input, at step 2326, the patient diary application may initiate further modifications to the parameter settings, which may or may not result in immediate stimulation, wherein the modifications may include an increment or a decrement to any stimulation or timing variable.

Still optionally, in another embodiment, following step 2302 wherein the patient receives the EDP and downloads the patient diary application, the patient does not wear the EDP immediately at step 2308, but first turns the EDP on, pairs the EDP with the companion device, pairs the companion device with another wearable device, for example, a device, with physiological sensors, configured to be worn on the human body, such as around the wrist, in order to monitor, acquire, record, and/or transmit the physiological data, and begins recording key data parameters, such as pain, menstrual cycle, and well-being, as well as data from the other wearable device, such as fitness/exercise, in the patient diary application. At step 2332, once the patient diary application has accumulated key data and data from the other wearable device over a predefined time period, the patient is instructed by the application to wear the EDP. Then, at step 2334, once the companion device receives confirmation that the EDP is being worn, the patient diary application initiates a custom stimulation protocol developed by the patient diary application based on all accumulated data, which may or may not result in immediate stimulation. Based on on-going key data input and on-going input from the other wearable device, at step 2336, the patient diary application may initiate further modifications to the parameter settings, which may or may not result in immediate stimulation, wherein the modifications may include an increment or a decrement to any stimulation or timing variable.

In embodiments, the electro-dermal patch device and companion device of the present specification is used with a separate monitoring device, to treat symptoms of dysmenorrhea in a patient. The separate monitoring device is configured to measure a plurality of physiological parameters, including, but not limited to, patient weight, body fat, lean mass, and BMI, and wirelessly transmit monitored data to the companion device.

Figure 27:
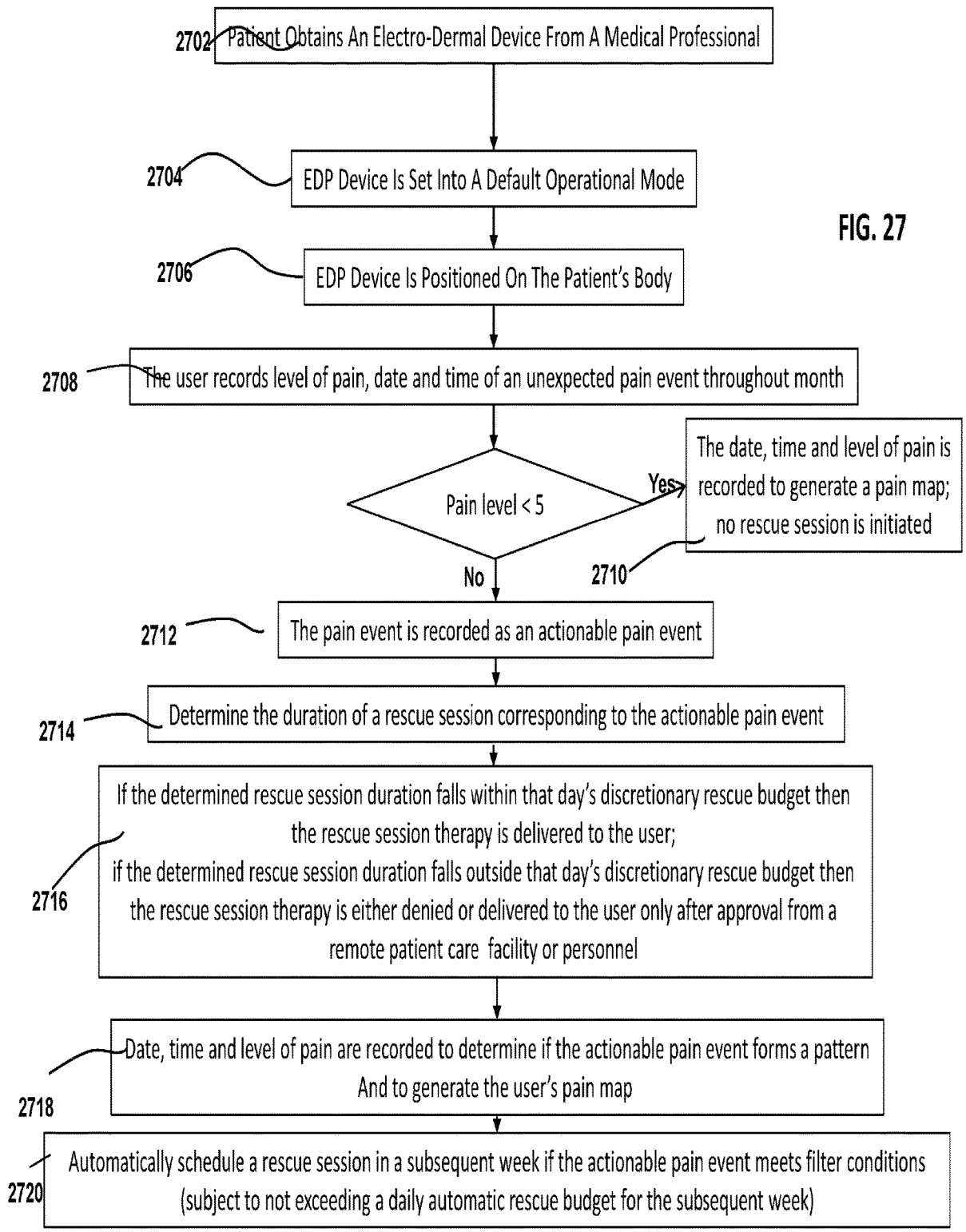
FIG. 27 is a flow chart illustrating exemplary steps involved in one embodiment of a method of using an electro-dermal device to automatically drive rescue therapy based on the user's individualized pain profile or map.

FIG. 27 is a flow chart illustrating the steps involved in one embodiment of a method of using an electro-dermal device to drive a rescue therapy based on the user's individualized pain profile or map. Rescue therapy, comprising rescue sessions, is driven and triggered by patient symptomatology and are used to target unpredictable pain and pain associated with ovulation. At step 2702, a patient obtains an electro-dermal (ED) device, in accordance with the devices disclosed in the present specification, from a medical professional.

The EDP device is set into either a default operational mode or an on-demand mode, by the patient or by the medical professional, at step 2704. In some embodiments, the default operational mode or the baseline stimulation protocol is set at 6-12 daily stimulation sessions of 30-60 minutes each having a pulse amplitude of 80 mA. Optionally, the on-demand mode is disabled if set into a default operational mode, and likewise the default operational mode is disabled if set into on-demand mode. Then, at step 2706, the EDP device is positioned on the patient's body, either by the patient or by the medical professional, to begin delivering stimulation treatment in accordance with the selected stimulation mode.

At step 2708, each day, the user records an intensity level of pain as well as the date and time of an unexpected pain event—that is, a pain event that does not regularly correlate with the onset or coincide with menses or ovulation. In various embodiments, the user uses a light bar Visual Analog Scale (VAS) on her smartphone (that functions as a companion device) to record the level of pain along with the date and time of the pain event. In some embodiments, the light bar VAS is configured as a 0 to 10 scale wherein 0 represents no pain while 10 represents a maximum level of pain. Thereafter, at step 2710, if the recorded level of pain intensity is less than 5, on the VAS, the pain event is recorded as a low intensity pain event along with the date and time of the pain event. The recorded date, time and level of the pain event are used to generate and display an individualized pain profile or map of the user.

At step 2712, if the recorded level of pain intensity is equal to or greater than 5, the pain event is recorded as an actionable pain event. Consequently, the following actions are taken: At step 2714, a rescue session duration is determined. In various embodiments, the rescue session duration is equal to the amount of time that is determined as part of the baseline stimulation protocol, for example, each rescue session duration is equal to 30 minutes or 1 hour. Therefore, if the baseline defines a protocol that delivers 30 min ON/30 min OFF stimulation, then the duration of the rescue session is determined to be equal to 30 minutes.

At step 2716, the determined rescue session duration is compared with the user's daily discretionary rescue budget. In some embodiments, the user's daily discretionary rescue budget is predefined to be equal to the amount of time that is allocated in the baseline protocol. Therefore, if the baseline protocol allocates 30 min ON/30 min OFF in 12 hour duration, the rescue budget is set at 360 minutes of stimulation therapy, to be allocated in increments that are determined by the user, with equivalent amounts of OFF time in between rescue sessions. In some embodiments, a total rescue budget is set at 12 hours (not including OFF time). If the determined rescue session duration falls outside that day's discretionary rescue budget then the user and a remote patient care facility or personnel are alerted and the rescue session therapy is either denied or delivered to the user only after approval from the remote patient care facility or personnel.

At step 2718, the date, time and level of pain are recorded to determine if filter or threshold condition(s) are met to ascertain if the pain event forms a pattern of recurrent pain spikes. As discussed earlier in the specification, the filter or threshold conditions may comprise a predefined period of time (ranging from a few days to a few months) and/or a predefined number of rescue sessions (ranging from 1 to 10 sessions). The recorded date, time and level of the pain event are also used to generate and display an individualized pain profile or map of the user.

At step 2720, if the actionable pain event meets or satisfies the filter or threshold condition(s) then a rescue session, for example, of 30 minutes duration, may be automatically scheduled, for additional therapies for the duration of the menses or ovulation event, at the recorded time of the actionable pain event.

The steps 2708 to 2720 are repeated for each occurrence of an unexpected pain event, throughout the duration of the stimulation therapy for the user.

As discussed earlier, the user is allowed a predefined amount of daily total rescue budget, for example, 360 or 720 minutes.

Figure 28:
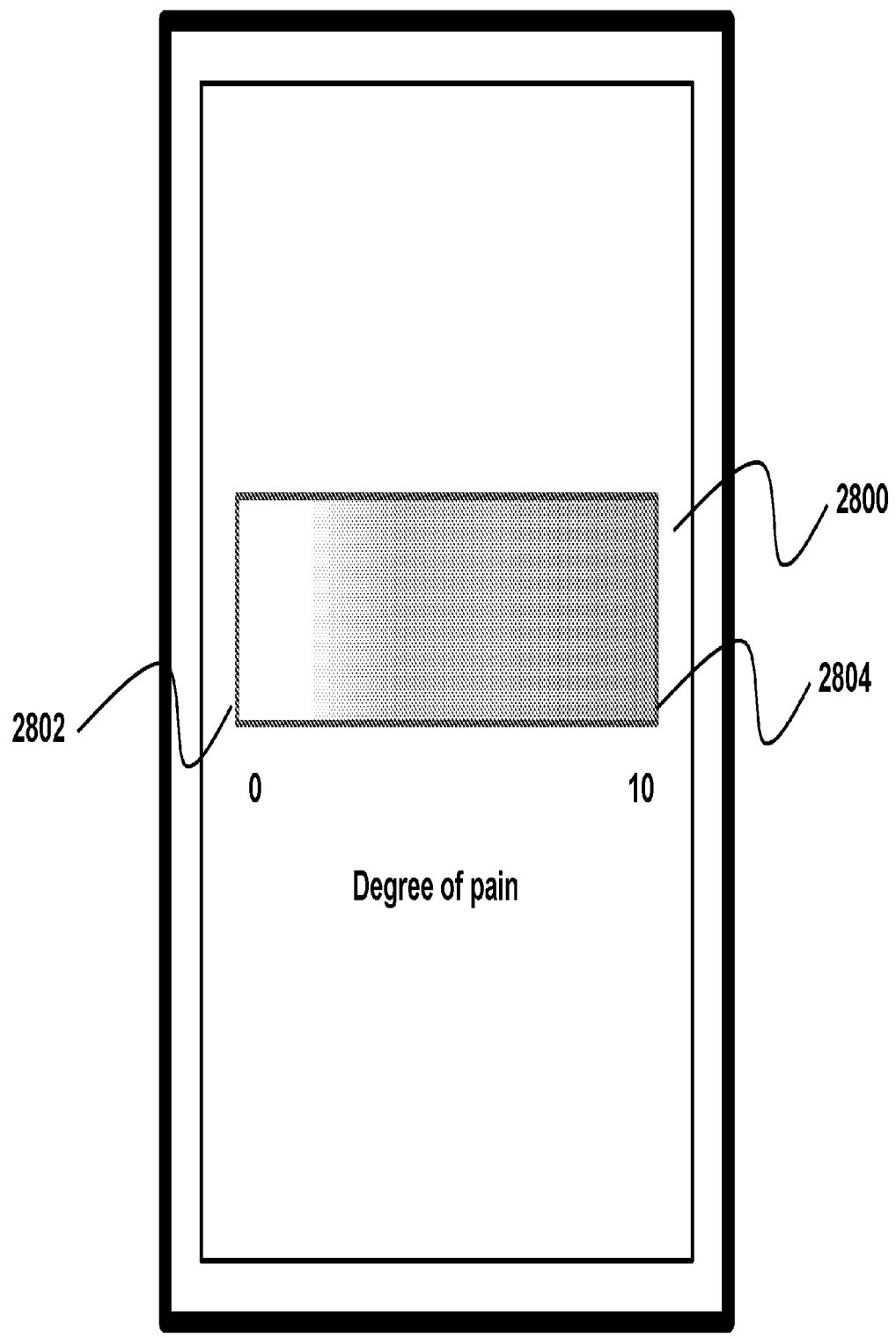
FIG. 28 is a depiction of a graphical user interface with a visual light bar.

FIG. 28 is a depiction of a graphical user interface with a visual light bar. It should be noted herein that while FIG. 28 is described in terms of a light bar having a scale from 0 to 10, any range may be employed, and any incremental iteration may correspond to any therapeutic length of time, in accordance with the present specification. For example, a range of 0 to 100 may be selected for the light bar to denote a patient's degree of pain.

As shown in FIG. 28, the light bar VAS 2800 extends or progresses, from 0 at the far left 2802 of the scale to 10 at the far right 2804 of the scale depending upon how long the user presses the button. In other words, the longer the user presses the button, the longer the light bar extends. In an embodiment, the closer to 10 that the light bar progresses from 2802 to 2804, the darker it becomes. In an embodiment, the user may repeatedly press light bar 2800 on a touchscreen device until the appropriate degree of pain is selected. In another embodiment, the user may slide the light bar 2800 from right to left or left to right, on a touchscreen device, to indicate the degree of pain.

In accordance with an aspect, the length or extent of the light bar VAS is not only indicative of the level of pain within a pain event but may also be indicative of the duration of a potential rescue session that may be triggered, as described above.

Figure 29:
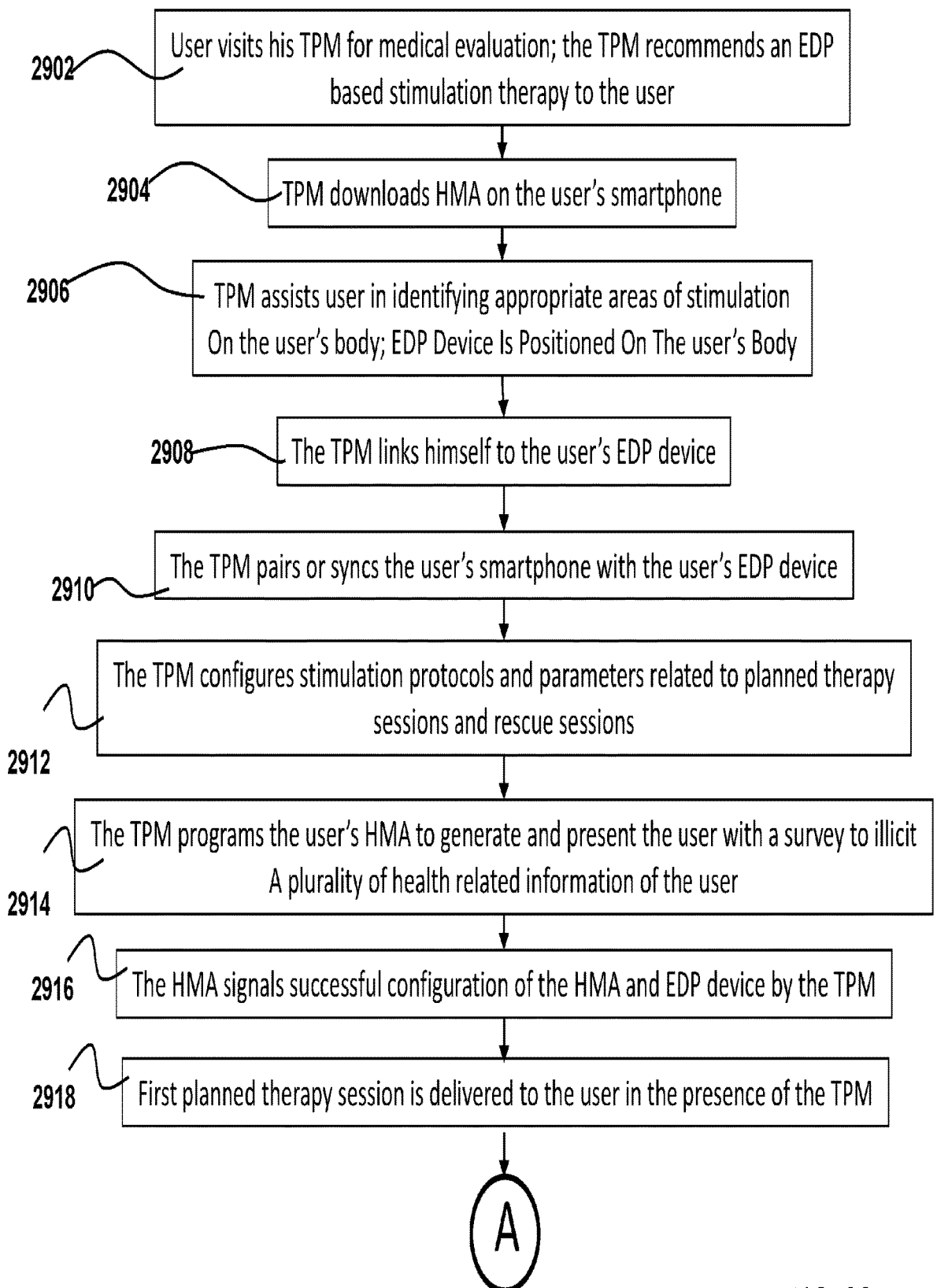
FIG. 29 is a flow chart illustrating a plurality of steps of a method for enabling a TPM to prescribe, configure, manage, monitor and intervene an EDP device based stimulation therapy for a user, in accordance with some embodiments.

FIG. 29 is a flow chart illustrating a plurality of steps of a method for enabling a TPM to prescribe, configure, manage, monitor and intervene an EDP device based stimulation therapy for a user, in accordance with some embodiments. At step 2902, a user visits her TPM for a medical check-up or evaluation. The TPM recommends an EDP device of the present specification to the user based on the user's medical condition, such as dysmenorrhea, for example. At step 2904, the TPM downloads the HMA on the user's smartphone (that works as a companion device). Thereafter, at step 2906, the TPM assists the user in identifying appropriate areas of stimulation (and therefore, placement of the EDP device on the user's body). The TPM also provides an orientation to the user regarding use and functions of the electro-dermal patch device. The EDP device is positioned on the identified location on the user's body. Next, at step 2908, the TPM associates or links to the user, the user's EDP device and HMA, such as, by inputting a unique code into the user's HMA. Associating or linking the TPM and the user enables a plurality of functions such as, but not limited to, allowing the TPM to regularly receive and access, in real time or near real time, the user's health related information and progress reports related to various therapeutic objectives, to accordingly modulate or titrate stimulation protocols and parameters when needed; and enabling the TPM to deactivate and reactivate the EDP device remotely, when needed.

The TPM pairs or syncs the user's smartphone with the user's EDP device, at step 2910. Thereafter, at step 2912, the TPM configures or programs the stimulation protocols and parameters, including various associated thresholds, ranges, related to planned therapy sessions as well as unplanned on-demand rescue sessions. In one embodiment, the TPM configures the planned stimulation therapy to be set at standard or baseline stimulation protocol, in absence of any initial health related information of the user. At step 2914, the TPM also programs the user's HMA to generate and present a survey to the user to illicit the user's health related information. The survey is programmed to be presented to the user, daily, within a time window preferred by the user. The TPM may, optionally, also prescribe a specific diet plan for the user. The HMA, at step 2916, acknowledges that the configuration (by the TPM) is successful and the EDP device also acknowledges successful configuration by, for example, vibratory, auditory and/or visual indications or signals (such as flashing LEDs of a specific color).

At step 2918, the TPM delivers a first planned therapy session to the user in the presence of the TPM to ensure that the HMA or therapy configuration is conducive to the user. If the user feels fine after the first session, the user is allowed to leave to continue the therapy at home, at step 2920. However, if the user reports inconvenience or deterioration in well-being, such as due to a feeling of nausea, the TPM reprograms the stimulation protocols and parameters at step 2922. At home, the user continues with the stimulation therapy, at step 2924, and generates a plurality of health related information (such as, but not limited to, the user's weight, scores related to pain, exercise, well-being (well-being profile) blood flow levels, individualized pain profile (as a result of recorded unexpected pain events and delivered rescue sessions)) during therapy. If and when needed, at step 2926, the TPM modulates the stimulation parameters and protocols, for both planned as well as rescue sessions, based on the plurality of user's health related information while the user is continuing with the stimulation therapy at home. The TPM also intervenes, by re-setting or reprogramming the EDP device and HMA and/or deactivating and reactivating the EDP device, when needed.

At step 2928, the user's stimulation is stopped, paused and/or the user prompted to revisit her TPM for re-evaluation of her medical condition or progress.

Therapeutic Objectives

In various embodiments, the systems and methods of the present specification employ an electro-dermal patch that provides pre-programmed and/or customized stimulation protocols to manage menstrual pain, dysmenorrhea related symptoms and/or well-being. In various embodiments, a Health Management application software, as described above, provides and/or enables the programming, either pre-programmed or set 'on demand' by the patient or medical personnel (in real time), of a plurality of therapeutic goals which are also customizable or adjustable in order to manage menstrual pain, dysmenorrhea related symptoms and/or well-being. It should be noted herein that any or a plurality of the methods of use or treatment examples provided above may be employed to achieve the therapeutic objectives.

It should also be noted that the percent changes in value listed below are represented by the following formula: [(New Value)−(Old Value)]/(Old Value)]. Thus, where a certain parameter is measured in percentage, the percentage change is reflected by the above formula and not a delta value.

The following are a plurality of non-limiting, exemplary goals:

In some embodiments, after at least one stimulation session or determinable time period after when stimulation terminates, the rate, level or amount of any patient parameter, as discussed throughout this specification is modified relative to the rate, level or amount of that patient parameter before stimulation. In one instance, after at least one stimulation session or determinable time period after when stimulation terminates, the rate, level or amount of that patient parameter is reduced relative to the rate, level or amount of that patient parameter before stimulation. In another instance, after at least one stimulation session or determinable time period after when stimulation terminates, the rate, level or amount of that patient parameter is increased relative to the rate, level or amount of that patient parameter before stimulation.

In some embodiments, application of stimulation therapy results in achieving a 10% reduction of overall amount of pain medication (such as aspirin, NSAID, Tylenol (acetaminophen) narcotics and any other medication used to control pain) usage during the course of a typical menstrual period (usually lasting 5-7 days).

In some embodiments, application of stimulation therapy results in achieving a lengthening of 10% of the average interval between the times for need of medication administration to treat menstrual related pain.

In some embodiments, after stimulation terminates, or at least one minute from when stimulation terminates, the patient experiences a decrease in pelvic and/or menstrual pain by at least 5%.

In some embodiments, after at least one minute from when stimulation terminates or after at least one stimulation session, the patient experiences a decrease in pelvic and/or menstrual pain such that it is equal to, or less than, 95% of the pre-stimulation menstrual pain levels.

In some embodiments, after at least one minute from when stimulation is initiated, the patient experiences a perceptible decrease in pelvic and/or menstrual pain.

In some embodiments, after at least one minute from when stimulation is initiated, the patient experiences an increase in well-being levels by at least 5%.

In some embodiments, after at least one minute from when stimulation terminates or after at least one stimulation session, the patient experiences an increase in well-being levels such that it is equal to, or greater than, 105% of the pre-stimulation well-being levels.

In some embodiments, after at least one stimulation session, an amount of a patient's pelvic and/or menstrual pain level is modified, relative to the corresponding amount before stimulation.

In some embodiments, after at least one stimulation session, an amount of a patient's well-being levels increases relative to the corresponding amount before stimulation.

In some embodiments, after at least one stimulation session, a patient's pelvic and/or menstrual pain level decreases, over a predefined period of time, relative to the patient's pelvic and/or menstrual pain level before stimulation and the patient's nausea and/or dyspepsia level does not increase, over the predefined period of time, relative to the patient's nausea level before stimulation, wherein the stimulation does not cause the patient to experience a pain sensation.

In some embodiments, after at least one stimulation session, a patient's well-being level increases, over a predefined period of time, relative to the patient's well-being level before stimulation and the patient's nausea and/or dyspepsia level does not increase, over the predefined period of time, relative to the patient's nausea level before stimulation, wherein the stimulation does not cause the patient to experience a pain sensation.

In some embodiments, after at least one stimulation session, a patient's prostaglandin level reduces by at least 1%, and preferably at least 3%, relative to the patient's prostaglandin level before stimulation. In some embodiments, after at least one stimulation session, a patient's prostaglandin level reduces by at least 1%, and preferably at least 3%, relative to the patient's prostaglandin level before stimulation.

In some embodiments, after at least one stimulation session, a post-stimulation prostaglandin level of a patient decreases by at least 1%, and preferably at least 3%, relative to a pre-stimulation prostaglandin level of the patient, wherein the pre-stimulation prostaglandin level is measured prior to stimulation and wherein the post-stimulation prostaglandin level is measured more than ten weeks after the at least one stimulation session.

In some embodiments, after at least one stimulation session, the level of a patient's beta-endorphin levels increases relative to the corresponding level of a patient's beta-endorphin levels before stimulation.

In some embodiments, after at least one stimulation session, a patient's beta-endorphin level increases by at least 1%, and preferably at least 3%, relative to the patient's beta-endorphin level before stimulation.

In some embodiments, after at least one session of stimulation session, the patient experiences a modification, and preferably, a perceptible decrease in pelvic and/or menstrual pain which lasts for at least one day.

In some embodiments, a patient's pelvic and/or menstrual pain is reduced by 5% over at least 1 day of stimulation therapy.

It should be appreciated that each of the pre-stimulation and post-stimulation levels, profiles or measurements may be assessed by comparing data from a single individual or by first aggregating pre-stimulation data from multiple individuals and post-stimulation data from multiple individuals and comparing the two aggregated data sets. Additionally, it should be appreciated that the effects of stimulation may be assessed by comparing measured parameters, as described above, from either an individual or group (in the form of aggregated data) to a control individual or group which has not undergone stimulation. In such cases, one would be comparing post-stimulation effects to no stimulation in a different individual or group of individuals (control) as opposed to comparing post-stimulation effects to pre-stimulation measurements from the same individual or group of individuals.

Telemedicine

As discussed earlier, the electro-dermal patch device is in data communication with and controlled by the companion device. The companion device is further capable of being in data communication with one or more remote patient care facilities and/or patient care personnel enabling telehealth or e-health and therefore allowing health care professionals to evaluate, diagnose and treat patients in remote locations using telecommunications technology.

In accordance with an aspect of the present specification, the user's plurality of health related information, such as the user's menstrual pain profile, menstrual cycle, well-being profile, weight trends, glucose data, daily or periodic scores related to exercise, stimulation induced nausea, dyspepsia and habituation events, including stimulation protocols, setting and parameters are recorded, archived and stored by the Health Management application software on the Cloud (for example). In various embodiments, such recorded and archived health related information as well as stimulation protocols, settings and parameters of the user are communicated to one or more remote care facilities and/or patient care personnel in real time, on-demand and/or periodically.

This enables the user to communicate her health status, trends, treatment or therapy details as well as therapeutic outcomes to the remote care facility and/or patient care personnel for evaluation, advice, support and further treatment and/or medication options. For example, the Health Management application software, which may be HIPAA compliant, enables continuous pain maintenance during a menstrual period by: enabling remote monitoring of the user's pain profile, well-being levels and overall activity level, for example; supporting a plurality of modes of communication such as, but not limited to, video-conferencing, tele-conferencing, email, and chat to enable interactive, real-time and/or asynchronous pain management or dysmenorrhea symptoms management related advice or stimulation regimen for the user. For example, the user's nutrition specialist, fitness trainer and/or a concierge service associated with the EDP device and Health Management application of the present specification may access, process and analyze the user's health related information and provide interventions in the form of adjusted or modified stimulation parameters, settings and protocols; and/or modifications to exercising routines, forms, frequency and period.

The above examples are merely illustrative of the many applications of the methods and systems of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. An electrical stimulation system configured to decrease a sensation of pain in a patient, comprising:
   an electrical stimulation device configured to be externally positioned on skin of the patient, comprising:
      a housing configured to adhere to the patient's skin;
      a memory, wherein the memory is configured to store a first plurality of stimulation parameters;
      a microcontroller positioned within the housing, wherein the microcontroller is adapted to cause a pulse generator to generate a plurality of electrical pulses in accordance with the first plurality of stimulation parameters;
      a transceiver positioned within the housing and in electrical communication with the microcontroller, wherein the transceiver is configured to communicate with a mobile computing device;
      at least one electrode in electrical contact with the microcontroller and in electrical contact with the patient's skin; and
      a pulse generator positioned within the housing and in electrical communication with the microcontroller and the at least one electrode, wherein the pulse generator is configured to generate the plurality of electrical pulses adapted to penetrate, via the at least one electrode, a range of 0.1 mm to 10 mm through the patient's skin; and
   a plurality of programmatic instructions stored on the mobile computing device, wherein, when executed, the plurality of programmatic instructions:
      cause the mobile computing device to generate a prompt to the patient to input patient status data over a period of time, wherein the patient status data includes at least one of a level of pain, a level of well-being, or a level of nausea;
      after the period of time, generate a stimulation parameter modulation signal based upon the patient status data; and
      cause the stimulation parameter modulation signal to be transmitted from the mobile computing device to the electrical stimulation device, wherein the electrical stimulation device generates the plurality of electrical pulses, such that at least one of the patient's T9 to T12 dermatomes, L1, L2, L5 dermatomes, or a sacral dermatomes is electrically stimulated, wherein, upon initiation of operation, the microcontroller causes the plurality of electrical pulses to be generated using the first plurality of stimulation parameters and wherein, after a second period of time, the microcontroller causes the plurality of electrical pulses to be generated using a second plurality of stimulation parameters that a) is at least partially different from the first plurality of stimulation parameters, b) based at least partially upon the stimulation parameter modulation signal, and has at least one of a pulse width, a pulse amplitude, a pulse frequency, a pulse duty cycle, a session duration, or a number of sessions that is increased relative to the first plurality of stimulation parameters if the patient's level of pain is above a predefined level.

2. The electrical stimulation system of claim 1, wherein the electrical stimulation device further comprises a first visual indicator, wherein the first visual indicator provides information about at least one of a power of state of the electrical stimulation device, a commencement or conclusion of a stimulation session, a malfunction of the electrical stimulation device, or a state of the power source.

3. The electrical stimulation system of claim 1, wherein the electrical stimulation device further comprises a sensor, wherein the sensor is an impedance sensor configured to determine contact integrity of the at least one electrode to the patient's skin.

4. The electrical stimulation system of claim 1, wherein the housing further comprises a sensor and wherein the sensor is a neural sensor configured to detect an amount of neural activity and generate at least one of an indication that the electrical stimulation device is placed in a right location, an indication that the electrical stimulation device is increasing neural activity in accordance with a stimulation protocol, an indication that the patient's neural response rate is insufficient, or an indication that a stimulation protocol needs to be modified.

5. The electrical stimulation system of claim 1, wherein at least one of the stimulation pulse width is in a range of 10 μsec to 100 msec, the pulse amplitude is in a range of 1 mA to 100 mA, the pulse frequency is in a range of 1 to 250 pulses per second, the pulse shape is at least one of monophasic, biphasic, or sinusoidal, the duty cycle is in a range of 1% to 99%, the session duration is in a range of 1 min to 60 min, or the session frequency is based on the level of pain of the user.

6. An electrical stimulation system configured to decrease a sensation of pain in a patient, comprising:
   an electrical stimulation device configured to be externally positioned on skin of the patient, comprising:
      a housing configured to adhere to the patient's skin;
      a memory, wherein the memory is configured to store a first plurality of stimulation parameters;
      a microcontroller positioned within the housing, wherein the microcontroller is adapted to cause a pulse generator to generate a plurality of electrical pulses in accordance with the first plurality of stimulation parameters;

a transceiver positioned within the housing and in electrical communication with the microcontroller, wherein the transceiver is configured to communicate with a mobile computing device;

at least one electrode in electrical contact with the microcontroller and in electrical contact with the patient's skin; and a pulse generator positioned within the housing and in electrical communication with the microcontroller and the at least one electrode, wherein the pulse generator is configured to generate the plurality of electrical pulses adapted to penetrate, via the at least one electrode, a range of 0.1 mm to 10 mm through the patient's skin; and a plurality of programmatic instructions stored on the mobile computing device, wherein, when executed, the plurality of programmatic instructions:

cause the mobile computing device to generate a prompt to the patient to input patient status data over a period of time, wherein the patient status data includes at least one of a level of pain, a level of well-being, or a level of nausea;

after the period of time, generate a stimulation parameter modulation signal based upon the patient status data; and cause the stimulation parameter modulation signal to be transmitted from the mobile computing device to the electrical stimulation device, wherein the electrical stimulation device generates the plurality of electrical pulses, such that at least one of the patient's T9 to T12 dermatomes, L1, L2, L5 dermatomes, or a sacral dermatomes is electrically stimulated, wherein, upon initiation of operation, the microcontroller causes the plurality of electrical pulses to be generated using the first plurality of stimulation parameters and wherein, after a second period of time, the microcontroller causes the plurality of electrical pulses to be generated using a second plurality of stimulation parameters that a) is at least partially different from the first plurality of stimulation parameters, b) based at least partially upon the stimulation parameter modulation signal, and has at least one of a pulse width, a pulse amplitude, a pulse frequency, a pulse duty cycle, a session duration, or a number of sessions that is decreased relative to the first plurality of stimulation parameters if the patient's level of pain is below a predefined level.

7. The electrical stimulation system of claim 6, wherein the electrical stimulation device further comprises a first visual indicator, wherein the first visual indicator provides information about at least one of a power of state of the electrical stimulation device, a commencement or conclusion of a stimulation session, a malfunction of the electrical stimulation device, or a state of the power source.

8. The electrical stimulation system of claim 6, wherein the electrical stimulation device further comprises a sensor, wherein the sensor is an impedance sensor configured to determine contact integrity of the at least one electrode to the patient's skin.

9. The electrical stimulation system of claim 6, wherein the housing further comprises a sensor and wherein the sensor is a neural sensor configured to detect an amount of neural activity and generate at least one of an indication that the electrical stimulation device is placed in a right location, an indication that the electrical stimulation device is increasing neural activity in accordance with a stimulation protocol, an indication that the patient's neural response rate is insufficient, or an indication that a stimulation protocol needs to be modified.

10. The electrical stimulation system of claim 6, wherein at least one of the stimulation pulse width is in a range of 10 μsec to 100 msec, the pulse amplitude is in a range of 1 mA to 100 mA, the pulse frequency is in a range of 1 to 250 pulses per second, the pulse shape is at least one of monophasic, biphasic, or sinusoidal, the duty cycle is in a range of 1% to 99%, the session duration is in a range of 1 min to 60 min, or the session frequency is based on the level of pain of the user.

11. An electrical stimulation system configured to decrease a sensation of pain in a patient, comprising:

an electrical stimulation device configured to be externally positioned on skin of the patient, comprising:

a housing configured to adhere to the patient's skin;

a memory, wherein the memory is configured to store a first plurality of stimulation parameters;

a microcontroller positioned within the housing, wherein the microcontroller is adapted to cause a pulse generator to generate a plurality of electrical pulses in accordance with the first plurality of stimulation parameters;

a transceiver positioned within the housing and in electrical communication with the microcontroller, wherein the transceiver is configured to communicate with a mobile computing device;

at least one electrode in electrical contact with the microcontroller and in electrical contact with the patient's skin; and a pulse generator positioned within the housing and in electrical communication with the microcontroller and the at least one electrode, wherein the pulse generator is configured to generate the plurality of electrical pulses adapted to penetrate, via the at least one electrode, a range of 0.1 mm to 10 mm through the patient's skin; and a plurality of programmatic instructions stored on the mobile computing device, wherein, when executed, the plurality of programmatic instructions:

cause the mobile computing device to generate a prompt to the patient to input patient status data over a period of time, wherein the patient status data includes at least one of a level of pain, a level of well-being, or a level of nausea;

after the period of time, generate a stimulation parameter modulation signal based upon the patient status data; and cause the stimulation parameter modulation signal to be transmitted from the mobile computing device to the electrical stimulation device, wherein the electrical stimulation device generates the plurality of electrical pulses, such that at least one of the patient's T9 to T12 dermatomes, L1, L2, L5 dermatomes, or a sacral dermatomes is electrically stimulated, wherein, upon initiation of operation, the microcontroller causes the plurality of electrical pulses to be generated using the first plurality of stimulation parameters and wherein, after a second period of time, the microcontroller causes the plurality of electrical pulses to be generated using a second plurality of stimulation parameters that a) is at least partially different from the first plurality of stimulation parameters, b) based at least partially upon the stimulation parameter modulation signal, and has at least one of a pulse width, a pulse amplitude, a pulse frequency, a pulse duty cycle, a session duration, or a number of sessions that is decreased relative to the first plurality of stimulation parameters if the patient's level of well-being is above a predefined level.

12. The electrical stimulation system of claim 11, wherein the electrical stimulation device further comprises a first visual indicator, wherein the first visual indicator provides information about at least one of a power of state of the electrical stimulation device, a commencement or conclusion of a stimulation session, a malfunction of the electrical stimulation device, or a state of the power source.

13. The electrical stimulation system of claim 11, wherein the electrical stimulation device further comprises a sensor, wherein the sensor is an impedance sensor configured to determine contact integrity of the at least one electrode to the patient's skin.

14. The electrical stimulation system of claim 11, wherein the housing further comprises a sensor and wherein the sensor is a neural sensor configured to detect an amount of neural activity and generate at least one of an indication that the electrical stimulation device is placed in a right location, an indication that the electrical stimulation device is increasing neural activity in accordance with a stimulation protocol, an indication that the patient's neural response rate is insufficient, or an indication that a stimulation protocol needs to be modified.

15. The electrical stimulation system of claim 11, wherein at least one of the stimulation pulse width is in a range of 10 μsec to 100 msec, the pulse amplitude is in a range of 1 mA to 100 mA, the pulse frequency is in a range of 1 to 250 pulses per second, the pulse shape is at least one of monophasic, biphasic, or sinusoidal, the duty cycle is in a range of 1% to 99%, the session duration is in a range of 1 min to 60 min, or the session frequency is based on the level of pain of the user.

16. An electrical stimulation system configured to decrease a sensation of pain in a patient, comprising:
an electrical stimulation device configured to be externally positioned on skin of the patient, comprising:
a housing configured to adhere to the patient's skin;
a memory, wherein the memory is configured to store a first plurality of stimulation parameters;
a microcontroller positioned within the housing, wherein the microcontroller is adapted to cause a pulse generator to generate a plurality of electrical pulses in accordance with the first plurality of stimulation parameters;
a transceiver positioned within the housing and in electrical communication with the microcontroller, wherein the transceiver is configured to communicate with a mobile computing device;
at least one electrode in electrical contact with the microcontroller and in electrical contact with the patient's skin; and
a pulse generator positioned within the housing and in electrical communication with the microcontroller and the at least one electrode, wherein the pulse generator is configured to generate the plurality of electrical pulses adapted to penetrate, via the at least one electrode, a range of 0.1 mm to 10 mm through the patient's skin; and a plurality of programmatic instructions stored on the mobile computing device, wherein, when executed, the plurality of programmatic instructions:
cause the mobile computing device to generate a prompt to the patient to input patient status data over a period of time, wherein the patient status data includes at least one of a level of pain, a level of well-being, or a level of nausea;
after the period of time, generate a stimulation parameter modulation signal based upon the patient status data; and
cause the stimulation parameter modulation signal to be transmitted from the mobile computing device to the electrical stimulation device, wherein the electrical stimulation device generates the plurality of electrical pulses, such that at least one of the patient's T9 to T12 dermatomes, L1, L2, L5 dermatomes, or a sacral dermatomes is electrically stimulated, wherein, upon initiation of operation, the microcontroller causes the plurality of electrical pulses to be generated using the first plurality of stimulation parameters and wherein, after a second period of time, the microcontroller causes the plurality of electrical pulses to be generated using a second plurality of stimulation parameters that a) is at least partially different from the first plurality of stimulation parameters, b) based at least partially upon the stimulation parameter modulation signal, and has at least one of a pulse width, a pulse amplitude, a pulse frequency, a pulse duty cycle, a session duration, or a number of sessions that is increased relative to the first plurality of stimulation parameters if the patient's level of well-being is below a predefined level.

17. The electrical stimulation system of claim 16, wherein the electrical stimulation device further comprises a first visual indicator, wherein the first visual indicator provides information about at least one of a power of state of the electrical stimulation device, a commencement or conclusion of a stimulation session, a malfunction of the electrical stimulation device, or a state of the power source.

18. The electrical stimulation system of claim 16, wherein the electrical stimulation device further comprises a sensor, wherein the sensor is an impedance sensor configured to determine contact integrity of the at least one electrode to the patient's skin.

19. The electrical stimulation system of claim 16, wherein the housing further comprises a sensor and wherein the sensor is a neural sensor configured to detect an amount of neural activity and generate at least one of an indication that the electrical stimulation device is placed in a right location, an indication that the electrical stimulation device is increasing neural activity in accordance with a stimulation protocol, an indication that the patient's neural response rate is insufficient, or an indication that a stimulation protocol needs to be modified.

20. The electrical stimulation system of claim 16, wherein at least one of the stimulation pulse width is in a range of 10 μsec to 100 msec, the pulse amplitude is in a range of 1 mA to 100 mA, the pulse frequency is in a range of 1 to 250 pulses per second, the pulse shape is at least one of monophasic, biphasic, or sinusoidal, the duty cycle is in a range of 1% to 99%, the session duration is in a range of 1 min to 60 min, or the session frequency is based on the level of pain of the user.

* * * * *